US011236889B2

(12) United States Patent
Raring et al.

(10) Patent No.: US 11,236,889 B2
(45) Date of Patent: Feb. 1, 2022

(54) VIOLET AND ULTRAVIOLET ILLUMINATION DEVICE CONFIGURED WITH A GALLIUM AND NITROGEN CONTAINING LASER SOURCE

(71) Applicant: KYOCERA SLD Laser, Inc., Goleta, CA (US)

(72) Inventors: James W. Raring, Santa Barbara, CA (US); Paul Rudy, Manhattan Beach, CA (US); Melvin McLaurin, Santa Barbara, CA (US); Troy Trottier, Cary, NC (US)

(73) Assignee: KYOCERA SLD Laser, Inc., Goleta, CA (US)

( * ) Notice: Subject to any disclaimer, the term of this patent is extended or adjusted under 35 U.S.C. 154(b) by 0 days.

(21) Appl. No.: 17/216,220

(22) Filed: Mar. 29, 2021

(65) Prior Publication Data

US 2021/0215319 A1 Jul. 15, 2021

Related U.S. Application Data

(63) Continuation-in-part of application No. 16/923,476, filed on Jul. 8, 2020, now Pat. No. 11,125,415, which
(Continued)

(51) Int. Cl.
*F21V 9/32* (2018.01)
*H01S 5/062* (2006.01)
(Continued)

(52) U.S. Cl.
CPC ............... *F21V 9/32* (2018.02); *F21V 7/30* (2018.02); *G02B 27/0955* (2013.01);
(Continued)

(58) Field of Classification Search
CPC . F21V 9/32; H01S 5/062; H01S 5/343; H01S 5/0071; H01S 5/3402
See application file for complete search history.

(56) References Cited

U.S. PATENT DOCUMENTS 5,029,999 A 7/1991 Kremer et al.
6,125,225 A 9/2000 Dianov et al.
(Continued)

FOREIGN PATENT DOCUMENTS

CN 203967503 U 11/2014
DE 10 2016 200 653 A1 7/2017
(Continued)

OTHER PUBLICATIONS

U.S. Appl. No. 15/841,053 Notice of Allowance dated Oct. 10, 2018, 9 pages.
(Continued)

*Primary Examiner* — Evan P Dzierzynski
(74) *Attorney, Agent, or Firm* — Kilpatrick Townsend & Stockton LLP

(57) ABSTRACT

A light source system or apparatus configured with an infrared illumination source includes a gallium and nitrogen containing laser diode based white light source. The light source system includes a first pathway configured to direct directional electromagnetic radiation from the gallium and nitrogen containing laser diode to a first wavelength converter and to output a white light emission. In some embodiments infrared emitting laser diodes are included to generate the infrared illumination. In some embodiments infrared emitting wavelength converter members are included to generate the infrared illumination. In some embodiments a second wavelength converter is optically excited by a UV or blue emitting gallium and nitrogen containing laser diode, a laser diode operating in the long wavelength visible spectrum such as a green laser diode or a red laser diode, by a
(Continued)

near infrared emitting laser diode, by the white light emission produced by the first wavelength converter, or by some combination thereof. A beam shaper may be configured to direct the white light emission and an infrared emission for illuminating a target of interest and transmitting a data signal. In some configurations, sensors and feedback loops are included.

23 Claims, 44 Drawing Sheets

Related U.S. Application Data is a continuation of application No. 16/512,903, filed on Jul. 16, 2019, now Pat. No. 10,718,491.

(51) Int. Cl.
| | |
|---|---|
| *H01S 5/343* | (2006.01) |
| *H01S 5/00* | (2006.01) |
| *H01S 5/34* | (2006.01) |
| *F21V 7/30* | (2018.01) |
| *H01S 5/40* | (2006.01) |
| *G02B 27/09* | (2006.01) |
| *H04B 10/116* | (2013.01) |
| *H04B 10/50* | (2013.01) |
| *H01S 5/0225* | (2021.01) |
| *H01S 5/02251* | (2021.01) |
| *G01S 7/481* | (2006.01) |
| *H01S 5/02212* | (2021.01) |
| *H01S 5/02216* | (2021.01) |
| *F21Y 113/13* | (2016.01) |
| *H01S 5/028* | (2006.01) |
| *H01S 5/10* | (2021.01) |
| *H01L 33/00* | (2010.01) |
| *F21V 29/502* | (2015.01) |
| *G02B 26/08* | (2006.01) |
| *F21Y 115/30* | (2016.01) |
| *G02B 26/10* | (2006.01) |
| *F21V 29/70* | (2015.01) |
| *H01L 33/50* | (2010.01) |
| *H01L 33/32* | (2010.01) |
| *H01S 5/22* | (2006.01) |
| *H01S 5/042* | (2006.01) |
| *H01S 5/02* | (2006.01) |
| *H01S 5/024* | (2006.01) |
| *H01S 5/0234* | (2021.01) |
| *H01S 5/02257* | (2021.01) |

(52) U.S. Cl.
CPC ........ *G02B 27/0977* (2013.01); *H01S 5/0071* (2013.01); *H01S 5/0225* (2021.01); *H01S 5/02251* (2021.01); *H01S 5/062* (2013.01); *H01S 5/3402* (2013.01); *H01S 5/343* (2013.01); *H01S 5/34333* (2013.01); *H01S 5/4087* (2013.01); *H04B 10/116* (2013.01); *H04B 10/503* (2013.01); *F21V 29/502* (2015.01); *F21V 29/70* (2015.01); *F21Y 2113/13* (2016.08); *F21Y 2115/30* (2016.08); *G01S 7/4814* (2013.01); *G02B 26/0833* (2013.01); *G02B 26/105* (2013.01); *H01L 33/0045* (2013.01); *H01L 33/32* (2013.01); *H01L 33/502* (2013.01); *H01S 5/028* (2013.01); *H01S 5/0215* (2013.01); *H01S 5/0217* (2013.01); *H01S 5/0234* (2021.01); *H01S 5/02212* (2013.01); *H01S 5/02216* (2013.01); *H01S 5/02257* (2021.01); *H01S 5/02469* (2013.01); *H01S 5/04252* (2019.08); *H01S 5/1039* (2013.01); *H01S 5/2206* (2013.01); *H01S 5/34346* (2013.01); *H01S 2304/04* (2013.01)

(56) References Cited

U.S. PATENT DOCUMENTS

| | | | |
|---|---|---|---|
| 6,791,103 | B2 | 9/2004 | Nakamura et al. |
| 7,532,311 | B2 | 5/2009 | Henderson et al. |
| 9,318,875 | B1 | 4/2016 | Goutain |
| 9,784,835 | B1 | 10/2017 | Droz et al. |
| 9,888,838 | B2 | 2/2018 | Ito et al. |
| 10,222,474 | B1 | 3/2019 | Raring et al. |
| 10,338,220 | B1 | 7/2019 | Raring et al. |
| 10,345,446 | B2 | 7/2019 | Raring et al. |
| 10,649,086 | B2 | 5/2020 | Raring et al. |
| 10,718,491 | B1 | 7/2020 | Raring et al. |
| 2006/0227317 | A1 | 10/2006 | Henderson et al. |
| 2009/0101930 | A1* | 4/2009 | Li .............................. F21K 9/64 257/98 |
| 2013/0314711 | A1 | 11/2013 | Cantin et al. |
| 2014/0086539 | A1 | 3/2014 | Goutain et al. |
| 2015/0229107 | A1 | 8/2015 | McLaurin et al. |
| 2016/0265729 | A1* | 9/2016 | Goutain ................. B82Y 20/00 |
| 2017/0051883 | A1* | 2/2017 | Raring ................... H01S 5/3203 |
| 2017/0051884 | A1 | 2/2017 | Raring et al. |
| 2017/0301799 | A1 | 10/2017 | Boles et al. |
| 2018/0316160 | A1 | 11/2018 | Raring et al. |
| 2018/0323581 | A1 | 11/2018 | Stojetz et al. |
| 2019/0187284 | A1 | 6/2019 | Raring et al. |
| 2020/0064476 | A1 | 2/2020 | Raring et al. |
| 2020/0174123 | A1 | 6/2020 | Raring et al. |
| 2020/0174124 | A1 | 6/2020 | Raring et al. |
| 2021/0018161 | A1 | 1/2021 | Raring et al. |

FOREIGN PATENT DOCUMENTS

| | | |
|---|---|---|
| WO | 2017/019725 A1 | 2/2017 |
| WO | 2019/067416 A1 | 4/2019 |
| WO | 2019/118140 A1 | 6/2019 |

OTHER PUBLICATIONS

U.S. Appl. No. 16/002,422 Notice of Allowance dated Feb. 12, 2019, 9 pages.
U.S. Appl. No. 16/011,443 Notice of Allowance dated Feb. 19, 2019, 10 pages.
U.S. Appl. No. 16/270,448 Non-Final Office Action dated Sep. 11, 2019, 7 pages.
U.S. Appl. No. 16/270,448 Notice of Allowance dated Jan. 8, 2020, 7 pages.
U.S. Appl. No. 16/512,903 Notice of Allowance dated Mar. 26, 2020, 11 pages.
International Search Report and Written Opinion for Application No. PCT/US2018/062092, dated Jan. 31, 2019, 13 pages.
International Search Report and Written Opinion for Application No. PCT/US2020/042361, dated Sep. 21, 2020, 6 pages.
U.S. Appl. No. 16/672,266 Non-Final Office Action dated Nov. 17, 2020, 8 pages.
U.S. Appl. No. 16/672,266 Final Office Action dated Apr. 8, 2021, 8 pages.
U.S. Appl. No. 16/783,993 Non-Final Office Action dated Feb. 18, 2021, 9 pages.
U.S. Appl. No. 16/783,993 Final Office Action dated Jun. 1, 2021, 7 pages.
U.S. Appl. No. 16/784,008 Non-Final Office Action dated Feb. 26, 2021, 9 pages.
U.S. Appl. No. 16/784,008 Final Office Action dated Jun. 16, 2021, 8 pages.
U.S. Appl. No. 16/923,476 Notice of Allowance dated May 17, 2021, 11 pages.

(56) References Cited

OTHER PUBLICATIONS

Extended European Search Report for Application No. 18889537.9-1206, dated Jun. 24, 2021, 13 pages.
U.S. Appl. No. 16/784,008 Notice of Allowance dated Sep. 29, 2021, 8 pages.
U.S. Appl. No. 17/165,827 Notice of Allowance dated Nov. 24, 2021, 8 pages.

* cited by examiner

Figure 1: YAG: Ce3+ Absorption Spectra

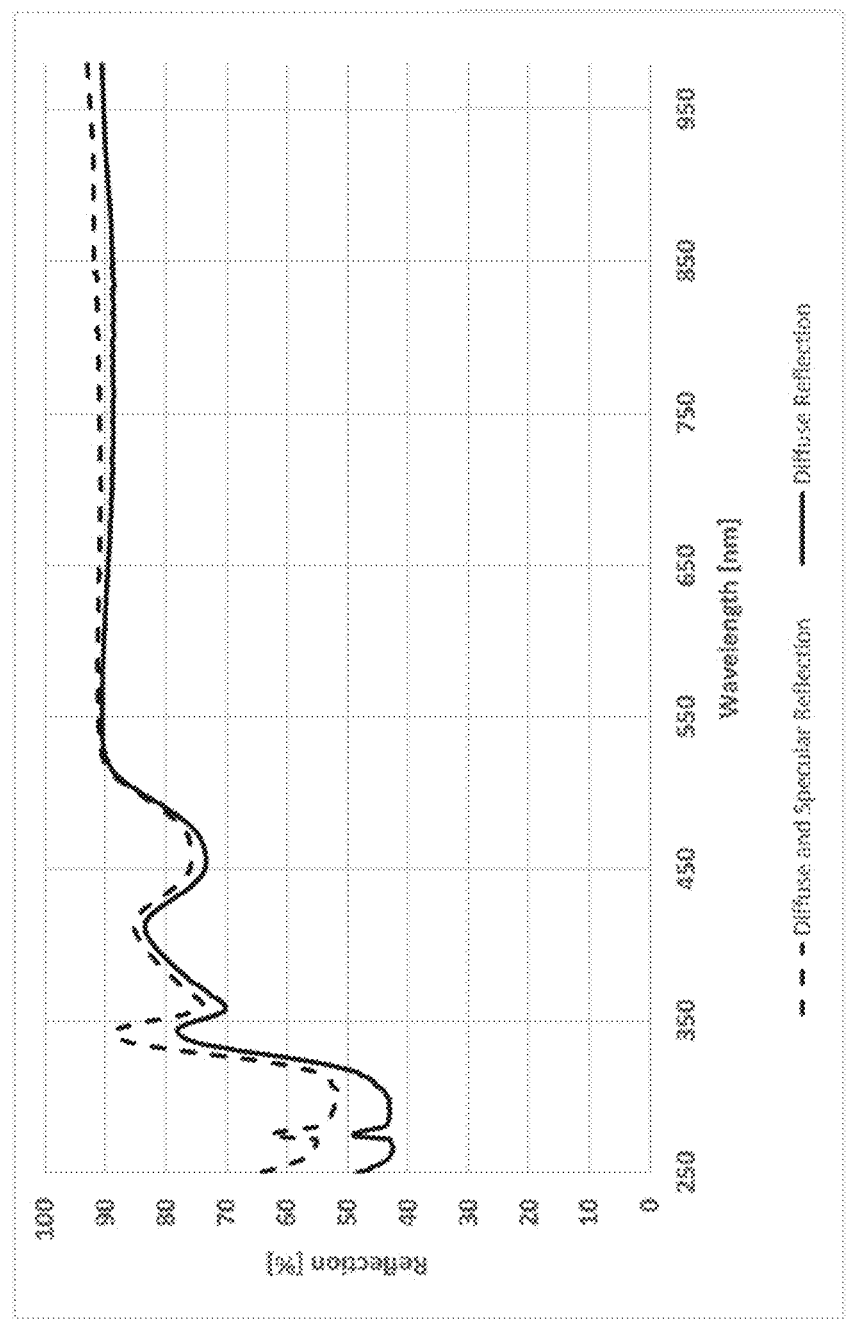
Figure 11: Diffuse Reflection of YAG: Ce3+ Component

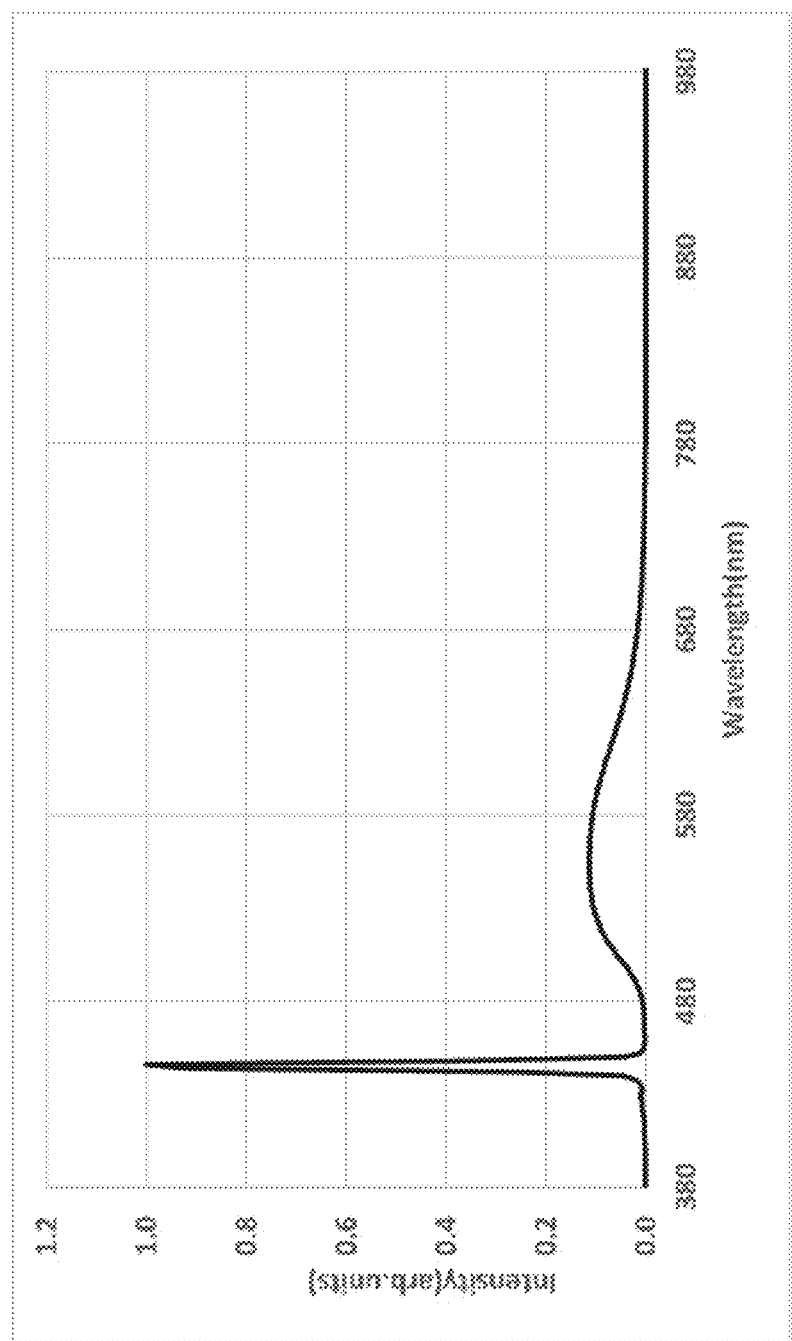
Figure 12: White Laser based Spectra 6000K

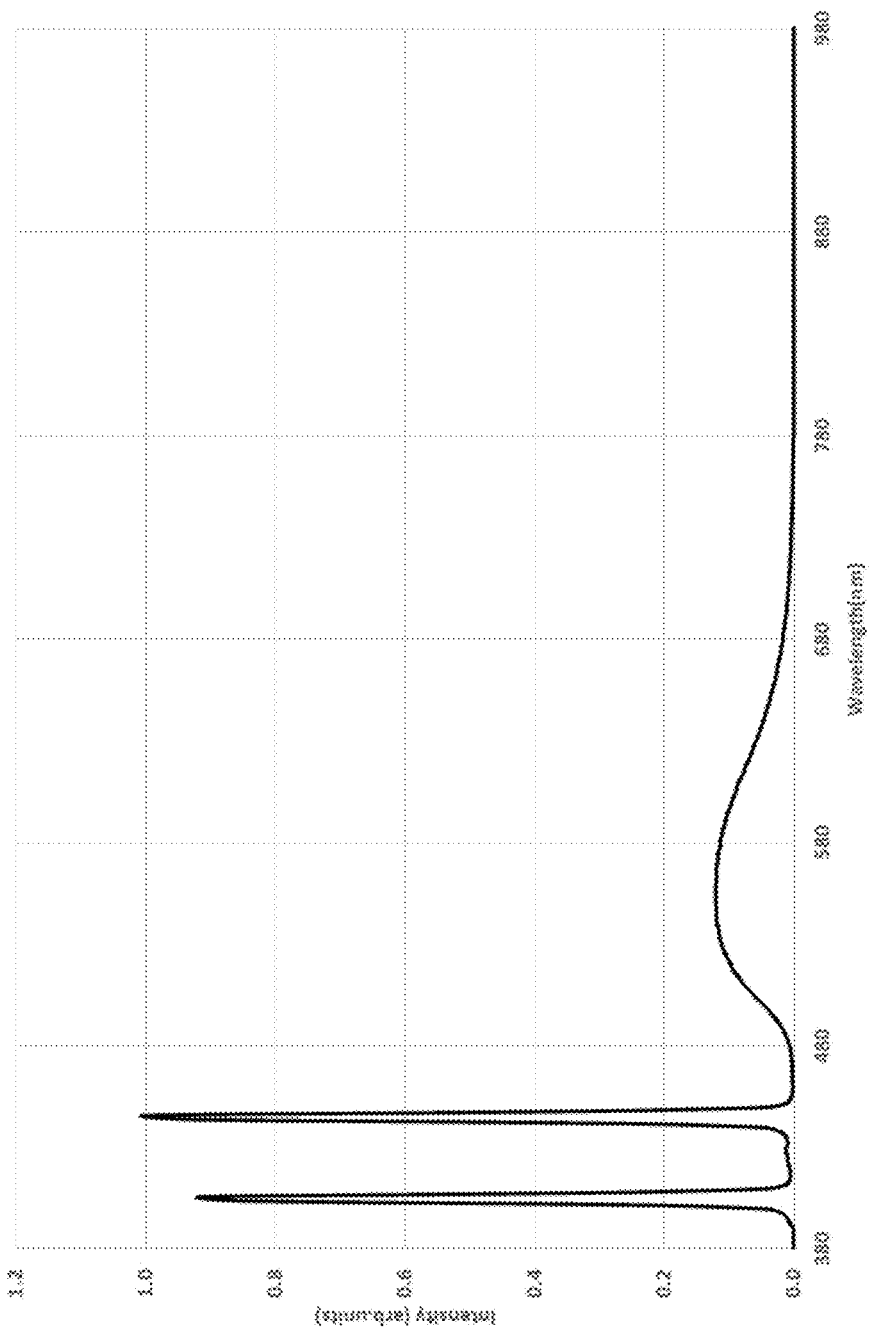
Figure 13: Laser based White 6000K with 405nm addition

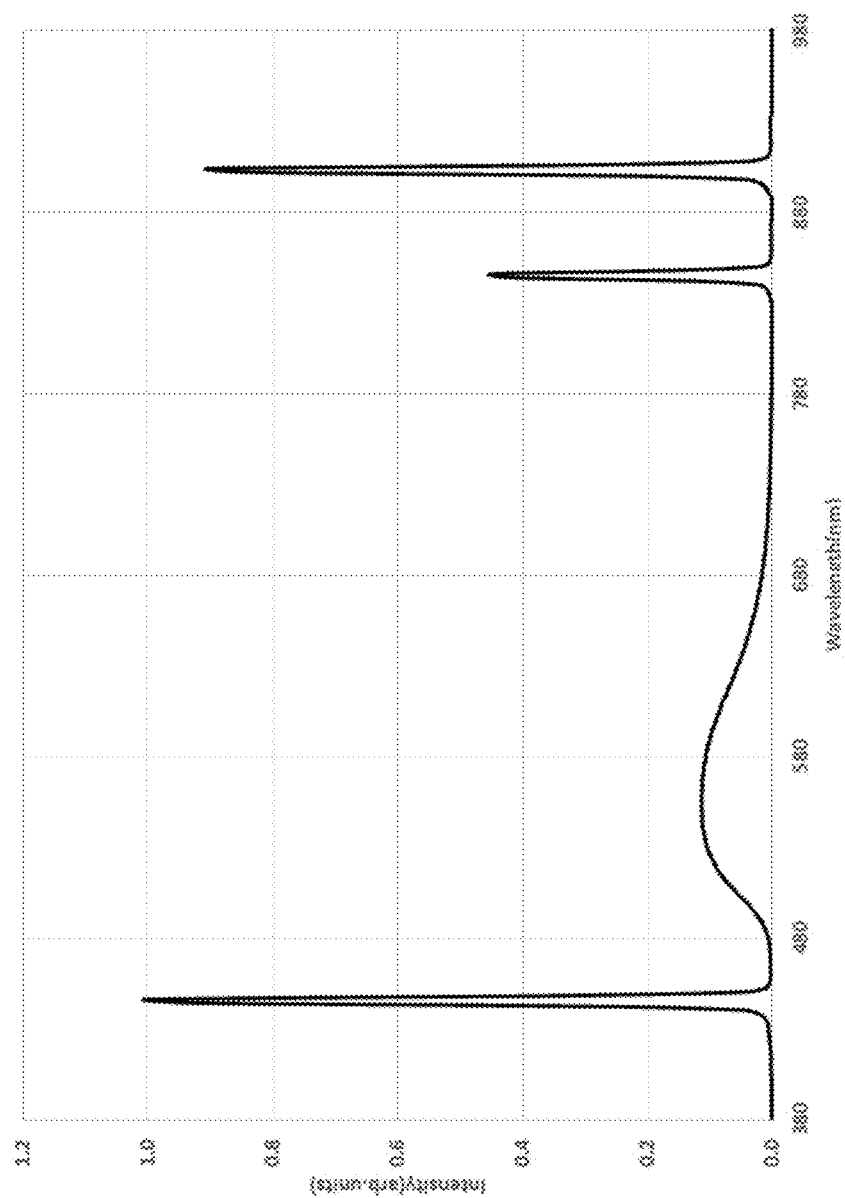
Figure 14: Laser based White Light 6000K with 850 and 905 IR additions

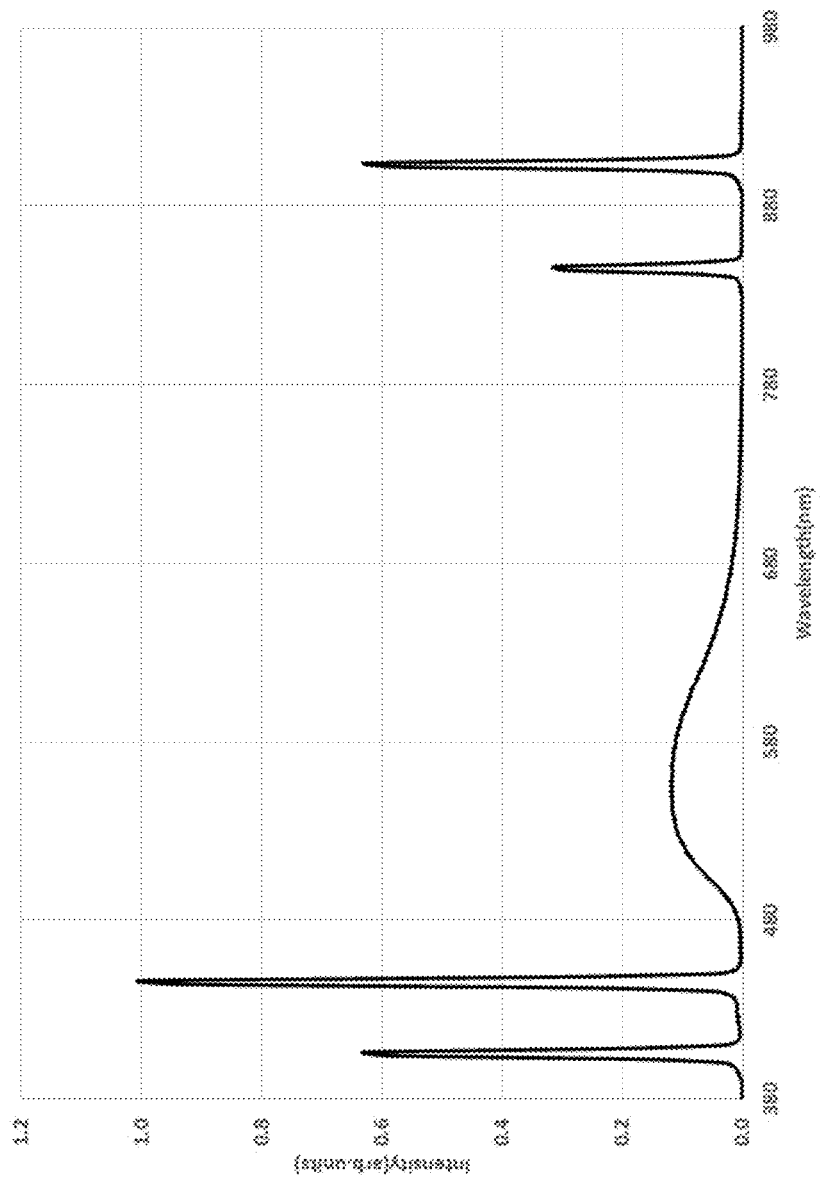
Figure 15: Laser Based White 6000K with Near UV and Near IR additions

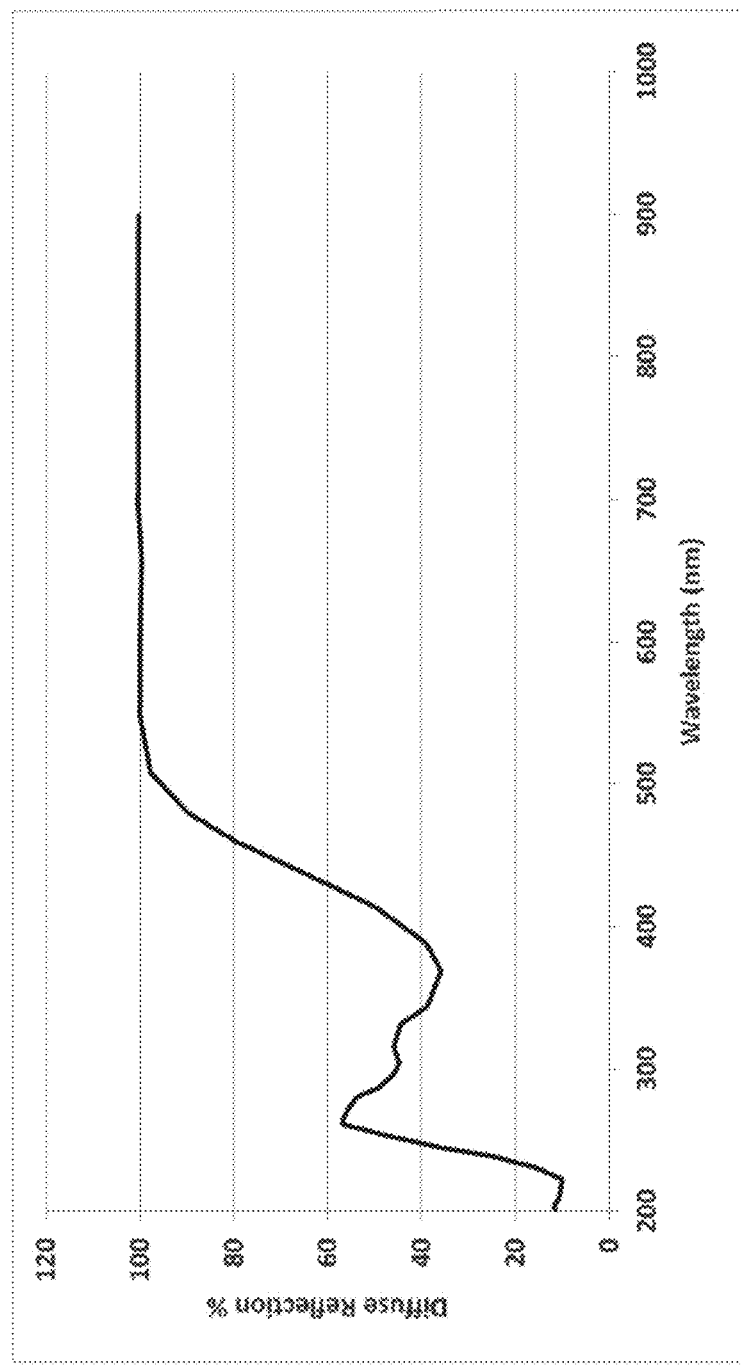
Figure 16: CASN: Eu2+ Red Phosphor Diffuse Reflection Spectra

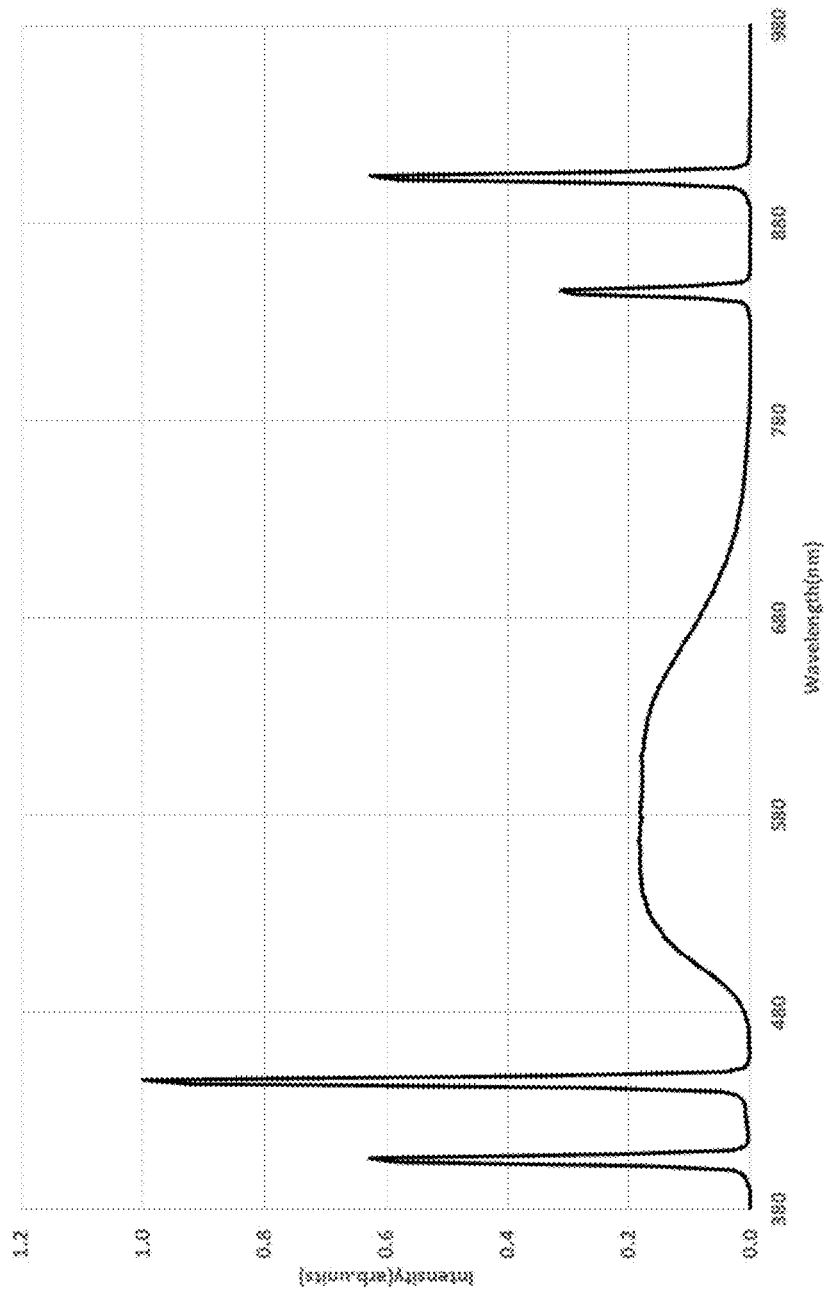
Figure 17: Laser based White 4000K with near UV and Near IR additions

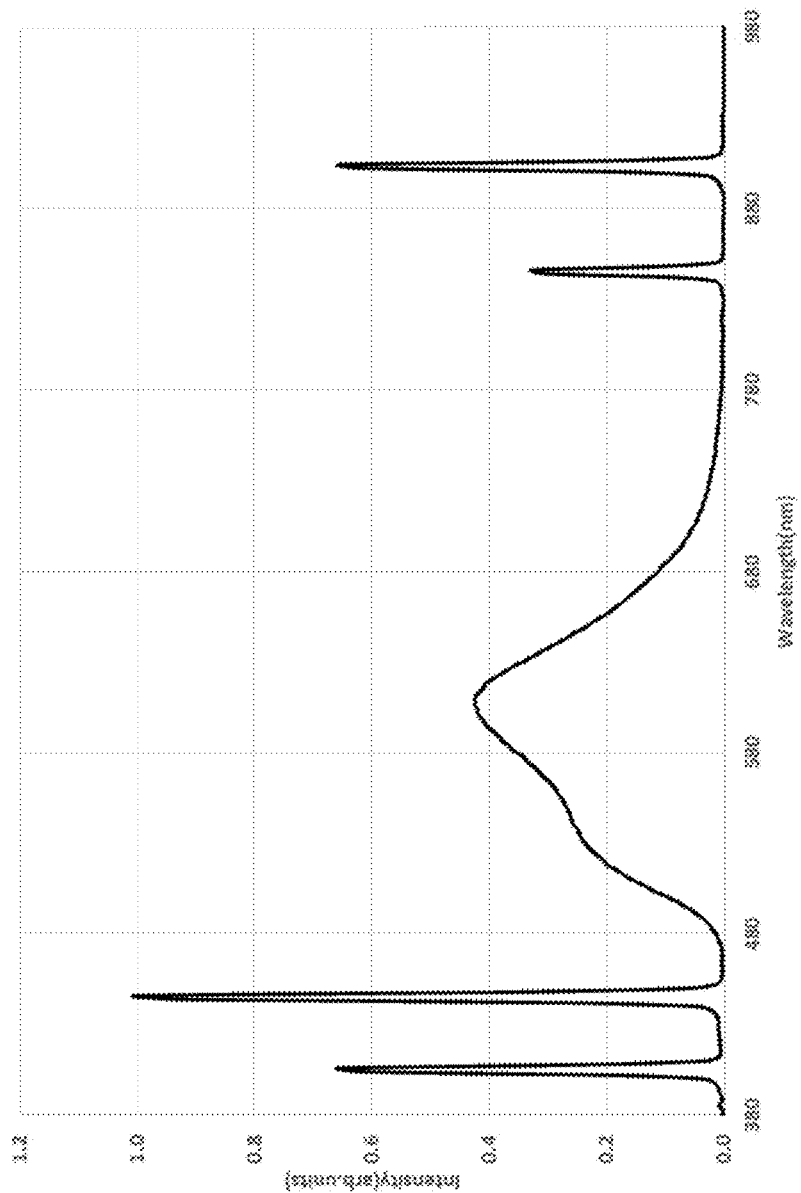

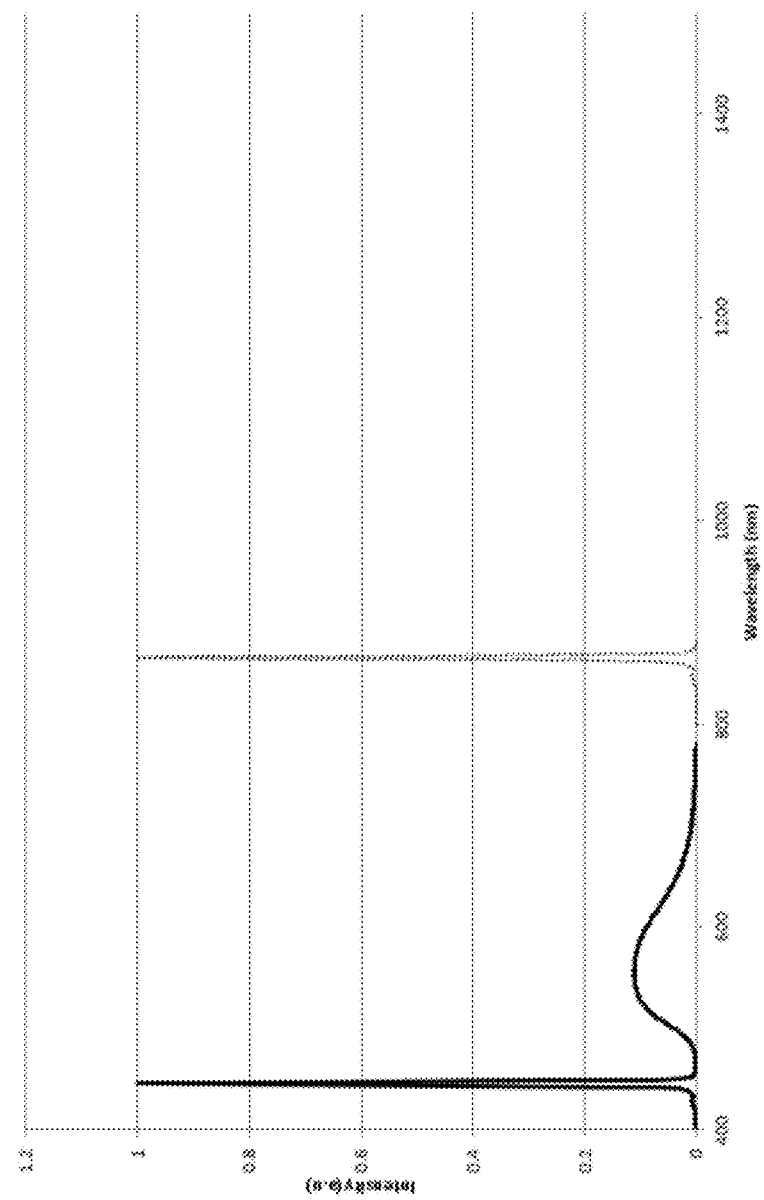

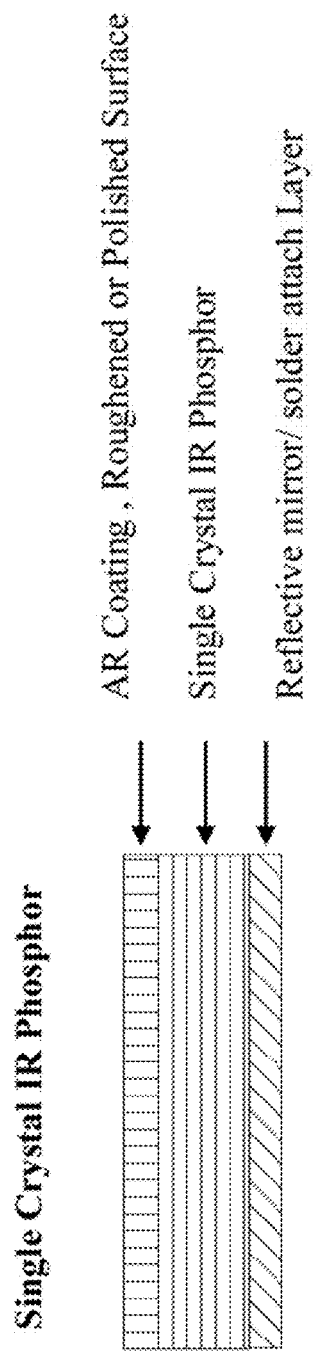

Stacked Single Crystal/PolyCrystal/Phosphor in Glass VIS/IR Phosphor

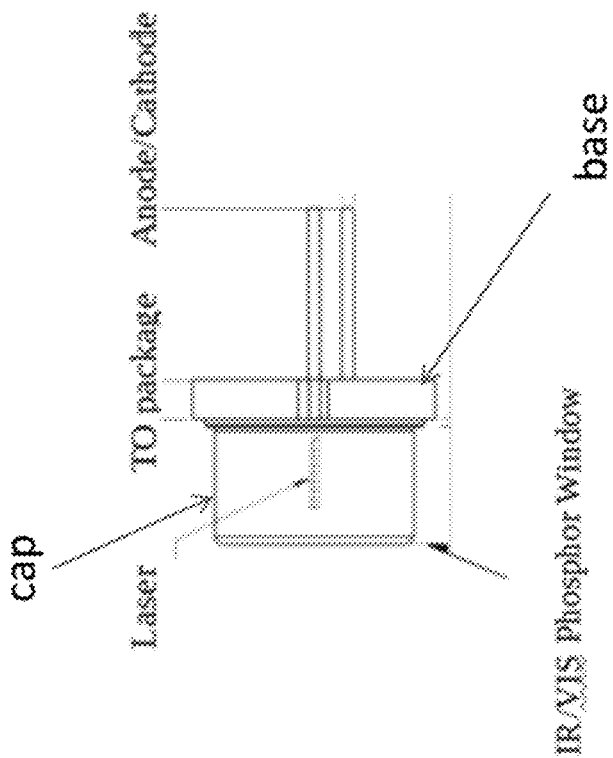
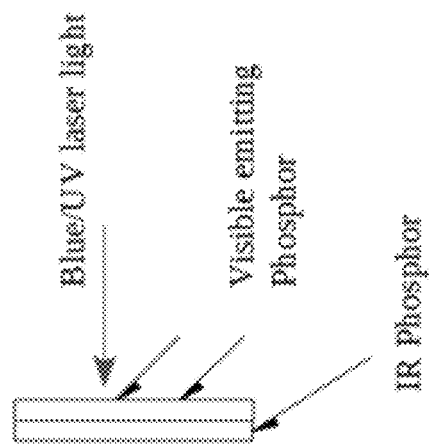
Figure 25C
Figure 25D

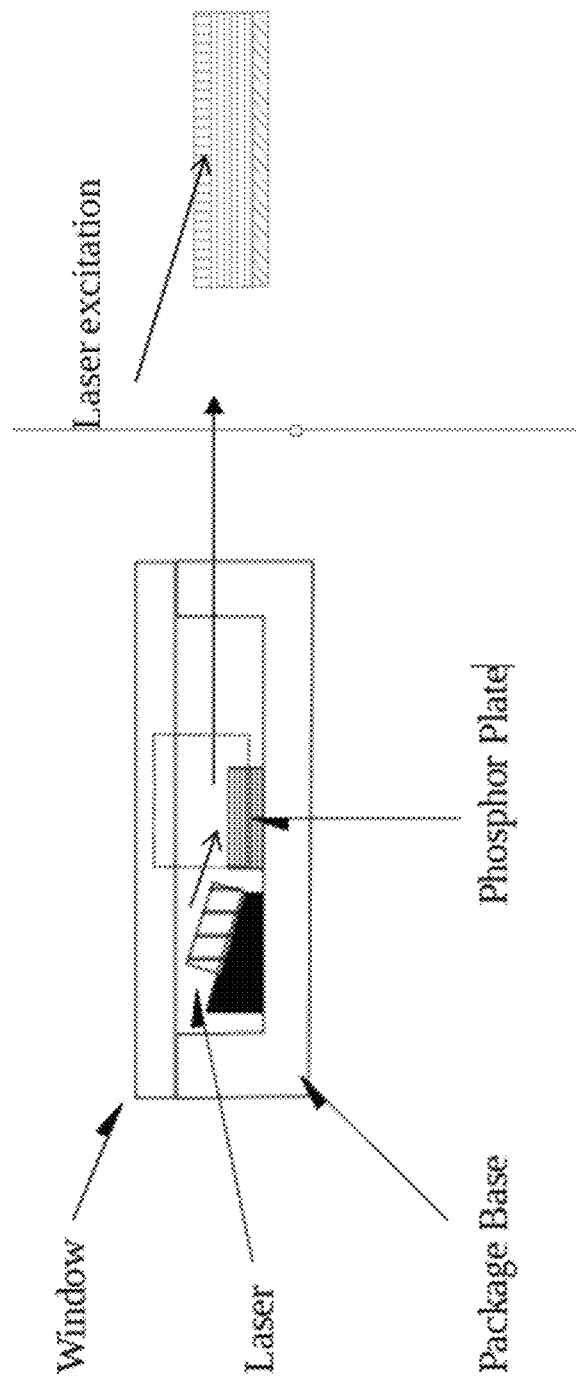

VIOLET AND ULTRAVIOLET ILLUMINATION DEVICE CONFIGURED WITH A GALLIUM AND NITROGEN CONTAINING LASER SOURCE

CROSS-REFERENCE TO RELATED APPLICATIONS

This application is a Continuation-In-Part of U.S. application Ser. No. 16/923,476, filed Jul. 8, 2020, which is a Continuation of U.S. application Ser. No. 16/512,903, filed Jul. 16, 2019, the entire contents of which are incorporated herein by reference for all purposes.

BACKGROUND

In the late 1800's, Thomas Edison invented the light bulb. The conventional light bulb, commonly called the "Edison bulb," has been used for over one hundred years for a variety of applications including lighting and displays. The conventional light bulb uses a tungsten filament enclosed in a glass bulb sealed in a base, which is screwed into a socket. The socket is coupled to an AC power or DC power source. The conventional light bulb can be found commonly in houses, buildings, and outdoor lightings, and other areas requiring light or displays. Unfortunately, drawbacks exist with the conventional light bulb:

The conventional light bulb dissipates more than 90% of the energy used as thermal energy.

The conventional light bulb routinely fails due to thermal expansion and contraction of the filament element.

The conventional light bulb emits light over a broad spectrum, much of which is not perceived by the human eye.

The conventional light bulb emits in all directions, which is undesirable for applications requiring strong directionality or focus, e.g. projection displays, optical data storage, etc.

To overcome some of the drawbacks of the conventional light bulb, several alternatives have been developed including fluorescent lamps, Mercury vapor lamps, sodium vapor lamps, other high-intensity discharge (HID) lamps, gas discharge lamps such as neon lamps, among others. These lamp technologies in general suffer from similar problems to Edison lamps as well as having their own unique drawbacks. For example, fluorescent lamps require high voltages to start, which can be in the range of a thousand volts for large lamps, and also emit highly non-ideal spectra that are dominated by spectral lines.

In the past decade, solid state lighting has risen in importance due to several key advantages it has over conventional lighting technology. Solid state lighting is lighting derived from semiconductor devices such as diodes which are designed and optimized to emit photons. Due to the high efficiency, long lifetimes, low cost, and non-toxicity offered by solid state lighting technology, light emitting diodes (LED) have rapidly emerged as the illumination technology of choice. An LED is a two-lead light source typically based on a p-i-n junction diode, which emits electromagnetic radiation when activated. The emission from an LED is spontaneous and is typically in a Lambertian pattern. When a suitable voltage is applied to the leads, electrons and holes recombine within the device releasing energy in the form of photons. This effect is called electroluminescence, and the color of the light is determined by the energy band gap of the semiconductor.

Appearing as practical electronic components in 1962 the earliest LEDs emitted low-intensity infrared light. Infrared LEDs are still frequently used as transmitting elements in remote-control circuits, such as those in remote controls for a wide variety of consumer electronics. The first visible-light LEDs were also of low intensity, and limited to red. Modern LEDs are available across the ultraviolet and infrared wavelengths, with very high brightness.

The earliest blue and violet gallium nitride (GaN)-based LEDs were fabricated using a metal-insulator-semiconductor structure due to a lack of p-type GaN. The first p-n junction GaN LED was demonstrated by Amano et al. using the LEEBI treatment to obtain p-type GaN in 1989. They obtained the current-voltage (I-V) curve and electroluminescence of the LEDs, but did not record the output power or the efficiency of the LEDs. Nakamura et al. demonstrated the p-n junction GaN LED using the low-temperature GaN buffer and the LEEBI treatment in 1991 with an output power of 42 µW at 20 mA. The first p-GaN/n-InGaN/n-GaN DH blue LEDs were demonstrated by Nakamura et al. in 1993. The LED showed a strong band-edge emission of InGaN in a blue wavelength regime with an emission wavelength of 440 nm under a forward biased condition. The output power and the EQE were 125 µW and 0.22%, respectively, at a forward current of 20 mA. In 1994, Nakamura et al. demonstrated commercially available blue LEDs with an output power of 1.5 mW, an EQE of 2.7%, and the emission wavelength of 450 nm. On Oct. 7, 2014, the Nobel Prize in Physics was awarded to Isamu Akasaki, Hiroshi Amano and Shuji Nakamura for "the invention of efficient blue light-emitting diodes which has enabled bright and energy-saving white light sources" or, less formally, LED lamps.

By combining GaN-based LEDs with wavelength converting materials such as phosphors, solid-state white light sources were realized. This technology utilizing GaN-based LEDs and phosphor materials to produce white light is now illuminating the world around us as a result of the many advantages over incandescent light sources including lower energy consumption, longer lifetime, improved physical robustness, smaller size, and faster switching. LEDs are now used in applications as diverse as aviation lighting, automotive headlamps, advertising, general lighting, traffic signals, and camera flashes. LEDs have allowed new text, video displays, and sensors to be developed, while their high switching rates can be very useful in communications technology. LEDs, however, are not the only solid-state light source and may not be preferable light sources for certain lighting applications. Alternative solid state light sources utilizing stimulated emission, such as laser diodes (LDs) or super-luminescent light emitting diodes (SLEDs), provide many unique features advantageously over LEDs.

In 1960, the laser was demonstrated by Theodore H. Maiman at Hughes Research Laboratories in Malibu. This laser utilized a solid-state flash lamp-pumped synthetic ruby crystal to produce red laser light at 694 nm. Early visible laser technology comprised lamp pumped infrared solid state lasers with the output wavelength converted to the visible using specialty crystals with nonlinear optical properties. For example, a green lamp pumped solid state laser had 3 stages: electricity powers lamp, lamp excites gain crystal which lases at 1064 nm, 1064 nm goes into frequency conversion crystal which converts to visible 532 nm. The resulting green and blue lasers were called "lamped pumped solid state lasers with second harmonic generation" (LPSS with SHG) had wall plug efficiency of ~1%, and were more efficient than Ar-ion gas lasers, but were still too inefficient, large, expensive, fragile for broad deployment outside of specialty scientific and medical applications. To improve the efficiency of these visible lasers, high power diode (or semiconductor) lasers were utilized. These "diode pumped solid state lasers with SHG" (DPSS with SHG) had 3 stages: electricity powers 808 nm diode laser, 808 nm excites gain crystal, which lases at 1064 nm, 1064 nm goes into frequency conversion crystal which converts to visible 532 nm. As high power laser diodes evolved and new specialty SHG crystals were developed, it became possible to directly convert the output of the infrared diode laser to produce blue and green laser light output. These "directly doubled diode lasers" or SHG diode lasers had 2 stages: electricity powers 1064 nm semiconductor laser, 1064 nm goes into frequency conversion crystal which converts to visible 532 nm green light. These lasers designs are meant to improve the efficiency, cost and size compared to DPSS-SHG lasers, but the specialty diodes and crystals required make this challenging today.

YAG:$Ce^{3+}$ phosphor is used throughout the LED and laser light industries as it provides absorption of blue light with emission of yellow light. The combination of blue and yellow in correct proportions results in white light. As shown in FIG. 1, the absorption is constrained to narrow wavelength regimes, nominally 455 nm+/−25 nm, a weaker absorption centered on 340 nm and lastly a peak near 225 nm. The efficient conversion of blue light to yellow takes advantage of the strong absorption of blue light near 455 nm. Outside of these absorption regions, the response of the YAG:$Ce^{3+}$ phosphor must be reflective, transmissive or absorption which does not result in luminescence.

Solid-state laser light sources, due to the narrowness of their spectra which enables efficient spectral filtering, high modulation rates, and short carrier lifetimes, smaller in size, and far greater surface brightness compared to LEDs, can be more preferable as visible light sources as a means of transmitting information with high bandwidth in many applications including lighting fixtures, lighting systems, displays, projectors and the like. Advancements of new GaN-based blue laser technology based on improved processes have substantially reduced manufacture cost and opened opportunities for utilizing the modulated laser signal and the light spot directly to measure and or interact with the surrounding environment, transmit data to other electronic systems, and respond dynamically to inputs from various sensors. Such applications are herein referred to as "smart lighting" applications to be disclosed throughout the specification herein.

SUMMARY

The present invention provides a system or apparatus configured with an infrared (IR) illumination source integrated with a gallium and nitrogen containing laser diodes based white light source. With the capability to emit light in both the visible light spectrum and the infrared light spectrum, the system or apparatus is at least a dual band emitting light source. In some embodiments the gallium and nitrogen containing laser diode is fabricated with a process to transfer gallium and nitrogen containing layers and methods of manufacture and use thereof. In some embodiments the system or apparatus contains sensors to form feedback loops that can activate the infrared illumination source and/or the laser based white light illumination source. Merely by examples, the invention provides remote and integrated smart laser lighting devices and methods, configured with infrared and visible illumination capability for spotlighting, detection, imaging, projection display, spatially dynamic lighting devices and methods, LIDAR, LiFi, and visible light communication devices and methods, and various combinations of above in applications of general lighting, commercial lighting and display, automotive lighting and communication, defense and security, search and rescue, industrial processing, internet communications, agriculture or horticulture. The integrated light source according to this invention can be incorporated into an automotive headlight, a general illumination source, a security light source, a search light source, a defense light source, as a light fidelity (LiFi) communication device, for horticulture purposes to optimize plant growth, or many other applications.

In an aspect, this invention provides novel uses and configurations of gallium and nitrogen containing laser diodes in lighting systems configured for IR illumination, which can be deployed in dual spectrum spotlighting, imaging, sensing, and searching applications. Configured with a laser based white light source and an IR light source, this invention is capable of emitting light both in the visible wavelength band and in the IR wavelength band, and is configured to selectively operate in one band or simultaneously in both bands. This dual band emission source can be deployed in communication systems such as visible light communication systems such as Li-Fi systems, communications using the convergence of lighting and display with static or dynamic spatial patterning using beam shaping elements such as MEMS scanning mirrors or digital light processing units, and communications triggered by integrated sensor feedback. Specific embodiments of this invention employ a transferred gallium and nitrogen containing material process for fabricating laser diodes or other gallium and nitrogen containing devices enabling benefits over conventional fabrication technologies.

The present invention is configured for both visible light emission and IR light emission. While the necessity and utility of visible light is clearly understood, it is often desirable to provide illumination wavelength bands that are not visible. In one example, IR illumination is used for night vision. Night vision or IR detection devices play a critical role in defense, security, search and rescue, and recreational activities in both the private sector and at the municipal or government sectors. By providing the ability to see in no or low ambient light conditions, night vision technology is widely deployed to the consumer markets for several applications including hunting, gaming, driving, locating, detecting, personal protection, and others. Whether by biological or technological means, night vision and IR detection are made possible by a combination of sufficient spectral range and sufficient intensity range. Such detection can be for two dimensional imaging, or three dimensional distance measurement such as range-finding, or three dimensional imaging such as LIDAR.

The present invention provides a light source configured for emission of laser based visible light such as white light and an infrared light, to form an illumination source capable of providing visible and IR illumination. The light source includes a gallium and nitrogen containing laser diode excitation source configured with an optical cavity. The optical cavity includes an optical waveguide region and one or more facet regions. The optical cavity is configured with electrodes to supply a first driving current to the gallium and nitrogen containing material. The first driving current provides an optical gain to an electromagnetic radiation propagating in the optical waveguide region of the gallium and nitrogen containing material. The electromagnetic radiation is outputted through at least one of the one or more facet regions as a directional electromagnetic radiation characterized by a first peak wavelength in the ultra-violet, blue, green, or red wavelength regime. Furthermore, the light source includes a wavelength converter, such as a phosphor member, optically coupled to the pathway to receive the directional electromagnetic radiation from the excitation source. The wavelength converter is configured to convert at least a fraction of the directional electromagnetic radiation with the first peak wavelength to at least a second peak wavelength that is longer than the first peak wavelength. In a preferred embodiment the output is comprised of a white-color spectrum with at least the second peak wavelength and partially the first peak wavelength forming the laser based visible light spectrum component according to the present invention. In one example, the first peak wavelength is a blue wavelength and the second peak wavelength is a yellow wavelength. The light source optionally includes a beam shaper configured to direct the white-color spectrum for illuminating a target or area of interest.

In one preferred embodiment of the present invention an IR emitting laser diode or light emitting diode is included to form the IR emission component of the dual band emitting light source. The IR laser diode contains an optical cavity configured with electrodes to supply a second driving current. The second driving current provides an optical gain to an IR electromagnetic radiation propagating in the optical waveguide region. The electromagnetic radiation is outputted through at least one of the one or more facet regions as a directional electromagnetic radiation characterized by a third peak wavelength in the IR regime. In one configuration the directional IR emission is optically coupled to the wavelength converter member such that the wavelength converter member is within the optical pathway of the IR emission to receive the directional electromagnetic radiation from the excitation source. Once incident on the wavelength converter member, the IR emission with the third peak wavelength would be at least partially reflected from the wavelength converter member and redirected into the same optical pathway as the white light emission with the first and second peak wavelengths. The IR emission would be directed through the optional beam shaper configured to direct the output IR light for illuminating approximately the same target or area of interest as the visible light. In this embodiment the first and second driving current could be activated independently such that the apparatus could provide a visible light source with only the first driving current activated, an IR light source with the second driving current activated, or could simultaneously provide both a visible and IR light source. In some applications it would be desirable to only use the IR illumination source for IR detection. Once an object was detected, the visible light source could be activated.

In a second preferred embodiment of the present invention a second wavelength converter member is included to provide emission in the IR regime at a third peak wavelength, to provide the IR emission component of the dual band emitting light source. The IR wavelength converter member, such as a phosphor member, would be configured to receive and absorb a pump light and emit a longer wavelength IR light. In this embodiment, the dual band light source comprises the first wavelength converter member for emitting visible light and the second wavelength converter member for emitting IR light. In one example, the first and second wavelength converter members are configured in a side by side, or adjacent arrangement such that the white light emission from the first wavelength converter member is emitted from a separate spatial location than the IR emission from the second wavelength converter member. In this example, the first and second wavelength converter members could be excited by separate laser diode members wherein in one embodiment the first wavelength converter member would be excited by a first gallium and nitrogen containing laser diodes such as violet, blue, or green laser diodes, and the second wavelength converter member would be excited by a second gallium and nitrogen containing laser diodes such as violet, blue, or green laser diodes. In a second embodiment of this example the first wavelength converter member is excited by a first gallium and nitrogen containing laser diode such as a violet or blue laser diode, and the second wavelength converter member is excited by a second laser diode formed from a different material system operating in the red or IR wavelength region, such as a gallium and arsenic containing material or an indium and phosphorous containing material. In these embodiments the first laser diode would be excited by a first drive current and the second laser diode would be excited by a second drive current. Since the first and second drive currents could be activated independently, the dual band light emitting source could provide a visible light source with only the first driving current activated, an IR light source with only the second driving current activated, or could simultaneously provide both a visible and IR light source with both the first and second drive currents activated. In some applications it would be desirable to only use the IR illumination source for IR detection. Once an object is detected with the IR illumination, the visible light source can be activated to visibly illuminate the target.

In another example according to this invention, the first wavelength converter member and the second wavelength converter member could be configured in a vertically stacked arrangement. Preferably the first wavelength converter member would be arranged on the same side as the primary emission surface of the stacked wavelength converter arrangement such that the IR light emitted from the second wavelength converter can pass through the first wavelength converter member without appreciable absorption. That is, in a reflective mode configuration, the first wavelength converter member emitting the visible light would be arranged on top of the second wavelength converter member emitting the IR light such that the visible and IR emission exiting the emission surface of the first wavelength converter would be collected as useful light. That is, the IR emission with the third peak wavelength would be emitted into the same optical pathway as the white light emission with the first and second peak wavelengths. In this stacked configuration, a common gallium and nitrogen containing laser diode member could be configured as the excitation source for both the first and second wavelength member. Since the IR and visible light emission would exit the stacked wavelength converter members from the same surface and within approximately the same area, a simple optical system such as collection and collimation optics can be used to project and direct both the visible emission and the IR emission to the same target area. In this configuration activating the laser diode member with a first drive current would excite both the emission of the visible light and the IR light such that independent control of the emission of the visible light and IR light would be difficult. Other vertically stacked wavelength converter members are possible such as positioning the IR emitting second wavelength converter member on the emission side of the stack such that the visible light emission from the first wavelength converter member would function to excite IR emission from the second wavelength converter member.

In another example of the present example with the vertically stacked wavelength converter members the first and second wavelength converter members could be excited by separate laser diode members wherein in one embodiment the first wavelength converter member would be excited by a first gallium and nitrogen containing laser diodes such as violet or blue laser diode and the second wavelength converter member would be excited by a second gallium and nitrogen containing laser diodes such as a green emitting or longer wavelength laser diode. In a second embodiment of this example the first wavelength converter member is excited by a first gallium and nitrogen containing laser diode such as a violet or blue laser diode, and the second wavelength converter member is excited by a second laser diode formed from a different material system operating in the red or IR wavelength region, such as a gallium and arsenic containing material or an indium and phosphorous containing material. The key consideration for this embodiment is to select the second laser diode with an operating wavelength that will not be substantially absorbed in the first wavelength converter member, but will be absorbed in the second wavelength converter member such that when the second laser diode is activated the emission will pass through the first wavelength converter to excite the second wavelength converter and generate the IR emission. The result is that the first laser diode member primarily activates the first wavelength converter member to generate visible light and the second laser diode member primarily activates the second wavelength converter to generate IR light. The benefit to this version of the stacked wavelength converter configuration is that since the first laser diode would be excited by a first drive current and the second laser diode would be excited by a second drive current the first and second wavelength converter members could be activated independently such that the dual band light emitting source could provide a visible light source with only the first driving current activated, an IR light source with only the second driving current activated, or could simultaneously provide both a visible and IR light source with both the first and second drive currents activated. In some applications it would be desirable to only use the IR illumination source for IR detection. Once an object was detected, the visible light source could be activated.

In yet another example according to this invention, the first wavelength converter member and the second wavelength converter member are combined to form single hybrid wavelength converter member. This can be achieved in various ways such as sintering a mixture of wavelength converters elements such as phosphors into a single solid body. In this composite wavelength converter configuration, a common gallium and nitrogen containing laser diode member could be configured as the excitation source to generate both the visible light and the IR light. In this configuration the activating the laser diode member with a first drive current would excite both the emission of the visible light and the IR light such that independent control of the emission of the visible light and IR light would be difficult.

Alternatively, the visible light emission could be excited by a first gallium and nitrogen containing laser diode such as a violet or blue laser diode, and the IR emission could be excited by a second laser diode formed from a different material system operating in the red or IR wavelength region, such as a gallium and arsenic containing material or an indium and phosphorous containing material. The key consideration for this embodiment is to select the second laser diode with an operating wavelength that will not be substantially absorbed in the visible light emitting element of the composite wavelength converter member, but will be absorbed in IR emitting element of the composite wavelength converter member such that when the second laser diode is activated it will not excite the visible light emission, but will excite the IR emission. The result is that the first laser diode member primarily activates the first wavelength converter member to generate visible light and the second laser diode member primarily activates the second wavelength converter to generate IR light. Since the IR emission with the third peak wavelength would be emitted from the same surface and spatial location as the visible emission with the first and second peak wavelengths, the IR emission would be easily directed into the same optical pathway as the white light emission with the first and second peak wavelengths. The IR emission and white light emission could then be directed through the optional beam shaper configured to direct the output light for illuminating a target of interest. In this embodiment the first and second driving current could be activated independently such that the apparatus could provide a visible light source with only the first driving current activated, an IR light source with the second driving current activated, or could simultaneously provide both a visible and IR light source. In some applications it would be desirable to only use the IR illumination source for IR detection. Once an object is detected with the IR illumination, the visible light source can be activated to visibly illuminate the target.

The benefit to this version of the stacked wavelength converter configuration is that since the first laser diode would be excited by a first drive current and the second laser diode would be excited by a second drive current the first and second wavelength converter members could be activated independently such that the dual band light emitting source could provide a visible light source with only the first driving current activated, an IR light source with only the second driving current activated, or could simultaneously provide both a visible and IR light source with both the first and second drive currents activated. In some applications it would be desirable to only use the IR illumination source for IR detection. Once an object was detected, the visible light source could be activated.

In preferred embodiments according to the present invention, the wavelength converter element is comprised of one or more phosphor members. Such phosphor members can be implemented in solid body form such as single crystal phosphor element, a ceramic element, or a phosphor in a glass, or could be in a powder form wherein the powder is bound by a binder material. There is a wide range of phosphor chemistries to select from to ensure the proper emission and performance properties. Moreover, such phosphor members can be operated in several architectural arrangements such as a reflective mode, a transmissive mode, a hybrid mode, or any other mode.

In some embodiments, the present disclosure provides a dual band light source configured for visible light communication. The light source includes a controller comprising a modem and a driver. The modem is configured to receive a data signal. The controller is configured to generate one or more control signals to operate the driver to generate a driving current and a modulation signal based on the data signal. Additionally, the light source includes a light emitter configured as a pump-light device comprised of a gallium and nitrogen containing material and an optical cavity. The optical cavity includes an optical waveguide region and one or more facet regions. The optical cavity is configured with electrodes to supply the driving current based on at least one of the one or more control signals to the gallium and nitrogen containing material. The driving current provides an optical gain to an electromagnetic radiation propagating in the optical waveguide region. The electromagnetic radiation is outputted through at least one of the one or more facet regions as a directional electromagnetic radiation characterized by a first peak wavelength in the ultra-violet or blue wavelength regime. The directional electromagnetic radiation is modulated to carry the data signal using the modulation signal provided by the driver. The light source further includes a pathway configured to direct, filter, or split the directional electromagnetic radiation. Furthermore, the light source includes a wavelength converter optically coupled to the pathway to receive the directional electromagnetic radiation from the pump-light device. The wavelength converter is configured to convert at least a fraction of the directional electromagnetic radiation with the first peak wavelength to at least a second peak wavelength that is longer than the first peak wavelength and to output a white-color spectrum comprising at least the second peak wavelength and partially the first peak wavelength. Moreover, the light source includes a beam shaper configured to direct the white-color spectrum for illuminating a target of interest and transmitting the data signal through at least the fraction of the directional electromagnetic radiation with the first peak wavelength to a receiver at the target of interest.

Optionally, as used herein, the term "modem" refers to a communication device. The device can also include a variety of other data receiving and transferring devices for wireless, wired, cable, or optical communication links, and any combination thereof. In an example, the device can include a receiver with a transmitter, or a transceiver, with suitable filters and analog front ends. In an example, the device can be coupled to a wireless network such as a meshed network, including Zigbee, Zeewave, and others. In an example, the wireless network can be based upon a 802.11 wireless standard or equivalents. In an example, the wireless device can also interface to telecommunication networks, such as 3G, LTE, 5G, and others. In an example, the device can interface into a physical layer such as Ethernet or others. The device can also interface with an optical communication including a laser coupled to a drive device or an amplifier. Of course, there can be other variations, modifications, and alternatives.

Optionally, the pump-light device includes a laser diode device. Optionally, the pump-light device includes a superluminescent diode (SLED) device.

Optionally, the laser diode device includes a carrier chip singulated from a carrier substrate. Additionally, the laser diode device includes one or more epitaxial material die transferred to the carrier substrate from a substrate. The epitaxial material includes an n-type cladding region, an active region including at least one active layer overlying the n-type cladding region, and a p-type cladding region overlying the active layer region. Furthermore, the laser diode device includes one or more laser diode stripe regions formed in the epitaxial material die.

Optionally, the directional electromagnetic radiation with the first peak wavelength includes a violet spectrum with the first peak wavelength in a range of 380-420 nm, and/or a blue spectrum with the first peak wavelength in a range of 420-480 nm.

According to the present invention, the directional IR electromagnetic radiation with the third peak wavelength is emitted from a laser diode operating in a range from about 700 nm to about 15000 nm. In one example the laser diode operates with wavelength in the 700 nm to 1100 nm range based on GaAs for near-IR night vision illumination, range finding and LIDAR sensing, and communication could be included. In another example the laser diode operates with wavelength in the 1100 to 2500 nm range based on InP for eye-safe wavelength IR illumination, range finding, LIDAR sensing, and communication could be included. The IR emitting laser diode could be comprised of compound semiconductor materials including GaAs, InP, InGaAs, InAs, InAlAs, AlGaAs, AlInGaP, InGaAsP, or InGaAsSb, or some combination thereof.

Additionally, the IR emitting laser diode could be based on interband electron-hole recombination such as a quantum well laser diode, or could be based on quantum cascade laser diode operating with intraband or interband transitions. In another example the laser diode operates with wavelength in the 2500 nm to 15000 nm wavelength range based on quantum cascade laser technology for mid-IR thermal imaging, sensing, and communication could be included. For example, GaInAs/AlInAs quantum cascade lasers operate at room temperature in the wavelength range of 3 μm to 8 μm. The IR emitting laser diode is based on an edge-emitting design or a vertical cavity emitting design.

Optionally, the output of the driver includes at least a driving current for controlling an intensity of the directional electromagnetic radiation emitted from the pump-light device and a modulation signal of a pre-defined format based on either amplitude modulation or frequency modulation based on the data signal.

Optionally, the directional electromagnetic radiation includes multiple pulse-modulated light signals at a modulation frequency range selected from about 50 MHz to 300 MHz, 300 MHz to 1 GHz, and 1 GHz to 100 GHz based on the data signal.

Optionally, the white-color spectrum includes the multiple pulse-modulated light signals modulated based on the data signal carried by at least a fraction of the directional electromagnetic radiation from the light emitter.

Optionally, the wavelength converter includes a phosphor material configured as in a reflection mode to have a surface receiving the directional electromagnetic radiation in an incident angle. The white-color spectrum is a combination of a spectrum of the second peak wavelength converted by the phosphor material, a fraction of the directional electromagnetic radiation with the first peak wavelength reflected from the surface of the phosphor material, and a fraction of the directional electromagnetic radiation scattered from interior of the phosphor material.

Optionally, the wavelength converter includes a phosphor material configured as in a transmission mode to receive the directional electromagnetic radiation passed through. The white-color spectrum is a combination of a fraction of the directional electromagnetic radiation not absorbed by the phosphor material and a spectrum of the second peak wavelength converted by the phosphor material.

Optionally, the wavelength converter includes a plurality of wavelength converting regions that respectively convert blue or violet wavelength regime to a predominantly red spectrum, or a predominantly green spectrum, and/or a predominantly blue spectrum with a longer peak wavelength than the first peak wavelength of the directional electromagnetic radiation.

Optionally, the beam shaper includes a plurality of color-specific optical elements for independently manipulating the predominantly red spectrum, the predominantly green spectrum, and the predominantly blue spectrum for transmitting to different targets of interests carrying different streams of the data signal for different receivers.

Optionally, the beam shaper includes one or a combination of more optical elements selected a list of slow axis collimating lens, fast axis collimating lens, aspheric lens, ball lens, total internal reflector (TIR) optics, parabolic lens optics, refractive optics, and micro-electromechanical system (MEMS) mirrors configured to direct, collimate, focus the white-color spectrum to at least modify an angular distribution thereof.

Optionally, the beam shaper is configured to direct the white-color spectrum as an illumination source for illuminating the target of interest along a preferred direction.

Optionally, the light source includes a beam steering device wherein the beam steering device is configured to direct the white-color spectrum for dynamically scanning a spatial range around the target of interest.

Optionally, the pathway includes an optical fiber to guide the directional electromagnetic radiation to the wavelength converter member disposed remotely to generate the white-color spectrum. Optionally, the pathway includes a waveguide for guide the directional electromagnetic radiation to the wavelength converter member. Optionally, the pathway includes free-space optics devices.

Optionally, the receiver at the target of interest comprises a photodiode, avalanche photodiode, photomultiplier tube, and one or more band-pass filters to detect pulse-modulated light signals at a modulation frequency range of about 50 MHz to 100 GHz, the receiver being coupled to a modem configured to decode the light signals into binary data.

In another aspect, the present invention provides gallium and nitrogen based lasers light sources configured for one or more predetermined light characteristic responses such as a light movement response, a light color response, a light brightness response, or other responses. Specific embodiments of this invention employ a transferred gallium and nitrogen containing material process for fabricating laser diodes or other gallium and nitrogen containing devices enabling benefits over conventional fabrication technologies.

In another embodiment, the present disclosure provides an integrated light source for communication and dynamic spatial illumination. The integrated light source includes a modem configured for receiving data signals and a laser modulation driver coupled to the modem to generate a driving current and provide a modulation format based on the data signals. Additionally, the integrated light source includes a laser device driven by the driving current to emit a laser light with a first peak wavelength modulated according to the modulation format. The integrated light source further includes an optical pathway for guiding the laser light. Furthermore, the integrated light source includes a wavelength converting element configured to couple with the optical pathway to receive the laser light with a first peak wavelength and reemit a white-color light excited by converting a fraction of the laser light with the first peak wavelength to a spectrum with a second peak wavelength longer than the first peak wavelength and combining the fraction of fraction of the laser light with a first peak wavelength and the spectrum with the second peak wavelength. The white-color light carries the data signal in the modulation format. Moreover, the integrated light source includes a beam shaping optical element configured to collimate the white-color light and a beam steering optical element configured to receive one or more voltage and current signals generated by a beam steering driver based on input information to dynamically scan the white-color light to provide patterned illuminations to multiple areas and simultaneously transmit the data signals to different receivers at the multiple areas.

Optionally, the modulation format based on the data signal includes one selected from double-sideband modulation (DSB), double-sideband modulation with carrier (DSB-WC), double-sideband suppressed-carrier transmission (DSB-SC), double-sideband reduced carrier transmission (DSB-RC), single-sideband modulation (SSB, or SSB-AM), single-sideband modulation with carrier (SSB-WC), single-sideband modulation suppressed carrier modulation (SSB-SC), vestigial sideband modulation (VSB, or VSB-AM), quadrature amplitude modulation (QAM), pulse amplitude modulation (PAM), phase-shift keying (PSK), frequency-shift keying (FSK), continuous phase modulation (CPM), minimum-shift keying (MSK), Gaussian minimum-shift keying (GMSK), continuous-phase frequency-shift keying (CPFSK), orthogonal frequency-division multiplexing (OFDM), and discrete multitone (DMT).

Optionally, the wavelength converting element is disposed via a thermal conductor material on a submount structure commonly supporting the laser device. The wavelength converting element includes a phosphor material selected for absorbing at least partially one of the violet spectrum, the blue spectrum, the green spectrum, and the red spectrum to reemit a broader spectrum with a peak wavelength respectively longer than the peak wavelength of the wavelength ranges of violet spectrum, the blue spectrum, the green spectrum, and the red spectrum.

Optionally, the beam steering optical element further is selected from one of a micro-electromechanical system (MEMS) mirror, a digital light processing (DLP) chip, a digital mirror device (DMD), and a liquid crystal on silicon (LCOS) chip for steering, patterning, or pixelating the white-color light.

Optionally, the integrated light source further includes a controller having an interface configured as a user input dial, switch, or joystick mechanism or a feedback loop module for receiving input information to activate the MEMS mirror, or DLP chip, or DMD, or LCOS chip. The input information includes an illumination spatial pattern inputted by user or a dynamically varying illumination spatial pattern updated from sensor feedback. The beam steering optical element further is configured to spatially modulate and dynamically direct the white-color light based on the input information to provide spatially modulated illumination onto a first area of a target surface or into first direction of a target space in a first period and onto a second area of the target surface or into a second direction of a target space in a second period, and to independently transmit the data signals to a first receiver at the first area or downstream in the first direction in the first period and to a second receiver at the second area or downstream in the second direction in the second period.

Optionally, the integrated light source further includes a reflector disposed at downstream of the white-color light. The reflector is a parabolic reflector to reflect and propagate a collimated beam along an axis thereof.

Optionally, the integrated light source further includes a lens used to collimate the white-color light into a projected beam. The lens includes an aspheric lens positioned the wavelength converting element to collimate the white-color light.

Optionally, the integrated light source further includes a housing having an aperture for dynamically outputting the white-color light. The housing is configured to have a common submount to support at least the laser device, the wavelength converting element, and the beam steering optical element. The housing includes one of a TO canister package, a butterfly package, a chip and phosphor on submount (CPoS) package, a surface mount device (SMD) type package.

In yet another embodiment, the present disclosure provides a dynamic light source with color and brightness control for visible light communication. The dynamic light source includes a modem configured to receive digital information for communication. Additionally, the dynamic light source includes a laser driver configured to generate a driving current and at least one modulation signal based on the digital information. The dynamic light source further includes a laser device configured to be driven by the driving current to emit a laser beam with a first peak wavelength in a color range of violet or blue spectrum. The laser beam is modulated by the at least one modulation signal to carry the digital information. Furthermore, the dynamic light source includes a beam shaping optical element configured to dynamically direct the laser beam with a varying angle through an aperture into a pathway. The dynamic light source further includes a wavelength converting member comprising at least two color phosphor regions spatially distributed to respectively receive the laser beam with different angle outputted from the pathway and configured to convert a fraction of the laser beam with the first peak wavelength to at least two color spectra respectively by the at least two color phosphor regions. Each of the at least two color spectra includes a second peak wavelength longer than the first peak wavelength but varying with the fraction of the laser beam being absorbed by each of the at least two color phosphor regions. The at least two color spectra are respectively combined with remaining fraction of the laser beam with the first peak wavelength to reemit an output light beam of a broader spectrum with a dynamically varied color point. The dynamic light source also includes a beam steering optical element configured to spatially direct the output light beam. Moreover, the dynamic light source includes a beam steering driver configured to generate control signals based on input information for the beam steering optical element to dynamically scan the output light beam to provide spatially modulated illumination with dynamically varied color point onto one or more of multiple target areas or into one or more of multiple target directions in one or more selected periods while simultaneously transmit digital information to a receiver in one or more of multiple target areas or one or more of multiple target directions in one or more selected periods.

Optionally, the gallium and nitrogen containing laser device includes one or more laser diodes for emitting the laser beam with the first peak wavelength in violet spectrum ranging from 380 to 420 nm, in blue spectrum ranging from 420 to 480 nm, in the cyan and green spectrum ranging from 480 to 560 nm, or longer.

According to the present invention, the directional IR electromagnetic radiation with the third peak wavelength is emitted from a laser diode operating in a range from about 700 nm to about 15000 nm. In one example the laser diode operates with wavelength in the 700 nm to 1100 nm range based on GaAs for near-IR night vision illumination, range finding and LIDAR sensing, and communication could be included. In another example the laser diode operates with wavelength in the 1100 to 2500 nm range based on InP for eye-safe wavelength IR illumination, range finding, LIDAR sensing, and communication could be included. The IR emitting laser diode could be comprised of compound semiconductor materials including GaAs, InP, InGaAs, InAs, InAlAs, AlGaAs, AlInGaP, InGaAsP, or InGaAsSb, or some combination thereof.

Additionally, the IR emitting laser diode could be based on interband electron-hole recombination such as a quantum well laser diode, or could be based on quantum cascade laser diode operating with intraband or interband transitions. In another example the laser diode operates with wavelength in the 2500 nm to 15000 nm wavelength range based on quantum cascade laser technology for mid-IR thermal imaging, sensing, and communication could be included. For example, GaInAs/AlInAs quantum cascade lasers operate at room temperature in the wavelength range of 3 μm to 8 μm. The IR emitting laser diode is based on an edge-emitting design or a vertical cavity emitting design.

Optionally, the at least two color phosphor regions of the wavelength converting member include a first phosphor material configured to absorb a first ratio of the laser beam with the first peak wavelength in the violet spectrum and convert to a first color spectrum with a second wavelength longer than the first peak wavelength to emit the output light beam with a first color point, a second phosphor material configured to absorb a second ratio of the laser beam with the first peak wavelength in the blue spectrum and convert to a second color spectrum with a second wavelength longer than the first peak wavelength to emit the output light beam with a second color point, a third phosphor material configured to absorb a third ratio of the laser beam with the first peak wavelength in the violet or blue spectrum and convert to a third color spectrum with a second wavelength longer than the first peak wavelength to emit the output light beam with a third color point.

Extending the usable wavelength range for Laser based lighting, it is possible to use Infrared down-converting phosphors to generate emission in the NIR (0.7-1.4 um) and mid-IR (1.4-3.0 um) spectrum. This could be purely Infrared emission, or a combination of visible and infrared emission depending on application requirements. A large number of potential IR phosphors exist, but their suitability depends on the application wavelength, and the phosphors inherent properties for conversion of visible light to IR light.

Optionally, the dynamic light source further includes a second beam shaping optical element configured to collimate and direct the output light beam by at least modifying an angular distribution thereof. The second beam shaping optical element includes one or a combination of several optical devices including slow axis collimating lens, fast axis collimating lens, aspheric lens, ball lens, total internal reflector (TIR) optics, parabolic lens optics, refractive optics, and micro-electromechanical system (MEMS) mirrors.

In an alternative embodiment, the present disclosure provides a dynamic light source with color and brightness control for visible light communication. The dynamic light source includes a modem configured to receive digital information for communication and a laser driver configured to generate one or more driving currents and a modulation signal based on the digital information. Additionally, the dynamic light source includes a laser device configured to be driven by the one or more driving currents to emit at lease a first laser beam with a first peak wavelength in a color range of violet or blue spectrum and a second laser beam with a second peak wavelength longer than the first peak wavelength. At least one of the first laser beam and the second laser beam is modulated by the modulation signal to carry the digital information. The dynamic light source further includes a beam shaping optical element configured to collimate, focus, and dynamically direct the first laser beam and the second laser beam respectively through a pathway. Furthermore, the dynamic light source includes a wavelength converting member configured to receive either the first laser beam or the second laser beam from the pathway and configured to convert a first fraction of the first laser beam with the first peak wavelength to a first spectrum with a third peak wavelength longer than the first peak wavelength or convert a second fraction of the second laser beam with the second peak wavelength to a second spectrum with a fourth peak wavelength longer than the second peak wavelength. The first spectrum and the second spectrum respectively combine with remaining fraction of the first laser beam with the first peak wavelength and the second laser beam with the second peak wavelength to reemit an output light beam of a broader spectrum dynamically varied from a first color point to a second color point. The dynamic light source further includes a beam steering optical element configured to spatially direct the output light beam. Moreover, the dynamic light source includes a beam steering driver configured to generate control signals based on input information for the beam steering optical element to dynamically scan the output light beam to provide spatially modulated illumination with dynamically varied color point onto one or more of multiple target areas or into one or more of multiple target directions in one or more selected periods while simultaneously transmit digital information to a receiver in one or more of multiple target areas or one or more of multiple target directions in one or more selected periods.

Optionally, the laser device includes one or more first laser diodes for emitting the first laser beam with the first peak wavelength in violet spectrum ranging from 380 to 420 nm or blue spectrum ranging from 420 to 480 nm. The one or more first laser diodes include an active region including a gallium and nitrogen containing material configured to be driven by the one or more driving currents. The gallium and nitrogen containing material comprises one or more of GaN, AlN, InN, InGaN, AlGaN, InAlN, InAlGaN.

Optionally, the laser device includes one or more second laser diodes for emitting the second laser beam with the second peak wavelength in red spectrum ranging from 600 nm to 670 nm, or in green spectrum ranging from 480 nm to 550 nm, or a blue spectrum with a longer wavelength than that of the first peak wavelength. The one or more second laser diodes include an active region including a gallium and arsenic containing material configured to be driven by the one or more driving currents.

According to the present invention, the directional IR electromagnetic radiation with the third peak wavelength is emitted from a laser diode operating in a range from about 700 nm to about 15000 nm. In one example the laser diode operates with wavelength in the 700 nm to 1100 nm range based on GaAs for near-IR night vision illumination, range finding and LIDAR sensing, and communication could be included. In another example the laser diode operates with wavelength in the 1100 to 2500 nm range based on InP for eye-safe wavelength IR illumination, range finding, LIDAR sensing, and communication could be included. The IR emitting laser diode could be comprised of compound semiconductor materials including GaAs, InP, InGaAs, InAs, InAlAs, AlGaAs, AlInGaP, InGaAsP, or InGaAsSb, or some combination thereof.

Additionally, the IR emitting laser diode could be based on interband electron-hole recombination such as a quantum well laser diode, or could be based on quantum cascade laser diode operating with intraband or interband transitions. In another example the laser diode operates with wavelength in the 2500 nm to 15000 nm wavelength range based on quantum cascade laser technology for mid-IR thermal imaging, sensing, and communication could be included. For example, GaInAs/AlInAs quantum cascade lasers operate at room temperature in the wavelength range of 3 µm to 8 µm. The IR emitting laser diode is based on an edge-emitting design or a vertical cavity emitting design.

Optionally, the first laser, second, and/or third laser beams are independently modulated by the modulation signal to act as independent channels to communicate the digital information.

Optionally, the wavelength converting member includes a first phosphor material selected for absorbing a first ratio of the first laser beam with the first peak wavelength in the violet spectrum and converting to a first spectrum with a second wavelength longer than the first peak wavelength to emit a first output light beam with a first color point, a second phosphor material selected for absorbing partially second ratio of the first laser beam with the first peak wavelength in the blue spectrum and converting to a second spectrum with a second wavelength longer than the first peak wavelength to emit a second output light beam with a second color point, a third phosphor material selected for absorbing a third ratio of the second laser beam with the first peak wavelength in the red spectrum and converting to a third spectrum with a second wavelength longer than the first peak wavelength to emit a third output light beam with a third color point.

Optionally, the beam shaping optical element includes one or a combination of more optical elements selected a list of slow axis collimating lens, fast axis collimating lens, aspheric lens, ball lens, total internal reflector (TIR) optics, parabolic lens optics, refractive optics, and micro-electro-mechanical system (MEMS) mirrors configured to direct, collimate, focus each of the first laser beam and second laser beam with modified angular distributions as incident beams into corresponding first, second, third phosphor material for tuning the first, second, third ratio of the first and second laser beams being converted thereof for dynamically adjusting the first, second, third color point of the respective first, second, third output light beam.

In yet another aspect, the present invention provides gallium and nitrogen laser based illumination sources integrated with IR illumination sources coupled to one or more sensors with a feedback loop or control circuitry to trigger the light source to react with one or more predetermined responses such as activating the visible light emission for a visible light illumination, activating IR light emission for an IR illumination, activating aVLC signal or dynamic spatial patterning of light, a light movement response, a light color response, a light brightness response, a spatial light pattern response, other response, or a combination of responses. Specific embodiments of this invention employ a transferred gallium and nitrogen containing material process for fabricating laser diodes or other gallium and nitrogen containing devices enabling benefits over conventional fabrication technologies.

In still another embodiment, the present disclosure describing a laser based light source integrated with an IR illumination source provides a smart light source configured for visible light communication. The smart light source includes a controller comprising a modem and a driver. The modem is configured to receive data signal and operate the driver to generate a driving current and a modulation signal. Additionally, the smart light source includes a light emitter configured as a pump-light device comprised of a gallium and nitrogen containing material and an optical cavity comprising an optical waveguide region and one or more facet regions. The optical cavity is configured with electrodes to supply the driving current from the driver to the gallium and nitrogen containing material to provide optical gain to an electromagnetic radiation propagating in the optical waveguide region and output a directional electromagnetic radiation through at least one of the one or more facet regions. The directional electromagnetic radiation is characterized by a first peak wavelength in the ultra-violet or blue wavelength regime and modulated to carry the data signal using the modulation signal by the controller. The smart light source further includes a wavelength converter optically coupled to the directional electromagnetic radiation from the pump-light device, wherein the wavelength converter is configured to convert at least a fraction of the directional electromagnetic radiation with the first peak wavelength to at least a second peak wavelength that is longer than the first peak wavelength and to output a white-color spectrum comprising at least the second peak wavelength and partially the first peak wavelength. Furthermore, the smart light source includes a beam shaper configured to collimate and focus a beam of the white-color spectrum to a certain direction or a certain focal point. The smart light source further includes a beam steering element configured to manipulate the beam of the white-color spectrum for illuminating a target of interest and transmitting the data signal through at least the fraction of the directional electromagnetic radiation with the first peak wavelength to a receiver at the target of interest. Moreover, the smart light source includes one or more sensors being configured in a feedback loop circuit coupled to the controller. The one or more sensors are configured to provide one or more feedback currents or voltages based on the various parameters associated with the target of interest detected in real time to the controller with one or more of light movement response, light color response, light brightness response, spatial light pattern response, and data signal communication response being triggered.

Optionally, the wavelength converter includes a phosphor material configured as in a reflection mode to have a surface receiving the directional electromagnetic radiation in an incident angle. The white-color spectrum is a combination of a spectrum of the second peak wavelength converted by the phosphor material, a fraction of the directional electromagnetic radiation with the first peak wavelength reflected from the surface of the phosphor material, and a fraction of the directional electromagnetic radiation scattered from interior of the phosphor material.

Optionally, the wavelength converter includes a phosphor material configured as in a transmission mode to receive the directional electromagnetic radiation passed through. The white-color spectrum is a combination of a fraction of the directional electromagnetic radiation not absorbed by the phosphor material and a spectrum of the second peak wavelength converted by the phosphor material.

Optionally, the wavelength converter includes a plurality of wavelength converting regions that respectively convert blue or violet wavelength regime to a predominantly red spectrum, or a predominantly green spectrum, and/or a predominantly blue spectrum with a longer peak wavelength than the first peak wavelength of the directional electromagnetic radiation.

Optionally, the beam steering element includes a plurality of color-specific optical elements for independently manipulating the predominantly red spectrum, the predominantly green spectrum, and the predominantly blue spectrum for transmitting to different targets of interests carrying different streams of the data signal for different receivers.

Optionally, the beam steering element is configured to manipulate and direct the beam of the white-color spectrum as an illumination source with spatial modulation for illuminating a surface at the target of interest along a preferred direction.

Optionally, the beam steering element further is configured to direct the white-color spectrum for dynamically scanning a spatial range around the target of interest.

Optionally, the one or more sensors include one or a combination of multiple of sensors selected from microphone, geophone, motion sensor, radio-frequency identification (RFID) receivers, hydrophone, chemical sensors including a hydrogen sensor, $CO_2$ sensor, or electronic nose sensor, flow sensor, water meter, gas meter, Geiger counter, altimeter, airspeed sensor, speed sensor, range finder, piezoelectric sensor, gyroscope, inertial sensor, accelerometer, MEMS sensor, Hall effect sensor, metal detector, voltage detector, photoelectric sensor, photodetector, photoresistor, pressure sensor, strain gauge, thermistor, thermocouple, pyrometer, temperature gauge, motion detector, passive infrared sensor, Doppler sensor, biosensor, capacitance sensor, video cameras, transducer, image sensor, infrared sensor, radar, SONAR, LIDAR.

Optionally, the one or more sensors is configured in the feedback loop circuit to provide a feedback current or voltage to tune a control signal for operating the driver to adjust brightness and color of the directional electromagnetic radiation from the light-emitter.

Optionally, the one or more sensors is configured in the feedback loop circuit to provide a feedback current or voltage to tune a control signal for operating the beam steering optical element to adjust a spatial position and pattern illuminated by the beam of the white-color spectrum.

Optionally, the one or more sensors is configured in the feedback loop circuit to send a feedback current or voltage back to the controller to change the driving current and the modulation signal for changing the data signal to be communicated through at least a fraction of the directional electromagnetic radiation modulated by the modulation signal.

Optionally, the controller further is configured to provide control signals to tune the beam shaper for dynamically modulating the white-color spectrum based on feedback from the one or more sensors.

Optionally, the controller is a microprocessor disposed in a smart phone, a smart watch, a computerized wearable device, a tablet computer, a laptop computer, a vehicle-built-in computer, a drone.

Optionally, the beam steering element further is configured to independently transmit the data signal to different receivers in different direction in different period synchronized with the spatial modulation of the white-color spectrum illuminated into the particular direction.

Optionally, the beam steering element includes an optical device selected from one of a micro-electromechanical system (MEMS) mirror, a digital light processing (DLP) chip, a digital mirror device (DMD), and a liquid crystal on silicon (LCOS) chip for steering, patterning, or pixelating the white-color spectrum.

Optionally, the MEMS mirror is configured to produce high deflection angles more than 10 degrees, low in power consumption of less than 100 mW, and high scan frequencies capable of producing HD resolution.

Optionally, the MEMS mirror is configured to perform resonant operation for vector pointing and provide high reflectivity of >80% for high power operation.

Optionally, the beam steering element includes a 2-dimensional array of micro-mirrors to steer, pattern, and/or pixelate a beam of the white-color light by reflecting from corresponding pixels at a predetermined angle to turn each pixel on or off.

Optionally, the 2-dimensional array of micro-mirrors is formed on a silicon chip configured for providing dynamic spatial modulation of the beam of white-color spectrum.

Optionally, the beam steering element further is configured to spatially modulate and dynamically direct the white-color light based on the input information to provide spatially modulated illumination onto a first area of a target surface or into first direction of a target space in a first period and onto a second area of the target surface or into a second direction of a target space in a second period, and to independently transmit the data signals to a first receiver at the first area or downstream in the first direction in the first period and to a second receiver at the second area or downstream in the second direction in the second period.

Optionally, each of the first receiver and the second receiver comprises a photodiode, avalanche photodiode, photomultiplier tube, and one or more band-pass filters to detect pulse-modulated light signals, and is coupled to a modem configured to decode the light signals into binary data.

In yet still another embodiment, the present disclosure provides a smart light source with spatial illumination and color dynamic control. The smart light source includes a microcontroller for generating one or more control signals and a laser device configured to be driven by at least one of the one or more control signals to emit a laser beam with a first peak wavelength in a color range of violet or blue spectrum. The laser beam is modulated by the at least one modulation signal to carry the digital information. Additionally, the smart light source includes a beam shaping optical element configured to dynamically direct the laser beam with a varying angle through an aperture into a pathway. The smart light source further includes a wavelength converting member comprising at least two color phosphor regions spatially distributed to respectively receive the laser beam with different angle outputted from the pathway and configured to convert a fraction of the laser beam with the first peak wavelength to at least two color spectra respectively by the at least two color phosphor regions. Each of the at least two color spectra includes a second peak wavelength longer than the first peak wavelength but varying with the fraction of the laser beam being absorbed by each of the at least two color phosphor regions. The at least two color spectra are respectively combined with remaining fraction of the laser beam with the first peak wavelength to reemit an output light beam of a broader spectrum with a dynamically varied color point. Furthermore, the smart light source includes a beam steering optical element configured to spatially direct the output light beam. Moreover, the light source includes a beam steering driver coupled to the microcontroller to receive some of the one or more control signals based on input information for the beam steering optical element to dynamically scan the output light beam substantially in white color to provide spatially modulated illumination and selectively direct one or more of the multiple laser beams with the first peak wavelengths in different color ranges onto one or more of multiple target areas or into one or more of multiple target directions in one or more selected periods.

In yet still an alternative embodiment, the present disclosure provides a smart light source with spatially modulated illumination. The smart light source includes a controller configured to receive input information for generating one or more control signals. The smart light source further includes a light emitter configured as a pump-light device comprised of a gallium and nitrogen containing material and an optical cavity; the optical cavity comprising an optical waveguide region and one or more facet regions. The optical cavity is configured with electrodes to supply a driving current based on at least one of the one or more control signals to the gallium and nitrogen containing material. The driving current provides an optical gain to an electromagnetic radiation propagating in the optical waveguide region. The electromagnetic radiation is outputted through at least one of the one or more facet regions as a directional electromagnetic radiation characterized by a first peak wavelength in the ultra-violet or blue wavelength regime. Furthermore, the smart light source includes a beam shaper configured to collimate and focus the directional electromagnetic radiation to a certain direction and focal point and a wavelength converter optically coupled to the directional electromagnetic radiation from the pump-light device. The wavelength converter is configured to absorb at least a fraction of the directional electromagnetic radiation with the first peak wavelength to excite a spectrum with a second peak wavelength that is longer than the first peak wavelength and to reemit an output electromagnetic radiation with a broader spectrum comprising at least the second peak wavelength and partially the first peak wavelength. The smart light source further includes a beam steering optical element configured to manipulate the output electromagnetic radiation for providing spatially modulated illuminations onto a target area or into a target direction. Moreover, the smart light source includes one or more sensors being configured in a feedback loop circuit coupled to the controller. The one or more sensors are configured to provide one or more feedback currents or voltages based on the various parameters associated with the target of interest detected in real time to the controller with one or more of light movement response, light color response, light brightness response, spatial light pattern response, and data signal communication response being triggered.

In yet still another alternative embodiment, the present disclosure provides a smart light system with color and brightness dynamic control. The smart light system includes a microcontroller configured to receive input information for generating one or more control signals. Additionally, the smart light system includes a laser device configured to be driven by at least one of the one or more control signals to emit at lease a first laser beam with a first peak wavelength in a color range of violet or blue spectrum and a second laser beam with a second peak wavelength longer than the first peak wavelength. The smart light system further includes a pathway configured to dynamically guide the first laser beam and the second laser beam. Furthermore, the smart light system includes a wavelength converting member configured to receive either the first laser beam or the second laser beam from the pathway and configured to convert a first fraction of the first laser beam with the first peak wavelength to a first spectrum with a third peak wavelength longer than the first peak wavelength or convert a second fraction of the second laser beam with the second peak wavelength to a second spectrum with a fourth peak wavelength longer than the second peak wavelength. The first spectrum and the second spectrum respectively combine with remaining fraction of the first laser beam with the first peak wavelength and the second laser beam with the second peak wavelength to reemit an output light beam of a broader spectrum dynamically varied from a first color point to a second color point. The smart light system includes a beam shaping optical element configured to collimate and focus the output light beam and a beam steering optical element configured to direct the output light beam. Moreover, the smart light system includes a beam steering driver coupled to the microcontroller to receive some of the one or more control signals based on input information for the beam steering optical element to dynamically scan the output light beam substantially in white color to provide spatially modulated illumination and selectively direct one or more of the multiple laser beams with the first peak wavelengths in different color ranges onto one or more of multiple target areas or into one or more of multiple target directions in one or more selected periods. Even further, the smart light system includes one or more sensors being configured in a feedback loop circuit coupled to the controller. The one or more sensors are configured to provide one or more feedback currents or voltages based on the various parameters associated with the target of interest detected in real time to the controller with one or more of light movement response, light color response, light brightness response, spatial light pattern response, and data signal communication response being triggered.

Merely by way of example, the present invention can be applied to applications such as white lighting, white spot lighting, flash lights, automobile headlights, all-terrain vehicle lighting, light sources used in recreational sports such as biking, surfing, running, racing, boating, light sources used for drones, planes, robots, other mobile or robotic applications, safety, counter measures in defense applications, multi-colored lighting, lighting for flat panels, medical, metrology, beam projectors and other displays, high intensity lamps, spectroscopy, entertainment, theater, music, and concerts, analysis fraud detection and/or authenticating, tools, water treatment, laser dazzlers, targeting, communications, LiFi, visible light communications (VLC), sensing, detecting, distance detecting, Light Detection And Ranging (LIDAR), transformations, transportations, leveling, curing and other chemical treatments, heating, cutting and/or ablating, pumping other optical devices, other optoelectronic devices and related applications, and source lighting and the like. The integrated light source according to this invention can be incorporated into an automotive headlight, a general illumination source, a security light source, a search light source, a defense light source, as a light fidelity (LiFi) communication device, for horticulture purposes to optimize plant growth, or many other applications.

BRIEF DESCRIPTION OF THE FIGURES

The following drawings are merely examples for illustrative purposes according to various disclosed embodiments and are not intended to limit the scope of the present invention.

FIG. 11 is a plot showing the measured diffuse and specular reflection from a YAG:Ce3+ phosphor configured for use in reflection mode where the blue light source and white light emission occur on the same side according to an embodiment of the present invention.

FIG. 12 is an example laser based spectra showing a typical laser based spectra with no additional modifications.

FIG. 13 is an example laser based spectra showing the addition of a 405 nm near UV peak to the base spectra according to an embodiment of the present invention.

FIG. 14 is an example laser based spectra showing the inclusion of 850 nm and 905 nm laser light near IR spectra according to an embodiment of the present invention.

FIG. 15 is an example laser based spectra showing both the near UV and Near IR spectra with the base White light spectra of FIG. 12 according to an embodiment of the present invention.

FIG. 16 is an example laser based spectra showing diffuse reflection for CASN:Eu2+.

FIG. 17 is an example laser based spectra showing full example of 4000K Neutral White which utilizes YAG:Ce3+ and CASN:Eu3+ phosphors in conjunction with near UV and Near IR lasers according to an embodiment of the present invention.

FIG. 18 is an example laser based spectra showing the addition of the Sr containing s-CASN red phosphor can also be used to further extend the color to the warm white spectral region according to an embodiment of the present invention.

FIG. 19C is an example optical spectrum of a laser based white light source configured with an IR emitting laser diode for IR illumination according to an embodiment of the present invention.

FIG. 20A is a schematic diagram of a single crystal IR emitting phosphor configured for reflection mode operation according to an embodiment of the present invention.

FIG. 25C is a side view schematic diagram of a laser based white light source with an IR illumination capability operating in transmission mode and housed in a TO canister style package with an IR and visible light emitting based wavelength converter member configured with the transparent window of the cap according to an embodiment of the present invention.

FIG. 25D is a side view schematic diagram of an IR and visible light emitting based wavelength converter member configured with the transparent window of the cap according to an embodiment of the present invention.

FIG. 28A is a side-view schematic diagram of a laser based white light source with an IR illumination capability operating in reflection mode in an enclosed surface mount package according to an embodiment of the present invention.

DETAILED DESCRIPTION

Figure 1:
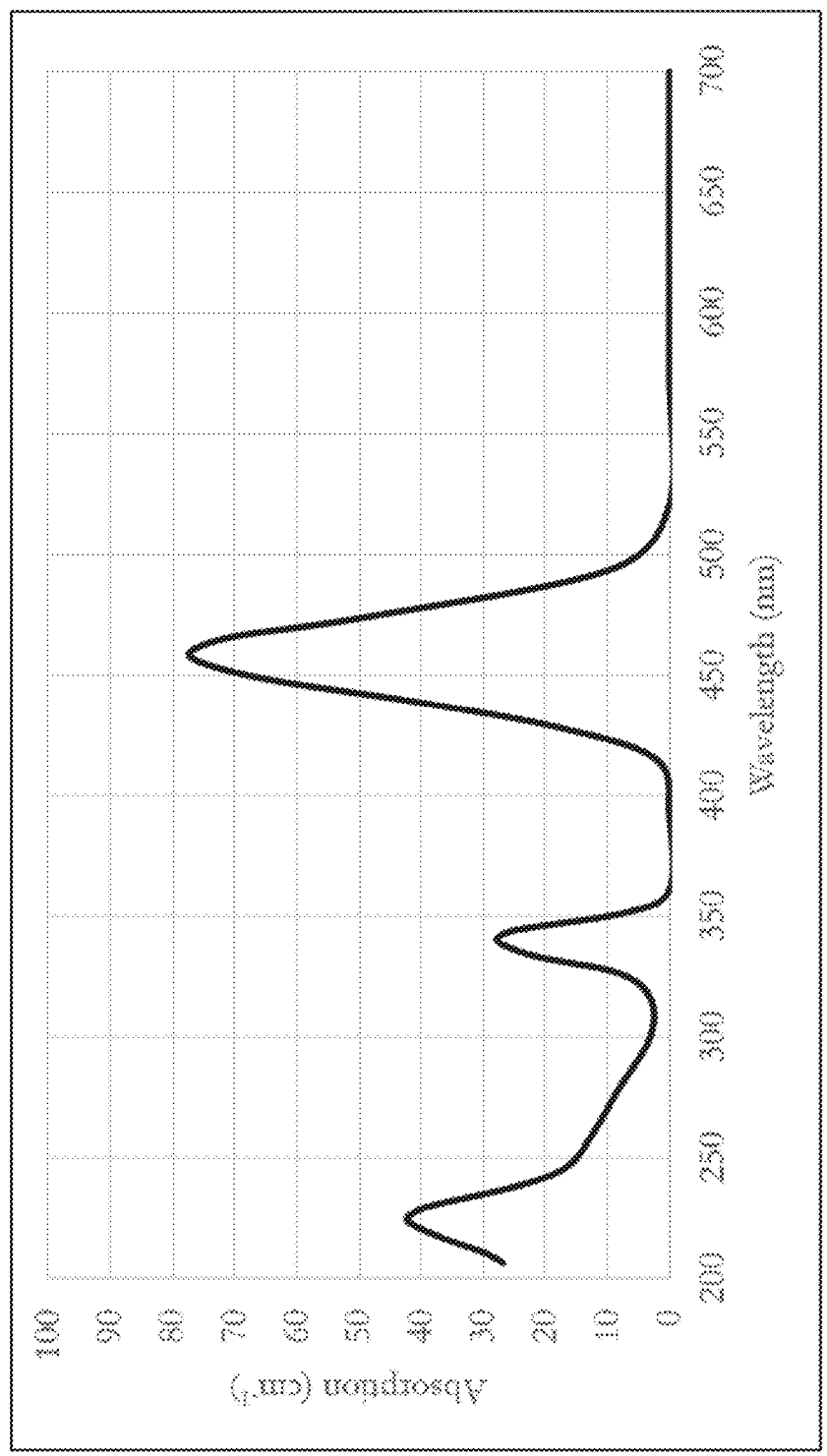
FIG. 1 is an example absorption spectra of YAG:Ce$^{3+}$ phosphor.

The present invention provides a system or apparatus configured with an infrared illumination source integrated with a gallium and nitrogen containing laser diodes based white light source. With the capability to emit light in both the visible light spectrum and the infrared light spectrum, the system or apparatus is at least a dual band emitting light source. In some embodiments the gallium and nitrogen containing laser diode is fabricated with a process to transfer gallium and nitrogen containing layers and methods of manufacture and use thereof. In some embodiments the system or apparatus contains sensors to form feedback loops that can activate the infrared illumination source and/or the laser based white light illumination source. Merely by examples, the invention provides remote and integrated smart laser lighting devices and methods, configured with infrared and visible illumination capability for spotlighting, detection, imaging, projection display, spatially dynamic lighting devices and methods, LIDAR, LiFi, and visible light communication devices and methods, and various combinations of above in applications of general lighting, commercial lighting and display, automotive lighting and communication, defense and security, search and rescue, industrial processing, internet communications, agriculture or horticulture. The integrated light source according to this invention can be incorporated into an automotive headlight, a general illumination source, a security light source, a search light source, a defense light source, as a light fidelity (LiFi) communication device, for horticulture purposes to optimize plant growth, or many other applications.

In an aspect, this invention provides novel uses and configurations of gallium and nitrogen containing laser diodes in lighting systems configured for IR illumination, which can be deployed in dual spectrum spotlighting, imaging, sensing, and searching applications. Configured with a laser based white light source and an IR light source, this invention is capable of emitting light both in the visible wavelength band and in the IR wavelength band, and is configured to selectively operate in one band or simultaneously in both bands. This dual band emission source can be deployed in communication systems such as visible light communication systems such as Li-Fi systems, communications using the convergence of lighting and display with static or dynamic spatial patterning using beam shaping elements such as MEMS scanning mirrors or digital light processing units, and communications triggered by integrated sensor feedback. Specific embodiments of this invention employ a transferred gallium and nitrogen containing material process for fabricating laser diodes or other gallium and nitrogen containing devices enabling benefits over conventional fabrication technologies.

The present invention is configured for both visible light emission and IR light emission. While the necessity and utility of visible light is clearly understood, it is often desirable to provide illumination wavelength bands that are not visible. In one example, IR illumination is used for night vision. Night vision or IR detection devices play a critical role in defense, security, search and rescue, and recreational activities in both the private sector and at the municipal or government sectors. By providing the ability to see in no or low ambient light conditions, night vision technology is widely deployed to the consumer markets for several applications including hunting, gaming, driving, locating, detecting, personal protection, and others. Whether by biological or technological means, night vision and IR detection are made possible by a combination of sufficient spectral range and sufficient intensity range. Such detection can be for two dimensional imaging, or three dimensional distance measurement such as range-finding, or three dimensional imaging such as LIDAR.

Figure 2:
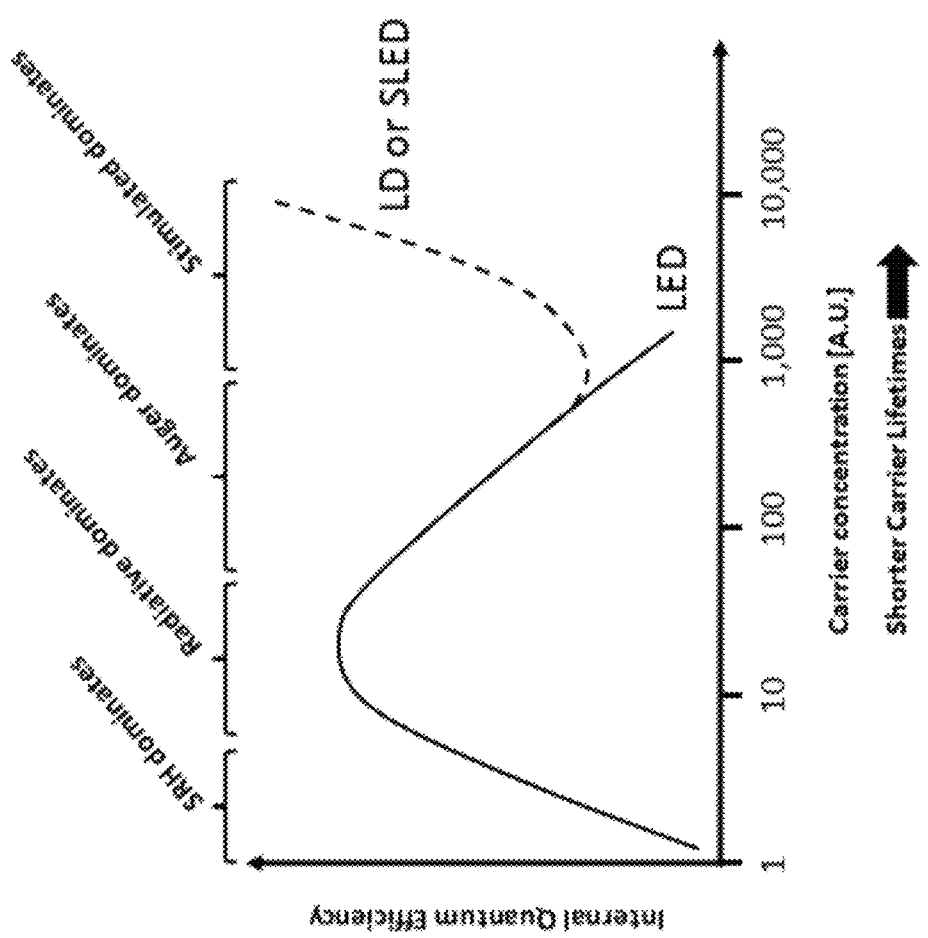
FIG. 2 is a schematic diagram showing dependence of internal quantum efficiency in a laser diode on carrier concentration in the light emitting layers of the device.
Figure 3:
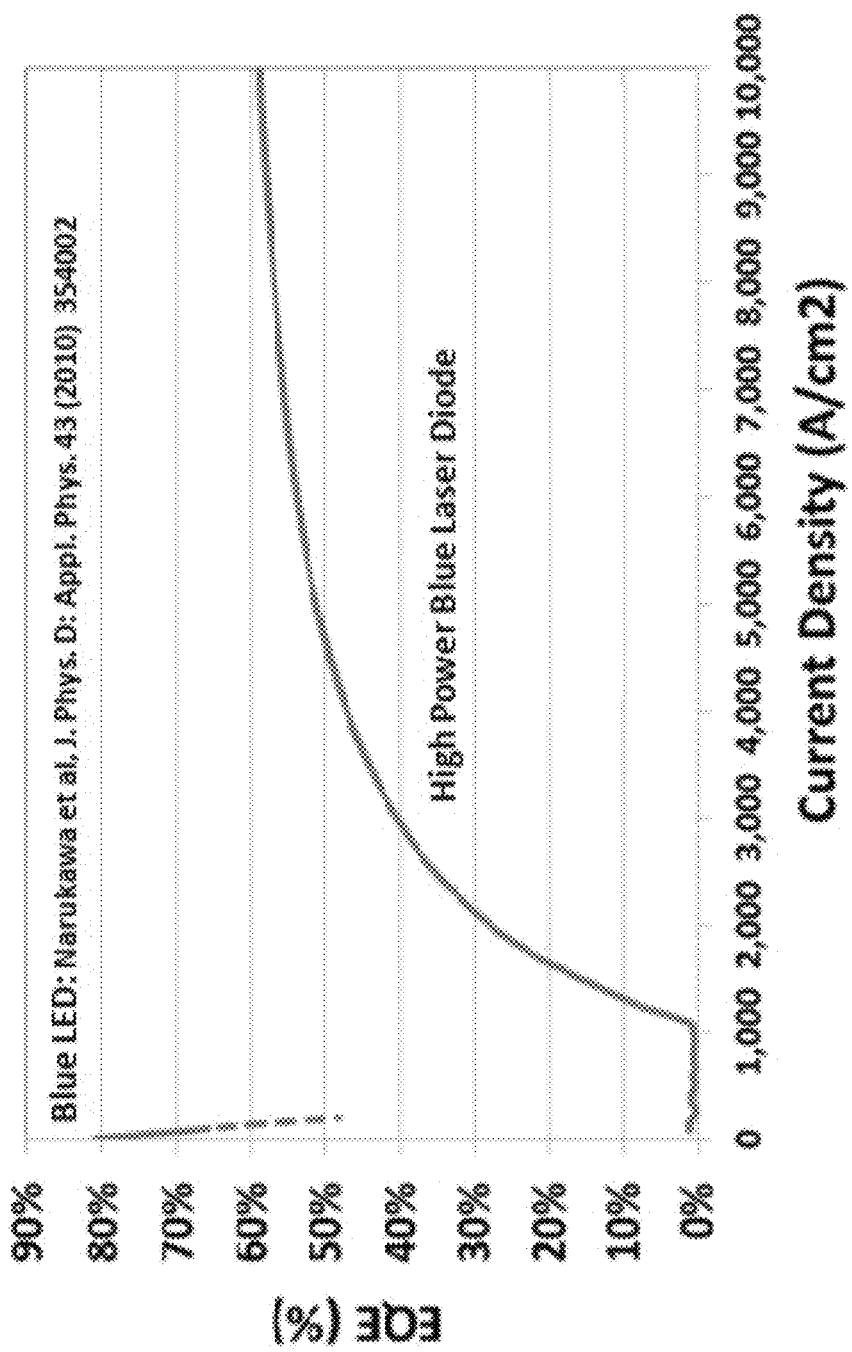
FIG. 3 is a plot of external quantum efficiency as a function of current density for a high power blue laser diode compared to the high power blue light emitting diode.

As background, while LED-based light sources offer great advantages over incandescent based sources, there are still challenges and limitations associated with LED device physics. The first limitation is the so called "droop" phenomenon that plagues GaN based LEDs. The droop effect leads to power rollover with increased current density, which forces LEDs to hit peak external quantum efficiency at very low current densities in the 10-200 A/cm$^2$ range. FIG. 2 shows a schematic diagram of the relationship between internal quantum efficiency (IQE) and carrier concentration in the light emitting layers of a light emitting diode (LED) and light-emitting devices where stimulated emission is significant such as laser diodes (LDs) or super-luminescent LEDs. IQE is defined as the ratio of the radiative recombination rate to the total recombination rate in the device. At low carrier concentrations Shockley-Reed-Hall recombination at crystal defects dominates recombination rates such that IQE is low. At moderate carrier concentrations, spontaneous radiative recombination dominates such that IQE is relatively high. At high carrier concentrations, non-radiative auger recombination dominates such that IQE is again relatively low. In devices such as LDs or SLEDs, stimulated emission at very high carrier densities leads to a fourth regime where IQE is relatively high. FIG. 3 shows a plot of the external quantum efficiency (EQE) for a typical blue LED and for a high power blue laser diode. EQE is defined as the product of the IQE and the fraction of generated photons that are able to exit the device. While the blue LED achieves a very high EQE at very low current densities, it exhibits very low EQE at high current densities due to the dominance of auger recombination at high current densities. The LD, however, is dominated by stimulated emission at high current densities, and exhibits very high EQE. At low current densities, the LD has relatively poor EQE due to reabsorption of photons in the device. Thus, to maximize efficiency of the LED based light source, the current density must be limited to low values where the light output is also limited. The result is low output power per unit area of LED die (flux), which forces the use large LED die areas to meet the brightness requirements for most applications. For example, a typical LED based light bulb will require 3 mm$^2$ to 30 mm$^2$ of epi area.

A second limitation of LEDs is also related to their brightness, more specifically it is related to their spatial brightness. A conventional high brightness LED emits ~1 W per mm$^2$ of epi area. With some advances and breakthrough perhaps this can be increased up to 5-10× to 5-10 W per mm$^2$ of epi area. Finally, LEDs fabricated on conventional c-plane GaN suffer from strong internal polarization fields, which spatially separate the electron and hole wave functions and lead to poor radiative recombination efficiency. Since this phenomenon becomes more pronounced in InGaN layers with increased indium content for increased wavelength emission, extending the performance of UV or blue GaN-based LEDs to the blue-green or green regime has been difficult.

An exciting new class of solid-state lighting based on laser diodes is rapidly emerging. Like an LED, a laser diode is a two-lead semiconductor light source that that emits electromagnetic radiation. However, unlike the output from an LED that is primarily spontaneous emission, the output of a laser diode is comprised primarily of stimulated emission. The laser diode contains a gain medium that functions to provide emission through the recombination of electron-hole pairs and a cavity region that functions as a resonator for the emission from the gain medium. When a suitable voltage is applied to the leads to sufficiently pump the gain medium, the cavity losses are overcome by the gain and the laser diode reaches the so-called threshold condition, wherein a steep increase in the light output versus current input characteristic is observed. At the threshold condition, the carrier density clamps and stimulated emission dominates the emission. Since the droop phenomenon that plagues LEDs is dependent on carrier density, the clamped carrier density within laser diodes provides a solution to the droop challenge. Further, laser diodes emit highly directional and coherent light with orders of magnitude higher spatial brightness than LEDs. For example, a commercially available edge emitting GaN-based laser diode can reliably produce about 2 W of power in an aperture that is 15 µm wide by about 0.5 µm tall, which equates to over 250,000 W/mm$^2$. This spatial brightness is over 5 orders of magnitude higher than LEDs or put another way, 10,000 times brighter than an LED.

Based on essentially all the pioneering work on GaN LEDs, visible laser diodes based on GaN technology have rapidly emerged over the past 20 years. Currently the only viable direct blue and green laser diode structures are fabricated from the wurtzite AlGaInN material system. The manufacturing of light emitting diodes from GaN related materials is dominated by the heteroepitaxial growth of GaN on foreign substrates such as Si, SiC and sapphire. Laser diode devices operate at such high current densities that the crystalline defects associated with heteroepitaxial growth are not acceptable. Because of this, very low defect-density, free-standing GaN substrates have become the substrate of choice for GaN laser diode manufacturing. Unfortunately, such bulk GaN substrates are costly and not widely available in large diameters. For example, 2" diameter is the most common laser-quality bulk GaN c-plane substrate size today with recent progress enabling 4" diameter, which are still relatively small compared to the 6" and greater diameters that are commercially available for mature substrate technologies. Further details of the present invention can be found throughout the present specification and more particularly below.

Additional benefits are achieved over pre-existing techniques using the present invention. In particular, the present invention enables a cost-effective white light source. In a specific embodiment, the present optical device can be manufactured in a relatively simple and cost effective manner. Depending upon the embodiment, the present apparatus and method can be manufactured using conventional materials and/or methods according to one of ordinary skill in the art. In some embodiments of this invention the gallium and nitrogen containing laser diode source is based on c-plane gallium nitride material and in other embodiments the laser diode is based on nonpolar or semipolar gallium and nitride material. In one embodiment the white source is configured from a chip on submount (CoS) with an integrated phosphor on the submount to form a chip and phosphor on submount (CPoS) white light source. In some embodiments intermediate submount members may be included. In some embodiments the laser diode and the phosphor member are supported by a common support member such as a package base. In this embodiment there could be submount members or additional support members included between the laser diode and the common support member. Similarly there could be submount members or additional support members included between the phosphor member and the common support member.

In various embodiments, the laser device and phosphor device are co-packaged or mounted on a common support member with or without intermediate submounts and the phosphor materials are operated in a transmissive mode, a reflective mode, or a side-pumped mode to result in a white emitting laser-based light source. In additional various embodiments, the electromagnetic radiation from the laser device is remotely coupled to the phosphor device through means such as free space coupling or coupling with a waveguide such as a fiber optic cable or other solid waveguiding material, and wherein the phosphor materials are operated in a transmissive mode, a reflective mode, or a side-pumped mode to result in a white emitting laser-based light source. Merely by way of example, the invention can be applied to applications such as white lighting, white spot lighting, flash lights, automobile headlights, all-terrain vehicle lighting, flash sources such as camera flashes, light sources used in recreational sports such as biking, surfing, running, racing, boating, light sources used for drones, planes, robots, other mobile or robotic applications, safety, search and rescue, sensing, range finding, counter measures in defense applications, multi-colored lighting, lighting for flat panels, medical, metrology, beam projectors and other displays, high intensity lamps, spectroscopy, entertainment, theater, music, and concerts, analysis fraud detection and/or authenticating, tools, water treatment, laser dazzlers, targeting, communications, LiFi, visible light communications (VLC), sensing, detecting, distance detecting, Light Detection And Ranging (LIDAR), transformations, transportations, leveling, curing and other chemical treatments, heating, cutting and/or ablating, pumping other optical devices, other optoelectronic devices and related applications, and source lighting and the like.

Laser diodes are ideal as phosphor excitation sources. With a spatial brightness (optical intensity per unit area) greater than 10,000 times higher than conventional LEDs and the extreme directionality of the laser emission, laser diodes enable characteristics unachievable by LEDs and other light sources. Specifically, since the laser diodes output beams carrying over 1 W, over 5 W, over 10 W, or even over 100 W can be focused to very small spot sizes of less than 1 mm in diameter, less than 500 µm in diameter, less than 100 µm in diameter, or even less than 50 µm in diameter, power densities of over 1 W/mm$^2$, 100 W/mm$^2$, or even over 2,500 W/mm$^2$ can be achieved. When this very small and powerful beam of laser excitation light is incident on a phosphor material the ultimate point source of white light can be achieved. Assuming a phosphor conversion ratio of 200 lumens of emitted white light per optical watt of excitation light, a 5 W excitation power could generate 1000 lumens in a beam diameter of 100 µm, or 50 µm, or less. Such a point source is game changing in applications such as spotlighting or range finding where parabolic reflectors or lensing optics can be combined with the point source to create highly collimated white light spots that can travel drastically higher distances than ever possible before using LEDs or bulb technology.

In some embodiments of the present invention the gallium and nitrogen containing light emitting device may not be a laser device, but instead may be configured as a superluminescent diode or superluminescent light emitting diode (SLED) device. For the purposes of this invention, a SLED device and laser diode device can be used interchangeably. A SLED is similar to a laser diode as it is based on an electrically driven junction that when injected with current becomes optically active and generates amplified spontaneous emission (ASE) and gain over a wide range of wavelengths. When the optical output becomes dominated by ASE there is a knee in the light output versus current (LI) characteristic wherein the unit of light output becomes drastically larger per unit of injected current. This knee in the LI curve resembles the threshold of a laser diode, but is much softer. The advantage of a SLED device is that SLED it can combine the unique properties of high optical emission power and extremely high spatial brightness of laser diodes that make them ideal for highly efficient long throw illumination and high brightness phosphor excitation applications with a broad spectral width of (>5 nm) that provides for an improved eye safety and image quality in some cases. The broad spectral width results in a low coherence length similar to an LED. The low coherence length provides for an improved safety such has improved eye safety. Moreover, the broad spectral width can drastically reduce optical distortions in display or illumination applications. As an example, the well-known distortion pattern referred to as "speckle" is the result of an intensity pattern produced by the mutual interference of a set of wavefronts on a surface or in a viewing plane. The general equations typically used to quantify the degree of speckle are inversely proportional to the spectral width. In the present specification, both a laser diode (LD) device and a superluminescent light emitting diode (SLED) device are sometime simply referred to "laser device".

A gallium and nitrogen containing laser diode (LD) or super luminescent light emitting diode (SLED) may include at least a gallium and nitrogen containing device having an active region and a cavity member and are characterized by emitted spectra generated by the stimulated emission of photons. In some embodiments a laser device emitting red laser light, i.e. light with wavelength between about 600 nm to 750 nm, are provided. These red laser diodes may include at least a gallium phosphorus and arsenic containing device having an active region and a cavity member and are characterized by emitted spectra generated by the stimulated emission of photons. The ideal wavelength for a red device for display applications is ~635 nm, for green ~530 nm and for blue 440-470 nm. There may be tradeoffs between what colors are rendered with a display using different wavelength lasers and also how bright the display is as the eye is more sensitive to some wavelengths than to others.

In some embodiments according to the present invention, multiple laser diode sources are configured to be excite the same phosphor or phosphor network. Combining multiple laser sources can offer many potential benefits according to this invention. First, the excitation power can be increased by beam combining to provide a more powerful excitation spit and hence produce a brighter light source. In some embodiments, separate individual laser chips are configured within the laser-phosphor light source. By including multiple lasers emitting 1 W, 2 W, 3 W, 4 W, 5 W or more power each, the excitation power can be increased and hence the source brightness would be increased. For example, by including two 3 W lasers exciting the same phosphor area, the excitation power can be increased to 6 W for double the white light brightness. In an example where about 200 lumens of white are generated per 1 watt of laser excitation power, the white light output would be increased from 600 lumens to 1200 lumens. Beyond scaling the power of each single laser diode emitter, the total luminous flux of the white light source can be increased by continuing to increasing the total number of laser diodes, which can range from 10s, to 100s, and even to 1000s of laser diode emitters resulting in 10s to 100s of kW of laser diode excitation power. Scaling the number of laser diode emitters can be accomplished in many ways such as including multiple lasers in a co-package, spatial beam combining through conventional refractive optics or polarization combining, and others. Moreover, laser diode bars or arrays, and mini-bars can be utilized where each laser chip includes many adjacent laser diode emitters. For example, a bar could include from 2 to 100 laser diode emitters spaced from about 10 microns to about 400 microns apart. Similarly, the reliability of the source can be increased by using multiple sources at lower drive conditions to achieve the same excitation power as a single source driven at more harsh conditions such as higher current and voltage.

As used herein, the term GaN substrate is associated with Group III-nitride based materials including GaN, InGaN, AlGaN, or other Group III containing alloys or compositions that are used as starting materials. Such starting materials include polar GaN substrates (i.e., substrate where the largest area surface is nominally an (h k l) plane wherein h=k=0, and l is non-zero), non-polar GaN substrates (i.e., substrate material where the largest area surface is oriented at an angle ranging from about 80-100 degrees from the polar orientation described above towards an (h k l) plane wherein l=0, and at least one of h and k is non-zero) or semi-polar GaN substrates (i.e., substrate material where the largest area surface is oriented at an angle ranging from about +0.1 to 80 degrees or 110-179.9 degrees from the polar orientation described above towards an (h k l) plane wherein l=0, and at least one of h and k is non-zero). Of course, there can be other variations, modifications, and alternatives.

The laser diode device can be fabricated on a conventional orientation of a gallium and nitrogen containing film or substrate (e.g., GaN) such as the polar c-plane, on a nonpolar orientation such as the m-plane, or on a semipolar orientation such as the {30-31}, {20-21}, {30-32}, {11-22}, {10-11}, {30-3-1}, {20-2-1}, {30-3-2}, or offcuts of any of these polar, nonpolar, and semipolar planes within +/−10 degrees towards a c-plane, and/or +/−10 degrees towards an a-plane, and/or +/−10 degrees towards an m-plane. In some embodiments, a gallium and nitrogen containing laser diode laser diode includes a gallium and nitrogen containing substrate. The substrate member may have a surface region on the polar {0001} plane (c-plane), nonpolar plane (m-plane, a-plane), and semipolar plain ({11-22}, {10-1-1}, {20-21}, {30-31}) or other planes of a gallium and nitrogen containing substrate. The laser device can be configured to emit a laser beam characterized by one or more wavelengths from about 390 nm to about 540 nm. In some embodiments the laser diode is comprised from a III-nitride material emitting in the ultraviolet region with a wavelength of about 270 nm to about 390 nm.

Figure 4:
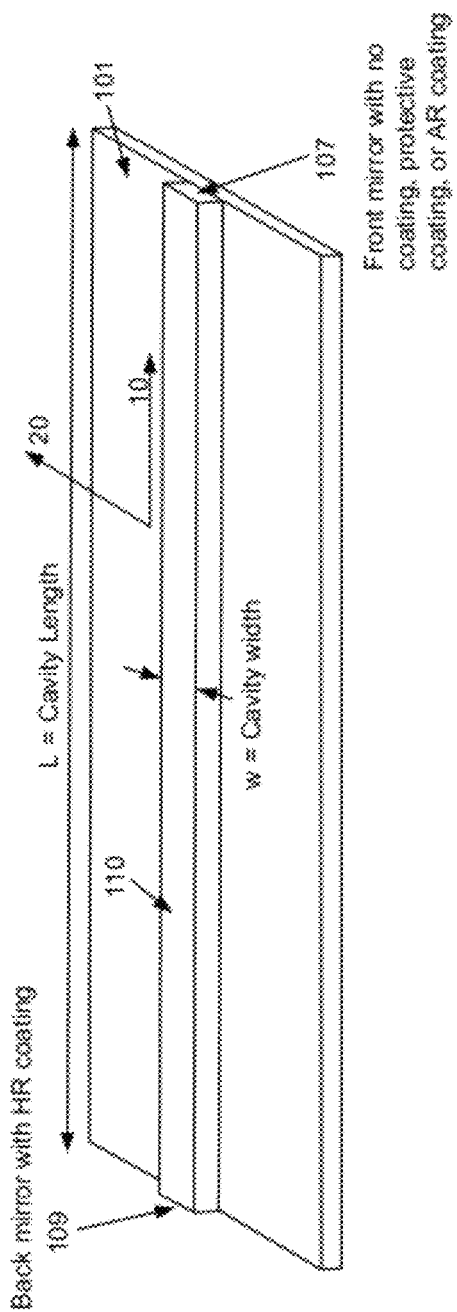
FIG. 4 is a simplified schematic diagram of a laser diode formed on a gallium and nitrogen containing substrate with the cavity aligned in a direction ended with cleaved or etched mirrors according to some embodiments of the present invention.

FIG. 4 is a simplified schematic diagram of a laser diode formed on a gallium and nitrogen containing substrate with the cavity aligned in a direction ended with cleaved or etched mirrors according to some embodiments of the present invention. In an example, the substrate surface 101 is a polar c-plane and the laser stripe region 110 is characterized by a cavity orientation substantially in an m-direction 10, which is substantially normal to an a-direction 20, but can be others such as cavity alignment substantially in the a-direction. The laser strip region 110 has a first end 107 and a second end 109 and is formed on an m-direction on a {0001} gallium and nitrogen containing substrate having a pair of cleaved or etched mirror structures, which face each other. In another example, the substrate surface 101 is a semipolar plane and the laser stripe region 110 is characterized by a cavity orientation substantially in a projection of a c-direction 10, which is substantially normal to an α-direction 20, but can be others such as cavity alignment substantially in the a-direction. The laser strip region 110 has a first end 107 and a second end 109 and is formed on a semipolar substrate such as a {40-41}, {30-31}, {20-21}, {40-4-1}, {30-3-1}, {20-2-1}, {20-21}, or an offcut of these planes within +/−5 degrees from the c-plane and a-plane gallium and nitrogen containing substrate. Optionally, the gallium nitride substrate member is a bulk GaN substrate characterized by having a nonpolar or semipolar crystalline surface region, but can be others. The bulk GaN substrate may have a surface dislocation density below $10^5$ cm$^{-2}$ or $10^5$ to $10^7$ cm$^{-2}$. The nitride crystal or wafer may include $Al_xIn_yGa_{1-x-y}N$, where $0 \leq x$, y, $x+y \leq 1$. In one specific embodiment, the nitride crystal includes GaN. In a embodiments, the GaN substrate has threading dislocations, at a concentration between about $10^5$ cm$^{-2}$ and about $10^8$ cm$^{-2}$, in a direction that is substantially orthogonal or oblique with respect to the surface.

The exemplary laser diode devices in FIG. 4 have a pair of cleaved or etched mirror structures 109 and 107, which face each other. The first cleaved or etched facet 109 includes a reflective coating and the second cleaved or etched facet 107 includes no coating, an antireflective coating, or exposes gallium and nitrogen containing material. The first cleaved or etched facet 109 is substantially parallel with the second cleaved or etched facet 107. The first and second cleaved facets 109 and 107 are provided by a scribing and breaking process according to an embodiment or alternatively by etching techniques using etching technologies such as reactive ion etching (ME), inductively coupled plasma etching (ICP), or chemical assisted ion beam etching (CAIBE), or other method. The reflective coating is selected from silicon dioxide, hafnia, and titania, tantalum pentoxide, zirconia, aluminum oxide, aluminum nitride, and aluminum oxynitride including combinations, and the like. Depending upon the design, the mirror surfaces can also include an anti-reflective coating.

In a specific embodiment, the method of facet formation includes subjecting the substrates to a laser for pattern formation. In a preferred embodiment, the pattern is configured for the formation of a pair of facets for a ridge lasers. In a preferred embodiment, the pair of facets faces each other and is in parallel alignment with each other. In a preferred embodiment, the method uses a UV (355 nm) laser to scribe the laser bars. In a specific embodiment, the laser is configured on a system, which allows for accurate scribe lines configured in a different patterns and profiles. In an embodiment, the laser scribing can be performed on the back-side, front-side, or both depending upon the application. Of course, there can be other variations, modifications, and alternatives.

In a specific embodiment, the method uses backside laser scribing or the like. With backside laser scribing, the method preferably forms a continuous line laser scribe that is perpendicular to the laser bars on the backside of the GaN substrate. In a specific embodiment, the laser scribe is generally about 15-20 μm deep or other suitable depth. Preferably, backside scribing can be advantageous. That is, the laser scribe process does not depend on the pitch of the laser bars or other like pattern. Accordingly, backside laser scribing can lead to a higher density of laser bars on each substrate according to a preferred embodiment. In a specific embodiment, backside laser scribing, however, may lead to residue from the tape on the facets. In a specific embodiment, backside laser scribe often requires that the substrates face down on the tape. With front-side laser scribing, the backside of the substrate is in contact with the tape. Of course, there can be other variations, modifications, and alternatives.

It is well known that etch techniques such as chemical assisted ion beam etching (CAIBE), inductively coupled plasma (ICP) etching, or reactive ion etching (RIE) can result in smooth and vertical etched sidewall regions, which could serve as facets in etched facet laser diodes. In the etched facet process a masking layer is deposited and patterned on the surface of the wafer. The etch mask layer could be comprised of dielectrics such as silicon dioxide ($SiO_2$), silicon nitride ($Si_xN_y$), a combination thereof or other dielectric materials. Further, the mask layer could be comprised of metal layers such as Ni or Cr, but could be comprised of metal combination stacks or stacks comprising metal and dielectrics. In another approach, photoresist masks can be used either alone or in combination with dielectrics and/or metals. The etch mask layer is patterned using conventional photolithography and etch steps. The alignment lithography could be performed with a contact aligner or stepper aligner. Such lithographically defined mirrors provide a high level of control to the design engineer. After patterning of the photoresist mask on top of the etch mask is complete, the patterns in then transferred to the etch mask using a wet etch or dry etch technique. Finally, the facet pattern is then etched into the wafer using a dry etching technique selected from CAIBE, ICP, RIE and/or other techniques. The etched facet surfaces must be highly vertical of between about 87 and about 93 degrees or between about 89 and about 91 degrees from the surface plane of the wafer. The etched facet surface region must be very smooth with root mean square roughness values of less than about 50 nm, 20 nm, 5 nm, or 1 nm. Lastly, the etched must be substantially free from damage, which could act as nonradiative recombination centers and hence reduce the catastrophic optical mirror damage (COMD) threshold. CAIBE is known to provide very smooth and low damage sidewalls due to the chemical nature of the etch, while it can provide highly vertical etches due to the ability to tilt the wafer stage to compensate for any inherent angle in etch.

The laser stripe region 110 is characterized by a length and width. The length ranges from about 50 μm to about 3000 μm, but is preferably between about 10 μm and about 400 μm, between about 400 μm and about 800 μm, or about 800 μm and about 1600 μm, but could be others. The stripe also has a width ranging from about 0.5 μm to about 50 μm, but is preferably between about 0.8 μm and about 2.5 μm for single lateral mode operation or between about 2.5 μm and about 50 μm for multi-lateral mode operation, but can be other dimensions. In a specific embodiment, the present device has a width ranging from about 0.5 μm to about 1.5 μm, a width ranging from about 1.5 μm to about 3.0 μm, a width ranging from about 3.0 μm to about 50 μm, and others. In a specific embodiment, the width is substantially constant in dimension, although there may be slight variations. The width and length are often formed using a masking and etching process, which are commonly used in the art.

The laser stripe region 110 is provided by an etching process selected from dry etching or wet etching. The device also has an overlying dielectric region, which exposes a p-type contact region. Overlying the contact region is a contact material, which may be metal or a conductive oxide or a combination thereof. The p-type electrical contact may be deposited by thermal evaporation, electron beam evaporation, electroplating, sputtering, or another suitable technique. Overlying the polished region of the substrate is a second contact material, which may be metal or a conductive oxide or a combination thereof and which includes the n-type electrical contact. The n-type electrical contact may be deposited by thermal evaporation, electron beam evaporation, electroplating, sputtering, or another suitable technique.

In a specific embodiment, the laser device may emit red light with a center wavelength between 600 nm and 750 nm. Such a device may include layers of varying compositions of $Al_xIn_yGa_{1-x-y}As_zP_{1-z}$, where x+y≤1 and z≤1. The red laser device includes at least an n-type and p-type cladding layer, an n-type SCH of higher refractive index than the n-type cladding, a p-type SCH of higher refractive index than the p-type cladding and an active region where light is emitted. In a specific embodiment, the laser stripe is provided by an etching process selected from dry etching or wet etching. In a preferred embodiment, the etching process is dry, but can be others. The device also has an overlying dielectric region, which exposes the contact region. In a specific embodiment, the dielectric region is an oxide such as silicon dioxide, but can be others. Of course, there can be other variations, modifications, and alternatives. The laser stripe region is characterized by a length and width. The length ranges from about 50 μm to about 3000 μm, but is preferably between 10 μm and 400 μm, between about 400 μm and 800 μm, or about 800 μm and 1600 μm, but could be others such as greater than 1600 μm. The stripe region also has a width ranging from about 0.5 μm to about 80 μm, but is preferably between 0.8 and 2.5 μm for single lateral mode operation or between 2.5 μm and 60 μm for multi-lateral mode operation, but can be other dimensions. The laser strip region has a first end and a second end having a pair of cleaved or etched mirror structures, which face each other. The first facet includes a reflective coating and the second facet includes no coating, an antireflective coating, or exposes gallium and nitrogen containing material. The first facet is substantially parallel with the second cleaved or etched facet.

Given the high gallium and nitrogen containing substrate costs, difficulty in scaling up gallium and nitrogen containing substrate size, the inefficiencies inherent in the processing of small wafers, and potential supply limitations it becomes extremely desirable to maximize utilization of available gallium and nitrogen containing substrate and overlying epitaxial material. In the fabrication of lateral cavity laser diodes, it is typically the case that minimum die size is determined by device components such as the wire bonding pads or mechanical handling considerations, rather than by laser cavity widths. Minimizing die size is critical to reducing manufacturing costs as smaller die sizes allow a greater number of devices to be fabricated on a single wafer in a single processing run. The current invention is a method of maximizing the number of devices which can be fabricated from a given gallium and nitrogen containing substrate and overlying epitaxial material by spreading out the epitaxial material onto a carrier wafer via a die expansion process.

Similar to an edge emitting laser diode, a SLED is typically configured as an edge-emitting device wherein the high brightness, highly directional optical emission exits a waveguide directed outward from the side of the semiconductor chip. SLEDs are designed to have high single pass gain or amplification for the spontaneous emission generated along the waveguide. However, unlike laser diodes, they are designed to provide insufficient feedback to in the cavity to achieve the lasing condition where the gain equals the total losses in the waveguide cavity. In a typical example, at least one of the waveguide ends or facets is designed to provide very low reflectivity back into the waveguide. Several methods can be used to achieve reduced reflectivity on the waveguide end or facet. In one approach an optical coating is applied to at least one of the facets, wherein the optical coating is designed for low reflectivity such as less than 1%, less than 0.1%, less than 0.001%, or less than 0.0001% reflectivity. In another approach for reduced reflectivity the waveguide ends are designed to be tilted or angled with respect to the direction of light propagation such that the light that is reflected back into the chip does not constructively interfere with the light in the cavity to provide feedback. The tilt angle must be carefully designed around a null in the reflectivity versus angle relationship for optimum performance. The tilted or angled facet approach can be achieved in a number of ways including providing an etched facet that is designed with an optimized angle lateral angle with respect to the direction of light propagation. The angle of the tilt is pre-determined by the lithographically defined etched facet patter. Alternatively, the angled output could be achieved by curving and/or angling the waveguide with respect to a cleaved facet that forms on a pre-determined crystallographic plane in the semiconductor chip. Another approach to reduce the reflectivity is to provide a roughened or patterned surface on the facet to reduce the feedback to the cavity. The roughening could be achieved using chemical etching and/or a dry etching, or with an alternative technique. Of course there may be other methods for reduced feedback to the cavity to form a SLED device. In many embodiments a number of techniques can be used in combination to reduce the facet reflectivity including using low reflectivity coatings in combination with angled or tilted output facets with respect to the light propagation.

In a specific embodiment on a nonpolar Ga-containing substrate, the device is characterized by a spontaneously emitted light is polarized in substantially perpendicular to the c-direction. In a preferred embodiment, the spontaneously emitted light is characterized by a polarization ratio of greater than 0.1 to about 1 perpendicular to the c-direction. In a preferred embodiment, the spontaneously emitted light characterized by a wavelength ranging from about 430 nanometers to about 470 nm to yield a blue emission, or about 500 nanometers to about 540 nanometers to yield a green emission, and others. For example, the spontaneously emitted light can be violet (e.g., 395 to 420 nanometers), blue (e.g., 420 to 470 nm); green (e.g., 500 to 540 nm), or others. In a preferred embodiment, the spontaneously emitted light is highly polarized and is characterized by a polarization ratio of greater than 0.4. In another specific embodiment on a semipolar {20-21} Ga-containing substrate, the device is also characterized by a spontaneously emitted light is polarized in substantially parallel to the a-direction or perpendicular to the cavity direction, which is oriented in the projection of the c-direction.

In a specific embodiment, the present invention provides an alternative device structure capable of emitting 501 nm and greater light in a ridge laser embodiment. The device is provided with the following epitaxially grown elements:

an n-GaN or n-AlGaN cladding layer with a thickness from 100 nm to 3000 nm with Si doping level of $5\times10^{17}$ $cm^{-3}$ to $3 \times 10^{18}$ $cm^{-3}$;

an n-side SCH layer comprised of InGaN with molar fraction of indium of between 2% and 15% and thickness from 20 nm to 250 nm;

a single quantum well or a multiple quantum well active region comprised of at least two 2.0 nm to 8.5 nm InGaN quantum wells separated by 1.5 nm and greater, and optionally up to about 12 nm, GaN or InGaN barriers;

a p-side SCH layer comprised of InGaN with molar a fraction of indium of between 1% and 10% and a thickness from 15 nm to 250 nm or an upper GaN-guide layer;

an electron blocking layer comprised of AlGaN with molar fraction of aluminum of between 0% and 22% and thickness from 5 nm to 20 nm and doped with Mg;

a p-GaN or p-AlGaN cladding layer with a thickness from 400 nm to 1500 nm with Mg doping level of $2 \times 10^{17}$ $cm^{-3}$ to $2 \times 10^{19}$ cm-3; and a p++-GaN contact layer with a thickness from 20 nm to 40 nm with Mg doping level of $1 \times 10^{19}$ $cm^{-3}$ to $1 \times 10^{21}$ $cm^{-3}$.

A gallium and nitrogen containing laser diode laser device may also include other structures, such as a surface ridge architecture, a buried heterostructure architecture, and/or a plurality of metal electrodes for selectively exciting the active region. For example, the active region may include first and second gallium and nitrogen containing cladding layers and an indium and gallium containing emitting layer positioned between the first and second cladding layers. A laser device may further include an n-type gallium and nitrogen containing material and an n-type cladding material overlying the n-type gallium and nitrogen containing material. In a specific embodiment, the device also has an overlying n-type gallium nitride layer, an active region, and an overlying p-type gallium nitride layer structured as a laser stripe region. Additionally, the device may also include an n-side separate confinement hetereostructure (SCH), p-side guiding layer or SCH, p-AlGaN EBL, among other features. In a specific embodiment, the device also has a p++ type gallium nitride material to form a contact region. In a specific embodiment, the p++ type contact region has a suitable thickness and may range from about 10 nm 50 nm, or other thicknesses. In a specific embodiment, the doping level can be higher than the p-type cladding region and/or bulk region. In a specific embodiment, the p++ type region has doping concentration ranging from about $10^{19}$ to $10^{21}$ Mg/am³, and others. The p++ type region preferably causes tunneling between the semiconductor region and overlying metal contact region. In a specific embodiment, each of these regions is formed using at least an epitaxial deposition technique of metal organic chemical vapor deposition (MOCVD), molecular beam epitaxy (MBE), or other epitaxial growth techniques suitable for GaN growth. In a specific embodiment, the epitaxial layer is a high quality epitaxial layer overlying the n-type gallium nitride layer. In some embodiments the high quality layer is doped, for example, with Si or O to form n-type material, with a dopant concentration between about $10^{16}$ $cm^{-3}$ and $10^{20}$ $cm^{-3}$.

Figure 5:
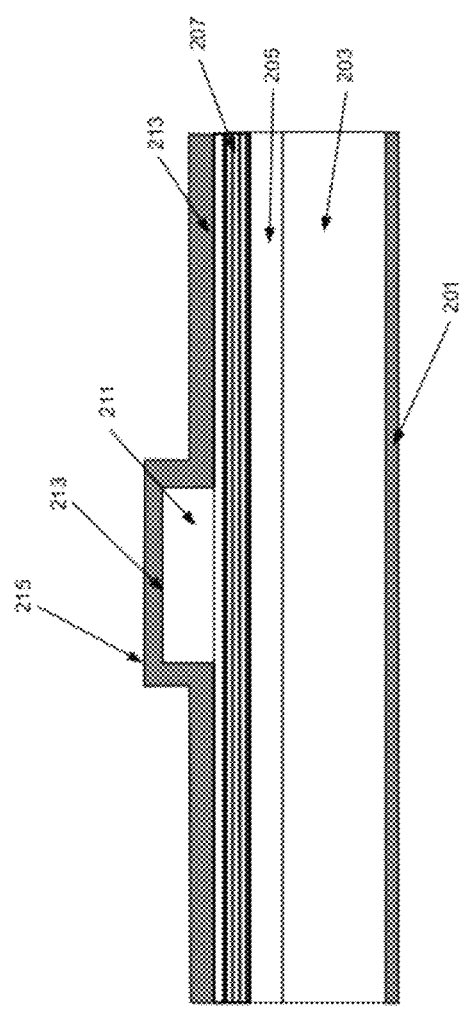
FIG. 5 is a cross-sectional view of a laser device according to an embodiment of the present invention.

FIG. 5 is a cross-sectional view of a laser device 200 according to some embodiments of the present disclosure. As shown, the laser device includes gallium nitride substrate 203, which has an underlying n-type metal back contact region 201. For example, the substrate 203 may be characterized by a semipolar or nonpolar orientation. The device also has an overlying n-type gallium nitride layer 205, an active region 207, and an overlying p-type gallium nitride layer structured as a laser stripe region 209. Each of these regions is formed using at least an epitaxial deposition technique of MOCVD, MBE, or other epitaxial growth techniques suitable for GaN growth. The epitaxial layer is a high quality epitaxial layer overlying the n-type gallium nitride layer. In some embodiments the high quality layer is doped, for example, with Si or O to form n-type material, with a dopant concentration between about $10^{16}$ $cm^{-3}$ and $10^{20}$ $cm^{-3}$.

An n-type $Al_uIn_vGa_{1-u-v}N$ layer, where 0≤u, v, u+v≤1, is deposited on the substrate. The carrier concentration may lie in the range between about $10^{16}$ $cm^{-3}$ and $10^{20}$ $cm^{-3}$. The deposition may be performed using MOCVD or MBE.

For example, the bulk GaN substrate is placed on a susceptor in an MOCVD reactor. After closing, evacuating, and back-filling the reactor (or using a load lock configuration) to atmospheric pressure, the susceptor is heated to a temperature between about 1000 and about 1200 degrees Celsius in the presence of a nitrogen-containing gas. The susceptor is heated to approximately 900 to 1200 degrees Celsius under flowing ammonia. A flow of a gallium-containing metalorganic precursor, such as trimethylgallium (TMG) or triethylgallium (TEG) is initiated, in a carrier gas, at a total rate between approximately 1 and 50 standard cubic centimeters per minute (sccm). The carrier gas may include hydrogen, helium, nitrogen, or argon. The ratio of the flow rate of the group V precursor (ammonia) to that of the group III precursor (trimethylgallium, triethylgallium, trimethylindium, trimethylaluminum) during growth is between about 2000 and about 12000. A flow of disilane in a carrier gas, with a total flow rate of between about 0.1 sccm and 10 sccm, is initiated.

In one embodiment, the laser stripe region is p-type gallium nitride layer 209. The laser stripe is provided by a dry etching process, but wet etching can be used. The dry etching process is an inductively coupled process using chlorine bearing species or a reactive ion etching process using similar chemistries. The chlorine bearing species are commonly derived from chlorine gas or the like. The device also has an overlying dielectric region, which exposes a contact region 213. The dielectric region is an oxide such as silicon dioxide or silicon nitride, and a contact region is coupled to an overlying metal layer 215. The overlying metal layer is preferably a multilayered structure containing gold and platinum (Pt/Au), palladium and gold (Pd/Au), or nickel gold (Ni/Au), or a combination thereof. In some embodiments, barrier layers and more complex metal stacks are included.

Active region 207 preferably includes one to ten quantum well regions or a double heterostructure region for light emission. Following deposition of the n-type layer to achieve a desired thickness, an active layer is deposited. The quantum wells are preferably InGaN with GaN, AlGaN, InAlGaN, or InGaN barrier layers separating them. In other embodiments, the well layers and barrier layers include $Al_wIn_xGa_{1-w-x}N$ and $Al_yIn_zGa_{1-y-z}N$, respectively, where 0≤w, x, y, z, w+x, y+z≤1, where w≤u, y and/or x>v, z so that the bandgap of the well layer(s) is less than that of the barrier layer(s) and the n-type layer. The well layers and barrier layers each have a thickness between about 1 nm and about 20 nm. The composition and structure of the active layer are chosen to provide light emission at a preselected wavelength. The active layer may be left undoped (or unintentionally doped) or may be doped n-type or p-type.

The active region can also include an electron blocking region, and a separate confinement heterostructure. The electron-blocking layer may include $Al_sIn_tGa_{1-s-t}N$, where 0≤s, t, s+t≤1, with a higher bandgap than the active layer, and may be doped p-type. In one specific embodiment, the electron blocking layer includes AlGaN. In another embodiment, the electron blocking layer includes an AlGaN/GaN super-lattice structure, comprising alternating layers of AlGaN and GaN, each with a thickness between about 0.2 nm and about 5 nm.

As noted, the p-type gallium nitride or aluminum gallium nitride structure is deposited above the electron blocking layer and active layer(s). The p-type layer may be doped with Mg, to a level between about $10^{16}$ cm$^{-3}$ and $10^{22}$ cm$^{-3}$, with a thickness between about 5 nm and about 1000 nm. The outermost 1-50 nm of the p-type layer may be doped more heavily than the rest of the layer, so as to enable an improved electrical contact. The device also has an overlying dielectric region, for example, silicon dioxide, which exposes the contact region 213.

The metal contact is made of suitable material such as silver, gold, aluminum, nickel, platinum, rhodium, palladium, chromium, or the like. The contact may be deposited by thermal evaporation, electron beam evaporation, electroplating, sputtering, or another suitable technique. In a preferred embodiment, the electrical contact serves as a p-type electrode for the optical device. In another embodiment, the electrical contact serves as an n-type electrode for the optical device. The laser devices illustrated in FIG. 4 and FIG. 5 and described above are typically suitable for relative low-power applications.

In various embodiments, the present invention realizes high output power from a diode laser is by widening a portions of the laser cavity member from the single lateral mode regime of 1.0-3.0 µm to the multi-lateral mode range 5.0-20 µm. In some cases, laser diodes having cavities at a width of 50 µm or greater are employed.

The laser stripe length, or cavity length ranges from 100 to 3000 µm and employs growth and fabrication techniques such as those described in U.S. patent application Ser. No. 12/759,273, filed Apr. 13, 2010, which is incorporated by reference herein. As an example, laser diodes are fabricated on nonpolar or semipolar gallium containing substrates, where the internal electric fields are substantially eliminated or mitigated relative to polar c-plane oriented devices. It is to be appreciated that reduction in internal fields often enables more efficient radiative recombination. Further, the heavy hole mass is expected to be lighter on nonpolar and semipolar substrates, such that better gain properties from the lasers can be achieved.

Optionally, FIG. 5 illustrates an example cross-sectional diagram of a gallium and nitrogen based laser diode device. The epitaxial device structure is formed on top of the gallium and nitrogen containing substrate member 203. The substrate member may be n-type doped with O and/or Si doping. The epitaxial structures will contain n-side layers 205 such as an n-type buffer layer comprised of GaN, AlGaN, AlINGaN, or InGaN and n-type cladding layers comprised of GaN, AlGaN, or AlInGaN. The n-typed layers may have thickness in the range of 0.3 µm to about 3 µm or to about 5 µm and may be doped with an n-type carriers such as Si or O to concentrations between $1\times10^{16}$ cm$^{-3}$ to $1\times10^{19}$ cm$^{-3}$. Overlying the n-type layers is the active region and waveguide layers 207. This region could contain an n-side waveguide layer or separate confinement heterostructure (SCH) such as InGaN to help with optical guiding of the mode. The InGaN layer be comprised of 1 to 15% molar fraction of InN with a thickness ranging from about 30 nm to about 250 nm and may be doped with an n-type species such as Si. Overlying the SCH layer is the light emitting regions which could be comprised of a double heterostructure or a quantum well active region. A quantum well active region could be comprised of 1 to 10 quantum wells ranging in thickness from 1 nm to 20 nm comprised of InGaN. Barrier layers comprised of GaN, InGaN, or AlGaN separate the quantum well light emitting layers. The barriers range in thickness from 1 nm to about 25 nm. Overlying the light emitting layers are optionally an AlGaN or InAlGaN electron blocking layer with 5% to about 35% AlN and optionally doped with a p-type species such as Mg. Also optional is a p-side waveguide layer or SCH such as InGaN to help with optical guiding of the mode. The InGaN layer be comprised of 1 to 15% molar fraction of InN with a thickness ranging from 30 nm to about 250 nm and may be doped with an p-type species such as Mg. Overlying the active region and optional electron blocking layer and p-side waveguide layers is a p-cladding region and a p++ contact layer. The p-type cladding region is comprised of GaN, AlGaN, AlINGaN, or a combination thereof. The thickness of the p-type cladding layers is in the range of 0.3 µm to about 2 µm and is doped with Mg to a concentration of between $1\times10^{16}$ cm$^{-3}$ to $1\times10^{19}$ cm$^{-3}$. A ridge 211 is formed in the p-cladding region for lateral confinement in the waveguide using an etching process selected from a dry etching or a wet etching process. A dielectric material 213 such as silicon dioxide or silicon nitride or deposited on the surface region of the device and an opening is created on top of the ridge to expose a portion of the p++ GaN layer. A p-contact 215 is deposited on the top of the device to contact the exposed p++ contact region. The p-type contact may be comprised of a metal stack containing a of Au, Pd, Pt, Ni, Ti, or Ag and may be deposited with electron beam deposition, sputter deposition, or thermal evaporation. A n-contact 201 is formed to the bottom of the substrate member. The n-type contact may be comprised of a metal stack containing Au, Al, Pd, Pt, Ni, Ti, or Ag and may be deposited with electron beam deposition, sputter deposition, or thermal evaporation.

In multiple embodiments according to the present invention, the device layers include a super-luminescent light emitting diode or SLED. In all applicable embodiments a SLED device can be interchanged with or combined with laser diode devices according to the methods and architectures described in this invention. A SLED is in many ways similar to an edge emitting laser diode; however the emitting facet of the device is designed so as to have a very low reflectivity. A SLED is similar to a laser diode as it is based on an electrically driven junction that when injected with current becomes optically active and generates amplified spontaneous emission (ASE) and gain over a wide range of wavelengths. When the optical output becomes dominated by ASE there is a knee in the light output versus current (LI) characteristic wherein the unit of light output becomes drastically larger per unit of injected current. This knee in the LI curve resembles the threshold of a laser diode, but is much softer. A SLED would have a layer structure engineered to have a light emitting layer or layers clad above and below with material of lower optical index such that a laterally guided optical mode can be formed. The SLED would also be fabricated with features providing lateral optical confinement. These lateral confinement features may consist of an etched ridge, with air, vacuum, metal or dielectric material surrounding the ridge and providing a low optical-index cladding. The lateral confinement feature may also be provided by shaping the electrical contacts such that injected current is confined to a finite region in the device. In such a "gain guided" structure, dispersion in the optical index of the light emitting layer with injected carrier density provides the optical-index contrast needed to provide lateral confinement of the optical mode.

It is also possible for the laser diode or SLED ridge, or in the case of a gain-guided device the electrically injected region, would not be of uniform width. The purpose of this would be to produce a wave-guide or cavity of larger width at one or both ends. This has two main advantages over a ridge or injected region of uniform width. Firstly, the waveguide can be shaped such that the resulting cavity can only sustain a single lateral mode while allowing the total area of the device to be significantly larger than that achievable in a device having a waveguide of uniform width. This increases the achievable optical power achievable in a device with a single lateral mode. Secondly, this allows for the cross-sectional area of the optical mode at the facets to be significantly larger than in a single-mode device having a waveguide of uniform width. Such a configuration reduces the optical power density of the device at the facet, and thereby reduces the likelihood that operation at high powers will result in optical damage to the facets. Single lateral mode devices may have some advantages in spectroscopy or in visible light communication where the single later mode results in a significant reduction in spectral width relative to a multi-lateral mode device with a wide ridge of uniform width. This would allow for more laser devices of smaller differences in center wavelength to be included in the same VLC emitter as the spectra would overlap less and be easier to demultiplex with filtered detectors. Optionally, both multi-mode and single-mode lasers would have significantly narrower spectra relative to LEDs with spectra of the same peak wavelength.

In an embodiment, the LD or SLED device is characterized by a ridge with non-uniform width. The ridge is comprised by a first section of uniform width and a second section of varying width. The first section has a length between 100 and 500 µm long, though it may be longer. The first section has a width of between 1 and 2.5 µm, with a width preferably between 1 and 1.5 µm. The second section of the ridge has a first end and a second end. The first end connects with the first section of the ridge and has the same width as the first section of the ridge. The second end of the second section of the ridge is wider than the first section of the ridge, with a width between 5 and 50 µm and more preferably with a width between 15 and 35 µm. The second section of the ridge waveguide varies in width between its first and second end smoothly. In some embodiments the second derivative of the ridge width versus length is zero such that the taper of the ridge is linear. In some embodiments, the second derivative is chosen to be positive or negative. In general the rate of width increase is chosen such that the ridge does not expand in width significantly faster than the optical mode. In specific embodiments, the electrically injected area is patterned such that only a part of the tapered portion of the waveguide is electrically injected.

In an embodiment, multiple laser dice emitting at different wavelengths are transferred to the same carrier wafer in close proximity to one another; preferably within one millimeter of each other, more preferably within about 200 micrometers of each other and most preferably within about 50 µm of each other. The laser die wavelengths are chosen to be separated in wavelength by at least twice the full width at half maximum of their spectra. For example, three dice, emitting at 440 nm, 450 nm and 460 nm, respectively, are transferred to a single carrier chip with a separation between die of less than 50 µm and die widths of less than 50 µm such that the total lateral separation, center to center, of the laser light emitted by the die is less than 200 µm. The closeness of the laser die allows for their emission to be easily coupled into the same optical train or fiber optic waveguide or projected in the far field into overlapping spots. In a sense, the lasers can be operated effectively as a single laser light source.

Such a configuration offers an advantage in that each individual laser light source could be operated independently to convey information using for example frequency and phase modulation of an RF signal superimposed on DC offset. The time-averaged proportion of light from the different sources could be adjusted by adjusting the DC offset of each signal. At a receiver, the signals from the individual laser sources would be demultiplexed by use of notch filters over individual photodetectors that filter out both the phosphor derived component of the white light spectra as well as the pump light from all but one of the laser sources. Such a configuration would offer an advantage over an LED based visible light communication (VLC) source in that bandwidth would scale easily with the number of laser emitters. Of course, a similar embodiment with similar advantages could be constructed from SLED emitters.

After the laser diode chip fabrication as described above, the laser diode can be mounted to a submount. In some examples the submount is comprised of AlN, SiC, BeO, diamond, or other materials such as metals, ceramics, or composites. The submount can be the common support member wherein the phosphor member of the CPoS would also be attached. Alternatively, the submount can be an intermediate submount intended to be mounted to the common support member wherein the phosphor material is attached. The submount member may be characterized by a width, length, and thickness. In an example wherein the submount is the common support member for the phosphor and the laser diode chip the submount would have a width and length ranging in dimension from about 0.5 mm to about 5 mm or to about 15 mm and a thickness ranging from about 150 µm to about 2 mm. In the example wherein the submount is an intermediate submount between the laser diode chip and the common support member it could be characterized by width and length ranging in dimension from about 0.5 mm to about 5 mm and the thickness may range from about 50 µm to about 500 µm. The laser diode is attached to the submount using a bonding process, a soldering process, a gluing process, or a combination thereof. In one embodiment the submount is electrically isolating and has metal bond pads deposited on top. The laser chip is mounted to at least one of those metal pads. The laser chip can be mounted in a p-side down or a p-side up configuration. After bonding the laser chip, wire bonds are formed from the chip to the submount such that the final chip on submount (CoS) is completed and ready for integration.

Figure 6:
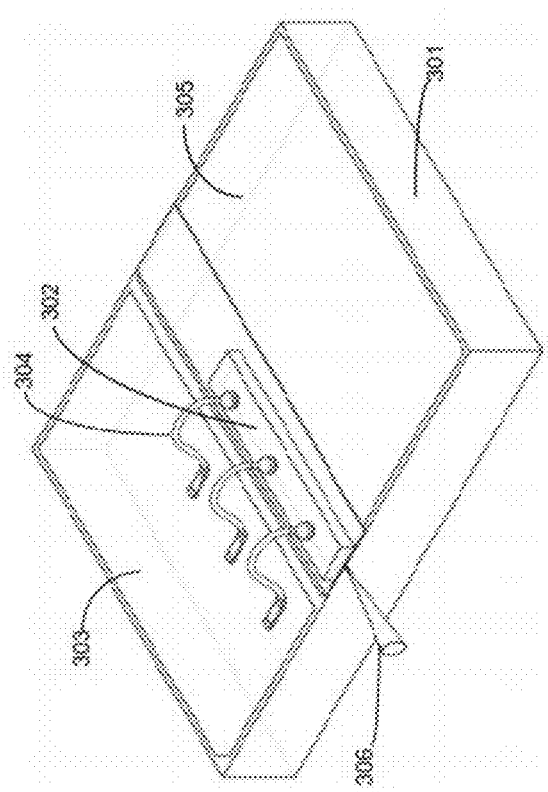
FIG. 6 is a schematic diagram illustrating a chip on submount (CoS) based on a conventional laser diode formed on gallium and nitrogen containing substrate technology according to an embodiment of the present invention.

A schematic diagram illustrating a CoS based on a conventional laser diode formed on gallium and nitrogen containing substrate technology according to this present invention is shown in FIG. 6. The CoS is comprised of submount material 301 configured to act as an intermediate material between a laser diode chip 302 and a final mounting surface. The submount is configured with electrodes 303 and 305 that may be formed with deposited metal layers such as Au. In one example, Ti/Pt/Au is used for the electrodes. Wirebonds 304 are configured to couple the electrical power from the electrodes 303 and 305 on the submount to the laser diode chip to generate a laser beam output 306 from the laser diode. The electrodes 303 and 305 are configured for an electrical connection to an external power source such as a laser driver, a current source, or a voltage source. Wirebonds 304 can be formed on the electrodes to couple electrical power to the laser diode device and activate the laser.

In another embodiment, the gallium and nitrogen containing laser diode fabrication includes an epitaxial release step to lift off the epitaxially grown gallium and nitrogen layers and prepare them for transferring to a carrier wafer which could include the submount after laser fabrication. The transfer step requires precise placement of the epitaxial layers on the carrier wafer to enable subsequent processing of the epitaxial layers into laser diode devices. The attachment process to the carrier wafer could include a wafer bonding step with a bond interface comprised of metal-metal, semiconductor-semiconductor, glass-glass, dielectric-dielectric, or a combination thereof.

In yet another preferred variation of this CPoS white light source, a process for lifting-off gallium and nitrogen containing epitaxial material and transferring it to the common support member can be used to attach the gallium and nitrogen containing laser epitaxial material to a submount member. In this embodiment, the gallium and nitrogen epitaxial material is released from the gallium and nitrogen containing substrate it was epitaxially grown on. As an example, the epitaxial material can be released using a photoelectrochemical (PEC) etching technique. It is then transferred to a submount material using techniques such as wafer bonding wherein a bond interface is formed. For example, the bond interface can be comprised of a Au—Au bond. The submount material preferably has a high thermal conductivity such as SiC, wherein the epitaxial material is subsequently processed to form a laser diode with a cavity member, front and back facets, and electrical contacts for injecting current. After laser fabrication is complete, a phosphor material is introduced onto the submount to form an integrated white light source. The phosphor material may have an intermediate material positioned between the submount and the phosphor. The intermediate material may be comprised of a thermally conductive material such as copper. The phosphor material can be attached to the submount using conventional die attaching techniques using solders such as AuSn solder, but can be other techniques such as SAC solders such as SAC305, lead containing solder, or indium, but can be others. In an alternative embodiment sintered Ag pastes or films can be used for the attach process at the interface. Sintered Ag attach material can be dispensed or deposited using standard processing equipment and cycle temperatures with the added benefit of higher thermal conductivity and improved electrical conductivity. For example, AuSn has a thermal conductivity of about 50 W/m-K and electrical conductivity of about 16 $\mu\Omega$cm whereas pressure-less sintered Ag can have a thermal conductivity of about 125 W/m-K and electrical conductivity of about 4 $\mu\Omega$cm, or pressured sintered Ag can have a thermal conductivity of about 250 W/m-K and electrical conductivity of about 2.5 $\mu\Omega$cm. Due to the extreme change in melt temperature from paste to sintered form, (260° C.-900° C.), processes can avoid thermal load restrictions on downstream processes, allowing completed devices to have very good and consistent bonds throughout. Optimizing the bond for the lowest thermal impedance is a key parameter for heat dissipation from the phosphor, which is critical to prevent phosphor degradation and thermal quenching of the phosphor material. The benefits of using this embodiment with lifted-off and transferred gallium and nitrogen containing material are the reduced cost, improved laser performance, and higher degree of flexibility for integration using this technology.

In this embodiment, gallium and nitrogen containing epitaxial layers are grown on a bulk gallium and nitrogen containing substrate. The epitaxial layer stack includes at least a sacrificial release layer and the laser diode device layers overlying the release layers. Following the growth of the epitaxial layers on the bulk gallium and nitrogen containing substrate, the semiconductor device layers are separated from the substrate by a selective wet etching process such as a PEC etch configured to selectively remove the sacrificial layers and enable release of the device layers to a carrier wafer. In one embodiment, a bonding material is deposited on the surface overlying the semiconductor device layers. A bonding material is also deposited either as a blanket coating or patterned on the carrier wafer. Standard lithographic processes are used to selectively mask the semiconductor device layers. The wafer is then subjected to an etch process such as dry etch or wet etch processes to define via structures that expose the sacrificial layers on the sidewall of the mesa structure. As used herein, the term mesa region or mesa is used to describe the patterned epitaxial material on the gallium and nitrogen containing substrate and prepared for transferring to the carrier wafer. The mesa region can be any shape or form including a rectangular shape, a square shape, a triangular shape, a circular shape, an elliptical shape, a polyhedron shape, or other shape. The term mesa shall not limit the scope of the present invention.

Following the definition of the mesa, a selective etch process is performed to fully or partially remove the sacrificial layers while leaving the semiconductor device layers intact. The resulting structure includes undercut mesas comprised of epitaxial device layers. The undercut mesas correspond to dice from which semiconductor devices will be formed on. In some embodiments a protective passivation layer can be employed on the sidewall of the mesa regions to prevent the device layers from being exposed to the selective etch when the etch selectivity is not perfect. In other embodiments a protective passivation is not needed because the device layers are not sensitive to the selective etch or measures are taken to prevent etching of sensitive layers such as shorting the anode and cathode. The undercut mesas corresponding to device dice are then transferred to the carrier wafer using a bonding technique wherein the bonding material overlying the semiconductor device layers is joined with the bonding material on the carrier wafer. The resulting structure is a carrier wafer comprising gallium and nitrogen containing epitaxial device layers overlying the bonding region.

In a preferred embodiment PEC etching is deployed as the selective etch to remove the a sacrificial layers. PEC is a photo-assisted wet etch technique that can be used to etch GaN and its alloys. The process involves an above-band-gap excitation source and an electrochemical cell formed by the semiconductor and the electrolyte solution. In this case, the exposed (Al,In,Ga)N material surface acts as the anode, while a metal pad deposited on the semiconductor acts as the cathode. The above-band-gap light source generates electron-hole pairs in the semiconductor. Electrons are extracted from the semiconductor via the cathode while holes diffuse to the surface of material to form an oxide. Since the diffusion of holes to the surface requires the band bending at the surface to favor a collection of holes, PEC etching typically works only for n-type material although some methods have been developed for etching p-type material. The oxide is then dissolved by the electrolyte resulting in wet etching of the semiconductor. Different types of electrolyte including HCl, KOH, and $HNO_3$ have been shown to be effective in PEC etching of GaN and its alloys. The etch selectivity and etch rate can be optimized by selecting a favorable electrolyte. It is also possible to generate an external bias between the semiconductor and the cathode to assist with the PEC etching process.

In one embodiment thermocompression bonding is used to transfer the gallium and nitrogen epitaxial semiconductor layers to the carrier wafer. In this embodiment thermocompression bonding involves bonding of the epitaxial semiconductor layers to the carrier wafer at elevated temperatures and pressures using a bonding media 408 disposed between the epitaxial layers and handle wafer. The bonding media 408 may be comprised of a number of different layers, but typically contain at least one layer (the bonding layer 408) that is composed of a relatively ductile material with a high surface diffusion rate. In many cases this material is comprised of Au, Al or Cu. The bonding media 408 may also include layers disposed between the bonding layer and the epitaxial materials or handle wafer that promote adhesion. For example an Au bonding layer on a Si wafer may result in diffusion of Si to the bonding interface, which would reduce the bonding strength. Inclusion of a diffusion barrier such as silicon oxide or nitride would limit this effect. Relatively thin layers of a second material may be applied on the top surface of the bonding layer in order to promote adhesion between the bonding layers disposed on the epitaxial material and handle. Some bonding layer materials of lower ductility than gold (e.g. Al, Cu etc.) or which are deposited in a way that results in a rough film (for example electrolytic deposition) may require planarization or reduction in roughness via chemical or mechanical polishing before bonding, and reactive metals may require special cleaning steps to remove oxides or organic materials that may interfere with bonding.

Gold-gold metallic bonding is used as an example in this work, although a wide variety of oxide bonds, polymer bonds, wax bonds, etc., are potentially suitable. Submicron alignment tolerances are possible using commercial available die bonding equipment. In another embodiment of the invention the bonding layers can be a variety of bonding pairs including metal-metal, oxide-oxide, soldering alloys, photoresists, polymers, wax, etc. Only epitaxial die which are in contact with a bond bad on the carrier wafer will bond. Sub-micron alignment tolerances are possible on commercially available die or flip chip bonders.

The carrier wafer can be chosen based on any number of criteria including but not limited to cost, thermal conductivity, thermal expansion coefficients, size, electrical conductivity, optical properties, and processing compatibility. The patterned epitaxy wafer, or donor, is prepared in such a way as to allow subsequent selective release of bonded epitaxy regions, here-in referred to as die. The patterned carrier wafer is prepared such that bond pads are arranged in order to enable the selective area bonding process. The bonding material can be a variety of media including but not limited to metals, polymers, waxes, and oxides. These wafers can be prepared by a variety of process flows, some embodiments of which are described below. In the first selective area bond step, the epitaxy wafer is aligned with the pre-patterned bonding pads on the carrier wafer and a combination of pressure, heat, and/or sonication is used to bond the mesas to the bonding pads.

In some embodiments of the invention the carrier wafer is another semiconductor material, a metallic material, or a ceramic material. Some potential candidates include silicon, gallium arsenide, sapphire, silicon carbide, diamond, gallium nitride, AlN, polycrystalline AlN, indium phosphide, germanium, quartz, copper, copper tungsten, gold, silver, aluminum, stainless steel, or steel.

In some embodiments, the carrier wafer is selected based on size and cost. For example, ingle crystal silicon wafers are available in diameters up to 300 mm or 12 inch, and are most cost effective. By transferring gallium and nitrogen epitaxial materials from 2" gallium and nitrogen containing bulk substrates to large silicon substrates of 150 mm, 200 mm, or 300 mm diameter the effective area of the semiconductor device wafer can be increases by factors of up to 36 or greater. This feature of this invention allows for high quality gallium and nitrogen containing semiconductor devices to be fabricated in mass volume leveraging the established infrastructure in silicon foundries.

In some embodiments of the invention, the carrier wafer material is chosen such that it has similar thermal expansion properties to group-III nitrides, high thermal conductivity, and is available as large area wafers compatible with standard semiconductor device fabrication processes. The carrier wafer is then processed with structures enabling it to also act as the submount for the semiconductor devices. Singulation of the carrier wafers into individual die can be accomplished either by sawing, cleaving, or a scribing and breaking process. By combining the functions of the carrier wafer and finished semiconductor device submount the number of components and operations needed to build a packaged device is reduced, thereby lowering the cost of the final semiconductor device significantly.

Figure 7:
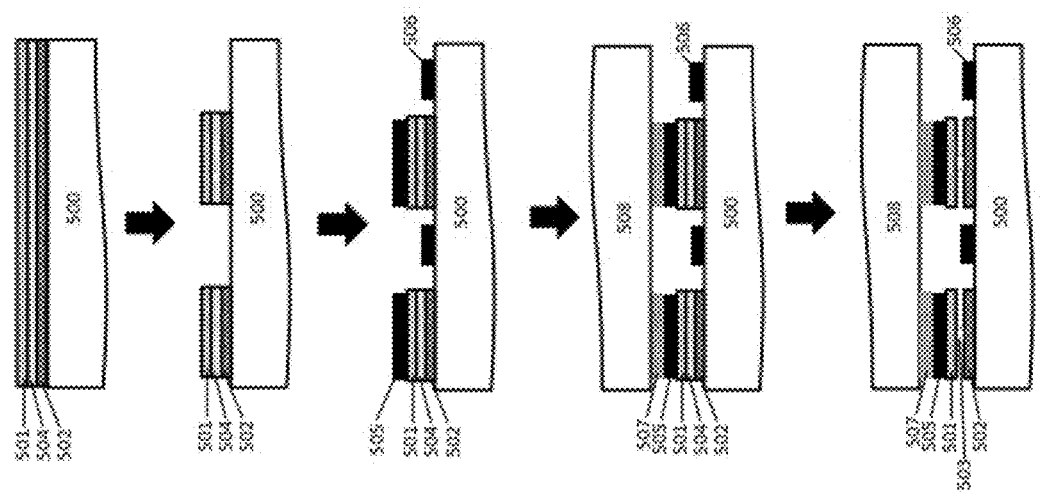
FIG. 7 is a schematic diagram illustrating a process comprised of first forming the bond between an epitaxial material formed on the gallium and nitrogen containing substrate and then subjecting a sacrificial release material to the PEC etch process to release the gallium and nitrogen containing substrate according to some embodiments of the present invention.

In one embodiment of this invention, the bonding of the semiconductor device epitaxial material to the carrier wafer process can be performed prior to the selective etching of the sacrificial region and subsequent release of the gallium and nitrogen containing substrate. FIG. 7 is a schematic illustration of a process comprised of first forming the bond between the gallium and nitrogen containing epitaxial material formed on the gallium and nitrogen containing substrate and then subjecting a sacrificial release material to the PEC etch process to release the gallium and nitrogen containing substrate. In this embodiment, an epitaxial material is deposited on the gallium and nitrogen containing substrate, such as a GaN substrate, through an epitaxial deposition process such as metal organic chemical vapor deposition (MOCVD), molecular beam epitaxy (MBE), or other. The epitaxial material includes at least a sacrificial release layer and a device layers. In some embodiments a buffer layer is grown on between the substrate surface region and the sacrificial release region. Referring to FIG. 7, substrate wafer 500 is overlaid by a buffer layer 502, a selectively etchable sacrificial layer 504 and a collection of device layers 501. The bond layer 505 is deposited along with a cathode metal 506 that will be used to facilitate the photoelectrochemical etch process for selectively removing the sacrificial layer 504.

In a preferred embodiment of this invention, the bonding process is performed after the selective etching of the sacrificial region. This embodiment offers several advantages. One advantage is easier access for the etchant to uniformly etch the sacrificial region across the semiconductor wafer comprising a bulk gallium and nitrogen containing substrate such as GaN and bulk gallium and nitrogen containing epitaxial device layers. A second advantage is the ability to perform multiple bond steps. In one example, the "etch-then-bond" process flow can be deployed where the mesas are retained on the substrate by controlling the etch process such that not all parts of the sacrificial layer is removed. Referring to FIG. 7, a substrate wafer 500 is overlaid by a buffer layer 502, a selectively etchable sacrificial layer 504 and a collection of device layers 501. A bond layer 505 is deposited along with a cathode metal 506 that will be used to facilitate the photoelectrochemical etch process for selectively removing the sacrificial layer 504. The selective etch process is carried out to the point where only a small fraction of the sacrificial layer 504 is remaining, such that multiple mesas or mesa regions are formed and retained on the substrate, but the unetched portions of the sacrificial layer 504 are easily broken during or after the mesas are bonded to a carrier wafer 508.

A critical challenge of the etch-then-bond embodiment is mechanically supporting the undercut epitaxial device layer mesa region from spatially shifting prior to the bonding step.

If the mesas shift the ability to accurately align and arrange them to the carrier wafer will be compromised, and hence the ability to manufacture with acceptable yields. This challenge mechanically fixing the mesa regions in place prior to bonding can be achieved in several ways. In a preferred embodiment anchor regions 503 are used to mechanically support the mesas to the gallium and nitrogen containing substrate prior to the bonding step wherein they are releases from the gallium and nitrogen containing substrate 500 and transferred to the carrier wafer 508.

Other than typical GaN based laser devices, undercut AlInGaAsP based laser devices can be produced in a manner similar to GaN based laser diodes described in this invention. There are a number of wet etches that etch some AlInGaAsP alloys selectively. In one embodiment, an AlGaAs or AlGaP sacrificial layer could be grown clad with GaAs etch stop layers. When the composition of $Al_xGa_{1-x}As$ and $Al_xGa_{1-x}P$ is high (x>0.5) AlGaAs can be etched with almost complete selectivity (i.e. etch rate of AlGaAs >$10^6$ times that of GaAs) when etched with HF. InGaP and AlInP with high InP and AlP compositions can be etched with HCl selectively relative to GaAs. GaAs can be etched selectively relative to AlGaAs using $C_6H_8O_7$:$H_2O_2$:$H_2O$. There are a number of other combinations of sacrificial layer, etch-stop layer and etch chemistry which are widely known to those knowledgeable in the art of micromachining AlInGaAsP alloys.

In an embodiment, the AlInGaAsP device layers are exposed to the etch solution which is chosen along with the sacrificial layer composition such that only the sacrificial layers experience significant etching. The active region can be prevented from etching during the compositionally selective etch using an etch resistant protective layer, such as like silicon dioxide, silicon nitride, metals or photoresist among others, on the sidewall. This step is followed by the deposition of a protective insulating layer on the mesa sidewalls, which serves to block etching of the active region during the later sacrificial region undercut etching step. A second top down etch is then performed to expose the sacrificial layers and bonding metal is deposited. With the sacrificial region exposed a compositionally selective etch is used to undercut the mesas. At this point, the selective area bonding process is used to continue fabricating devices. The device layers should be separated from the sacrificial layers by a layer of material that is resistant to etching. This is to prevent etching into the device layers after partially removing the sacrificial layers.

In a preferred embodiment, the semiconductor device epitaxy material with the underlying sacrificial region is fabricated into a dense array of mesas on the gallium and nitrogen containing bulk substrate with the overlying semiconductor device layers. The mesas are formed using a patterning and a wet or dry etching process wherein the patterning includes a lithography step to define the size and pitch of the mesa regions. Dry etching techniques such as reactive ion etching, inductively coupled plasma etching, or chemical assisted ion beam etching are candidate methods. Alternatively, a wet etch can be used. The etch is configured to terminate at or below a sacrificial region below the device layers. This is followed by a selective etch process such as PEC to fully or partially etch the exposed sacrificial region such that the mesas are undercut. This undercut mesa pattern pitch will be referred to as the 'first pitch'. The first pitch is often a design width that is suitable for fabricating each of the epitaxial regions on the substrate, while not large enough for the desired completed semiconductor device design, which often desire larger non-active regions or regions for contacts and the like. For example, these mesas would have a first pitch ranging from about 5 µm to about 500 µm or to about 5000 µm. Each of these mesas is a 'die'.

In a preferred embodiment, these dice are transferred to a carrier wafer at a second pitch using a selective bonding process such that the second pitch on the carrier wafer is greater than the first pitch on the gallium and nitrogen containing substrate. In this embodiment the dice are on an expanded pitch for so called "die expansion". In an example, the second pitch is configured with the dice to allow each die with a portion of the carrier wafer to be a semiconductor device, including contacts and other components. For example, the second pitch would be about 50 µm to about 1000 µm or to about 5000 µm, but could be as large at about 3-10 mm or greater in the case where a large semiconductor device chip is required for the application. The larger second pitch could enable easier mechanical handling without the expense of the costly gallium and nitrogen containing substrate and epitaxial material, allow the real estate for additional features to be added to the semiconductor device chip such as bond pads that do not require the costly gallium and nitrogen containing substrate and epitaxial material, and/or allow a smaller gallium and nitrogen containing epitaxial wafer containing epitaxial layers to populate a much larger carrier wafer for subsequent processing for reduced processing cost. For example, a 4 to 1 die expansion ratio would reduce the density of the gallium and nitrogen containing material by a factor of 4, and hence populate an area on the carrier wafer 4 times larger than the gallium and nitrogen containing substrate. This would be equivalent to turning a 2" gallium and nitrogen substrate into a 4" carrier wafer. In particular, the present invention increases utilization of substrate wafers and epitaxy material through a selective area bonding process to transfer individual die of epitaxy material to a carrier wafer in such a way that the die pitch is increased on the carrier wafer relative to the original epitaxy wafer. The arrangement of epitaxy material allows device components which do not require the presence of the expensive gallium and nitrogen containing substrate and overlying epitaxy material often fabricated on a gallium and nitrogen containing substrate to be fabricated on the lower cost carrier wafer, allowing for more efficient utilization of the gallium and nitrogen containing substrate and overlying epitaxy material.

Figure 8:
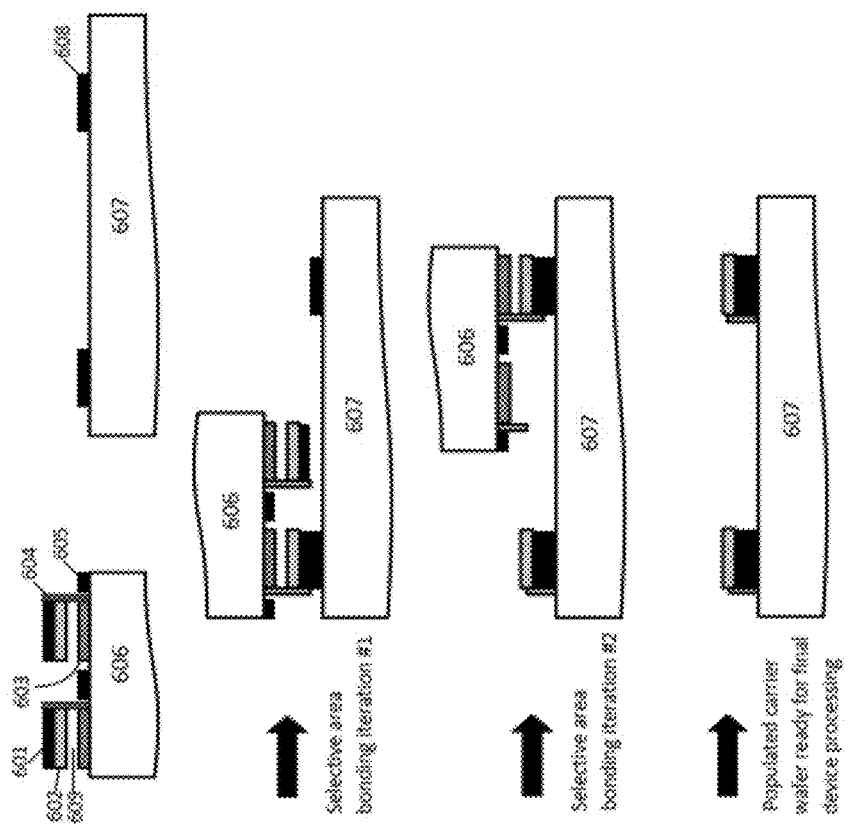
FIG. 8 is a schematic representation of the die expansion process with selective area bonding according to some embodiments of the present invention.

FIG. 8 is a schematic representation of the die expansion process with selective area bonding according to the present invention. A device wafer is prepared for bonding in accordance with an embodiment of this invention. The device wafer consists of a substrate 606, buffer layers 603, a fully removed sacrificial layer 609, device layers 602, bonding media 601, cathode metal 605, and an anchor material 604. The sacrificial layer 609 is removed in the PEC etch with the anchor material 604 is retained. The mesa regions formed in the gallium and nitrogen containing epitaxial wafer form dice of epitaxial material and release layers defined through processing. Individual epitaxial material die are formed at first pitch. A carrier wafer is prepared consisting of the carrier wafer substrate 607 and bond pads 608 at second pitch. The substrate 606 is aligned to the carrier wafer 607 such that a subset of the mesa on the gallium and nitrogen containing substrate 606 with a first pitch aligns with a subset of bond pads 608 on the carrier wafer 607 at a second pitch. Since the first pitch is greater than the second pitch and the mesas will include device die, the basis for die expansion is established. The bonding process is carried out and upon separation of the substrate from the carrier wafer 607 the subset of mesas on the substrate 606 are selectively transferred to the carrier wafer 607. The process is then repeated with a second set of mesas and bond pads 608 on the carrier wafer 607 until the carrier wafer 607 is populated fully by epitaxial mesas. The gallium and nitrogen containing epitaxy substrate 201 can now optionally be prepared for reuse.

In the example depicted in FIG. 8, one quarter of the epitaxial dice on the epitaxy wafer 606 are transferred in this first selective bond step, leaving three quarters on the epitaxy wafer 606. The selective area bonding step is then repeated to transfer the second quarter, third quarter, and fourth quarter of the epitaxial die to the patterned carrier wafer 607. This selective area bond may be repeated any number of times and is not limited to the four steps depicted in FIG. 8. The result is an array of epitaxial die on the carrier wafer 607 with a wider die pitch than the original die pitch on the epitaxy wafer 606. The die pitch on the epitaxial wafer 606 will be referred to as pitch 1, and the die pitch on the carrier wafer 607 will be referred to as pitch 2, where pitch 2 is greater than pitch 1.

In one embodiment the bonding between the carrier wafer and the gallium and nitrogen containing substrate with epitaxial layers is performed between bonding layers that have been applied to the carrier and the gallium and nitrogen containing substrate with epitaxial layers. The bonding layers can be a variety of bonding pairs including metal-metal, oxide-oxide, soldering alloys, photoresists, polymers, wax, etc. Only epitaxial dice which are in contact with a bond bad 608 on the carrier wafer 607 will bond. Sub-micron alignment tolerances are possible on commercial die bonders. The epitaxy wafer 606 is then pulled away, breaking the epitaxy material at a weakened epitaxial release layer 609 such that the desired epitaxial layers remain on the carrier wafer 607. Herein, a 'selective area bonding step' is defined as a single iteration of this process.

In one embodiment, the carrier wafer 607 is patterned in such a way that only selected mesas come in contact with the metallic bond pads 608 on the carrier wafer 607. When the epitaxy substrate 606 is pulled away the bonded mesas break off at the weakened sacrificial region, while the un-bonded mesas remain attached to the epitaxy substrate 606. This selective area bonding process can then be repeated to transfer the remaining mesas in the desired configuration. This process can be repeated through any number of iterations and is not limited to the two iterations depicted in FIG. 8. The carrier wafer can be of any size, including but not limited to about 2 inch, 3 inch, 4 inch, 6 inch, 8 inch, and 12 inch. After all desired mesas have been transferred, a second bandgap selective PEC etching can be optionally used to remove any remaining sacrificial region material to yield smooth surfaces. At this point standard semiconductor device processes can be carried out on the carrier wafer. Another embodiment of the invention incorporates the fabrication of device components on the dense epitaxy wafers before the selective area bonding steps.

In an example, the present invention provides a method for increasing the number of gallium and nitrogen containing semiconductor devices which can be fabricated from a given epitaxial surface area; where the gallium and nitrogen containing epitaxial layers overlay gallium and nitrogen containing substrates. The gallium and nitrogen containing epitaxial material is patterned into die with a first die pitch; the die from the gallium and nitrogen containing epitaxial material with a first pitch is transferred to a carrier wafer to form a second die pitch on the carrier wafer; the second die pitch is larger than the first die pitch.

Once the laser diode epitaxial structure has been transferred to the carrier wafer as described in this invention, wafer level processing can be used to fabricate the dice into laser diode devices. The wafer process steps may be similar to those described in this specification for more conventional laser diodes. For example, in many embodiments the bonding media and dice will have a total thickness of less than about 7 μm, making it possible to use standard photoresist, photoresist dispensing technology and contact and projection lithography tools and techniques to pattern the wafers. The aspect ratios of the features are compatible with deposition of thin films, such as metal and dielectric layers, using evaporators, sputter and CVD deposition tools.

The laser diode device may have laser stripe region formed in the transferred gallium and nitrogen containing epitaxial layers. In the case where the laser is formed on a polar c-plane, the laser diode cavity can be aligned in the m-direction with cleaved or etched mirrors. Alternatively, in the case where the laser is formed on a semipolar plane, the laser diode cavity can be aligned in a projection of a c-direction. The laser strip region has a first end and a second end and is formed on a gallium and nitrogen containing substrate having a pair of cleaved mirror structures, which face each other. The first cleaved facet includes a reflective coating and the second cleaved facet includes no coating, an antireflective coating, or exposes gallium and nitrogen containing material. The first cleaved facet is substantially parallel with the second cleaved facet. The first and second cleaved facets are provided by a scribing and breaking process according to an embodiment or alternatively by etching techniques using etching technologies such as reactive ion etching (ME), inductively coupled plasma etching (ICP), or chemical assisted ion beam etching (CAIBE), or other method. Typical gases used in the etching process may include Cl and/or BCl3. The first and second mirror surfaces each include a reflective coating. The coating is selected from silicon dioxide, hafnia, and titania, tantalum pentoxide, zirconia, including combinations, and the like. Depending upon the design, the mirror surfaces can also include an anti-reflective coating.

In a specific embodiment, the method of facet formation includes subjecting the substrates to a laser for pattern formation. In a preferred embodiment, the pattern is configured for the formation of a pair of facets for a ridge lasers. In a preferred embodiment, the pair of facets faces each other and is in parallel alignment with each other. In a preferred embodiment, the method uses a UV (355 nm) laser to scribe the laser bars. In a specific embodiment, the laser is configured on a system, which allows for accurate scribe lines configured in a different patterns and profiles. In some embodiments, the laser scribing can be performed on the back-side, front-side, or both depending upon the application. Of course, there can be other variations, modifications, and alternatives.

It is well known that etch techniques such as chemical assisted ion beam etching (CAIBE), inductively coupled plasma (ICP) etching, or reactive ion etching (RIE) can result in smooth and vertical etched sidewall regions, which could serve as facets in etched facet laser diodes. In the etched facet process a masking layer is deposited and patterned on the surface of the wafer. The etch mask layer could be comprised of dielectrics such as silicon dioxide ($SiO_2$), silicon nitride ($Si_xN_y$), a combination thereof or other dielectric materials. Further, the mask layer could be comprised of metal layers such as Ni or Cr, but could be comprised of metal combination stacks or stacks comprising metal and dielectrics. In another approach, photoresist masks can be used either alone or in combination with dielectrics and/or metals. The etch mask layer is patterned using conventional photolithography and etch steps. The alignment lithography could be performed with a contact aligner or stepper aligner. Such lithographically defined mirrors provide a high level of control to the design engineer. After patterning of the photoresist mask on top of the etch mask is complete, the patterns in then transferred to the etch mask using a wet etch or dry etch technique. Finally, the facet pattern is then etched into the wafer using a dry etching technique selected from CAIBE, ICP, RIE and/or other techniques. The etched facet surfaces must be highly vertical of between about 87 and about 93 degrees or between about 89 and about 91 degrees from the surface plane of the wafer. The etched facet surface region must be very smooth with root mean square roughness values of less than about 50 nm, 20 nm, 5 nm, or 1 nm. Lastly, the etched must be substantially free from damage, which could act as non-radiative recombination centers and hence reduce the COMD threshold. CAIBE is known to provide very smooth and low damage sidewalls due to the chemical nature of the etch, while it can provide highly vertical etches due to the ability to tilt the wafer stage to compensate for any inherent angle in etch.

In a specific embodiment, the plurality of donor epitaxial wafers may be comprised of device layers emitting at substantially different wavelengths. For example, a blue device emitting at around 450 nm may be bonded adjacent to both a green device emitting at around 530 nm and a red device made from AlInGaAsP layers emitting at around 630 nm. Such a configuration would result in a controllable light source emitting combinations or red, green and blue light that could be used for illumination or the generation of images.

In alternative embodiments, structures comprised of gallium and arsenic materials emitting in the 700 nm to 1100 nm range or structures comprised of indium and phosphorous materials emitting in the 1100 nm to 2000 nm range are transferred to the same carrier as the gallium and nitrogen containing structures emitting in the visible wavelength range. Such a configuration resulting in a controllable light source emitting in both the visible and IR wavelength ranges would be well suited for the present dual band emitting illumination source invention disclosed here.

In an embodiment, the device layers include a superluminescent light emitting diode or SLED. A SLED is in many ways similar to an edge emitting laser diode; however the emitting facet of the device is designed so as to have a very low reflectivity. A SLED is similar to a laser diode as it is based on an electrically driven junction that when injected with current becomes optically active and generates amplified spontaneous emission (ASE) and gain over a wide range of wavelengths. When the optical output becomes dominated by ASE there is a knee in the light output versus current (LI) characteristic wherein the unit of light output becomes drastically larger per unit of injected current. This knee in the LI curve resembles the threshold of a laser diode, but is much softer. A SLED would have a layer structure engineered to have a light emitting layer or layers clad above and below with material of lower optical index such that a laterally guided optical mode can be formed. The SLED would also be fabricated with features providing lateral optical confinement. These lateral confinement features may consist of an etched ridge, with air, vacuum, metal or dielectric material surrounding the ridge and providing a low optical-index cladding. The lateral confinement feature may also be provided by shaping the electrical contacts such that injected current is confined to a finite region in the device. In such a "gain guided" structure, dispersion in the optical index of the light emitting layer with injected carrier density provides the optical-index contrast needed to provide lateral confinement of the optical mode. The emission spectral width is typically substantially wider (>5 nm) than that of a laser diode and offer advantages with respect to reduced image distortion in displays, increased eye safety, and enhanced capability in measurement and spectroscopy applications.

The laser stripe is characterized by a length and width. The length ranges from about 50 µm to about 3000 µm, but is preferably between about 10 µm and about 400 µm, between about 400 µm and about 800 µm, or about 800 µm and about 1600 µm, but could be others such as greater than 1600 µm. The stripe also has a width ranging from about 0.5 µm to about 50 µm, but is preferably between about 0.8 µm and about 2.5 µm for single lateral mode operation or between about 2.5 µm and about 80 µm for multi-lateral mode operation, but can be other dimensions. In a specific embodiment, the present device has a width ranging from about 0.5 µm to about 1.5 µm, a width ranging from about 1.5 µm to about 3.0 µm, a width ranging from about 3.0 µm to about 360 µm, and others. In a specific embodiment, the width is substantially constant in dimension, although there may be slight variations. The width and length are often formed using a masking and etching process, which are commonly used in the art.

The laser stripe is provided by an etching process selected from dry etching or wet etching. The device also has an overlying dielectric region, which exposes a p-type contact region. Overlying the contact region is a contact material, which may be metal or a conductive oxide or a combination thereof. The p-type electrical contact may be deposited by thermal evaporation, electron beam evaporation, electroplating, sputtering, or another suitable technique. Overlying the polished region of the substrate is a second contact material, which may be metal or a conductive oxide or a combination thereof and which includes the n-type electrical contact. The n-type electrical contact may be deposited by thermal evaporation, electron beam evaporation, electroplating, sputtering, or another suitable technique.

Figure 9:
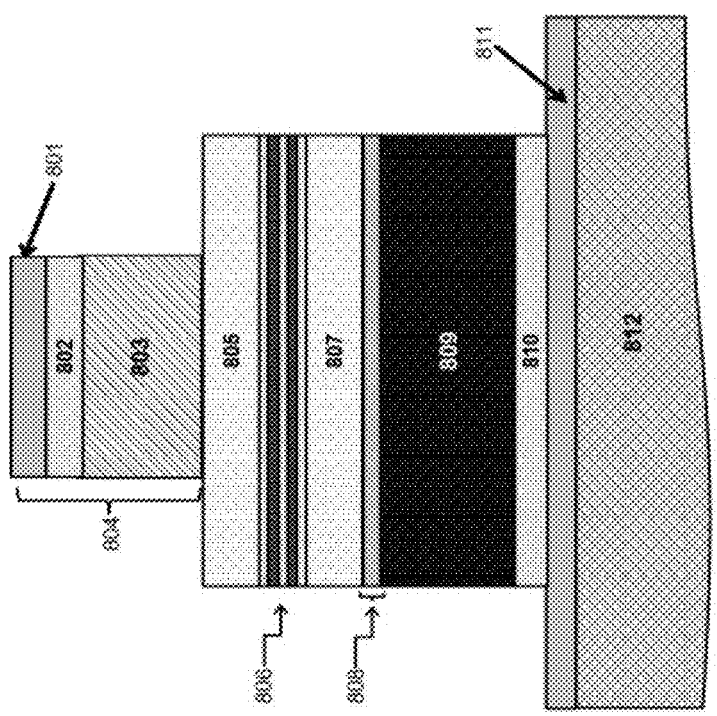
FIG. 9 is an example of a processed laser diode cross-section according to an embodiment of the present invention.

An example of a processed laser diode cross-section according to one embodiment of the present invention is shown in FIG. 9. In this example an n-contact 801 is formed on top of n-type gallium and nitrogen contact layer 802 and n-type cladding layer 803 that have been etched to form a ridge waveguide 804. The n-type cladding layer 803 overlies an n-side waveguide layer or separate confinement heterostructure (SCH) layer 805 and the n-side SCH overlies an active region 806 that contains light emitting layers such as quantum wells. The active region overlies an optional p-side SCH layer 807 and an electron blocking layer (EBL) 808. The optional p-side SCH layer overlies the p-type cladding 809 and a p-contact layer 810. Underlying the p-contact layer 810 is a metal stack 811 that contains the p-type contact and bond metal used to attach the transferred gallium and nitrogen containing epitaxial layers to the carrier wafer 812.

Once the laser diodes have been fully processed within the gallium and nitrogen containing layers that have been transferred to the carrier wafer, the carrier wafer must be diced. Several techniques can be used to dice the carrier wafer and the optimal process will depend on the material selection for the carrier wafer. As an example, for Si, InP, or GaAs carrier wafers that cleave very easily, a cleaving process can be used wherein a scribing and breaking process using conventional diamond scribe techniques may be most suitable. For harder materials such as GaN, AlN, SiC, sapphire, or others where cleaving becomes more difficult a laser scribing and breaking technique may be most suitable. In other embodiments a sawing process may be the most optimal way to dice the carrier wafer into individual laser chips. In a sawing process a rapidly rotating blade with hard cutting surfaces like diamond are used, typically in conjunction with spraying water to cool and lubricate the blade. Example saw tools used to commonly dice wafers include Disco saws and Accretech saws.

Figure 10:
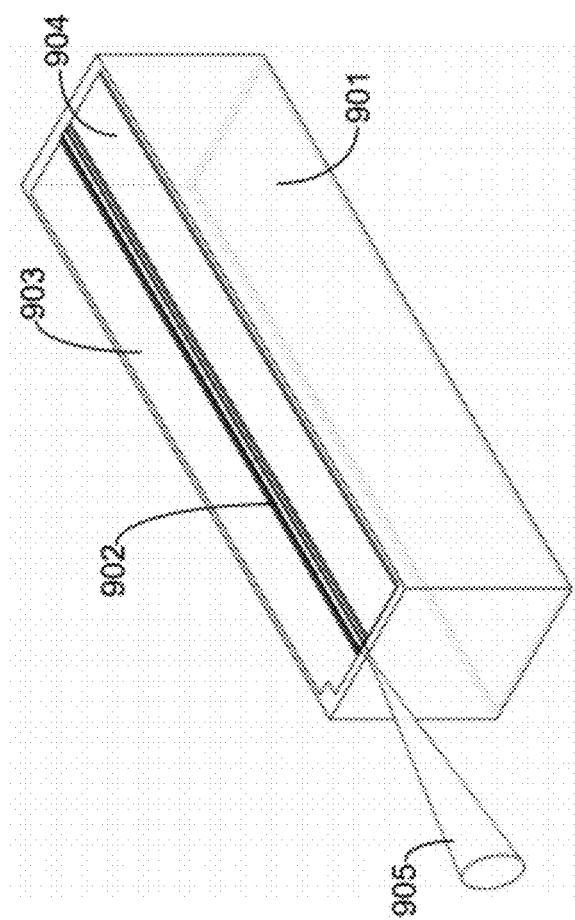
FIG. 10 is a schematic diagram illustrating a CoS based on lifted off and transferred epitaxial gallium and nitrogen containing layers according to an embodiment of this present invention.

A schematic diagram illustrating a CoS based on lifted off and transferred epitaxial gallium and nitrogen containing layers according to this present invention is shown in FIG. 10. The CoS is comprised of submount material 901 configured from the carrier wafer with the transferred epitaxial material with a laser diode configured within the epitaxy 902. Electrodes 903 and 904 are electrically coupled to the n-side and the p-side of the laser diode device and configured to transmit power from an external source to the laser diode to generate a laser beam output 905 from the laser diode. The electrodes are configured for an electrical connection to an external power source such as a laser driver, a current source, or a voltage source. Wirebonds can be formed on the electrodes to couple the power to the laser diode device. This integrated CoS device with transferred epitaxial material offers advantages over the conventional configuration such as size, cost, and performance due to the low thermal impedance.

Further process and device description for this embodiment describing laser diodes formed in gallium and nitrogen containing epitaxial layers that have been transferred from the native gallium and nitrogen containing substrates are described in U.S. patent application Ser. No. 14/312,427 and U.S. Patent Publication No. 2015/0140710, which are incorporated by reference herein. As an example, this technology of GaN transfer can enable lower cost, higher performance, and a more highly manufacturable process flow.

The present invention combines gallium and nitrogen containing laser with wavelength converter members emitting the in the visible spectrum to comprise a laser based white light source. In a preferred embodiment, the visible wavelength converter member is comprised of a phosphor member, wherein careful phosphor selection is a key consideration within the laser based white light source. The phosphor must be able to withstand the extreme optical intensity and associated heating induced by the laser excitation spot without severe degradation. Important characteristics to consider for phosphor selection include:

- A high conversion efficiency of optical excitation power to white light lumens. In the example of a blue laser diode exciting a yellow phosphor, a conversion efficiency of over 150 lumens per optical watt, or over 200 lumens per optical watt, or over 300 lumens per optical watt is desired.
- A high optical damage threshold capable of withstanding 1-20 W of laser power in a spot comprising a diameter of 1 mm, 500 µm, 200 µm, 100 µm, or even 50 µm.
- High thermal damage threshold capable of withstanding temperatures of over 150° C., over 200° C., or over 300° C. without decomposition.
- A low thermal quenching characteristic such that the phosphor remains efficient as it reaches temperatures of over 150° C., 200° C., or 250° C.
- A high thermal conductivity to dissipate the heat and regulate the temperature. Thermal conductivities of greater than 3 W/m-K, greater than 5 W/m-K, greater than 10 W/m-K, and even greater than 15 W/m-K are desirable.
- A proper phosphor emission color for the application.
- A suitable porosity characteristic that leads to the desired scattering of the coherent excitation without unacceptable reduction in thermal conductivity or optical efficiency.
- A proper form factor for the application. Such form factors include, but are not limited to blocks, plates, disks, spheres, cylinders, rods, or a similar geometrical element. Proper choice will be dependent on whether phosphor is operated in transmissive or reflective mode and on the absorption length of the excitation light in the phosphor.
- A surface condition optimized for the application. In an example, the phosphor surfaces can be intentionally roughened for improved light extraction.

In a preferred embodiment, the laser based white light source contains a blue laser diode operating in the 420 nm to 480 nm wavelength range combined with a phosphor material providing a yellowish emission in the 530 nm to 600 nm range such that when mixed with the blue emission of the laser diode a white light is produced. For example, to meet a white color point on the black body line the energy of the combined spectrum may be comprised of about 30% from the blue laser emission and about 70% from the yellow phosphor emission, or about 15% from the blue laser emission and about 85% from the yellow phosphor emission. In other embodiments phosphors with red, green, yellow, and even blue emission can be used in combination with the laser diode excitation sources in the violet, ultra-violet, or blue wavelength range to produce a white light with color mixing. Although such white light systems may be more complicated due to the use of more than one phosphor member, advantages such as improved color rendering could be achieved.

In an example, the light emitted from the laser diodes is partially converted by the phosphor element. In an example, the partially converted light emitted generated in the phosphor element results in a color point, which is white in appearance. In an example, the color point of the white light is located on the Planckian blackbody locus of points. In an example, the color point of the white light is located within du'v' of less than 0.010 of the Planckian blackbody locus of points. In an example, the color point of the white light is preferably located within du'v' of less than 0.03 of the Planckian blackbody locus of points.

The phosphor material can be operated in a transmissive mode, a reflective mode, or a combination of a transmissive mode and reflective mode, or other modes. The phosphor material is characterized by a conversion efficiency, a resistance to thermal damage, a resistance to optical damage, a thermal quenching characteristic, a porosity to scatter excitation light, and a thermal conductivity. In a preferred embodiment the phosphor material is comprised of a yellow emitting YAG material doped with Ce with a conversion efficiency of greater than 100 lumens per optical watt, greater than 200 lumens per optical watt, or greater than 300 lumens per optical watt, and can be a polycrystalline ceramic material or a single crystal material.

In some embodiments of the present invention, the environment of the phosphor can be independently tailored to result in high efficiency with little or no added cost. Phosphor optimization for laser diode excitation can include high transparency, scattering or non-scattering characteristics, and use of ceramic phosphor plates. Decreased temperature sensitivity can be determined by doping levels. A reflector can be added to the backside of a ceramic phosphor, reducing loss. The phosphor can be shaped to increase in-coupling, increase out-coupling, and/or reduce back reflections. Surface roughening is a well-known means to increase extraction of light from a solid material. Coatings, mirrors, or filters can be added to the phosphors to reduce the amount of light exiting the non-primary emission surfaces, to promote more efficient light exit through the primary emission surface, and to promote more efficient in-coupling of the laser excitation light. Of course, there can be additional variations, modifications, and alternatives.

In some embodiments, certain types of phosphors will be best suited in this demanding application with a laser excitation source. As an example, ceramic yttrium aluminum garnets (YAG) doped with $Ce^{3+}$ ions, or YAG based phosphors can be ideal candidates. They are doped with species such as Ce to achieve the proper emission color and are often comprised of a porosity characteristic to scatter the excitation source light, and nicely break up the coherence in laser excitation. As a result of its cubic crystal structure the YAG:Ce can be prepared as a highly transparent single crystal as well as a polycrystalline bulk material. The degree of transparency and the luminescence are depending on the stoichiometric composition, the content of dopant, and entire processing and sintering route. The transparency and degree of scattering centers can be optimized for a homogenous mixture of blue and yellow light. The YAG:Ce can be configured to emit a green emission. In some embodiments the YAG can be doped with Eu to emit a red emission. In some embodiments the phosphor peak emission wavelength is about 525 nm, about 540 nm, about 660 nm, or at a wavelength in between these peak wavelengths.

In a preferred embodiment according to this invention, the white light source is configured with a ceramic polycrystalline YAG:Ce phosphors comprising an optical conversion efficiency of greater than 100 lumens per optical excitation watt, of greater than 200 lumens per optical excitation watt, or even greater than 300 lumens per optical excitation watt. Additionally, the ceramic YAG:Ce phosphors is characterized by a temperature quenching characteristics above 150° C., above 200° C., or above 250° C. and a high thermal conductivity of 5-10 W/m-K to effectively dissipate heat to a heat sink member and keep the phosphor at an operable temperature.

In another preferred embodiment according to this invention, the white light source is configured with a single crystal phosphor (SCP) such as YAG:Ce. In one example the Ce:$Y_3Al_5O_{12}$ SCP can be grown by the Czochralski technique. In this embodiment according the present invention the SCP based on YAG:Ce is characterized by an optical conversion efficiency of greater than 100 lumens per optical excitation watt, of greater than 200 lumens per optical excitation watt, or even greater than 300 lumens per optical excitation watt. Additionally, the single crystal YAG:Ce phosphors is characterized by a temperature quenching characteristics above 150° C., above 200° C., or above 300° C. and a high thermal conductivity of 8-20 W/m-K to effectively dissipate heat to a heat sink member and keep the phosphor at an operable temperature. In addition to the high thermal conductivity, high thermal quenching threshold, and high conversion efficiency, the ability to shape the phosphors into tiny forms that can act as ideal "point" sources when excited with a laser is an attractive feature.

In some embodiments the YAG:Ce can be configured to emit a yellow emission. In alternative or the same embodiments a YAG:Ce can be configured to emit a green emission.

In yet alternative or the same embodiments the YAG can be doped with Eu to emit a red emission. In some embodiments a LuAG is configured for emission. In alternative embodiments, silicon nitrides or aluminum-oxi-nitrides can be used as the crystal host materials for red, green, yellow, or blue emissions. In some embodiments the phosphor peak emission wavelength is about 525 nm, about 540 nm, about 660 nm, or at a wavelength in between these peak wavelengths.

In an alternative embodiment, a powdered single crystal or ceramic phosphor such as a yellow phosphor or green phosphor is included. The powdered phosphor can be dispensed on a transparent member for a transmissive mode operation or on a solid member with a reflective layer on the back surface of the phosphor or between the phosphor and the solid member to operate in a reflective mode. The phosphor powder may be held together in a solid structure using a binder material wherein the binder material is preferable in inorganic material with a high optical damage threshold and a favorable thermal conductivity. The phosphor power may be comprised of colored phosphors and configured to emit a white light when excited by and combined with the blue laser beam or excited by a violet laser beam. The powdered phosphors could be comprised of YAG, LuAG, or other types of phosphors. In some embodiments the phosphor peak emission wavelength is about 525 nm, about 540 nm, about 660 nm, or at a wavelength in between these peak wavelengths.

In one embodiment of the present invention the phosphor material contains a yttrium aluminum garnet host material and a rare earth doping element, and others. In an example, the wavelength conversion element is a phosphor which contains a rare earth doping element, selected from one of Ce, Nd, Er, Yb, Ho, Tm, Dy and Sm, combinations thereof, and the like. In an example, the phosphor material is a high-density phosphor element. In an example, the high-density phosphor element has a density greater than 90% of pure host crystal. Cerium (III)-doped YAG (YAG:$Ce^{3+}$, or $Y_3Al_5O_{12}$:$Ce^{3+}$) can be used wherein the phosphor absorbs the light from the blue laser diode and emits in a broad range from greenish to reddish, with most of output in yellow. This yellow emission combined with the remaining blue emission gives the "white" light, which can be adjusted to color temperature as warm (yellowish) or cold (bluish) white. The yellow emission of the $Ce^{3+}$:YAG can be tuned by substituting the cerium with other rare earth elements such as terbium and gadolinium and can even be further adjusted by substituting some or all of the aluminum in the YAG with gallium. In some embodiments the phosphor peak emission wavelength is about 525 nm, about 540 nm, about 660 nm, or at a wavelength in between these peak wavelengths.

In alternative examples, various phosphors can be applied to this invention, which include, but are not limited to organic dyes, conjugated polymers, semiconductors such as AlInGaP or InGaN, yttrium aluminum garnets (YAGs) doped with $Ce^{3+}$ ions $(Y_{1-a}Gd_a)_3(Al_{1-b}Ga_b)_5O_{12}$:$Ce^{3+}$, $SrGa_2S_4$:$Eu^{2+}$, SrS:$Eu^{2+}$, terbium aluminum based garnets (TAGs) ($Tb_3Al_5O_5$), colloidal quantum dot thin films containing CdTe, ZnS, ZnSe, ZnTe, CdSe, or CdTe.

In further alternative examples, some rare-earth doped SiAlONs can serve as phosphors. Europium(II)-doped β-SiAlON absorbs in ultraviolet and visible light spectrum and emits intense broadband visible emission. Its luminance and color does not change significantly with temperature, due to the temperature-stable crystal structure. In an alternative example, green and yellow SiAlON phosphor and a red $CaAlSiN_3$-based (CASN) phosphor may be used.

In yet a further example, white light sources can be made by combining near ultraviolet emitting laser diodes with a mixture of high efficiency europium based red and blue emitting phosphors plus green emitting copper and aluminum doped zinc sulfide (ZnS:Cu,Al).

In an example, a phosphor or phosphor blend can be selected from a of (Y, Gd, Tb, Sc, Lu, La)$_3$(Al, Ga, In)$_5$O$_{12}$: Ce$^{3+}$, SrGa$_2$S$_4$:Eu$^{2+}$, SrS:Eu$^{2+}$, and colloidal quantum dot thin films comprising CdTe, ZnS, ZnSe, ZnTe, CdSe, or CdTe. In an example, a phosphor is capable of emitting substantially red light, wherein the phosphor is selected from a of the group consisting of (Gd,Y,Lu,La)$_2$O$_3$:Eu$^{3+}$, Bi$^{3+}$; (Gd,Y,Lu,La)$_2$O$_2$S:Eu$^{3+}$, Bi$^{3+}$; (Gd,Y,Lu,La)VO$_4$: Eu$^{3+}$, Bi$^{3+}$; Y$_2$(O,S)$_3$: Eu$^{3+}$; Ca$_{1-x}$Mo$_{1-y}$Si$_y$O$_4$: where $0.05<x<0.5$, $0<y<0.1$; (Li,Na,K)$_5$Eu(W,Mo)O$_4$; (Ca,Sr)S: Eu$^{2+}$; SrY$_2$S$_4$:Eu$^{2+}$; CaLa$_2$S$_4$:Ce$^{3+}$; (Ca,Sr)S:Eu$^{2+}$; 3.5MgO×0.5MgF$_2$×GeO$_2$:Mn$^{4+}$ (MFG); (Ba,Sr,Ca)Mg$_x$P$_2$O$_7$:Eu$^{2+}$, Mn$^{2+}$; (Y,Lu)$_2$WO$_6$:Eu$^{3+}$, Mo$^{6+}$; (Ba,Sr,Ca)$_3$Mg$_x$Si$_2$O$_8$:Eu$^{2+}$, Mn$^{2+}$, wherein $1<x<2$; (RE$_{1-y}$Ce$_y$)Mg$_{2-x}$Li$_x$Si$_{3-x}$P$_x$O$_{12}$, where RE is at least one of Sc, Lu, Gd, Y, and Tb, $0.0001<x<0.1$ and $0.001<y<0.1$; (Y, Gd, Lu, La)$_{2-x}$Eu$_x$W$_{1-y}$Mo$_y$O$_6$, where $0.5<x<1.0$, $0.01<y<1.0$; (SrCa)$_{1-x}$Eu$_x$Si$_5$N$_8$, where $0.01<x<0.3$; SrZnO$_2$:Sm$^{+3}$; M$_m$O$_n$X, wherein M is selected from the group of Sc, Y, a lanthanide, an alkali earth metal and mixtures thereof; X is a halogen; $1<m<3$; and $1<n<4$, and wherein the lanthanide doping level can range from 0.1 to 40% spectral weight; and Eu$^+$ activated phosphate or borate phosphors; and mixtures thereof. Further details of other phosphor species and related techniques can be found in U.S. Pat. No. 8,956,894, in the name of Raring et al. issued Feb. 17, 2015, and titled "White light devices using non-polar or semipolar gallium containing materials and phosphors", which is commonly owned, and hereby incorporated by reference herein.

In some embodiments of the present invention, ceramic phosphor materials are embedded in a binder material such as silicone. This configuration is typically less desirable because the binder materials often have poor thermal conductivity, and thus get very hot wherein the rapidly degrade and even burn. Such "embedded" phosphors are often used in dynamic phosphor applications such as color wheels where the spinning wheel cools the phosphor and spreads the excitation spot around the phosphor in a radial pattern.

Sufficient heat dissipation from the phosphor is a critical design consideration for the integrated white light source based on laser diode excitation. Specifically, the optically pumped phosphor system has sources of loss in the phosphor that result is thermal energy and hence must be dissipated to a heat-sink for optimal performance. The two primary sources of loss are the Stokes loss which is a result of converting photons of higher energy to photons of lower energy such that difference in energy is a resulting loss of the system and is dissipated in the form of heat. Additionally, the quantum efficiency or quantum yield measuring the fraction of absorbed photons that are successfully re-emitted is not unity such that there is heat generation from other internal absorption processes related to the non-converted photons. Depending on the excitation wavelength and the converted wavelength, the Stokes loss can lead to greater than 10%, greater than 20%, and greater than 30%, and greater loss of the incident optical power to result in thermal power that must be dissipated. The quantum losses can lead to an additional 10%, greater than 20%, and greater than 30%, and greater of the incident optical power to result in thermal power that must be dissipated. With laser beam powers in the 1 W to 100 W range focused to spot sizes of less than 1 mm in diameter, less than 500 µm in diameter, or even less than 100 µm in diameter, power densities of over 1 W/mm$^2$, 100 W/mm$^2$, or even over 2,500 W/mm$^2$ can be generated. As an example, assuming that the spectrum is comprised of 30% of the blue pump light and 70% of the converted yellow light and a best case scenario on Stokes and quantum losses, we can compute the dissipated power density in the form of heat for a 10% total loss in the phosphor at 0.1 W/mm$^2$, 10 W/mm$^2$, or even over 250 W/mm$^2$. Thus, even for this best case scenario example, this is a tremendous amount of heat to dissipate. This heat generated within the phosphor under the high intensity laser excitation can limit the phosphor conversion performance, color quality, and lifetime.

For optimal phosphor performance and lifetime, not only should the phosphor material itself have a high thermal conductivity, but it should also be attached to the submount or common support member with a high thermal conductivity joint to transmit the heat away from the phosphor and to a heat-sink. In this invention, the phosphor is either attached to the common support member as the laser diode as in the CPoS or is attached to an intermediate submount member that is subsequently attached to the common support member. Candidate materials for the common support member or intermediate submount member are SiC, AlN, BeO, diamond, copper, copper tungsten, sapphire, aluminum, or others. The interface joining the phosphor to the submount member or common support member must be carefully considered. The joining material should be comprised of a high thermal conductivity material such as solder (or other) and be substantially free from voids or other defects that can impede heat flow. In some embodiments, glue materials can be used to fasten the phosphor. Ideally the phosphor bond interface will have a substantially large area with a flat surface on both the phosphor side and the support member sides of the interface.

In the present invention, the laser diode output beam must be configured to be incident on the phosphor material to excite the phosphor. In some embodiments the laser beam may be directly incident on the phosphor and in other embodiments the laser beam may interact with an optic, reflector, waveguide, or other object to manipulate the beam prior to incidence on the phosphor. Examples of such optics include, but are not limited to ball lenses, aspheric collimator, aspheric lens, fast or slow axis collimators, dichroic mirrors, turning mirrors, optical isolators, but could be others.

In some embodiments, the apparatus typically has a free space with a non-guided laser beam characteristic transmitting the emission of the laser beam from the laser device to the phosphor material. The laser beam spectral width, wavelength, size, shape, intensity, and polarization are configured to excite the phosphor material. The beam can be configured by positioning it at the precise distance from the phosphor to exploit the beam divergence properties of the laser diode and achieve the desired spot size. In one embodiment, the incident angle from the laser to the phosphor is optimized to achieve a desired beam shape on the phosphor. For example, due to the asymmetry of the laser aperture and the different divergent angles on the fast and slow axis of the beam the spot on the phosphor produced from a laser that is configured normal to the phosphor would be elliptical in shape, typically with the fast axis diameter being larger than the slow axis diameter. To compensate this, the laser beam incident angle on the phosphor can be optimized to stretch the beam in the slow axis direction such that the beam is more circular on phosphor. In other embodiments free space optics such as collimating lenses can be used to shape the beam prior to incidence on the phosphor. The beam can be characterized by a polarization purity of greater than 50% and less than 100%. As used herein, the term "polarization purity" means greater than 50% of the emitted electromagnetic radiation is in a substantially similar polarization state such as the transverse electric (TE) or transverse magnetic (TM) polarization states, but can have other meanings consistent with ordinary meaning.

The white light apparatus also has an electrical input interface configured to couple electrical input power to the laser diode device to generate the laser beam and excite the phosphor material. In an example, the laser beam incident on the phosphor has a power of less than 0.1 W, greater than 0.1 W, greater than 0.5 W, greater than 1 W, greater than 5 W, greater than 10 W, or greater than 20 W. The white light source configured to produce greater than 1 lumen, 10 lumens, 100 lumens, 1000 lumens, 10,000 lumens, or greater of white light output.

The support member is configured to transport thermal energy from the at least one laser diode device and the phosphor material to a heat sink. The support member is configured to provide thermal impedance of less than 10 degrees Celsius per watt, less than 5 degrees Celsius per watt, or less than 3 degrees Celsius per watt of dissipated power characterizing a thermal path from the laser device to a heat sink. The support member is comprised of a thermally conductive material such as copper with a thermal conductivity of about 400 W/(m-K), aluminum with a thermal conductivity of about 200 W/(mK), 4H—SiC with a thermal conductivity of about 370 W/(m-K), 6H—SiC with a thermal conductivity of about 490 W/(m-K), AlN with a thermal conductivity of about 230 W/(m-K), a synthetic diamond with a thermal conductivity of about >1000 W/(m-K), sapphire, or other metals, ceramics, or semiconductors. The support member may be formed from a growth process such as SiC, AlN, or synthetic diamond, and then mechanically shaped by machining, cutting, trimming, or molding. Alternatively the support member may be formed from a metal such as copper, copper tungsten, aluminum, or other by machining, cutting, trimming, or molding.

Currently, solid state lighting is dominated by systems utilizing blue or violet emitting light emitting diodes (LEDs) to excite phosphors which emit a broader spectrum. The combined spectrum of the so called pump LEDs and the phosphors can be optimized to yield white light spectra with controllable color point and good color rendering index. Peak wall plug efficiencies for state of the art LEDs are quite high, above 70%, such that LED based white lightbulbs are now the leading lighting technology for luminous efficacy. As laser light sources, especially high-power blue laser diodes made from gallium and nitrogen containing material based novel manufacture processes, have shown many advantageous functions on quantum efficiency, power density, modulation rate, surface brightness over conventional LEDs. This opens up the opportunity to use lighting fixtures, lighting systems, displays, projectors and the like based on solid-state light sources as a means of transmitting information with high bandwidth using visible light. It also enables utilizing the modulated laser signal or direct laser light spot manipulation to measure and or interact with the surrounding environment, transmit data to other electronic systems and respond dynamically to inputs from various sensors. Such applications are herein referred to as "smart lighting" applications.

In some embodiments, the present invention provides novel uses and configurations of gallium and nitrogen containing laser diodes in communication systems such as visible light communication systems. More specifically the present invention provides communication systems related to smart lighting applications with gallium and nitrogen based lasers light sources coupled to one or more sensors with a feedback loop or control circuitry to trigger the light source to react with one or more predetermined responses and combinations of smart lighting and visible light communication. In these systems, light is generated using laser devices which are powered by one or more laser drivers. In some embodiments, individual laser devices are used and optical elements are provided to combine the red, green and blue spectra into a white light spectrum. In other embodiments, blue or violet laser light is provided by a laser source and is partially or fully converted by a wavelength converting element into a broader spectrum of longer wavelength light such that a white light spectrum is produced.

The blue or violet laser devices illuminate a wavelength converting element which absorbs part of the pump light and reemits a broader spectrum of longer wavelength light. The light absorbed by the wavelength converting element is referred to as the "pump" light. The light engine is configured such that some portion of both light from the wavelength converting element and the unconverted pump light are emitted from the light-engine. When the non-converted, blue pump light and the longer wavelength light emitted by the wavelength converting element are combined, they may form a white light spectrum. In an example, the partially converted light emitted generated in the wavelength conversion element results in a color point, which is white in appearance. In an example, the color point of the white light is located on the Planckian blackbody locus of points. In an example, the color point of the white light is located within du'v' of less than 0.010 of the Planckian blackbody locus of points. In an example, the color point of the white light is preferably located within du'v' of less than 0.03 of the Planckian blackbody locus of points.

In an example, the wavelength conversion element is a phosphor which contains garnet host material and a doping element. In an example, the wavelength conversion element is a phosphor, which contains an yttrium aluminum garnet host material and a rare earth doping element, and others. In an example, the wavelength conversion element is a phosphor which contains a rare earth doping element, selected from one or more of Nd, Cr, Er, Yb, Nd, Ho, Tm Cr, Dy, Sm, Tb and Ce, combinations thereof, and the like. In an example, the wavelength conversion element is a phosphor which contains oxy-nitrides containing one or more of Ca, Sr, Ba, Si, Al with or without rare-earth doping. In an example, the wavelength conversion element is a phosphor which contains alkaline earth silicates such as $M_2SiO_4$:$Eu^{2+}$ (where M is one or more of $Ba^{2+}$, $Sr^{2+}$ and $Ca^{2+}$). In an example, the wavelength conversion element is a phosphor which contains $Sr_2LaAlO_5$:$Ce^{3+}$, $Sr_3SiO_5$:$Ce^{3+}$ or $Mn^{4+}$-doped fluoride phosphors. In an example, the wavelength conversion element is a high-density phosphor element. In an example, the wavelength conversion element is a high-density phosphor element with density greater than 90% of pure host crystal. In an example, the wavelength converting material is a powder. In an example, the wavelength converting material is a powder suspended or embedded in a glass, ceramic or polymer matrix. In an example, the wavelength converting material is a single crystalline member. In an example, the wavelength converting material is a powder sintered to density of greater than 75% of the fully dense material. In an example, the wavelength converting material is a sintered mix of powders with varying composition and/or index of refraction. In an example, the wavelength converting element is one or more species of phosphor powder or granules suspended in a glassy or polymer matrix. In an example, the wavelength conversion element is a semiconductor. In an example, the wavelength conversion element contains quantum dots of semiconducting material. In an example, the wavelength conversion element is comprised by semiconducting powder or granules.

For laser diodes the phosphor may be remote from the laser die, enabling the phosphor to be well heat sunk, enabling high input power density. This is an advantageous configuration relative to LEDs, where the phosphor is typically in contact with the LED die. While remote-phosphor LEDs do exist, because of the large area and wide emission angle of LEDs, remote phosphors for LEDs have the disadvantage of requiring significantly larger volumes of phosphor to efficiently absorb and convert all of the LED light, resulting in white light emitters with large emitting areas and low luminance.

For LEDs, the phosphor emits back into the LED die where the light from the phosphor can be lost due to absorption. For laser diode modules, the environment of the phosphor can be independently tailored to result in high efficiency with little or no added cost. Phosphor optimization for laser diode modules can include highly transparent, non-scattering, ceramic phosphor plates. Decreased temperature sensitivity can be determined by doping levels. A reflector can be added to the backside of a ceramic phosphor, reducing loss. The phosphor can be shaped to increase in-coupling and reduce back reflections. Of course, there can be additional variations, modifications, and alternatives.

For laser diodes, the phosphor or wavelength converting element can be operated in either a transmission or reflection mode. In a transmission mode, the laser light is shown through the wavelength converting element. The white light spectrum from a transmission mode device is the combination of laser light not absorbed by the phosphor and the spectrum emitted by the wavelength converting element. In a reflection mode, the laser light is incident on the first surface of the wavelength converting element. Some fraction of the laser light is reflected off of the first surface by a combination of specular and diffuse reflection. Some fraction of the laser light enters the phosphor and is absorbed and converted into longer wavelength light. The white light spectrum emitted by the reflection mode device is comprised by the spectrum from the wavelength converting element, the fraction of the laser light diffusely reflected from the first surface of the wavelength converting element and any laser light scattered from the interior of the wavelength converting element.

In a specific embodiment, the laser light illuminates the wavelength converting element in a reflection mode. That is, the laser light is incident on and collected from the same side of the wavelength converting element. The element may be heat sunk to the emitter package or actively cooled. Rough surface is for scattering and smooth surface is for specular reflection. In some cases such as with a single crystal phosphor a rough surface with or without an AR coating of the wavelength converting element is provided to get majority of excitation light into phosphor for conversion and Lambertian emission while scattering some of the excitation light from the surface with a similar Lambertian as the emitted converted light. In other embodiments such as ceramic phosphors with internal built-in scattering centers are used as the wavelength converting elements, a smooth surface is provided to allow all laser excitation light into the phosphor where blue and wavelength converted light exits with a similar Lambertian pattern.

In a specific embodiment, the laser light illuminates the wavelength converting element in a transmission mode. That is, the laser light is incident on one side of the element, traverses through the phosphor, is partially absorbed by the element and is collected from the opposite side of the phosphor.

The wavelength converting elements, in general, can themselves contain scattering elements. When laser light is absorbed by the wavelength converting element, the longer wavelength light that is emitted by the element is emitted across a broad range of directions. In both transmission and reflection modes, the incident laser light must be scattered into a similar angular distribution in order to ensure that the resulting white light spectrum is substantially the same when viewed from all points on the collecting optical elements. Scattering elements may be added to the wavelength converting element in order to ensure the laser light is sufficiently scattered. Such scattering elements may include: low index inclusions such as voids, spatial variation in the optical index of the wavelength converting element which could be provided as an example by suspending particles of phosphor in a matrix of a different index or sintering particles of differing composition and refractive index together, texturing of the first or second surface of the wavelength converting element, and the like.

In a specific embodiment, a laser or SLED driver module is provided. For example, the laser driver module generates a drive current, with the drive currents being adapted to drive a laser diode to transmit one or more signals such as digitally encoded frames of images, digital or analog encodings of audio and video recordings or any sequences of binary values. In a specific embodiment, the laser driver module is configured to generate pulse-modulated light signals at a modulation frequency range of about 50 MHz to 300 MHz, 300 MHz to 1 GHz or 1 GHz to 100 GHz. In another embodiment the laser driver module is configured to generate multiple, independent pulse-modulated light signal at a modulation frequency range of about 50 MHz to 300 MHz, 300 MHz to 1 GHz or 1 GHz to 100 GHz. In an embodiment, the laser driver signal can be modulated by an analog voltage or current signal.

Some embodiments of the present invention provide a light source configured for emission of laser based visible light such as white light and an infrared light, to form an illumination source capable of providing visible and IR illumination. The light source includes a gallium and nitrogen containing laser diode excitation source configured with an optical cavity. The optical cavity includes an optical waveguide region and one or more facet regions. The optical cavity is configured with electrodes to supply a first driving current to the gallium and nitrogen containing material. The first driving current provides an optical gain to an electromagnetic radiation propagating in the optical waveguide region of the gallium and nitrogen containing material. The electromagnetic radiation is outputted through at least one of the one or more facet regions as a directional electromagnetic radiation characterized by a first peak wavelength in the ultra-violet, blue, green, or red wavelength regime. Furthermore, the light source includes a wavelength converter, such as a phosphor member, optically coupled to the electromagnet radiation pathway to receive the directional electromagnetic radiation from the excitation source. The wavelength converter is configured to convert at least a fraction of the directional electromagnetic radiation with the first peak wavelength to at least a second peak wavelength that is longer than the first peak wavelength. In a preferred embodiment the output is comprised of a white-color spectrum with at least the second peak wavelength and partially the first peak wavelength forming the laser based visible light spectrum component according to the present invention. In one example, the first peak wavelength is a blue wavelength and the second peak wavelength is a yellow wavelength. The light source optionally includes a beam shaper configured to direct the white-color spectrum for illuminating a target or area of interest.

There are many wavelength regimes which are of interest for Solid State lighting for non-photopic reasons. Some examples industries and the wavelengths of interest are shown in Table 1. Broadly speaking, all wavelengths can be utilized for photochemistry applications, the wavelength regions carry different amounts of energy and thus interact with different bond strengths. For example, VUV with photon energies of 7-13 eV are strong enough to cleave Water and Oxygen into radicals. UV-A, though lower energy than VUV can promote Vitamin D production in skin and be used for air purification and bacterial disinfection. At the lowest energy region, the Near IR, recent developments in thermal imaging and LIDAR are noted.

TABLE 1

Wavelength Regimes and Exemplary Applications

| 100-200 nm VUV | 200-280 nm UV-C | 280-320 nm UV-B | 320-420 nm UV-A and violet | 380-780 nm Visible | 780-2500 nm Near IR |
|---|---|---|---|---|---|
| Photochemistry | Photochemistry | Photochemistry | Photochemistry | | Thermal Imaging, IR illumination |
| Wafer Cleaning Ozone Generation | Air Disinfection Water Disinfection Surface Disinfection | Tanning Skin Disease Treatment | Tanning Water Purification Air Purification and surface cleaning | | Topical Medicine Activation, tissue healing |
| | Communication Depth sensing, LIDAR | Communication Depth sensing, LIDAR | Communication Depth sensing, LIDAR | | Communication Depth sensing, LIDAR |

In general, there are many possible applications and benefits of including light sources in these ultraviolet (UV) and infrared (IR) wavelength regimes within visible light sources. For example, by including light sources such as lasers in the near IR region, the visible light source can also function to provide IR illumination or thermal imaging, provide a depth sensing or 3D imaging sensing signal in LIDAR applications, provide a communication link by enabling high speed data transmission, and provide medical benefits such as topical medicine activation and enhance tissue healing. With independent control of the visible light function and the IR light functions, these benefits or capabilities in the IR can be achieved either simultaneous to the white light illumination function or separately. In some embodiments of the present invention, IR light sources such as IR light sources are included within the laser based visible light source.

In some preferred embodiments of the present invention, the visible laser based white light source includes an additional light source on the high energy side of the visible light spectrum such as a light source in the UV-A or violet wavelength ranges. Here light sources ranging from 320 nm to 400 nm or even to longer violet wavelengths such as 400 nm to 420 nm, can be included in the light source to perform functions such as purification of water, purification of air, and cleaning of surfaces. The UV or visible light source can preferably be generated by a laser diode, but could also come from a light emitting diode. The cleaning action occurs as the light breaks down and eventually destroys bacteria, virus, and germs. At this lower energy end of the UV wavelength range longer exposure times may be required for highly effective cleaning and disinfecting. However, a strong benefit to this lower energy region of the UV is that it is safe for human exposure, especially as the wavelength is increased to the 390 to 415 nm range. By including these UV-A or violet sources with wavelengths in the 390 nm to 415 nm wavelength range, such as 405 nm, in visible light sources the UV-A light can be activated in a near continuous and safe fashion to provide a cleaning/disinfecting benefit to the environment.

In a preferred embodiment, the UV-A light or violet light is generated by a laser diode that is included within the visible laser based white light source. In alternative embodiments, the UV-A light or violet light is generated by a different type of light sources such as a light emitting diode. The UV-A light or violet light can be operated simultaneous to the visible white light illumination when the visible light is needed, or can be operated when the visible light is not needed such as during close of business or when there is sufficient ambient light. This can allow the UV-A or violet source to be emitting all the time for a continuous cleaning/disinfecting result. The net effect is a light source that can provide a safer and cleaner environment, which could find application in virtually any location including hospitals, schools, restaurants, hotels, shopping centers, offices, homes, etc. In some embodiments of the present invention, a UV-A light source or a light source in the 390 nm to 415 nm range such as a 405 nm light source is included within the laser based visible light source. The UV-A light source or the violet light source in the 400 nm to 415 nm range is a laser diode emitting in this wavelength range. In some embodiments, the laser based light source is equipped with sensors for feedback loops and/or computational power or inputs to establish a lighting algorithm that can control when the disinfecting UV light and the visible white light should be emitting from the source.

In some applications the UV-A light or violet light in the 320 nm to 420 nm range is generated by a laser diode and can function as a data transmission medium to send high data rate encoded data to a receiver to form a communication link as described in this invention. In other applications the UV-A light or violet light in the 320 nm to 420 nm range is generated by a laser diode and can function as a sensing light in a depth sensing or ranging device, such as sensing devices that use time of flight measurement to detect a distance. In yet other applications the UV-A light or violet light in the 320 nm to 420 nm range is generated by a laser diode and can function as a sensing light in a 3D LiDAR system where the depths of a 2D array of spatial coordinates are measured to create a 3D image.

In some embodiments of the present invention, a higher energy UV light source is included in the laser based white light source. In these embodiments the UV light source can operate in the UV-C wavelength range from 200 nm to 280 nm or the UV-B wavelength range from 280 nm to 320 nm. The addition of these higher energy wavelengths can provide more rapid and more intense purification and disinfecting properties to the laser based white light source, compared with that from the UV-A or violet wavelengths. When using these wavelengths for disinfecting, purification, and cleaning it is highly important to implement the proper safety considerations and controls since prolonged exposure to humans or animals can have adverse health effects. In a preferred embodiment, the UV-B or UV-C light is generated by a laser diode that is included within the visible laser based white light source. In alternative embodiments, the UV-B or UV-C light is generated by a different type of light sources such as a light emitting diode.

In some embodiments of the present invention, the laser based white light source including the UV-C or UV-B light source would be designed such that the UV light was only activated for fixed periods of time to avoid over exposure, or the UV light could be activated at specific times when no human beings or animals are present. The independent controls of the white light emission and the UV light emission could allow the light source to provide its cleaning and disinfecting function as determined by the user, which could be at nighttime in office spaces when there are no occupants, could be between patient visits/occupants in hospitals and healthcare settings, in stores and shopping centers during close of business, and so on, to enable safe and effective disinfecting. In some embodiments, the laser based light source is equipped with sensors for feedback loops and/or computational power or inputs to establish a lighting algorithm that can control when the disinfecting UV light and the visible white light should be emitting from the source.

In some applications the UV-C light or UV-B light in the 320 nm to 420 nm range can function as a data transmission medium to send high data rate encoded data to a receiver to form a communication link as described in this invention. In other applications the UV-C light or UV-B light in the 320 nm to 420 nm range can function as a sensing light in a depth sensing or ranging device, such as sensing devices that use time of flight measurement to detect a distance. In yet other applications the UV-C light or UV-B light in the 320 nm to 420 nm range can function as a sensing light in a 3D LiDAR system where the depths of a 2D array of spatial coordinates are measured to create a 3D image.

In other embodiments of the present invention, light sources operating in the VUV range from 100 nm to 200 nm are included in the laser based white light source. Such deep UV light sources can be used for various applications when combined with the white light source. Safety considerations would need to be employed to avoid unsafe use of the high energy VUV light.

Figures 30A, 30B, 30C:
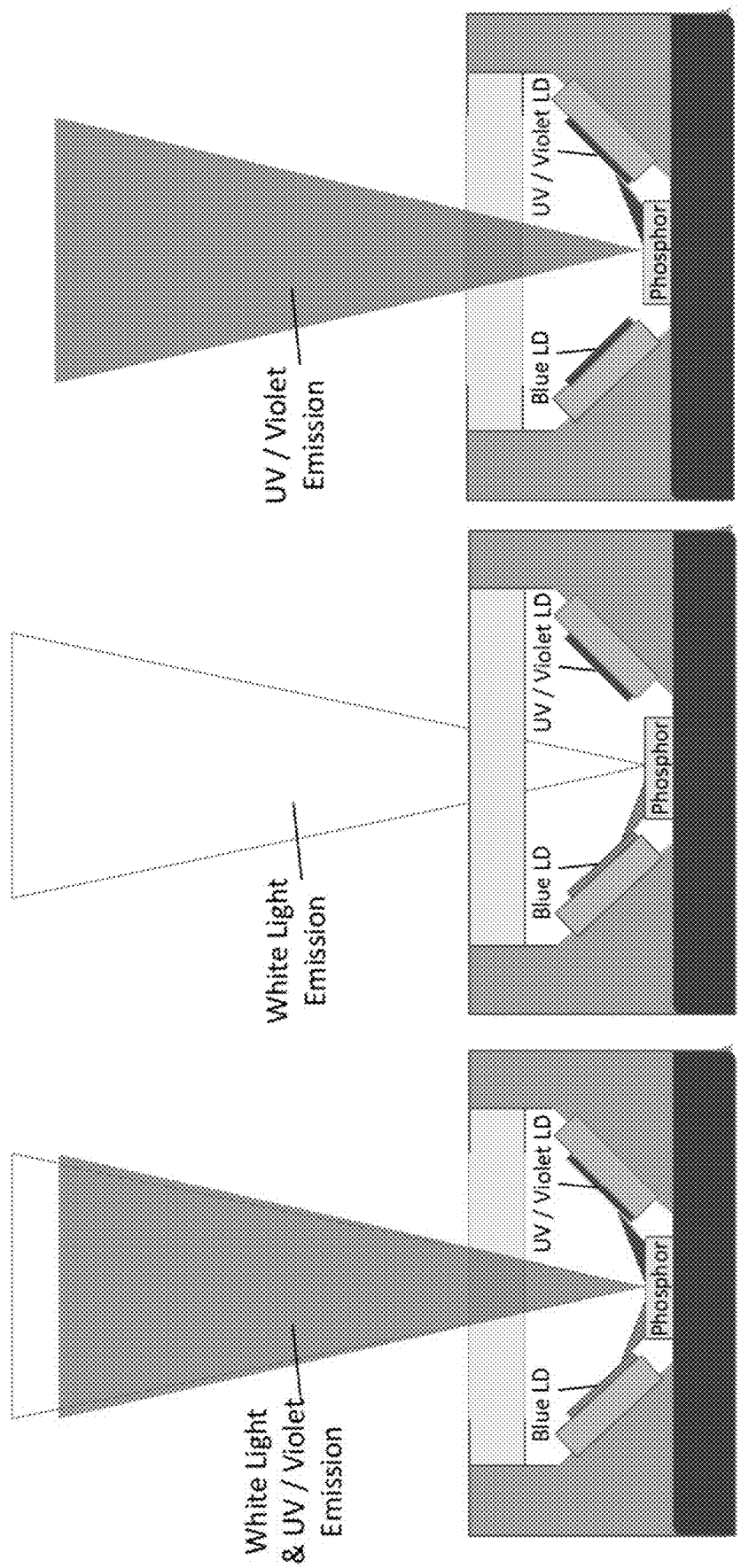
FIGS. 30A-30C are simplified block diagrams showing a laser diode source that includes a blue laser diode and a UV or violet laser diode according to some embodiments of the present invention.

In many preferred embodiments according to the present invention a UV laser with an emission peak wavelength in the 200 nm to 400 nm range, and/or a violet laser diode operating in the wavelength range of 400 nm to 410 nm or up to the 425 nm range is included in the laser based white light source. In certain preferred embodiments the laser based white light source uses a blue laser diode pumping a yellow emitting YAG based phosphor to generate a white light, wherein the phosphor is operated in a reflection mode. In an ideal configuration, the UV and/or violet emission is incident on the phosphor in substantially the same spot as the blue laser diode such that the generated white light emission and the scattered/reflected UV and/or violet emission are substantially spatially overlapping. An example is shown in FIGS. 30A-30C, where a combined white light and UV or violet emission may be emitted (FIG. 30A), a white light may be emitted (FIG. 30B), or a UV or violet emission may be emitted (FIG. 30C). In a similar manner, some embodiments may include a blue laser diode, a UV laser diode, and a violet laser diode. By having the emission of the white light and the UV and/or violet emission from the same spatial position, a common optic or optical system can be used to project and direct the white light and the UV and/or violet emission. In such reflective mode applications, careful consideration must be given to the UV and/or violet interaction with the YAG phosphor. In other embodiments of the present invention the phosphor member is operated in a transmission mode.

In this present invention that includes a UV and/or a violet laser diode, and/or an IR emitting laser diode in the white light source, the diffuse and specular reflection of YAG:Ce3+ phosphor must be understood such that the design can be optimized for the phosphor interaction with the UV and/or IR light in the wavelength regimes of interest. To this end, FIG. 11 shows the measured diffuse and specular reflection from a YAG:Ce3+ phosphor configured for use in reflection mode application where the blue light source and white light emission occur on the same side. It is clear for this configuration, the YAG:Ce3+ phosphor subcomponent acts as a good reflector for wavelengths between 350 and 1000 nm. Below 350 nm, the reflection decreases, coinciding with both increases in transmission and absorption.

Understanding that the YAG:$Ce^{3+}$ phosphor provides good reflectivity from 350 to 1000 nm means that many of the wavelength regimes described in Table 1, excepting VUV and part of UV-C, will be reflected from the YAG material. This allows solid state sources in the 350 nm-1000 nm range to be included in reflection mode geometries such that their light will be reflected off the surface of the YAG:Ce3+ phosphor and become part of the emission light which exits the device. This behavior in reflection mode geometry lends itself directly to the application of non-visual light applications based on the reflection characteristics and the reflection mode geometry. It should be noted that a transmission mode geometry would not result in the non-visual light exiting the device as this light would be reflected back inside the device and lost.

Consider the base spectra of a 6000K laser based white spectra and the possible additions to it. FIG. 12 shows a typical laser based spectra with no additional modifications. It consists of a blue laser 446 nm peak wavelength exciting a YAG:$Ce^{3+}$ phosphor with a broad peak centered near 560 nm.

With the reflection mode geometry of the device and the diffuse reflection in this configuration, it is possible to add additional spectral features with minimal changes in the color, flux or photopic parameters. FIG. 13 shows the addition of a 405 nm near UV peak to the base spectra. The 405 nm peak could be produced by the addition of a 405 nm laser to the device. GaN based near UV lasers have been demonstrated from 380-430 nm but the YAG phosphor reflection would support lasers as low as 350 nm prior to loss of reflection.

This type of spectral addition to the base spectra could be used for the near infrared region as well. Shown in FIG. 14 are the inclusion of 850 nm and 905 nm laser light near IR spectra. These 2 wavelengths are of particular interest for IR illumination, communication and LIDAR. These spectra could be added separately or combined as shown in FIG. 14. They could be operated concurrent with the white light or as separate channels. Near IR lasers are capable of producing light from 700 nm to 1500 nm and would be applicable to this geometry. These additions do not affect the overall photopic parameters of the light source as they are outside the visible range. The white light is still perceived with similar flux and color as the base white light of FIG. 12.

A further enhancement would combine both the near UV and Near IR spectra with the base white light spectra of FIG. 12 as shown in FIG. 15. All channels could be operated together or separately, white light, near UV, near IR.

Other standard white points for lighting could support the extended range of near UV and Near IR wavelengths dependent on the phosphor chosen to alter the white light spectrum and its diffuse reflection for the wavelengths of interest. One example of this is shown for the [Sr,Ca]AlSiN:Eu2+ phosphor family which is used in LED lighting to produce warm white spectra with high color rendering. The diffuse reflection for CASN:Eu2+ is shown in FIG. 16. It is clear that the standard red phosphor used for warm white applications provides good reflectivity in the near IR region, but low reflectivity in the near UV region. However, as the Red phosphor is only used in conjunction with yellow emitting materials such as YAG:Ce3+, LuAG:Ce3+ to produce warm white spectra, the near UV reflectivity is provided by the YAG:Ce3+ phosphor would allow both near UV and near IR reflectivity for warm white spectra.

A full example of 4000K Neutral White which utilizes YAG:Ce3+ and CASN:Eu3+ phosphors in conjunction with near UV and Near IR lasers is shown in FIG. 17.

The addition of the Sr containing s-CASN red phosphor can also be used to further extend the color to the warm white spectral region as is shown in FIG. 18. As with previous examples, the additions of near UV and near IR do not affect the overall photopic performance of the white light but rather enhance the spectra for non-visible functionalities.

In one embodiment of the present invention a laser diode or light emitting diode with a third peak wavelength is included to form an IR emission component of a dual band emitting light source. The IR laser diode contains an optical cavity configured with electrodes to supply a second driving current configured to the IR laser diode. The second driving current provides an optical gain to an electromagnetic radiation propagating in the optical waveguide region of the IR laser diode material. The electromagnetic radiation is outputted through at least one of the one or more facet regions as a directional electromagnetic radiation characterized by a third peak wavelength in the IR regime. In one configuration the directional IR emission is optically coupled to the wavelength converter member such that the wavelength converter member is within the optical pathway of the IR emission to receive the directional electromagnetic radiation from the excitation source. Once incident on the wavelength converter member, the IR emission with the third peak wavelength would be at least partially reflected from the wavelength converter member and redirected into the same optical pathway as the white light emission with the first and second peak wavelengths. The IR emission would be directed through the optional beam shaper configured to direct the output IR light for illuminating approximately the same target or area of interest as the visible light. In this embodiment the first and second driving current could be activated independently such that the apparatus could provide a visible light source with only the first driving current activated, an IR light source with the second driving current activated, or could simultaneously provide both a visible and IR light source. In some applications it would be desirable to only use the IR illumination source for IR detection. Once an object was detected, the visible light source could be activated.

Figure 19A:
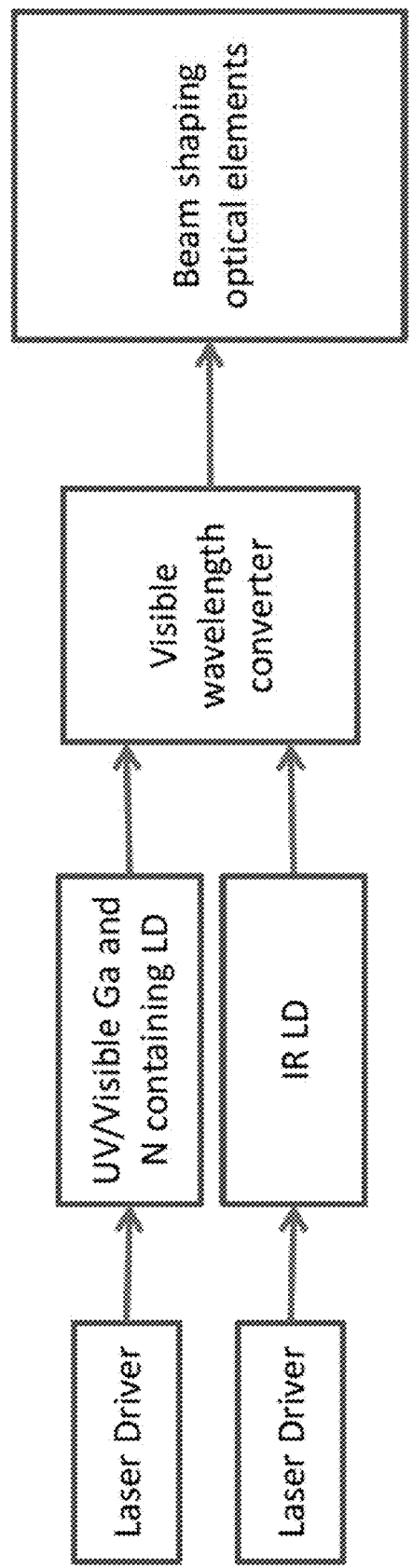
FIG. 19A is a functional block diagram for a laser-based white light source integrated with an IR illumination source containing a UV or blue pump laser, a visible wavelength converting element, and an IR emitting laser diode according to an embodiment of the present invention.

FIG. 19A is a functional block diagram for a laser-based white light source containing a gallium and nitrogen containing violet or blue pump laser and a wavelength converting element to generate a white light emission, and an infrared emitting laser diode to generate an IR emission according to an embodiment of the present invention. Referring to FIG. 19A, a violet or blue laser device emitting a spectrum with a center point wavelength between 390 and 480 nm is provided. The light from the violet or blue laser device is incident on a wavelength converting element, which partially or fully converts the blue light into a broader spectrum of longer wavelength light such that a white light spectrum is produced. In some embodiments the gallium and nitrogen containing laser diode operates in the 480 nm to 540 nm range. In some embodiments the laser diode is comprised from a III-nitride material emitting in the ultraviolet region with a wavelength of about 270 nm to about 390 nm. A laser driver is provided which powers the gallium and nitrogen containing laser device to excite the visible emitting wavelength member. In some embodiments, one or more beam shaping optical elements may be provided in order to shape or focus the white light spectrum. Additionally, an IR emitting laser device is included to generate an IR illumination. The directional IR electromagnetic radiation from the laser diode is incident on the wavelength converting element wherein it is reflected from or transmitted through the wavelength converting element such that it follows the same optical path as the white light emission. The IR emission could include a peak wavelength in the 700 nm to 1100 nm range based on gallium and arsenic material system (e.g., GaAs) for near-IR illumination, or a peak wavelength in the 1100 to 2500 nm range based on an indium and phosphorous containing material system (e.g., InP) for eye-safe wavelength IR illumination, or in the 2500 nm to 15000 nm wavelength range based on quantum cascade laser technology for mid-IR thermal imaging. For example, GaInAs/AlInAs quantum cascade lasers operate at room temperature in the wavelength range of 3 μm to 8 μm. A laser drive is included to power the IR emitting laser diode and deliver a controlled amount of current at a sufficiently high voltage to operate the IR laser diode. Optionally, the one or more beam shaping optical elements can be one selected from slow axis collimating lens, fast axis collimating lens, aspheric lens, ball lens, total internal reflector (TIR) optics, parabolic lens optics, refractive optics, or a combination of above. In other embodiments, the one or more beam shaping optical elements can be disposed prior to the laser light incident to the wavelength converting element.

In some embodiments the visible and/or IR emission from the light source are coupled into an optical waveguide such as an optical fiber, which could be a glass optical fiber or a plastic optical fiber. The optical fiber of an arbitrary length, including a single mode fiber (SMF) or a multi-mode fiber (MMF), with core diameters ranging from about 1 um to 10 um, about 10 um to 50 um, about 50 um to 150 um, about 150 um to 500 um, about 500 um to 1 mm, about 1 mm to 5 mm or greater than 5 mm. The optical fiber is aligned with a collimation optics member to receive the collimated white light and/or IR emission.

Figure 19B:
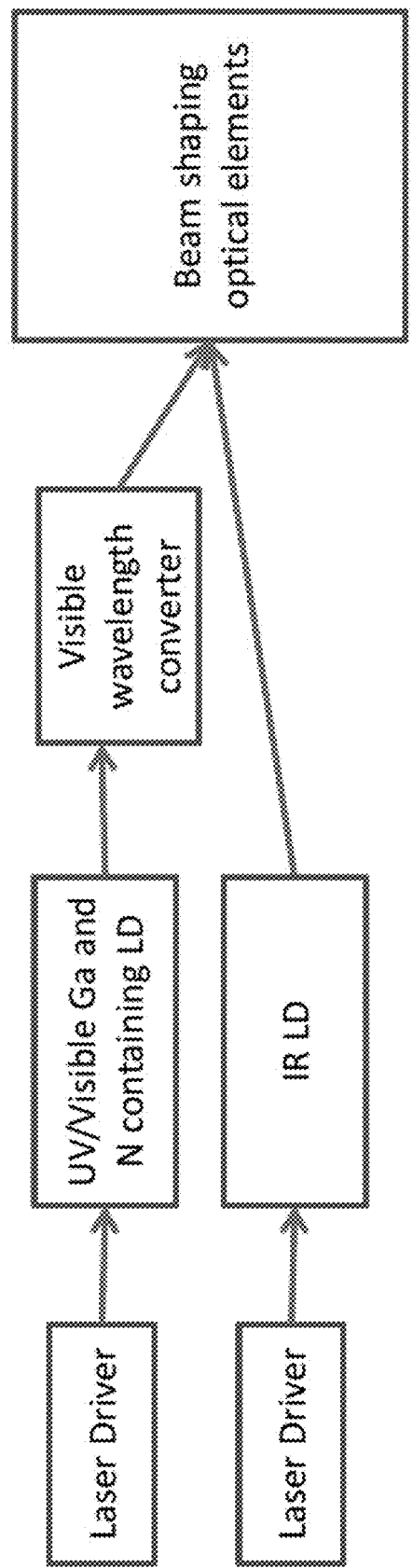
FIG. 19B is a functional block diagram for a laser-based white light source integrated with an IR illumination source containing a UV or blue pump laser, a visible emitting phosphor member, and an IR emitting laser diode according to an embodiment of the present invention.

In an additional configuration of the present embodiment that includes a direct laser diode IR illumination source, the IR illumination is optically coupled directly to the optical beam shaping elements rather than interacting with the wavelength converter element where it would be reflected and/or transmitted. FIG. 19B is a functional block diagram for a laser-based white light source containing a gallium and nitrogen containing violet or blue pump laser and a wavelength converting element to generate a white light emission, and an infrared emitting laser diode to generate an IR emission according to an embodiment of the present invention. In some embodiments, the white light source is used as a "light engine" for VLC or smart lighting applications. Referring to FIG. 19B, a blue or violet laser device emitting a spectrum with a center point wavelength between 390 and 480 nm is provided. In some embodiments the gallium and nitrogen containing laser diode operates in the 480 nm to 540 nm range. In some embodiments the laser diode is comprised from a III-nitride material emitting in the ultra-violet region with a wavelength of about 270 nm to about 390 nm. The light from the violet or blue laser device is incident on a wavelength converting element, which partially or fully converts the blue light into a broader spectrum of longer wavelength light such that a white light spectrum is produced. A laser driver is provided which powers the gallium and nitrogen containing laser device. In some embodiments, one or more beam shaping optical elements may be provided in order to shape or focus the white light spectrum. Additionally, an IR emitting laser device is included to generate an IR illumination. The directional IR electromagnetic radiation from the laser diode is directly optically coupled to the beam shaper elements, avoiding interactions with the wavelength converter element. The IR emission could include a peak wavelength in the 700 nm to 1100 nm range based on gallium and arsenic material system (e.g., GaAs) for near-IR illumination, or a peak wavelength in the 1100 to 2500 nm range based on an indium and phosphorous containing material system (e.g., InP) for eye-safe wavelength IR illumination, or in the 2500 nm to 15000 nm wavelength range based on quantum cascade laser technology for mid-IR thermal imaging. For example, GaInAs/AlInAs quantum cascade lasers operate at room temperature in the wavelength range of 3 μm to 8 μm. A laser drive is included to power the IR emitting laser diode. Optionally, the one or more beam shaping optical elements can be one selected from slow axis collimating lens, fast axis collimating lens, aspheric lens, ball lens, total internal reflector (TIR) optics, parabolic lens optics, refractive optics, or a combination of above. In other embodiments, the one or more beam shaping optical elements can be disposed prior to the laser light incident to the wavelength converting element.

In some embodiments the visible and/or IR emission from the light source are coupled into an optical waveguide such as an optical fiber, which could be a glass optical fiber or a plastic optical fiber. The optical fiber of an arbitrary length, including a single mode fiber (SMF) or a multi-mode fiber (MMF), with core diameters ranging from about 1 um to 10 um, about 10 um to 50 um, about 50 um to 150 um, about 150 um to 500 um, about 500 um to 1 mm, about 1 mm to 5 mm or greater than 5 mm. The optical fiber is aligned with a collimation optics member to receive the collimated white light and/or IR emission.

The resulting spectrum from the embodiment described in FIGS. 19A and 19B according to the present invention would be comprised of a relatively narrow band (about 0.5 to 3 nm) emission spectrum from the gallium and nitrogen containing laser diode in the UV or blue wavelength region, a broadband (about 10 to 100 nm) wavelength converter emission in the visible spectrum with a longer peak wavelength than the UV or blue laser diode, and the relatively narrow band (about 1 to 10 nm) emission from the IR laser diode with a longer wavelength than the peak emission wavelength from the visible phosphor member. FIG. 19C presents an example optical spectrum according to the present invention. In this figure, the gallium and nitrogen containing laser diode emits in the blue region at about 440 to 455 nm, the visible wavelength converter member emits in the yellow region, and the included IR illumination laser diode emits at 875 nm. Of course there can be many other configurations of the present invention, including different wavelength emitting gallium and nitrogen containing laser diodes, different wavelength visible phosphor emission, and different wavelength IR laser diode peak emission wavelengths. For example, the IR laser diode could operate with a peak wavelength of between 700 nm and 3 um.

The IR lasers according to the present invention could be configured to emit at wavelengths between 700 nm and 2.5 microns. The IR laser diode can be used to provide an IR illumination function or a LiFi/VLC communication function, or a combination of both functions. For example, a laser diode emitting in the 700 nm to 1100 nm range based on GaAs for NIR night vision illumination, range finding and LIDAR sensing, and communication could be included. In another example a laser diode operating in the 1100 to 2500 nm range based on InP for eye-safe wavelength IR illumination, range finding, LIDAR sensing, and communication could be included. In yet another example, a laser diode operating the in 2500 nm to 15000 nm wavelength range based on quantum cascade laser technology for mid-IR thermal imaging, sensing, and communication could be included. For example, GaInAs/AlInAs quantum cascade lasers operate at room temperature in the wavelength range of 3 μm to 8 μm. IR laser diode devices according to the present invention could be formed on InP substrates using the InGaAsP material system or formed on GaAs substrates using the InAlGaAsP. Quantum cascade lasers can be included for IR emission. In one embodiment one or more IR laser devices could be formed on the same carrier wafer as the visible violet or blue GaN laser diode source using the epitaxy transfer technology according to this invention. Such a device would be advantageous for IR illumination since it could be low cost, compact, and have similar emission aperture location as the visible laser diode to effectively superimpose the IR emission and the visible light emission. Additionally, such a device would be advantageous in communication applications as the IR laser diode, while not adding to the luminous efficacy of the light engine, would provide a non-visible channel for communications. This would allow for data transfer to continue under a broader range of conditions. For example, a VLC-enabled light engine using only visible emitters would be incapable of effectively transmitting data when the light source is nominally turned off as one would find in, for example, a movie theater, conference room during a presentation, a moodily lit restaurant or bar, or a bed-room at night among others. In another example, the non-converted laser device might emit a spectrum corresponding to blue or violet light, with a center wavelength between 390 and 480 nm. In some embodiments the gallium and nitrogen containing laser diode operates in the 480 nm to 540 nm range, or can operate in the UV range from about 270 nm to 390 nm. In another embodiment, the non-converted blue or violet laser may either be not incident on the wavelength converting element and combined with the white light spectrum in beam shaping and combining optics. In some embodiments the visible and/or IR emission from the light source are coupled into an optical waveguide such as an optical fiber, which could be a glass optical fiber or a plastic optical fiber.

In a second embodiment of the present invention a second wavelength converter element member is included to provide an emission in the IR regime at a third peak wavelength, to provide the IR emission component of the dual band emitting light source. The IR wavelength converter member, such as a phosphor member, is configured to receive and absorb a laser induced pump light and emit a longer wavelength IR light. In this embodiment, the dual band light source comprises the first wavelength converter member for emitting visible light and the second wavelength converter member for emitting IR light.

Typically, the difference in the down converters from LED to Laser is the change from a powder phosphor solution in a silicone binder matrix, to solid body phosphors of single crystals, sintered, hybrids and phosphors in Glass. The solid body phosphor is generally required to reduce the extreme heat generation under blue laser excitation in a small, controlled spot.

Extending the usable wavelength range for laser based lighting, it is possible to use Infrared down-converting phosphors to generate emission in the NIR (0.7-1.4 um) and mid-IR (1.4-3.0 um) spectrum, or into the deeper IR of beyond 3.0 um. This could be purely IR emission, or a combination of visible and infrared emission depending on application requirements. A large number of potential IR phosphors exist, but their suitability depends on the application wavelength, and the phosphors inherent properties for conversion of visible light to IR light. IN some embodiments the phosphor emission is characterized by a 1550 nm photoluminescence peak wavelength emission associated with the $Er+3$ ion 4f-4 intraband transition.

Some examples of phosphor materials that produce infrared light emission include $Lu_3Al_5O_{12}$: 0.05 $Ce3+$, 0.5% $Cr3+$ emitting in the 500-850 nm range, $La_3Ga_{4.95}GeO_{14}$: 0.05 $Cr3+$ emitting in the 600-1200 nm range, Bi-doped $GeO_2$ glass emitting in the 1000-1600 nm range, $Ca_2LuZr_2Al_3O_{12}$:0.08 $Cr3+$ emitting in the 650-850 nm range, $ScBO_3$:0.02 $Cr3+$ emitting in the 700-950 nm range, $YAl_3(BO_3)_4$:0.04 $Cr3+$, 0.01 $Yb3+$ emitting in the 650-850 nm and 980 nm range, and $NaScSi_2O_6$: 0.06 $Cr3+$ emitting in the 750-950 nm range.

Additionally, a large body of work for infrared phosphors has centered around the use of $Cr3+$ materials. For example, $ZnGa_2O_4$ emitting in the 650-750 nm range, $Zn(Ga_{1-x}Al_x)_2O_4$ emitting in the 675-800 nm range, $Zn_xGa_2O_{3+x}$ emitting in the 650-750 nm range, $MgGa_2O_4$ emitting in the 650-770 nm range, $Zn_3Ga_2Ge_2O_{10}$ emitting in the 650-1000 nm range, $Zn_{1+x}Ga_{2-2x}(Ge,Sn)_xO_4$ emitting in the 650-800 nm range, $Zn_3Ga_2Ge_2O_{10}$ emitting in the 600-800 nm range, $Zn_3Ga_2Sn_1O_8$ emitting in the 600-800 nm range, $Ca_3Ga_2Ge_3O_{12}$ emitting in the 670-1100 nm range, $Ca_{14}Zn_6Al_{10}O_{35}$ emitting in the 650-750 nm range, $Y_3Al_2Ga_3O_{10}$ emitting in the 500-800 nm range, $Gd_3Ga_5O_{10}$ emitting in the 650-800 nm range, $Lu_3Al_5O_{12}$ emitting in the 500-850 nm range, $La_3Ga_5GeO_{14}$ emitting in the 600-1200 nm range, $LiGa_5O_8$ emitting in the 650-850 nm range, $\beta$-$Ga_2O_3$ emitting in the 650-850 nm range, and $SrGa_{12}O_{19}$ emitting in the 650-950 nm range.

In some embodiments according to the present invention the IR wavelength converter members are comprised of semiconductor materials. In one example solid state structures employing semiconductor bulk material structures, quantum well structures, or quantum wire structures configured to emit infrared light are included. Some examples of such solid structures capable of emitting IR electromagnetic radiation include, Si emitting in the 700-1000 nm range, Ge emitting in the 800-2000 nm range, GaAs emitting in the 800-900 nm range, InP emitting in the 800-900 nm range, InGaAs emitting in the 900-1700 nm range, InAs emitting in the 2000-3000 nm range, InAlAs emitting in the 900-1600 nm range, AlGaAs emitting in the 700-900 nm range, AlInGaP emitting in the 600-800 nm range, InGaAsP emitting in the 1200-1800 nm range, InGaAsSb emitting in the 1800-3500 nm range, GaSb in the 1000-1300 nm range, GaInSb emitting in the 1600-1900 nm range, InSb emitting in the 2500-3000 nm range, CdTe emitting in the 700-800 nm range, HgTe emitting in the 3800-5000 nm range, $[Hg_xCd_{1-x}]Te$ emitting in the 700-5000 nm range.

Alternatively, infrared emitting quantum dot materials of the proper size can be incorporated as wavelength converter members in the present invention. Some examples of materials choices for infrared emitting quantum dots are Si emitting in the 700-1000 nm range, Ge emitting in the 800-2000 nm range, GeSn emitting in the 800-1500 nm range, PbS emitting in the 700-2000 nm range, PbSe emitting in the 800-5000 nm range, PbTe emitting in the 900-3000 nm range, InAs emitting in the 750-3000 nm range, InSb emitting in the 1000-2500 nm range, HgTe emitting in the 1000-5000 nm range, $Ag_2S$ emitting in the 700-1500 nm range, $Ag_2Se$ emitting in the 900-2000 nm range, $CuInSe_2$ emitting in the 650-1500 nm range, $AgInSe_2$ emitting in the 600-900 nm range, and $Cs_{1-x}F_{Ax}PbI_3$ emitting in the 650-850 nm range, but of course there could be others.

In order to incorporate IR emitting phosphors in a blue/near UV laser based device, a number of conditions should be met.

IR Phosphor fluoresces under laser emission wavelengths of near UV and/or Blue (e.g., 380 nm-480 nm).

IR phosphor fluoresces under secondary emission from visible emitting phosphors in device (e.g., 480 nm-700 nm). This reduces the stokes shift losses as compared to direct laser fluorescence, thereby reducing heating of the IR phosphor.

IR phosphor can be incorporated into a solid body element such as a single crystal, sintered, hybrid, or phosphor in glass structure. This structure could be composed of both Visible and IR emitting phosphor materials, or as separate structures.

The IR phosphor member can be comprised of different solid or powder micro-structures and configured for excitation by the laser diode excitation source. In some embodiments the phosphors would be configured with coating layers to modify the reflectivity of the excitation light and/or modify the reflectivity of the IR phosphor emission, and/or modify the reflectivity of the visible phosphor emission. In one example according to this invention, the phosphor would contain an antireflective coating layer on the excitation surface configured to reduce the reflectivity of the excitation beam such that it can be more efficiently converted to IR or visible light within the phosphor member. Such coating layers could be comprised of dielectric layers such as silicon dioxide, tantalum pentoxide, hafnia, aluminum oxide, silicon nitride, or others. In some embodiments the phosphor surface is intentionally roughened or patterned to reduce the reflectivity and induce an optical scattering effect.

In another example according to this invention, the phosphor is configured for a transmission mode operation wherein the excitation surface and the emission surface would be on opposite sides or faces of the phosphor. In this configuration, the phosphor could have an antireflective coating layer on the emission surface configured to reduce the reflectivity of the IR phosphor emission such that it can more efficiently exit the phosphor member as useful IR emission from the emission surface. Such coating reflectivity reducing layers could be comprised of dielectric layers such as silicon dioxide, tantalum pentoxide, hafnia, aluminum oxide, silicon nitride, or others. In some embodiments the phosphor surface is intentionally roughened or patterned to reduce the reflectivity and induce an optical scattering effect.

In another example according to this invention, the phosphor is configured for a reflective mode operation wherein the excitation beam is incident on the emission surface such that emission and excitation of the phosphor takes place on the same side or face of the phosphor member. In this configuration, the phosphor could have an antireflective coating layer on the emission surface configured to reduce the reflectivity of the IR phosphor emission such that it can more efficiently exit the phosphor member and/or reduce the reflectivity of the excitation light such that it can more efficiently penetrate into the phosphor where it can be converted to useful IR emission. Such coating layers could be comprised of dielectric layers such as silicon dioxide, tantalum pentoxide, hafnia, aluminum oxide, silicon nitride, or others. Moreover, in some embodiments comprised of a reflection mode phosphor the backside or bottom side of the phosphor member would be configured with a highly reflective coating or layer. The reflective coating would function to reflect the IR emitted light generated in the phosphor off the back surface so that it can be usefully emitted through the top or front side emission surface. The reflective coating could also be configured to reflect the excitation light. Such reflective coating layers could be comprised of metals such as Ag, Al, or others, or could be comprised of dielectric layers such as distributed Bragg reflector (DBR) stacks.

FIG. 11 provides schematic diagrams of different IR phosphor members. In FIG. 20A a single crystal phosphor member is configured for reflective mode operation. Single crystal phosphors can offer performance benefits such as high thermal conductivity to enable operation at high temperature and excitation density. The single crystal phosphor in FIG. 20A is contains a reflective mirror on the back or bottom side of the phosphor. The mirror stack can also be designed for a soldering attach process wherein diffusion barrier layers can be included to prevent damage to the mirror layer when the single crystal IR phosphor member is attached to a package or support member. The reflective mode single crystal phosphor of FIG. 20A is configured with an anti-reflective coating and/or a roughening or patterning of the top side emission surface.

Figure 20B:
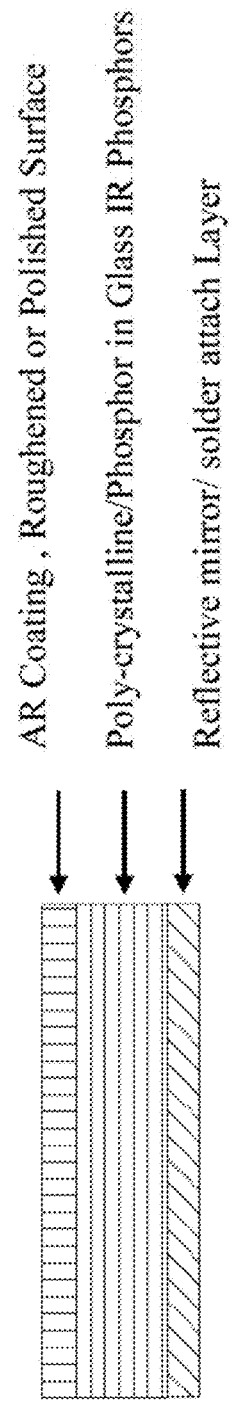
FIG. 20B is a schematic diagram of an IR emitting phosphor in glass member configured for reflection mode operation according to an embodiment of the present invention.

In FIG. 20B a phosphor in glass member is configured for reflective mode operation. Such phosphor in glass structures can offer performance benefits such as high optical scattering of the excitation emission and the phosphor emission to control and contain the emission area, while offering acceptable thermal conductivity for operation at high temperature and excitation density. The phosphor in glass structure in FIG. 20A is contains a reflective mirror on the back or bottom side of the phosphor. The mirror stack can also be designed for a soldering attach process wherein diffusion barrier layers can be included to prevent damage to the mirror layer when the phosphor in glass IR phosphor member is attached to a package or support member. The reflective mode phosphor in glass structure of FIG. 20B is configured with an anti-reflective coating and/or a roughening or patterning of the top side emission surface.

Figure 20C:
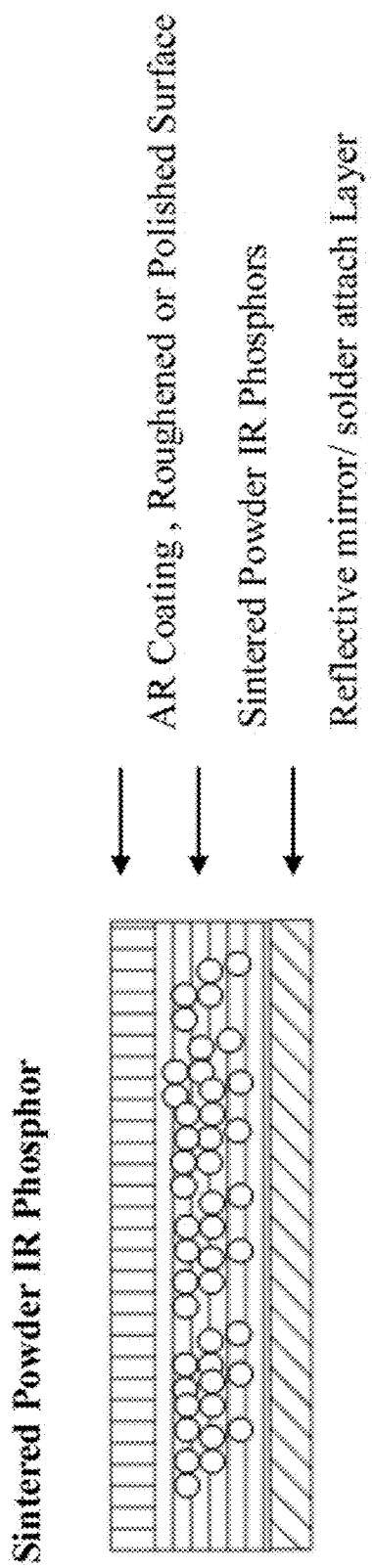
FIG. 20C is a schematic diagram of a sintered powder or ceramic IR emitting phosphor configured for reflection mode operation according to an embodiment of the present invention.

In FIG. 20C a sintered powder or ceramic phosphor is configured for reflective mode operation. Such sintered powder or ceramic phosphor structures can offer performance benefits such as high optical scattering of the excitation emission and the phosphor emission to control and contain the emission area, while offering acceptable thermal conductivity for operation at high temperature and excitation density. The sintered powder or ceramic phosphor in FIG. 20C is contains a reflective mirror on the back or bottom side of the phosphor. The mirror stack can also be designed for a soldering attach process wherein diffusion barrier layers can be included to prevent damage to the mirror layer when the sintered powder or ceramic IR phosphor member is attached to a package or support member. The reflective mode sintered powder or ceramic phosphor structure of FIG. 20C is configured with an anti-reflective coating and/or a roughening or patterning of the top side emission surface.

When integrating the IR emitting phosphor member with the laser based white light illumination source there are multiple arrangements that the visible emitting and IR emitting phosphor members can be configured with respect to each other. The examples provided in this application are not intended to coverall all such arrangements and shall not limit the scope of the present invention, because of course there could be other arrangements and architectures. Perhaps the most simple example phosphor arrangement would have the first and second wavelength converter members configured in a side by side, or adjacent arrangement such that the white light emission from the first wavelength converter member is emitted from a separate spatial location than the IR emission from the second wavelength converter member. In this example, the first and second wavelength converter members could be excited by separate laser diode members wherein in one embodiment the first wavelength converter member would be excited by a first gallium and nitrogen containing laser diodes such as violet, blue, or green laser diodes, and the second wavelength converter member would be excited by a second gallium and nitrogen containing laser diodes such as violet, blue, or green laser diodes. In a second embodiment of this example the first wavelength converter member is excited by a first gallium and nitrogen containing laser diode such as a violet or blue laser diode, and the second wavelength converter member is excited by a second laser diode formed from a different material system operating in the red or IR wavelength region, such as a gallium and arsenic containing material or an indium and phosphorous containing material. In these embodiments the first laser diode would be excited by a first drive current and the second laser diode would be excited by a second drive current. Since the first and second drive currents could be activated independently, the dual band light emitting source could provide a visible light source with only the first driving current activated, an IR light source with only the second driving current activated, or could simultaneously provide both a visible and IR light source with both the first and second drive currents activated. In some applications it would be desirable to only use the IR illumination source for IR detection. Once an object is detected with the IR illumination, the visible light source can be activated to visibly illuminate the target.

Figure 21A:
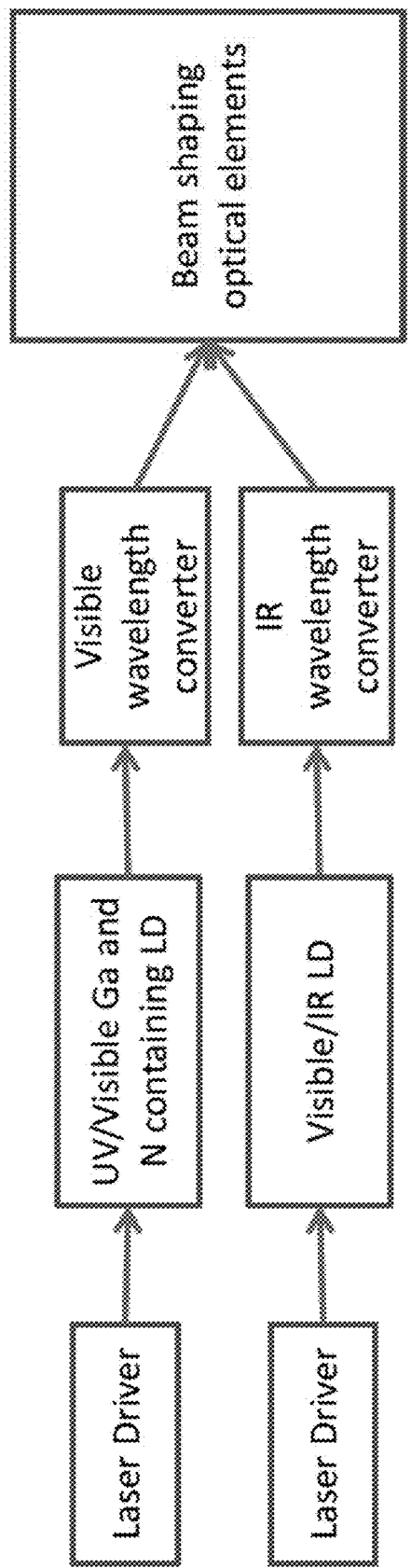
FIG. 21A is a functional block diagram for a laser-based white light source integrated with an IR illumination source containing a UV or blue pump laser, a red or near-IR emitting laser diode, a visible light emitting phosphor member, and a IR emitting phosphor member according to an embodiment of the present invention.

FIG. 21A is a functional block diagram for a laser-based white light source containing a gallium and nitrogen containing violet or blue pump laser and a wavelength converting element to generate a white light emission, and an infrared emitting wavelength converter member to generate an IR emission according to an embodiment of the present invention. Referring to FIG. 21A, a blue or violet laser device formed from a gallium and nitrogen containing material emitting a spectrum with a center point wavelength between 390 and 480 nm is provided. In some embodiments the gallium and nitrogen containing laser diode operates in the 480 nm to 540 nm range. In some embodiments the laser diode is comprised from a III-nitride material emitting in the ultraviolet region with a wavelength of about 270 nm to about 390 nm. The light from the violet or blue laser device is incident on a wavelength converting element, which partially or fully converts the blue light into a broader spectrum of longer wavelength light such that a white light spectrum is produced. A laser driver is provided which powers the gallium and nitrogen containing laser device. The light from the blue laser device is incident on a wavelength converting element, which partially or fully converts the blue light into a broader spectrum of longer wavelength light such that a white light spectrum is produced. In some embodiments, one or more beam shaping optical elements may be provided in order to shape or focus the white light spectrum. Additionally, an IR emitting wavelength converter member with a peak emission wavelength in the 650 nm to 2000 nm, or greater, range is included. A second laser device is included to excite the IR wavelength converter and generate the IR illumination emission. A laser driver is included to power the IR emitting laser diode. In some embodiments a beam shaper element is included to collect and direct the IR illumination emission. In a preferred embodiment, the IR illumination and the white light illumination emission share at least a common beam shaping element such that the illumination areas of the visible light and the IR light can be approximately super-imposed. Optionally, the one or more beam shaping optical elements can be one selected from slow axis collimating lens, fast axis collimating lens, aspheric lens, ball lens, total internal reflector (TIR) optics, parabolic lens optics such as parabolic reflectors, refractive optics, or a combination of above. In other embodiments, the one or more beam shaping optical elements can be disposed prior to the laser light incident to the wavelength converting element.

In some embodiments the visible and/or IR emission from the light source are coupled into an optical waveguide such as an optical fiber, which could be a glass optical fiber or a plastic optical fiber. The optical fiber of an arbitrary length, including a single mode fiber (SMF) or a multi-mode fiber (MMF), with core diameters ranging from about 1 um to 10 um, about 10 um to 50 um, about 50 um to 150 um, about 150 um to 500 um, about 500 um to 1 mm, about 1 mm to 5 mm or greater than 5 mm. The optical fiber is aligned with a collimation optics member to receive the collimated white light and/or IR emission.

In another embodiment of the above example, the adjacent or side by side wavelength converter elements are excited by the same gallium and nitrogen containing laser diode with a peak wavelength in the violet or blue wavelength range. This can be accomplished in several ways. One such way is to position the output laser excitation beam such that it is incident on both the first visible emitting wavelength converting member and the second IR emitting phosphor member. This configuration could be designed such that the proper fraction of the beam is incident on the first wavelength converting member for a desired visible light emission and a proper fraction incident on the second wavelength converter member for a desired IR light emission. In another such example, a beam steering element such as a MEMS scanning mirror could be included in the system. The beam steering element could be programmed or manually tuned to steer the excitation laser beam to be incident on the first wavelength converting element to generate a visible light when desired and to steer the beam to be incident on the IR emitting phosphor when desired. In this configuration, the dual band illumination source could selectively illuminate in either the visible or the IR spectrum, or simultaneously illuminate in both spectrums.

Figure 21B:
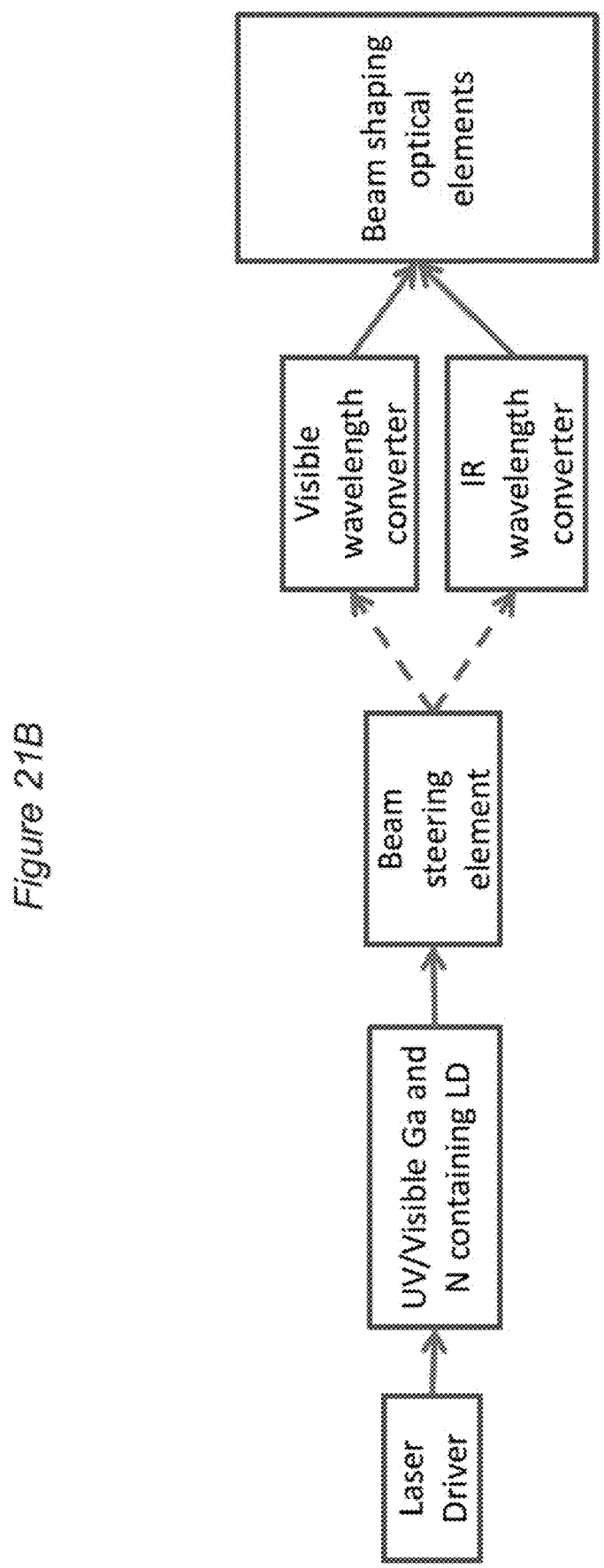
FIG. 21B is a functional block diagram for a laser-based white light source integrated with an IR illumination source containing a UV or blue pump laser diode, a beam steering element, a visible light emitting phosphor member, and an IR emitting phosphor member according to an embodiment of the present invention.

FIG. 21B is a functional block diagram for a laser-based white light source containing a gallium and nitrogen containing violet or blue pump laser and a wavelength converting element to generate a white light emission, and an infrared emitting wavelength converter member to generate an IR emission according to an embodiment of the present invention. Referring to FIG. 21B, a blue or violet laser device formed from a gallium and nitrogen containing material emitting a spectrum with a center point wavelength between 390 and 480 nm is provided. In some embodiments the gallium and nitrogen containing laser diode operates in the 480 nm to 540 nm range. In some embodiments the laser diode is comprised from a III-nitride material emitting in the ultraviolet region with a wavelength of about 270 nm to about 390 nm. The light from the violet or blue laser device is incident on a beam steering element such as a MEMS scanning mirror. The beam steering element functions to optionally steer the excitation beam to the first wavelength converting element to partially or fully converts the blue light into a broader spectrum of longer wavelength light such that a white light spectrum is produced or to a second wavelength converting element to generate an IR emission. A laser driver is provided which powers the gallium and nitrogen containing laser device. The IR emitting wavelength converter member can have a peak emission wavelength in the 650 nm to 2000 nm, or greater, range. In a preferred embodiment, the IR illumination and the white light illumination emission share at least a common beam shaping element such that the illumination areas of the visible light and the IR light can be approximately super-imposed. Optionally, the one or more beam shaping optical elements can be one selected from slow axis collimating lens, fast axis collimating lens, aspheric lens, ball lens, total internal reflector (TIR) optics, parabolic lens optics such as parabolic reflectors, refractive optics, or a combination of above. In other embodiments, the one or more beam shaping optical elements can be disposed prior to the laser light incident to the wavelength converting element. In some embodiments the visible and/or IR emission from the light source are coupled into an optical waveguide such as an optical fiber, which could be a glass optical fiber or a plastic optical fiber.

In another example according to this invention, the first wavelength converter member and the second wavelength converter member could be combined. In one combination configuration the visible emitting wavelength converter and the IR emitting wavelength converter are vertically stacked arrangement. Preferably the first wavelength converter member would be arranged on the same side as the primary emission surface of the stacked wavelength converter arrangement such that the IR light emitted from the second wavelength converter can pass through the first wavelength converter member without appreciable absorption. That is, in a reflective mode configuration, the first wavelength converter member emitting the visible light would be arranged on top of the second wavelength converter member emitting the IR light such that the visible and IR emission exiting the emission surface of the first wavelength converter would be collected as useful light. That is, the IR emission with the third peak wavelength would be emitted into the same optical pathway as the white light emission with the first and second peak wavelengths.

Figure 22A:
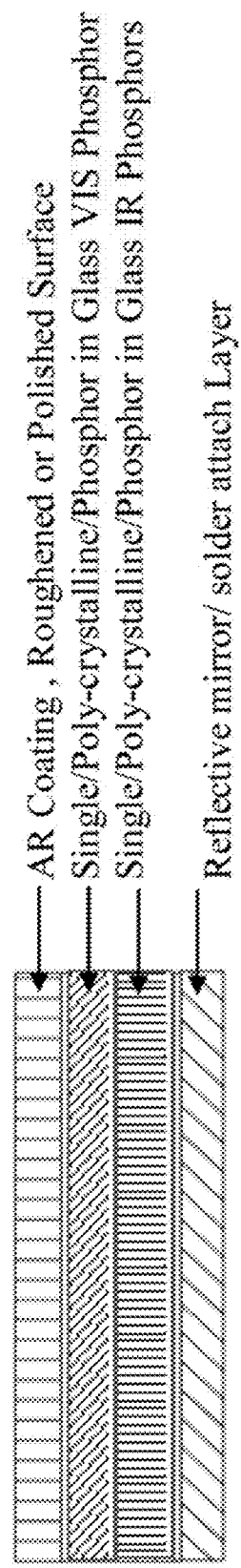
FIG. 22A is a schematic diagram of a stacked phosphor member comprised of a visible light emitting phosphor and a IR emitting phosphor configured for reflection mode operation according to an embodiment of the present invention.

FIG. 22A presents an example schematic diagram of a stacked phosphor configured for reflection mode operation wherein the IR emitting phosphor member is positioned below the visible emitting phosphor. The stacked phosphor member in FIG. 22A is contains a reflective mirror on the back or bottom side of the phosphor. The mirror stack can also be designed for a soldering attach process wherein diffusion barrier layers can be included to prevent damage to the mirror layer when the stacked phosphor member is attached to a package or support member. The stacked phosphor member of FIG. 22A is configured with an antireflective coating and/or a roughening or patterning of the top side emission surface.

In another combination configuration the visible emitting wavelength converter and the IR emitting wavelength converter are integrated into a single volume region to form single hybrid wavelength converter member. This can be achieved in various ways such as sintering a mixture of wavelength converters elements such as phosphors into a single solid body. For example, one would mix a visible light emitting phosphor member such as a YAG based phosphor with an IR emitting phosphor to form a composited phosphor or wavelength converter member. In this composite wavelength converter configuration, a common gallium and nitrogen containing laser diode member could be configured as the excitation source to generate both the visible light and the IR light. In this configuration the activating the laser diode member with a first drive current would excite both the emission of the visible light and the IR light such that independent control of the emission of the visible light and IR light would be difficult.

Figure 22B:
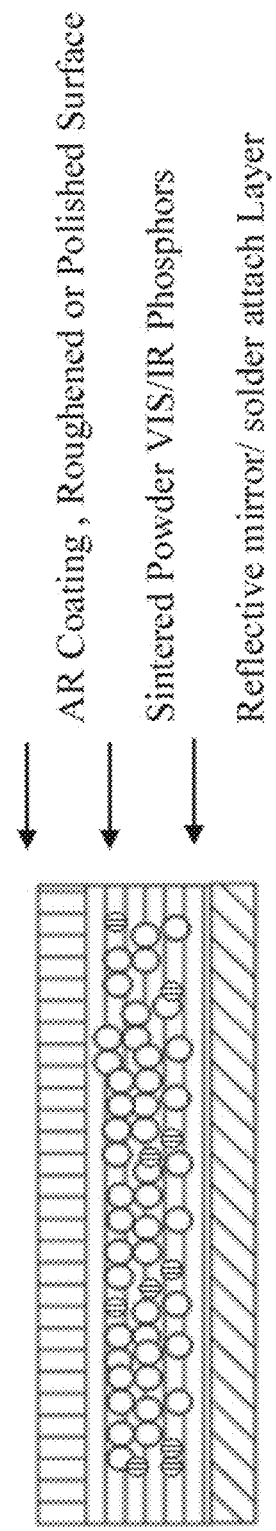
FIG. 22B is a schematic diagram of a composite phosphor member comprised of visible light emitting phosphor elements and IR emitting phosphor elements combined into a common volume region and configured for reflection mode operation according to an embodiment of the present invention.

FIG. 22B presents an example schematic diagram of a composite configured for reflection mode operation wherein the IR emitting phosphor elements are sintered into the same volume region as the visible emitting phosphor elements. The composite phosphor member in FIG. 22B is contains a reflective mirror on the back or bottom side of the phosphor. The mirror stack can also be designed for a soldering attach process wherein diffusion barrier layers can be included to prevent damage to the mirror layer when the composite phosphor member is attached to a package or support member. The composite phosphor member of FIG. 22B is configured with an anti-reflective coating and/or a roughening or patterning of the top side emission surface.

In this composite wavelength converter configuration, a common gallium and nitrogen containing laser diode member could be configured as the excitation source for both the first and second wavelength member. Since the IR and visible light emission would exit the stacked wavelength converter members from the same surface and within approximately the same area, a simple optical system such as collection and collimation optics can be used to project and direct both the visible emission and the IR emission to the same target area. In this configuration activating the laser diode member with a first drive current would excite both the emission of the visible light and the IR light such that independent control of the emission of the visible light and IR light would be difficult. Other vertically stacked wavelength converter members are possible such as positioning the IR emitting second wavelength converter member on the emission side of the stack such that the visible light emission from the first wavelength converter member would function to excite IR emission from the second wavelength converter member.

Figure 23A:
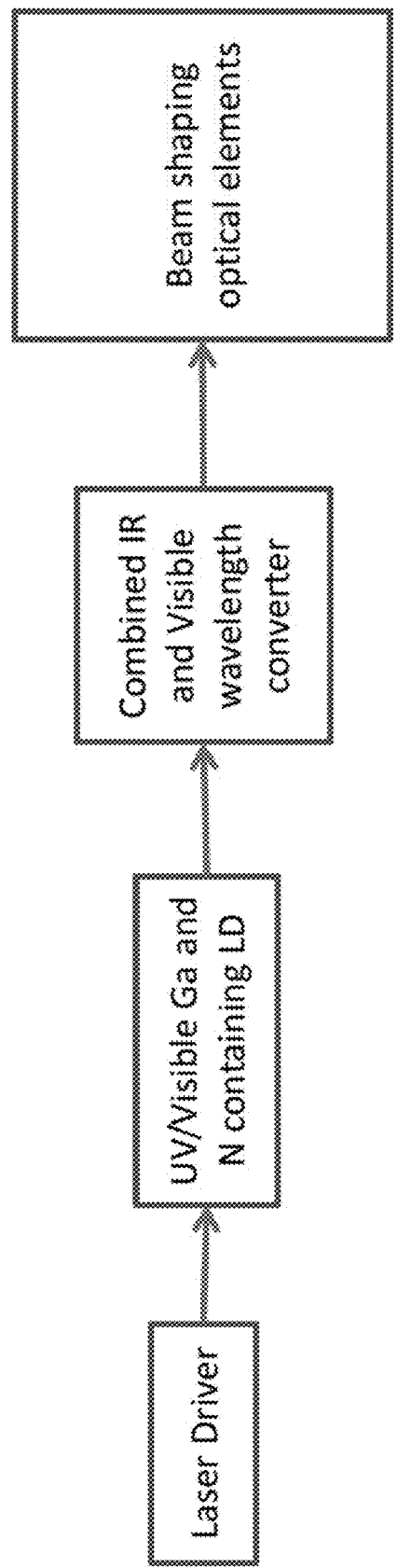
FIG. 23A is a functional block diagram for a laser-based white light source integrated with an IR illumination source containing a UV or blue pump laser diode and a phosphor member configured for both visible light emission and IR emission according to an embodiment of the present invention.

FIG. 23A is a functional block diagram for a laser-based white light source containing a gallium and nitrogen containing violet or blue pump laser configured to excite a wavelength converting element to generate a white light emission and a wavelength converting element to generate an IR emission according to an embodiment of the present invention. Referring to FIG. 23A, a blue or violet laser device formed from a gallium and nitrogen containing material emitting a spectrum with a center point wavelength between 390 and 480 nm is provided. In some embodiments the gallium and nitrogen containing laser diode operates in the 480 nm to 540 nm range. In some embodiments the laser diode is comprised from a III-nitride material emitting in the ultraviolet region with a wavelength of about 270 nm to about 390 nm. The light from the violet or blue laser device is incident on a wavelength converting element that is comprised of both a visible emitting element and an IR emitting element, which could be configured in a stacked or composite arrangement. The visible wavelength converter element, such as a phosphor, partially or fully converts the blue light into a broader spectrum of longer wavelength light such that a white light spectrum is produced. Moreover, the blue light from the laser diode and/or the visible light from the visible emitting wavelength converter member excites the IR emitting phosphor to generate an IR illumination. A laser driver is provided which powers the gallium and nitrogen containing laser device. In some embodiments, one or more beam shaping optical elements may be provided in order to shape or focus the white light spectrum. In a preferred embodiment, the IR illumination and the white light illumination emission share at least a common beam shaping element such that the illumination areas of the visible light and the IR light can be approximately superimposed. Optionally, the one or more beam shaping optical elements can be one selected from slow axis collimating lens, fast axis collimating lens, aspheric lens, ball lens, total internal reflector (TIR) optics, parabolic lens optics such as parabolic reflectors, refractive optics, or a combination of above. In other embodiments, the one or more beam shaping optical elements can be disposed prior to the laser light incident to the wavelength converting element. In some embodiments the visible and/or IR emission from the light source are coupled into an optical waveguide such as an optical fiber, which could be a glass optical fiber or a plastic optical fiber.

Figure 23B:
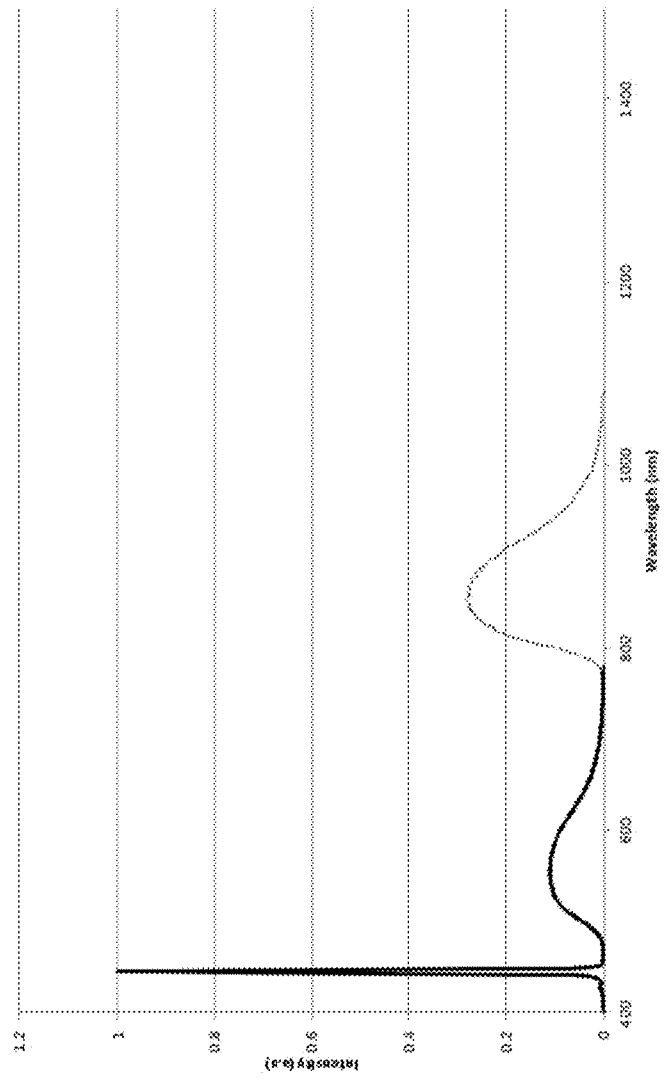
FIG. 23B is an example optical spectrum of a laser based white light source configured with an IR emitting wavelength converter to provide an IR illumination according to an embodiment of the present invention.

The resulting spectrum from the embodiment described in FIG. 23A according to the present invention would be comprised of a relatively narrow band (about 0.5 to 3 nm) emission spectrum from the gallium and nitrogen containing laser diode in the UV or blue wavelength region, a broadband (about 10 to 100 nm) wavelength converter emission in the visible spectrum with a longer peak wavelength than the UV or blue laser diode, and a relatively broadband (about 10 to 100 nm) wavelength converter emission in the IR spectrum with a longer peak wavelength than the peak emission wavelength from the visible phosphor member. FIG. 23B presents an example optical spectrum according to the present invention. In this figure, the gallium and nitrogen containing laser diode emits in the blue region at about 440 to 455 nm, the visible wavelength converter member emits in the yellow region, and the included IR emitting wavelength converter member emits with a peak wavelength of about 850 to 900 nm. Of course there can be many other configurations of the present invention, including different wavelength emitting gallium and nitrogen containing laser diodes, different wavelength emitting visible phosphor member, and different wavelength emitting IR phosphor members. For example, the IR emitting phosphor member could emit a peak wavelength of between 700 nm and 3 um.

In another example of the present example with the combined wavelength converter members the first and second wavelength converter members could be excited by separate laser diode members wherein in one embodiment the first wavelength converter member would be excited by a first gallium and nitrogen containing laser diodes such as violet or blue laser diode and the second wavelength converter member would be excited by a second gallium and nitrogen containing laser diodes such as a green emitting or longer wavelength laser diode. In a second embodiment of this example the first wavelength converter member is excited by a first gallium and nitrogen containing laser diode such as a violet or blue laser diode, and the second wavelength converter member is excited by a second laser diode formed from a different material system operating in the red or IR wavelength region, such as a gallium and arsenic containing material or an indium and phosphorous containing material. The key consideration for this embodiment is to select the second laser diode with an operating wavelength that will not be substantially absorbed in the first wavelength converter member, but will be absorbed in the second wavelength converter member such that when the second laser diode is activated the emission will pass through the first wavelength converter to excite the second wavelength converter and generate the IR emission. The result is that the first laser diode member primarily activates the first wavelength converter member to generate visible light and the second laser diode member primarily activates the second wavelength converter to generate IR light. The benefit to this version of the stacked wavelength converter configuration is that since the first laser diode would be excited by a first drive current and the second laser diode would be excited by a second drive current the first and second wavelength converter members could be activated independently such that the dual band light emitting source could provide a visible light source with only the first driving current activated, an IR light source with only the second driving current activated, or could simultaneously provide both a visible and IR light source with both the first and second drive currents activated. In some applications it would be desirable to only use the IR illumination source for IR detection. It is to be understood that the visible light emission from the from the first wavelength converter member may at least partially excite IR emission from the second wavelength converter member. In this case, the source may simultaneously emit both visible and IR emission when the visible light is activated. Thus, for dual emission of both the visible light and the IR emission, in one embodiment according to the present invention, only the first gallium and nitrogen containing laser diode operating in the violet or blue region may be required. However, and very importantly, when the longer wavelength laser diode is activated to excite the IR emitting wavelength converter member, no substantial visible light would be emitted. This would enable IR illumination of a target without revealing the presence of the illumination source. Once an object was detected, the visible light source could be activated.

Alternatively, the visible light emission could be excited by a first gallium and nitrogen containing laser diode such as a violet or blue laser diode, and the IR emission could be excited by a second laser diode formed from a different material system operating in the red or IR wavelength region, such as a gallium and arsenic containing material or an indium and phosphorous containing material. The key consideration for this embodiment is to select the second laser diode with an operating wavelength that will not be substantially absorbed in the visible light emitting element of the composite wavelength converter member, but will be absorbed in the IR emitting element of the composite wavelength converter member such that when the second laser diode is activated it will not substantially excite the visible light emission, but will excite the IR emission. The result is that the first laser diode member primarily activates the first wavelength converter member to generate visible light and the second laser diode member primarily activates the second wavelength converter to generate IR light. Since the IR emission with the third peak wavelength would be emitted from the same surface and spatial location as the visible emission with the first and second peak wavelengths, the IR emission would be easily directed into the same optical pathway as the white light emission with the first and second peak wavelengths. The IR emission and white light emission could then be directed through the optional beam shaper configured to direct the output light for illuminating a target of interest. In this embodiment the first and second driving current could be activated independently such that the apparatus could provide a visible light source with only the first driving current activated, an IR light source with the second driving current activated, or could simultaneously provide both a visible and IR light source. In some applications it would be desirable to only use the IR illumination source for IR detection. Once an object is detected with the IR illumination, the visible light source can be activated to visibly illuminate the target.

The benefit to this version of the stacked wavelength converter configuration is that since the first laser diode would be excited by a first drive current and the second laser diode would be excited by a second drive current the first and second wavelength converter members could be activated independently such that the dual band light emitting source could provide a visible light source with only the first driving current activated, an IR light source with only the second driving current activated, or could simultaneously provide both a visible and IR light source with both the first and second drive currents activated. It is to be understood that the visible light emission from the from the first wavelength converter member may at least partially excite IR emission from the second wavelength converter member. In this case, the source may simultaneously emit both visible and IR emission when the visible light is activated. Thus, for dual emission of both the visible light and the IR emission, in one embodiment according to the present invention only the first gallium and nitrogen containing laser diode operating in the violet or blue region may be required. However, and very importantly, when the longer wavelength laser diode is activated to excite the IR emitting wavelength converter member, no substantial visible light would be emitted. This would enable IR illumination of a target without revealing the presence of the illumination source. In some applications it would be desirable to only use the IR illumination source for IR detection. Once an object was detected, the visible light source could be activated.

Figure 24A:
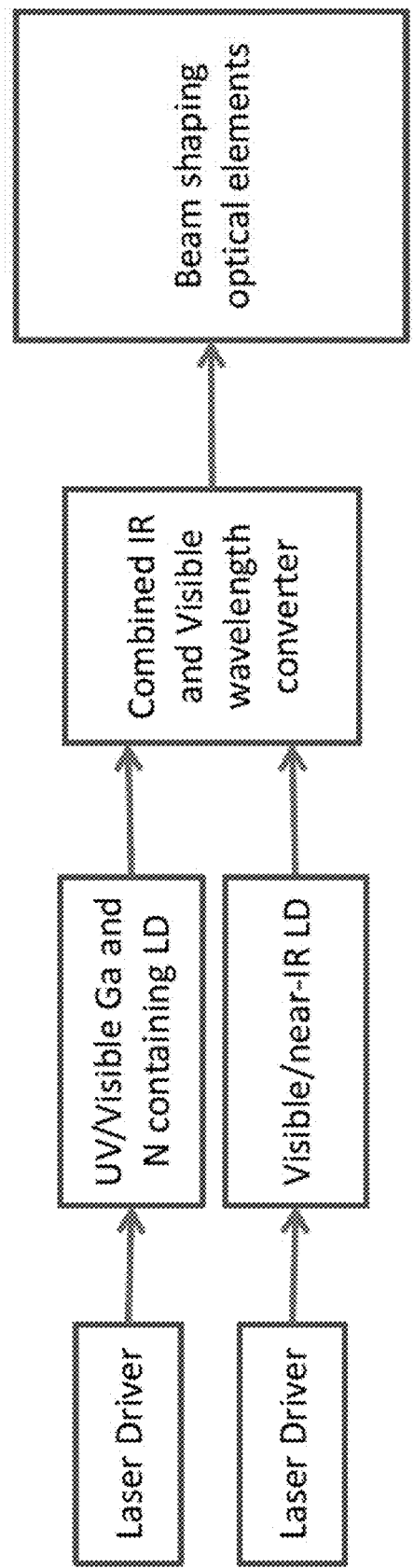
FIG. 24A is a functional block diagram for a laser-based white light source integrated with an IR illumination source containing a UV or blue pump laser, a red or near-IR emitting laser diode, and a phosphor member configured for both visible light emission and IR emission according to an embodiment of the present invention.

FIG. 24A is a functional block diagram for a laser-based white light source containing a gallium and nitrogen containing violet or blue pump laser configured to excite a wavelength converting element to generate a white light emission, and an IR emitting laser diode configured to pump an IR wavelength converting element to generate an IR emission according to an embodiment of the present invention. Referring to FIG. 24A, a blue or violet laser device formed from a gallium and nitrogen containing material emitting a spectrum with a center point wavelength between 390 and 480 nm is provided. In some embodiments the gallium and nitrogen containing laser diode operates in the 480 nm to 540 nm range. In some embodiments the laser diode is comprised from a III-nitride material emitting in the ultraviolet region with a wavelength of about 270 nm to about 390 nm. The light from the violet or blue laser device is incident on a wavelength converting element that is comprised of both a visible emitting element and an IR emitting element, which could be configured in a stacked or composite arrangement. The visible wavelength converter element, such as a phosphor, partially or fully converts the blue light into a broader spectrum of longer wavelength light such that a white light spectrum is produced. In some embodiments the blue light from the laser diode and/or the visible light from the visible emitting wavelength converter member could excite the IR emitting phosphor to generate an IR illumination. A laser driver is provided which powers the gallium and nitrogen containing laser device. A second laser diode is included. The second laser diode operates with a peak wavelength that is longer than the visible emission from the first wavelength converter member, but shorter than the peak wavelength of the IR emitting wavelength converter member. A second laser driver is configured to drive the second laser diode member. The output electromagnetic emission from the second laser diode member is configured to preferentially excite the IR emitting phosphor member without substantially exciting the visible phosphor member. In some embodiments, one or more beam shaping optical elements may be provided in order to shape or focus the white light and the IR emission spectrums. In a preferred embodiment, the IR illumination and the white light illumination emission share at least a common beam shaping element such that the illumination areas of the visible light and the IR light can be approximately super-imposed. Optionally, the one or more beam shaping optical elements can be one selected from slow axis collimating lens, fast axis collimating lens, aspheric lens, ball lens, total internal reflector (TIR) optics, parabolic lens optics such as parabolic reflectors, refractive optics, or a combination of above. In other embodiments, the one or more beam shaping optical elements can be disposed prior to the laser light incident to the wavelength converting element.

In some embodiments the visible and/or IR emission from the light source are coupled into an optical waveguide such as an optical fiber, which could be a glass optical fiber or a plastic optical fiber. The optical fiber of an arbitrary length, including a single mode fiber (SMF) or a multi-mode fiber (MMF), with core diameters ranging from about 1 um to 10 um, about 10 um to 50 um, about 50 um to 150 um, about 150 um to 500 um, about 500 um to 1 mm, about 1 mm to 5 mm or greater than 5 mm. The optical fiber is aligned with a collimation optics member to receive the collimated white light and/or IR emission.

Figure 24B:
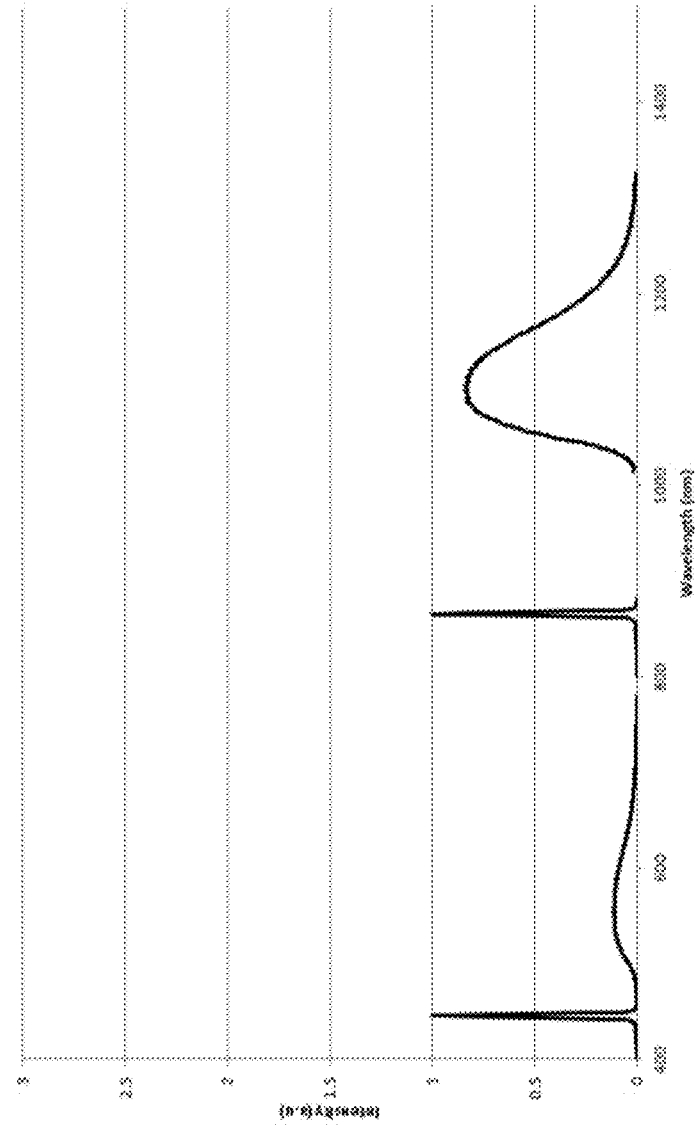
FIG. 24B is an example optical spectrum of a laser based white light source configured with a red or near IR emitting laser diode to excite an IR emitting wavelength converter to provide an IR illumination according to an embodiment of the present invention.

The resulting spectrum from the embodiment described in FIG. 24A according to the present invention would be comprised of a relatively narrow band (about 0.5 to 3 nm) emission spectrum from the gallium and nitrogen containing laser diode in the UV or blue wavelength region, a broadband (about 10 to 100 nm) wavelength converter emission in the visible spectrum with a longer peak wavelength than the UV or blue laser diode, a relatively narrow band (about 1 to 10 nm) emission from the second laser diode with a peak wavelength longer than the peak wavelength of the visible emitting phosphor, and a relatively broadband (about 10 to 100 nm) wavelength converter emission in the IR spectrum with a longer peak wavelength than the peak emission wavelength from the second laser diode. FIG. 24B presents an example optical spectrum according to the present invention. In this figure, the gallium and nitrogen containing laser diode emits in the blue region at about 440 to 455 nm, the visible wavelength converter member emits in the yellow region, the second laser diode member emits with a peak wavelength of 900 nm, and the included IR emitting wavelength converter member emits with a peak wavelength of about 1100 nm. Of course there can be many other configurations of the present invention, including different wavelength emitting gallium and nitrogen containing laser diodes, different wavelength emitting visible phosphor member, and different wavelength emitting IR phosphor members. For example, the IR emitting phosphor member could emit a peak wavelength of between 700 nm and 3 um.

In preferred embodiments according to the present invention, the wavelength converter element is comprised of one or more phosphor members. Such phosphor members can be implemented in solid body form such as single crystal phosphor element, a ceramic element, or a phosphor in a glass, or could be in a powder form wherein the powder is bound by a binder material. There is a wide range of phosphor chemistries to select from to ensure the proper emission and performance properties. Moreover, such phosphor members can be operated in several architectural arrangements such as a reflective mode, a transmissive mode, a hybrid mode, or any other mode.

In some embodiments, a deep UV laser is included wherein the deep UV laser is configured to excite a UV phosphor element to emit a UV light. In such a configuration, the UV emission could be deployed as a UV illumination source for UV imaging. In a further example of the present embodiment, deep UV laser could also be configured to excite a visible emitting wavelength converter member, and/or an IR emitting wavelength converter member.

In some embodiments, the light engine is provided with a plurality of blue or violet pump lasers which are incident on a first surface of the wavelength converting element. The plurality of blue or violet pump lasers is configured such that each pump laser illuminates a different region of the first surface of the wavelength converting element. In a specific embodiment, the regions illuminated by the pump lasers are not overlapping. In a specific embodiment, the regions illuminated by the pump lasers are partially overlapping. In a specific embodiment, a subset of pump lasers illuminate fully overlapping regions of the first surface of the wavelength converting element while one or more other pump lasers are configured to illuminate either a non-overlapping or partially overlapping region of the first surface of the wavelength converting element. Such a configuration is advantageous because by driving the pump lasers independently of one another the size and shape of the resulting light source can by dynamically modified such that the resulting spot of white light once projected through appropriate optical elements can by dynamically configured to have different sizes and shapes without the need for a moving mechanism.

In an alternative embodiment, the laser or SLED pump light sources and the wavelength converting element are contained in a sealed package provided with an aperture to allow the white light spectrum to be emitted from the package. In specific embodiments, the aperture is covered or sealed by a transparent material, though in some embodiments the aperture may be unsealed. In an example, the package is a TO canister with a window that transmits all or some of the pump and down-converted light. In an example, the package is a TO canister with a window that transmits all or some of the pump and down-converted light.

Figure 25A:
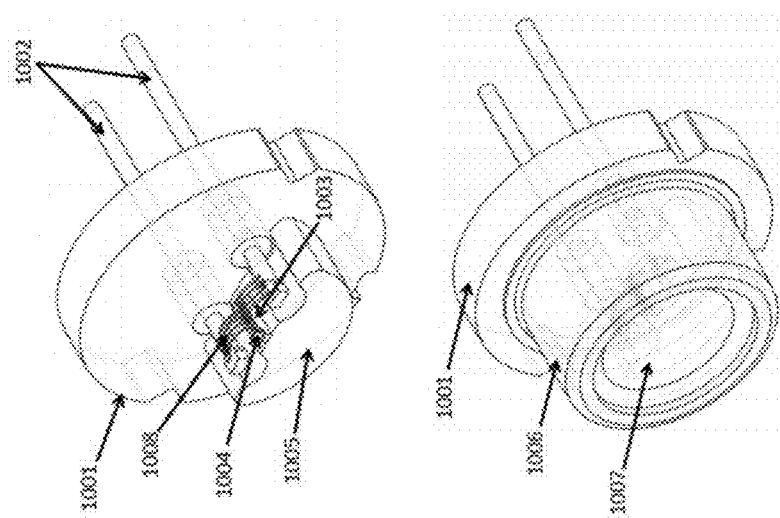
FIG. 25A is a schematic diagram of a laser based white light source with an IR illumination capability operating in transmission mode and housed in a TO canister style package according to an embodiment of the present invention.

FIG. 25A is a schematic diagram of a laser based white light source configured with an IR illumination capability operating in transmission mode and housed in a TO canister style package according to an embodiment of the present invention. Referring to FIG. 25A, the TO canister package includes a base member 1001, a shaped pedestal 1005 and pins 1002. The base member 1001 can be comprised of a metal such as copper, copper tungsten, aluminum, or steel, or other. The pins 1002 are either grounded to the base or are electrically insulated from it and provide a means of electrically accessing the laser device. The pedestal member 1005 is configured to transmit heat from the pedestal to the base member 1001 where the heat is subsequently passed to a heat sink. A cap member 1006 is provided with a window 1007 hermetically sealed. The cap member 1006 itself also is hermetically sealed to the base member 1001 to enclose the laser based white light source in the TO canister package.

A laser device 1003 and a wavelength converting member 104 are mounted on the pedestal 1005. In some embodiments intermediate submount members are included between the laser diode and the pedestal and/or between the wavelength converter member and the pedestal. The mounting to the pedestal can be accomplished using a soldering or gluing technique such as using AuSn solders, SAC solders such as SAC305, lead containing solder, or indium, but can be others. In an alternative embodiment sintered Ag pastes or films can be used for the attach process at the interface. Sintered Ag attach material can be dispensed or deposited using standard processing equipment and cycle temperatures with the added benefit of higher thermal conductivity and improved electrical conductivity. For example, AuSn has a thermal conductivity of about 50 W/m-K and electrical conductivity of about 16 $\mu\Omega$cm whereas pressureless sintered Ag can have a thermal conductivity of about 125 W/m-K and electrical conductivity of about 4 $\mu\Omega$cm, or pressured sintered Ag can have a thermal conductivity of about 250 W/m-K and electrical conductivity of about 2.5 $\mu\Omega$cm. Due to the extreme change in melt temperature from paste to sintered form, for example, 260° C.-900° C., processes can avoid thermal load restrictions on downstream processes, allowing completed devices to have very good and consistent bonds throughout. Electrical connections from the p-electrode and n-electrode of the laser diode are made using wire bonds 1008 which connect to the pins 1002. The pins are then electrically coupled to a power source to electrify the white light source and generate white light emission. In this configuration the white light source is not capped or sealed such that is exposed to the open environment.

The laser light emitted from the laser device 1003 shines through the wavelength converting element 1004 and is either fully or partially converted to longer wavelength light. The down-converted light and remaining laser light is then emitted from the wavelength converting element 1004. The laser activated phosphor member white light source configured in a can type package as shown in FIG. 25A includes an additional cap member 1006 to form a sealed structure around the white light source on the base member 1001. The cap member 1006 can be soldered, brazed, welded, or glue to the base. The cap member 1006 has a transparent window 1007 configured to allow the emitted white light to pass to the outside environment where it can be harnessed in application. The sealing type can be an environmental seal or a hermetic seal, and in an example the sealed package is backfilled with a nitrogen gas or a combination of a nitrogen gas and an oxygen gas. Optionally, the window 1007 and cap member 1006 are joined using epoxy, glue, metal solder, glass frit sealing and friction welding among other bonding techniques appropriate for the window material. Optionally, the cap member 1006 is either crimped onto the header of the base member 1001 or sealed in place using epoxy, glue, metal solder, glass frit sealing and friction welding among other bonding techniques appropriate for the cap material such that a hermetic seal is formed.

The laser devices are configured such that they illuminate the wavelength converting element 1004 and any non-converted pump light is transmitted through the wavelength converting element 1004 and exits the canister through the window 1007 of the cap member 1006. Down-converted light emitted by the wavelength converting element is similarly emitted from the TO canister through the window 1007.

Figure 25B:
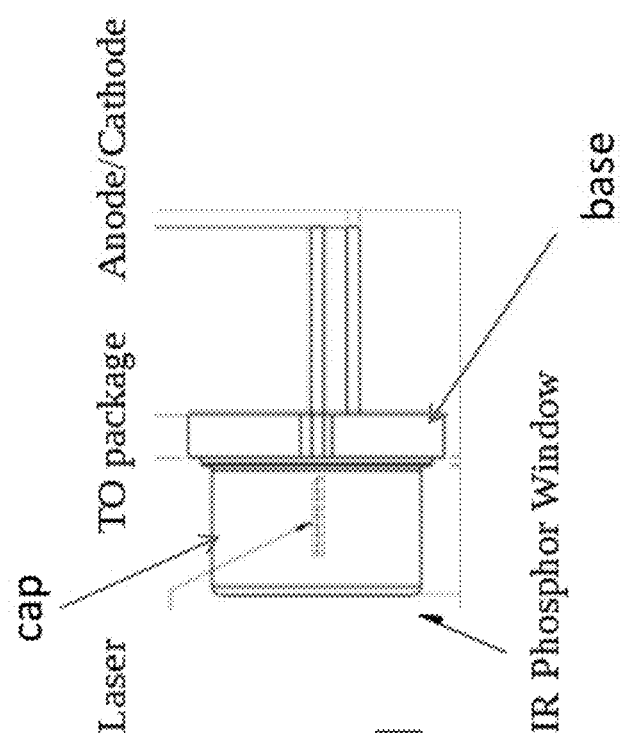
FIG. 25B is a side view schematic diagram of a laser based white light source with an IR illumination capability operating in transmission mode and housed in a TO canister style package with an IR emitting wavelength converter member configured with the transparent window of the cap according to an embodiment of the present invention.

In some configurations of the present invention, TO can type packages can be used to package the laser based IR illumination source. FIG. 25B presents a side view schematic diagram of a laser based IR illumination source capable for operating in transmission mode and housed in a TO canister style package with an IR emitting wavelength converter member configured with the transparent window of the cap according to an embodiment of the present invention. Referring to FIG. 25B, the TO can comprises a base member configured for transporting the heat generated in the package to a heat-sink member. Electrical feedthrough pins are configured to supply current to the anode and cathode of the laser diode from an external power source. A laser diode is mounted on a pedestal member within the TO can package, and the package is sealed with a cap member. The cap member comprises a transparent window member configured to allow visible and IR light to pass through the window to the outside environment. The transparent window member comprises an IR emitting wavelength converting member, configured to emit IR illumination when the laser diode excitation beam is incident on the window member. In some embodiments, the wavelength converter member serves as the window member.

In some configurations of the present invention, TO can type packages can be used to package the laser based white light source configured with an IR illumination source. FIG. 25C presents a side view schematic diagram of a laser based white light source with an IR illumination capable of operating in a transmission mode and housed in a TO canister style package with a visible and IR emitting wavelength converter member configured with the transparent window of the cap according to an embodiment of the present invention. Referring to FIG. 25C, the TO can comprises a base member configured for transporting the heat generated in the package to a heat-sink member. Electrical feedthrough pins are configured to supply current to the anode and cathode of the laser diode from an external power source. A laser diode is mounted on a pedestal member within the TO can package, and the package is sealed with a cap member. The cap member comprises a transparent window member configured to allow visible and IR light to pass through the window to the outside environment. The transparent window member comprises a visible and IR emitting wavelength converting member, configured to emit visible light such as white light and IR illumination when the laser diode excitation beam is incident on the window member. In some embodiments, the wavelength converter member serves as the window member.

FIG. 25D is a side view schematic diagram of an IR and visible light emitting based wavelength converter member configured with the transparent window of the cap according to an embodiment of the present invention. In this embodiment the wavelength converter member is comprised of a stacked IR emitting wavelength converter and visible light emitting wavelength converter. According to this example, the UV or blue laser diode excitation illumination is incident on the visible light emitting wavelength converter first, wherein the excitation light and the emitted visible light excites the IR emitting phosphor. In other embodiments the UV of blue laser diode excitation beam could be incident on the IR wavelength converter member first such that the light that penetrates the IR illumination phosphor would enter into the visible emitting wavelength converter member to excite a visible light. In other configurations, composite wavelength converter structures are configured to create the visible light and IR light.

Figure 25E:
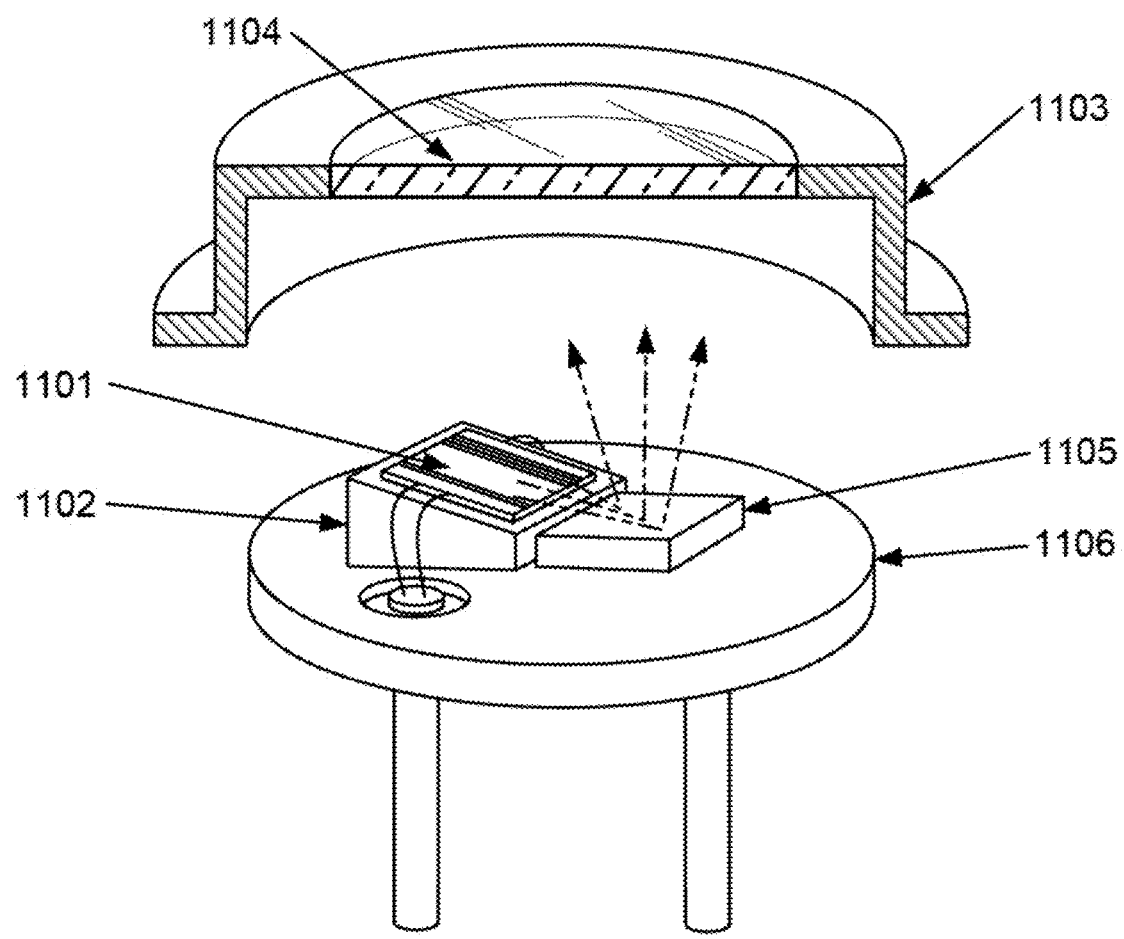
FIG. 25E is a schematic diagram of a laser based white light source operating in reflection mode and housed in a TO canister style package according to another embodiment of the present invention.

In an embodiment, the laser based white light source configured with an IR illumination source is packaged in a TO canister with a window that transmits all or some of the pump and down-converted light and the wavelength converting element is illuminated in a reflection mode. FIG. 25E is a schematic diagram of a laser based white light source operating in reflection mode and housed in a TO canister style package according to another embodiment of the present invention. The canister base consists of a header 1106, wedge shaped member 1102 and electrically isolated pins that pass-through the header. The laser devices 1101 and the wavelength converting element 1105 are mounted to the wedge shaped member 1102 and pedestal, respectively, using a thermally conductive bonding media such as silver epoxy or with a solder material, preferably chosen from one or more of AuSn, AgCuSn, PbSn, or In. The package is sealed with a cap 1103 which is fitted with a transparent window 1104. The window 1104 and cap 1103 are joined using epoxy, glue, metal solder, glass frit sealing and friction welding among other bonding techniques appropriate for the window material. The cap 1103 is either crimped onto the header 1106 or sealed in place using epoxy, glue, metal solder, glass frit sealing and friction welding among other bonding techniques appropriate for the cap material such that a hermetic seal is formed. The laser devices are configured such that they illuminate the wavelength converting element 1105 and any non-converted pump light is reflected or scattered from the wavelength converting element 1105 and exits the canister through the cap window 1104. Down-converted light emitted by the wavelength converting element 1105 is similarly emitted from the canister through the window 1104.

In another embodiment, a reflective mode integrated white light source is configured in a flat type package with a lens member to create a collimated white beam. The flat type package has a base or housing member with a collimated white light source mounted to the base and configured to create a collimated white beam to exit a window configured in the side of the base or housing member. The mounting to the base or housing can be accomplished using a soldering or gluing technique such as using AuSn solders, SAC solders such as SAC305, lead containing solder, or indium, but can be others. In an alternative embodiment sintered Ag pastes or films can be used for the attach process at the interface. Sintered Ag attach material can be dispensed or deposited using standard processing equipment and cycle temperatures with the added benefit of higher thermal conductivity and improved electrical conductivity. For example, AuSn has a thermal conductivity of about 50 W/m-K and electrical conductivity of about 16 μΩcm whereas pressureless sintered Ag can have a thermal conductivity of about 125 W/m-K and electrical conductivity of about 4 μΩcm, or pressured sintered Ag can have a thermal conductivity of about 250 W/m-K and electrical conductivity of about 2.5 μΩcm. Due to the extreme change in melt temperature from paste to sintered form, (260° C.-900° C.), processes can avoid thermal load restrictions on downstream processes, allowing completed devices to have very good and consistent bonds throughout. Electrical connections to the white light source can be made with wire bonds to the feed-throughs that are electrically coupled to external pins. In this example, the collimated reflective mode white light source includes the laser diode, the phosphor wavelength converter configured to accept the laser beam, and a collimating lens such as an aspheric lens configured in front of the phosphor to collect the emitted white light and form a collimated beam. The collimated beam is directed toward the window wherein the window region is formed from a transparent material. The transparent material can be a glass, quartz, sapphire, silicon carbide, diamond, plastic, or any suitable transparent material. The external pins are electrically coupled to a power source to electrify the white light source and generate white light emission.

In one embodiment according to the present invention, a transmissive mode integrated white light source is configured in a flat type package with a lens member to create a collimated white beam. In one example of this embodiment, the white light emission is collimated and projected toward a window configured on the flat-type package wherein the collimated white beam of light exits the transparent window and is guided by free space optical path or a fiber coupled optical path to the target subject or area.

There are several configurations that enable a remote pumping of phosphor material using one or more laser diode excitation sources. In an embodiment one or more laser diodes are remotely coupled to one or more phosphor members with a free-space optics configuration. That is, at least part of the optical path from the emission of the laser diode to the phosphor member is comprised of a free-space optics setup. In such a free-space optics configuration the optical beam from the laser diode may be shaped using optical elements such as collimating lens including a fast axis collimator, slow axis collimator, aspheric lens, ball lens, or other elements such as glass rods. In other embodiments of a free-space optical pumping the beam may not be shaped and simply directly coupled to the phosphor. In another embodiment a waveguide element is used to couple the optical excitation power from the one or more laser diodes to the phosphor member. The waveguide element includes one or more materials selected from Si, SiN, GaN, GaInP, Oxides, or others.

In another embodiment, an optical fiber is used as the waveguide element wherein on one end of the fiber the electromagnetic radiation from the one or more laser diodes is in-coupled to enter the fiber and on the other end of the fiber the electromagnetic radiation is out-coupled to exit the fiber wherein it is then incident on the phosphor member. The optical fiber could be comprised of a glass material such as silica, a polymer material, or other, and could have a length ranging from 100 μm to about 100 m or greater.

In alternative examples, the waveguide element could consist of glass rods, optical elements, specialized waveguide architectures such as silicon photonics devices.

In one embodiment the laser diode members are comprised of laser bars, wherein the laser bar includes a number of emitters with cavity members formed by ridge structures, the cavity members are electrically coupled to each other by the electrode. The laser diodes, each having an electrical contact through its cavity member, share a common n-side electrode. Depending on the application, the n-side electrode can be electrically coupled to the cavity members in different configurations. In a preferred embodiment, the common n-side electrode is electrically coupled to the bottom side of the substrate. In certain embodiments, n-contact is on the top of the substrate, and the connection is formed by etching deep down into the substrate from the top and then depositing metal contacts. For example, laser diodes are electrically coupled to one another in a parallel configuration. In this configuration, when current is applied to the electrodes, all laser cavities can be pumped relatively equally. Further, since the ridge widths will be relatively narrow in the 1.0 to 5.0 µm range, the center of the cavity member will be in close vicinity to the edges of the ridge (e.g., via) such that current crowding or non-uniform injection will be mitigated. In an additional embodiment including laser bars, the individual laser diode comprising the laser bar are electrically coupled in series. In yet an additional embodiment including laser bars, the individual laser diode comprising the laser bar are individually addressable. For example, electrodes can be individually coupled to the emitters so that it is possible to selectively turning a emitter on and off.

It is to be appreciated that the laser device with multiple cavity members has an effective ridge width of n×w, which could easily approach the width of conventional high power lasers having a width in the 10 to 50 µm range. Typical lengths of this multi-stripe laser could range from 400 µm to 2000 µm, but could be as much as 3000 µm. These laser devices have a wide range of applications. For example, the laser device can be coupled to a power source and operate at a power level of 0.5 to 10 W. In certain applications, the power source is specifically configured to operate at a power level of greater than 10 W. The operating voltage of the laser device can be less than 5 V, 5.5 V, 6 V, 6.5 V, 7 V, and other voltages. In various embodiments, the wall plug efficiency (e.g., total electrical-to-optical power efficiency) can be 15% or greater, 20% or greater, 25% or greater, 30% or greater, 35% or greater.

In some embodiments of the present invention, multi-chip laser diode modules are utilized. For example an enclosed free-space beam combined multi-chip laser module with an extended delivery fiber plus phosphor converter could be included according to the present invention. The enclosed free space multi-chip laser module produces a laser light beam in violet or blue light spectrum, with optional IR emitting laser diodes included. The multiple laser chips in the package provide substantially high intensity for the light source that is desired for many new applications. Additionally, an extended optical fiber with one end is coupled with the light guide output for further guiding the laser light beam to a desired distance for certain applications up to 100 m or greater. Optionally, the optical fiber can be also replaced by multiple waveguides built in a planar structure for integrating with silicon photonics devices. At the other end of the optical fiber, a phosphor material based wavelength converter may be disposed to receive the laser light, where the violet or blue color laser light is converted to white color light and emitted out through an aperture or collimation device. As a result, a white light source with small size, remote pump, and flexible setup is provided.

In another example, the package is a custom package made from one or more of plastic, metal, ceramics and composites.

In another embodiment, the laser devices are co-packaged on a common substrate along with the wavelength converting element. A shaped member may be provided separating either the laser devices or the wavelength converting element from the common substrate such that the pump light is incident on the wavelength converting element at some angle which is not parallel to the surface normal of the wavelength covering member. Transmission mode configurations are possible, where the laser light is incident on a side of the wavelength converting element not facing the package aperture. The package can also contain other optical, mechanical and electrical elements.

In an embodiment, the common substrate is a solid material with thermal conductivity greater than 100 W/m-K. In an example, the common substrate is preferably a solid material with thermal conductivity greater than 200 W/m-K. In an example, the common substrate is preferably a solid material with thermal conductivity greater than 400 W/m-K. In an example, the common substrate is preferably a solid material with electrical insulator with electrical resistivity greater than $1 \times 10^6$ Ω cm. In an example, the common substrate is preferably a solid material with thin film material providing electrical $1 \times 10^6$ Ω cm. In an example, the common substrate selected from one or more of $Al_2O_3$, AlN, SiC, BeO and diamond. In an example, the common substrate is preferably comprised of crystalline SiC. In an example, the common substrate is preferably comprised of crystalline SiC with a thin film of $Si_3N_4$ deposited onto the top surface. In an example, the common substrate contains metal traces providing electrically conductive connections between the one or more laser diodes. In an example, the common substrate contains metal traces providing thermally conductive connections between the one or more laser diodes and the common substrate.

In an embodiment, the common substrate is a composite structure comprised by a plurality or layers or regions of differing composition or electrical conductivity. In an example, the common substrate is a metal-core printed circuit board comprised by a core layer of aluminum or copper surrounded by layers of insulating plastic. Through vias, solder masks and solder pads may be provided. In an example, the common substrate is a ceramic substrate comprised by a ceramic core plate clad in patterned metallic pads for bonding and electrical contact. The ceramic substrate may contain metal filled vias for providing electrical communication between both faces of the ceramic plate. In an example, the common substrate consists of a metal core or slug surrounded by an insulating material such as plastic or ceramic. The surrounding insulating material may contain through vias for electrical communication between the front and back faces of the substrate. The insulating material may also have metallic or otherwise conducting pads patterned on it for wire-bonding.

In an embodiment, the one or more laser diodes are attached to the common substrate with a solder material. In an example, the one or more laser diodes are attached to the metal traces on the common substrate with a solder material, preferably chosen from one or more of AuSn, AgCuSn, PbSn, or In.

In an embodiment, the wavelength conversion material is attached to the common substrate with a solder material. In an example, the wavelength conversion material is attached to the metal traces on the common substrate with a solder material, preferably chosen from one or more of AuSn, AgCuSn, PbSn, or In.

In an example, the wavelength conversion element contains an optically reflective material interposed between the wavelength conversion element and the thermally conductive connection to the common substrate.

In an embodiment, the optically reflective material interposed between the wavelength conversion element and the thermally conductive connection to the common substrate has a reflectivity value of greater than 50%. In an embodiment the optically reflective material interposed between the wavelength conversion element and the thermally conductive connection to the common substrate has a reflectivity value of greater than 80%. In an example, the optically reflective material interposed between the wavelength conversion element and the thermally conductive connection to the common substrate has a reflectivity value of greater than 90%. In an example, optical beam shaping elements are placed between the laser diodes and the wavelength conversion element.

In an embodiment, the wavelength conversion element contains geometrical features aligned to each of the one or more laser diodes. In an example, the wavelength conversion element further contains an optically reflective material on the predominate portion of the edges perpendicular to the common substrate and one or more laser diodes, and where the geometrical features aligned to each of the laser diodes does not contain an optically reflective material. In an example, the common substrate is optically transparent. In an example, the wavelength conversion element is partially attached to the transparent common substrate. In an example, the wavelength converted light is directed through the common substrate. In an example, the wavelength converter contains an optically reflective material on at least the top surface. In an example, the one or more laser diodes and the wavelength conversion element are contained within a sealing element to reduce the exposure to the ambient environment. In an example, the one or more laser diodes and the wavelength conversion element are contained within a sealing element to reduce the exposure to the ambient environment.

Figure 26A:
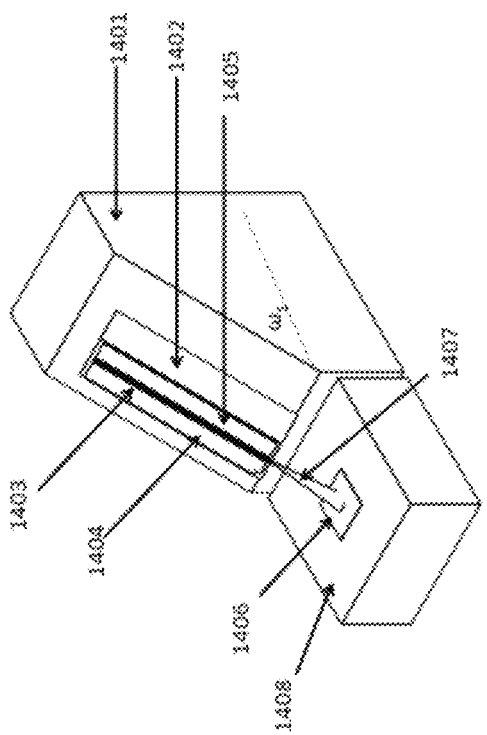
FIG. 26A is a schematic diagram of a laser based white light source with an IR illumination capability operating in reflection mode according to an embodiment of the present invention.

FIG. 26A is a schematic diagram illustrating an off-axis reflective mode embodiment of an integrated laser-phosphor white light source according to the present invention. In this embodiment the gallium and nitrogen containing lift-off and transfer technique is deployed to fabricate a very small and compact submount member with the laser diode chip formed from transferred epitaxy layers. Further, in this example the phosphor is tilted with respect to the fast axis of the laser beam at an angle $\omega_1$. The laser based white light device is comprised of a support member 1401 that serves as the support member for the laser diode CoS 1402 formed in transferred gallium and nitrogen containing epitaxial layers 1403. The phosphor material 1406 is mounted on a support member 1408 wherein the support members 1401 and 1408 would be attached to a common support member such as a surface in a package member such as a surface mount package. The laser diode or CoS is configured with electrodes 1404 and 1405 that may be formed with deposited metal layers and combination of metal layers including, but not limited to Au, Pd, Pt, Ni, Al, Ag titanium, or others such as transparent conductive oxides such as indium tin oxide. The laser beam output excites the phosphor material 1406 positioned in front of the output laser facet. The electrodes 1404 and 1405 are configured for an electrical connection to an external power source such as a laser driver, a current source, or a voltage source. Wirebonds can be formed on the electrodes to couple electrical power to the laser diode device to generate a laser beam 1407 output from the laser diode and incident on the phosphor 1406. Of course this is merely an example of a configuration and there could be many variants on this embodiment including but not limited to different shape phosphors, different geometrical designs of the submount, support members, different orientations of the laser output beam with respect to the phosphor, different electrode and electrical designs, and others.

Figure 26B:
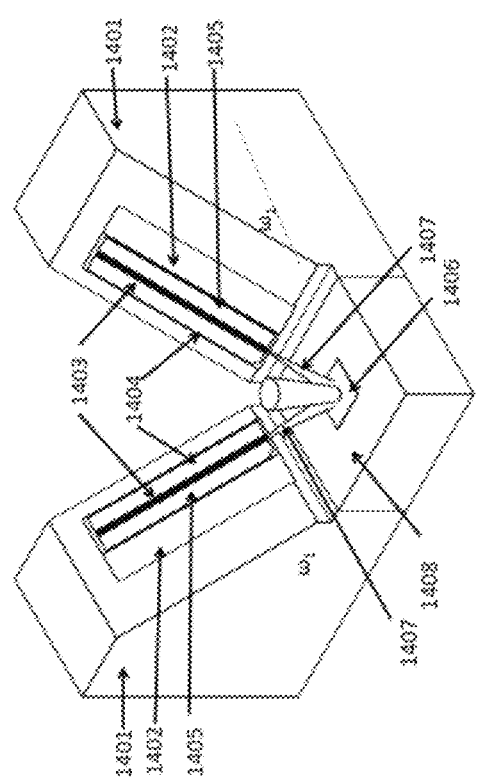
FIG. 26B is a schematic diagram of a laser based white light source with an IR illumination capability operating in reflection mode according to an embodiment of the present invention.

FIG. 26B is a schematic diagram illustrating an off-axis reflective mode phosphor with two laser diode devices embodiment of an integrated laser-phosphor white light source according to the present invention. In this embodiment the gallium and nitrogen containing lift-off and transfer technique is deployed to fabricate a very small and compact submount member with the laser diode chip formed from transferred epitaxy layers. Further, in this example the phosphor is tilted with respect to the fast axis of the laser beam at an angle $\omega_1$. The laser based white light sources is comprised of two or more laser diodes including support members 1401 that serves as the support member for the two laser diodes 1402 formed in transferred gallium and nitrogen containing epitaxial layers 1403. The phosphor material 1406 is mounted on a support member 408 wherein the support members 1401 and 1408 would be attached to a common support member such as a surface in a package member such as a surface mount package. The laser diodes or CoS devices are configured with electrodes 1404 and 1405 that may be formed with deposited metal layers and combination of metal layers including, but not limited to Au, Pd, Pt, Ni, Al, Ag titanium, or others such as transparent conductive oxides such as indium tin oxide. The multiple laser beams 1407 excite the phosphor material 1406 positioned in front of the output laser facet.

Referring to FIG. 26B the laser diode excitation beams 1407 are rotated with respect to each other such that the fast axis of the first beam is aligned with the slow axis of the second beam to form a more circular excitation spot. The electrodes 1404 and 1405 are configured for an electrical connection to an external power source such as a laser driver, a current source, or a voltage source. Wirebonds can be formed on the electrodes to couple electrical power to the laser diode device to generate the multiple laser beams 1407 incident on the phosphor 1406. Of course this is merely an example of a configuration and there could be many variants on this embodiment including but not limited to more than two laser diodes such as three of four laser diodes, different shape phosphors, different geometrical designs of the submount, support members, different orientations of the laser output beam with respect to the phosphor, wiring the laser diodes in series or parallel, different electrode and electrical designs including individually addressable lasers, and others.

Figure 27A:
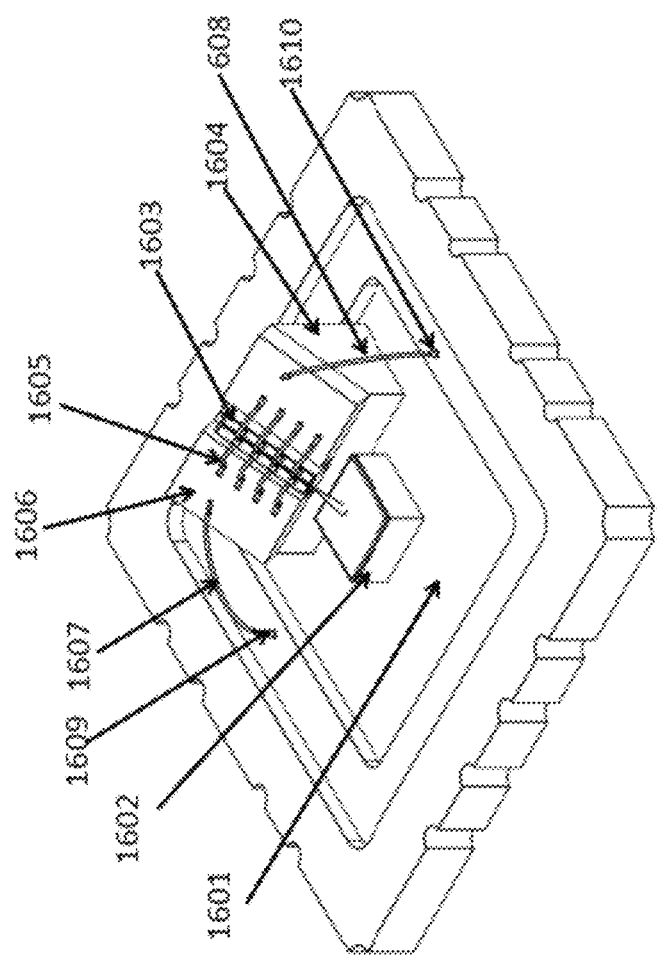
FIG. 27A is a schematic diagram of a laser based white light source with an IR illumination capability operating in reflection mode in a surface mount package according to an embodiment of the present invention.

FIG. 27A is a schematic diagram of an exemplary laser based white light source operating in reflection mode and housed in a surface mount package according to an embodiment of the present invention. Referring to FIG. 27A, a reflective mode white light source is configured in a surface mount device (SMD) type package. The SMD package has a common support base member 1601. The reflective mode phosphor member 1602 is attached to the base member 1601. Optionally, an intermediate submount member may be included between the phosphor member 1602 and the base member 1601. The laser diode 1603 is mounted on an angled support member 1604, wherein the angled support member 1604 is attached to the base member 1601. The base member 1601 is configured to conduct heat away from the white light source and to a heat sink. The base member 1601 is comprised of a thermally conductive material such as copper, copper tungsten, aluminum, SiC, steel, diamond, composite diamond, AN, sapphire, or other metals, ceramics, or semiconductors.

The mounting to the base member 1601 can be accomplished using a soldering or gluing technique such as using AuSn solders, SAC solders such as SAC305, lead containing solder, or indium, but can be others. Alternatively, sintered Ag pastes or films can be used for the attach process at the interface. Sintered Ag attach material can be dispensed or deposited using standard processing equipment and cycle temperatures with the added benefit of higher thermal conductivity and improved electrical conductivity. For example, AuSn has a thermal conductivity of about 50 W/m-K and electrical conductivity of about 16 μΩcm whereas pressure-less sintered Ag can have a thermal conductivity of about 125 W/m-K and electrical conductivity of about 4 μΩcm, or pressured sintered Ag can have a thermal conductivity of about 250 W/m-K and electrical conductivity of about 2.5 μΩcm. Due to the extreme change in melt temperature from paste to sintered form, 260° C.-900° C., processes can avoid thermal load restrictions on downstream processes, allowing completed devices to have very good and consistent bonds throughout. The mounting joint could also be formed from thermally conductive glues, thermal epoxies such as silver epoxy, and other materials.

Electrical connections from the electrodes of the laser diode are made to using wirebonds 1605 to electrode members 1606. Wirebonds 1607 and 1608 are formed to internal feedthroughs 1609 and 1610. The feedthroughs are electrically coupled to external leads. The external leads can be electrically coupled to a power source to electrify the white light source and generate white light emission.

The top surface of the base member 1601 may be comprised of, coated with, or filled with a reflective layer to prevent or mitigate any losses relating from downward directed or reflected light. Moreover, all surfaces within the package including the laser diode and submount member may be enhanced for increased reflectivity to help improve the useful white light output.

In this configuration the white light source is not capped or sealed such that is exposed to the open environment. In some examples of this embodiment of the integrated white light source apparatus, an electrostatic discharge (ESD) protection element such as a transient voltage suppression (TVS) element is included. Of course, FIG. 27A is merely an example and is intended to illustrate one possible simple configuration of a surface mount packaged white light source. Specifically, since surface mount type packages are widely popular for LEDs and other devices and are available off the shelf they could be one option for a low cost and highly adaptable solution.

Figure 27B:
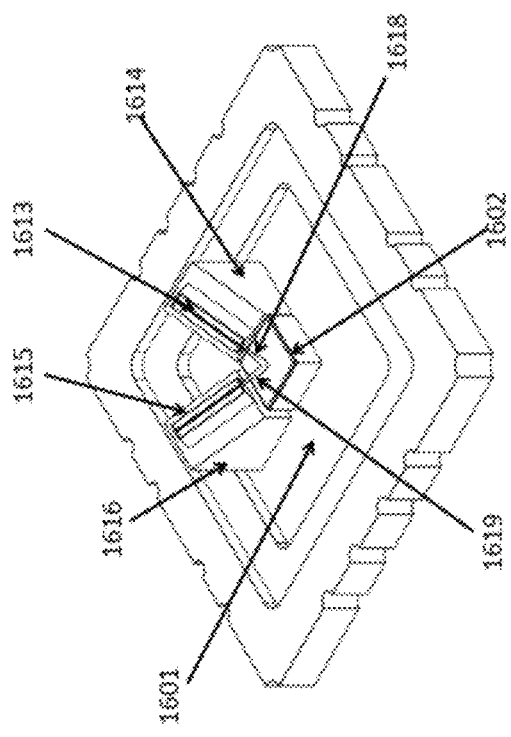
FIG. 27B is a schematic diagram of a laser based white light source with an IR illumination capability operating in reflection mode in a surface mount package according to another embodiment of the present invention.

FIG. 27B is an alternative example of a packaged white light source including 2 laser diode chips according to the present invention. In this example, a reflective mode white light source is configured also in a SMD type package. The SMD package has a base member 1601 with the reflective mode phosphor member 1602 mounted on a support member or on a base member. A first laser diode device 1613 may be mounted on a first support member 1614 or a base member 1601. A second laser diode device 1615 may be mounted on a second support member 1616 or a base member 1601. The support members and base member are configured to conduct heat away from the phosphor member 1602 and laser diode devices 1613 and 1615.

The external leads can be electrically coupled to a power source to electrify the laser diode sources to emit a first laser beam 1618 from the first laser diode device 1613 and a second laser beam 1619 from a second laser diode device 1615. The laser beams are incident on the phosphor member 1602 to create an excitation spot and a white light emission. The laser beams are preferably overlapped on the phosphor member 1602 to create an optimized geometry and/or size excitation spot. For example, the laser beams from the first and second laser diodes are rotated by 90 degrees with respect to each other such that the slow axis of the first laser beam 1618 is aligned with the fast axis of the second laser beam 1619.

The top surface of the base member 1601 may be comprised of, coated with, or filled with a reflective layer to prevent or mitigate any losses relating from downward directed or reflected light. Moreover, all surfaces within the package including the laser diode member and submount member may be enhanced for increased reflectivity to help improve the useful white light output. In this configuration the white light source is not capped or sealed such that is exposed to the open environment. In some examples of this embodiment of the integrated white light source apparatus, an ESD protection element such as a TVS element is included. Of course, FIG. 27B is merely an example and is intended to illustrate one possible simple configuration of a surface mount packaged white light source. Specifically, since surface mount type packages are widely popular for LEDs and other devices and are available off the shelf they could be one option for a low cost and highly adaptable solution.

Figure 27C:
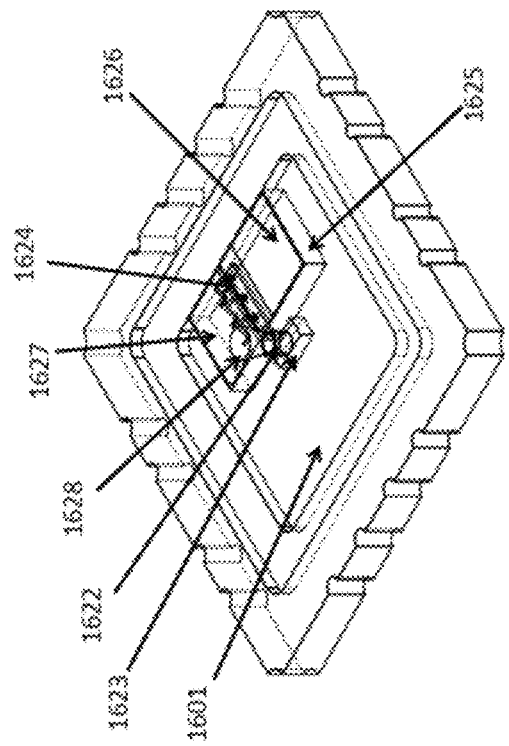
FIG. 27C is a schematic diagram of a laser based white light source with an IR illumination capability operating with side-pumped phosphor in a surface mount package according to another embodiment of the present invention.

FIG. 27C is an alternative example of a packaged white light source according to the present invention. In this example, a reflective mode white light source is configured also in a SMD type package. The SMD package has a base member 1601 serving as a common support member for a side-pumped phosphor member 1622 mounted on a submount or support member 1623 and a laser diode device 1624 mounted on a submount or support member 1625. In some embodiments, the laser diode 1624 and or the phosphor member 1622 may be mounted directly to the base member 1601 of the package. The support members and base member 1601 are configured to conduct heat away from the phosphor member 1622 and laser diode device 1624. The base member 1601 is substantially the same type as that in FIG. 27A and FIG. 27B in the SMD type package.

Electrical connections from the p-electrode and n-electrode can be electrically coupled to 1626 and 1627 electrodes on a submount member 1625 which would then be coupled to internal feedthroughs in the package. The feedthroughs are electrically coupled to external leads. The external leads can be electrically coupled to a power supply source to electrify the laser diode and generate a laser beam incident on the side of the phosphor member 1622. The phosphor member 1622 may preferably be configured for primary white light emission 1628 from the top surface of the phosphor member 1622. The top surface of the base member 1601 may be comprised of, coated with, or filled with a reflective layer to prevent or mitigate any losses relating from downward directed or reflected light. Moreover, all surfaces within the package including the laser diode member and submount member may be enhanced for increased reflectivity to help improve the useful white light output. In this configuration the white light source is not capped or sealed such that is exposed to the open environment. In some examples of this embodiment of the integrated white light source apparatus, an ESD protection element such as a TVS element is included. Of course, the example in FIG. 27C is merely an example and is intended to illustrate one possible simple configuration of a surface mount packaged white light source. Specifically, since surface mount type packages are widely popular for LEDs and other devices and are available off the shelf they could be one option for a low cost and highly adaptable solution.

The white light sources shown in FIGS. 27A, 27B, and 27C can be enclosed in a number of ways to form a light engine. Optionally, the light engine is encapsulated in a molded epoxy or plastic cover (not shown). The molded cover may have a flat top or can be molded to have a curved or spherical surface to aid in light extraction. It is possible for the cover to be pre-molded and glued in place, or to be molded in place from liquid or gel precursors. Because a polymer cover or molded encapsulating material may absorb laser light or down converted light from the wavelength converting element there is a large risk that the encapsulating material will age due to heating and light absorption. When such a material ages, it tends to become more optically absorbing, leading to a runaway process that inevitably leads to device failure. In a laser based device, where the laser devices emit light with a very high brightness and optical flux, this aging effect is expected to be quite severe. It is preferred, then, for a polymer cover to be absent from the region near the emitting facets of the lasers as well as from the path of the laser beams between the laser devices and the wavelength converting element. Optionally, the molded cover does not contact the laser device nor the wavelength converting element nor does it intersect the laser light beams prior to their intersecting the wavelength converting element. Optionally, the molded cover overlays and is in contact with a part or majority of the laser devices and the wavelength converting element, but does not cover the emitting facet of the lasers nor the surface of the wavelength converting element, nor does it intersect the beam path of the laser light between the laser devices and the wavelength converting element. Optionally, the encapsulating material is molded over the device after wire bonding of the laser devices, and no air gaps or voids are included.

In another embodiment, the light engine is encapsulated using a rigid, member such as a ceramic or metal housing. For example, a stamped metal wall could be provided with dimensions close to those of the outer edge of the common substrate. The wall could be attached to the common substrate and an airtight seal formed using epoxy or another glue, metal solder, glass fit sealing and friction welding among other bonding techniques. The top edge of the wall could, for example, be sealed by attaching a transparent cover. The transparent cover may be composed of any transparent material, including silica-containing glass, sapphire, spinel, plastic, diamond and other various minerals. The cover may be attached to the wall using epoxy, glue, metal solder, glass frit sealing and friction welding among other bonding techniques appropriate for the cover material.

In some embodiments the enclosure may be fabricated directly on the common substrate using standard lithographic techniques similar to those used in processing of MEMS devices. Many light emitters such as laser diodes could be fabricated on the same common substrate and, once fabrication is complete, singulated in to separate devices using sawing, laser scribing or a like process.

FIG. 28A is a side-view schematic diagram of a laser based white light source with an IR illumination capability operating in reflection mode in an enclosed surface mount package according to an embodiment of the present invention. As seen in the figure, the surface mount device package is comprised of a package base member configured as a support member. The phosphor plate overlies the support member and is configured in an optical pathway of the light emission from one or more laser diode members. The one or more laser diode members are configured on an elevated mounting surface that is not parallel to the mounting surface that the phosphor plate is mounted on. The result is an angle of incidence of the laser excitation beam on the phosphor plate. The phosphor plate is configured in a reflection mode wherein the plate receives the emission from the laser diode member on a top excitation surface and emits a visible light and an IR light from the same top surface. A transparent window member is included to provide a seal around the laser based visible and IR emitting source.

Figure 28B:
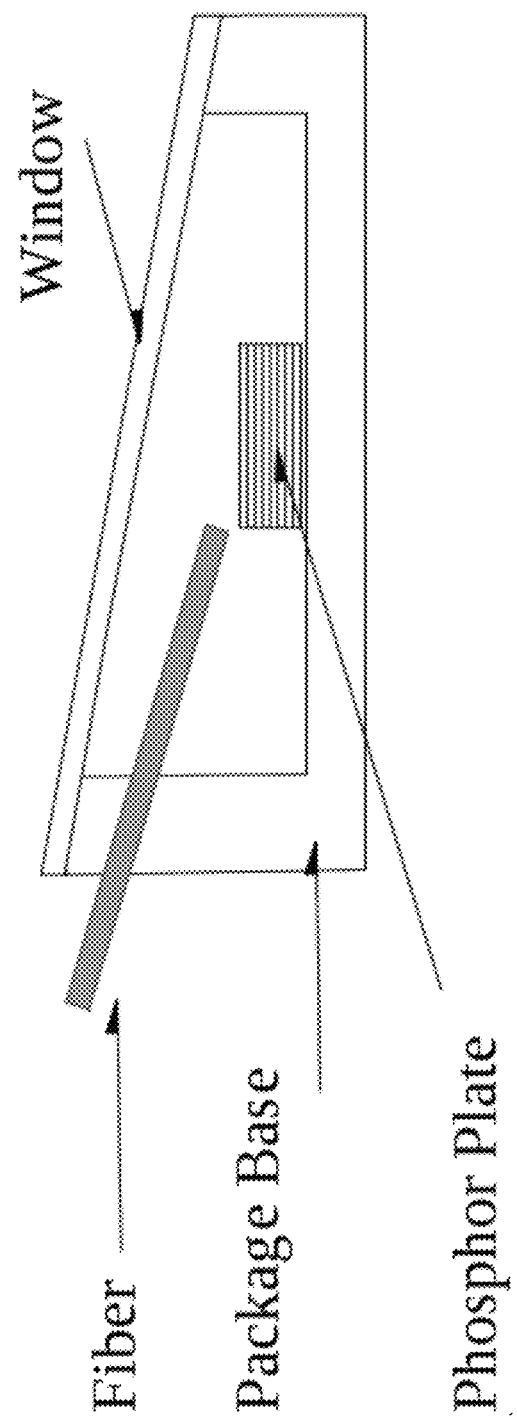
FIG. 28B is a side-view schematic diagram of a fiber-coupled laser based white light source with an IR illumination capability operating in reflection mode in an enclosed package according to an embodiment of the present invention.

FIG. 28B is a side-view schematic diagram of a fiber-coupled laser based white light source with an IR illumination capability operating in reflection mode in an enclosed package according to an embodiment of the present invention. As seen in the figure, the surface mount device package is comprised of a package base member configured as a support member. The phosphor plate overlies the support member and is configured in an optical pathway of the light emission from one or more optical fiber members that transport the excitation emission from one or more laser diodes into the package. The fiber is positioned at an off-normal angle relative to the that the phosphor plate such that the excitation beam exciting the fiber is incident on a top surface of the phosphor. The phosphor plate is configured in a reflection mode wherein the plate receives the emission from the laser diode member on a top excitation surface and emits a visible light and an IR light from the same top surface.

Referring to FIGS. 26A, 26B, 27A, 27B, 27C, 28A, and 28B showing several embodiments of the laser based white light source configured with an IR illumination source in a SMD type package. Optionally, the wedge-shaped members 1401, 1604, 1614, and 1616 in the SMD package are configured such that the laser light from each of multiple laser devices is incident on the wavelength converting element 1406 or 1602 with an angle of 10 to 45 degrees from the plane of the wavelength converting element's upper. Optionally, the wavelength converting element 1602 is bonded to the common substrate 1601 using a solder material. Optionally, the bonded surface of the wavelength converting element 1602 is provided with an adhesion promoting layer such as a Ti/Pt/Au metal stack. Optionally, the adhesion promoting layer includes as first layer that is highly reflective. Optionally, the adhesion promoting layers could be Ag/Ti/Pt/Au, where Ag is adjacent to the wavelength converting element and provides a highly-reflective surface below the wavelength converting element. The laser devices are connected electrically to the backside solder pads using wire bonding between electrical contact pads on the laser device chips and the top-side wire-bond pads on the common substrate. Optionally, only one of the multiple laser devices in the SMD packaged white light source is a blue pump light source with a center wavelength of between 405 and 470 nm. Optionally, the first wavelength converting element is a YAG-based phosphor plate which absorbs the pump light and emits a broader spectrum of yellow-green light such that the combination of the pump light spectra and phosphor light spectra produces a white light spectrum. The color point of the white light is preferably located within du'v' of less than 0.03 of the Planckian blackbody locus of points.

In some embodiments the laser based white light source configured with an IR illumination source is configured with an IR sensor or an IR imaging system. The IR illumination source of the present invention would be used to direct IR electromagnetic radiation toward a target area or subject and IR sensor or imaging system would be deployed to detect the presence, movement, or other characteristics of a subject matter or object within the illumination area. Once a certain characteristic was detected by the IR sensor, a response could be triggered. In one example, the visible laser based white light would be triggered to be activated to illuminate the target matter with visible white light. In some embodiments according to the present invention an infrared tracking, also known as infrared homing, is included wherein the infrared electromagnetic radiation emitted from a target is used to track the objects motion. Infrared is radiated strongly by hot bodies such as people, vehicles and aircraft.

Infrared waves are not visible to the human eye. In the electromagnetic spectrum, infrared radiation can be found between the visible and microwave regions. The infrared waves typically have wavelengths between 0.75 and 1000 μm. The infrared spectrum can be split into near IR, mid IR and far IR. The wavelength region from 0.75 to 3 μm is known as the near infrared region. The region between 3 and 6 μm is known as the mid-infrared region, and infrared radiation which has a wavelength greater higher than 6 μm is known as far infrared.

Thermal imaging systems use mid- or long wavelength IR energy and are considered passive, sensing only differences in heat. These heat signatures are then displayed on a screen, monitor, or some other readout device. Thermal imagers do not see reflected light and are therefore not affected by surrounding light sources such as oncoming headlights.

Night vision and other lowlight cameras rely on reflected ambient light such as moonlight or starlight. Night vision is not effective when there is too much light, but not enough light for you to see with the naked eye such as during the twilight hours. Perhaps, even more limiting, the sensitivity of night vision imaging technology is limited if there is not enough ambient visible light available since the imaging performance of anything that relies on reflected light is limited by the amount and strength of the light being reflected. In many instances there are no natural sources of illumination available in places such as caves, tunnels, basements, etc. In these situations, active illumination with IR sources that are not detectable to the human eye, night vision goggles, or silicon cameras can be used to illuminate an area or a target. These active imaging systems include IR illumination sources to generate their own reflected light by projecting a beam of near-IR energy that can be detected in the imager when it is reflected from an object. Such active IR systems can use short wavelength infrared light to illuminate an area of interest wherein some of the IR energy is reflected back to a camera and interpreted to generate an image. Such "covert" illumination without detection from common imaging technologies including visible light imaging technologies can be advantageous. In some embodiments, active IR systems can use mid-IR or deep-IR illumination sources.

Since this technology relies on reflected IR light to make an image with conventional IR illumination sources such as LED illumination sources, the range and contrast of the imaging system can be limited. The laser based white light system configured with an IR illumination source according to the present invention offers a superior illumination source that can overcome these challenges of range and contrast. Since the IR illumination is originating from either directly from a highly directional IR emitting laser diode or from a laser diode excited IR emitting wavelength converter member, the IR emission can be orders of magnitude brighter than conventional LED IR emission. This 10 to 10,000× increased brightness using a laser based IR illumination source can increase the range by 10 to 1000× over LED sources and provide superior contrast.

IR detectors are used to detect the radiation which has been collected. In some embodiments, the current or voltage output from the detectors is very small, requiring preamplifiers coupled with circuitry to further process the received signals. The two main types of IR detectors are thermal detectors and photodetectors. The response time and sensitivity of photonic detectors can be much higher, but often these have to be cooled to reduce thermal noise. The materials in these are semiconductors with narrow band gaps. Incident IR photons cause electronic excitations. In photoconductive detectors, the resistivity of the detector element is monitored. Photovoltaic detectors contain a p-n junction or a p-i-n junction on which photoelectric current appears upon illumination.

In one embodiment, the detector technology used to generate the resulting image can be an IR photodiode which is sensitive to IR light of the same wavelength as that emitted by the IR illumination source. When the reflected IR light is incident on the photodiode, a photocurrent is generated which induces an output voltage proportional to the magnitude of the IR light received. These infrared cameras should have a high signal-to-noise ratio with a high sensitivity or responsivity. In one example, an InGaAs based photodiode is used for the IR detector. In other examples, InAs based photodiodes, InSb based photodiodes, InAsSb based photodiodes, PbSe based photodiodes, or PbS based photodiodes can be included. In some configurations according to the present invention, photodiode arrays are included for IR detection. Additionally, avalanche photodiodes (APD) are included in the present invention. The detectors can be configured to operate as photovoltaic or photoconductive conductors. In some examples according to the present invention, some combination of the described detector technologies are included two color detectors. In some examples amplifiers and photomultipliers are included.

The thermal effects of the incident IR radiation can be followed through many temperature dependent phenomena. Bolometers and microbolometers are based on changes in resistance. Thermocouples and thermopiles use the thermoelectric effect. Golay cells follow thermal expansion. In IR spectrometers the pyroelectric detectors are the most widespread.

In several preferred embodiments of the laser based white light source including an IR illumination source is configured for communication. The communication could be intended for biological media such as humans such as pedestrians, consumers, athletes, police officers and other public servants, military, travelers, drivers, commuters, recreation activities, or other living things such as animals, plants, or other living objects. The communication could also be intended for objects such as cars or any type of auto including autonomous examples, airplanes, drones or other aircraft, which could be autonomous, or any wide range of objects such as street signs, roadways, tunnels, bridges, buildings, interior spaces in offices and residential and objects contained within, work areas, sports areas including arenas and fields, stadiums, recreational areas, and any other objects or areas. In some preferred embodiments the smart light source is used in Internet of Things (IoT), wherein the laser based smart light is used to communicate with objects such as household appliances (i.e., refrigerator, ovens, stove, etc.), lighting, heating and cooling systems, electronics, furniture such as couches, chairs, tables, beds, dressers, etc., irrigation systems, security systems, audio systems, video systems, etc. Clearly, the laser based smart lights can be configured to communicate with computers, smart phones, tablets, smart watches, augmented reality (AR) components, virtual reality (VR) components, games including game consoles, televisions, and any other electronic devices.

According to some embodiments of the present invention, the laser light source can communicate with various methods. In one preferred method, the smart light is configured as a visible light communication (VLC) system such as a LiFi system wherein at least one spectral component of the electromagnetic radiation in the light source is modulated to encode data such that the light is transmitting data. In some examples, a portion of the visible spectrum is modulated and in other examples a non-visible source such as an infrared or ultraviolet source is included for communication. The modulation pattern or format could be a digital format or an analog format, and would be configured to be received by an object or device. In some embodiments, communication could be executed using a spatial patterning of the light emission from the laser based smart light system. In an embodiment, a micro-display is used to pixelate or pattern the light, which could be done in a rapid dynamic fashion to communicate continuously flowing information or wherein the pattern is periodically changed to a static pattern to communicate a static message that could be updated. Examples of communication could be to inform individuals or crowds about upcoming events, what is contained inside a store, special promotions, provide instructions, education, sales, and safety. In an alternative embodiment, the shape or divergence angle of the emission beam is changed to a spotlight from a diffuse light or vice versa using a micro-display or a tunable lens such as a liquid crystal lens. Examples of communication could be to direct an individual or crowd, to warn about dangers, educate, or promote. In yet another embodiment of laser light based communication, the color of the smart lighting system could be changed from a cool white to a warm white, or even to a single color such as red, green, blue, or yellow, etc.

It is to be understood that in embodiments, the VLC light engine is not limited to a specific number of laser devices. In a specific embodiment, the light engine includes a single laser device acting as a "pump" light-source, and which is either a laser diode or SLED device emitting at a center wavelength between 390 nm and 480 nm. In some embodiments the gallium and nitrogen containing laser diode operates in the 480 nm to 540 nm range. In some embodiments the laser diode is comprised from a III-nitride material emitting in the ultraviolet region with a wavelength of about 270 nm to about 390 nm. Herein, a "pump" light-source is a laser diode or SLED device that illuminates as wavelength converting element such that a part or all laser light from the laser diode or SLED device is converted into longer wavelength light by the wavelength converting element. The spectral width of the pump light-source is preferably less than 2 nm, though widths up to 20 nm would be acceptable. In another embodiment, the VLC light engine consists of two or more laser or SLED "pump" light-sources emitting with center wavelengths between 380 nm and 480 nm, with the center wavelengths of individual pump light sources separated by at least 5 nm. The spectral width of the laser light source is preferably less than 2 nm, though widths up to 75% of the center wavelength separation would be acceptable. The pump light source illuminates a phosphor which absorbs the pump light and reemits a broader spectrum of longer wavelength light. Each pump light source is individually addressable, such that they may be operated independently of one another and act as independent communication channels.

Encoding of information for communication by the laser or SLED can be accomplished through a variety of methods. Most basically, the intensity of the LD or SLED could be varied to produce an analog or digital representation of an audio signal, video image or picture or any type of information. An analog representation could be one where the amplitude or frequency of variation of the LD or SLED intensity is proportional to the value of the original analog signal.

A primary benefit of the present invention including a laser diode-based or SLED-based lighting systems when applied to a LiFi or VLC application is that both laser diodes and SLEDs operate with stimulated emission wherein the direct modulation rates are not governed by carrier lifetime such as LEDs, which operate with spontaneous emission. Specifically, the modulation rate or frequency response of LEDs is inversely proportional to the carrier lifetime and proportional to the electrical parasitics (e.g., RC time constant) of the diode and device structure. Since carrier lifetimes are on the order of nanoseconds for LEDs, the frequency response is limited to the MHz range, typically in the 100s of MHz (i.e., 300-500 MHz). Additionally, since high power or mid power LEDs typically used in lighting require large diode areas on the order of 0.25 to 2 $mm^2$, the intrinsic capacitance of the diode is excessive and can further limit the modulation rate. On the contrary, laser diodes operate under stimulated emission wherein the modulation rates are governed by the photon lifetime, which is on the order of picoseconds, and can enable modulation rates in the GHz range, from about 1 to about 30 GHz depending on the type of laser structure, the differential gain, the active region volume, and optical confinement factor, and the electrical parasitics. As a result, VLC systems based on laser diodes can offer 10×, 100×, and potentially 1000× higher modulation rates, and hence data rates, compared to VLC systems based on LEDs. Since VLC (i.e., LiFi) systems in general can provide higher data rates than WiFi systems, laser based LiFi systems can enable 100× to 10,000× the data rate compared to conventional WiFi systems offering enormous benefits for delivering data in applications demand high data volumes such as where there are a large number of users (e.g., stadiums) and/or where the nature of the data being transferred requires a volume of bits (e.g., gaming).

Vertical cavity surface emitting lasers (VCSELs) are laser diode devices wherein the optical cavity is orthogonal to the epitaxial growth direction. These structures have very short cavity lengths dictated by the epitaxial growth thickness wherein high reflectivity distributed bragg reflectors (DBR) terminating each end of the cavity. The extremely small cavity length and hence cavity area of VCSELs makes them ideal for high speed modulation, wherein 3 modulation bandwidths of greater than 10 GHz, greater than 20 GHz, and greater than 30 GHz are possible. In some embodiments of the present invention VCSELs can be included. Such VCSELs may be based on GaN and related materials, InP and related material, or GaAs and related materials.

Digital encoding is common encoding scheme where the data to be transmitted is represented as numerical information and then varying the LD or SLED intensity in a way that corresponds to the various values of the information. As an example, the LD or SLED could be turned fully on and off with the on and off states correlated to binary values or could be turned to a high intensity state and a low intensity state that represent binary values. The latter would enable higher modulation rates as the turn-on delay of the laser diode would be avoided. The LD or SLED could be operated at some base level of output with a small variation in the output representing the transmitted data superimposed on the base level of output. This is analogous to having a DC offset or bias on a radio-frequency or audio signal. The small variation may be in the form of discrete changes in output that represent one or more bits of data, though this encoding scheme is prone to error when many levels of output are used to more efficiently encode bits. For example two levels may be used, representing a single binary digit or bit. The levels would be separated by some difference in light output. A more efficient encoding would use 4 discrete light output levels relative to the base level, enabling one value of light output to represent any combination of two binary digits or bits. The separation between light output levels is proportional to n−1, where n is the number of light output levels. Increasing the efficiency of the encoding in this way results in smaller differences in the signal differentiating encoded values and thus to a higher rate of error in measuring encoded values.

In some embodiments, additional beam shapers would be included between the laser diode members and the wavelength converter element to precondition the pump light beam before it is incident on the phosphor. For example, in a preferred embodiment the laser or SLED emission would be collimated prior to incidence with the wavelength converter such that the laser light excitation spot would have a specified and controlled size and location. The light signal then leaves the light engine and propagates either through free-space or via a waveguide such as an optical fiber. In an embodiment, the non-converted laser light is incident on the wavelength converting element 1527, however the non-converted laser light is efficiently scattered or reflected by the wavelength converting element 1527 such that less than 10% of the incident light is lost to absorption by the wavelength converting element 1527.

Use of multiple lasers of same wavelength allows for running each laser at a lower power than what one would do with only one pump laser for a fixed power of emitted white light spectrum. Addition of red and green lasers which are not converted allow for adjusting the color point of the emitted spectrum. Given a single blue emitter, so long as the conversion efficiency of the wavelength converting element does not saturate with pump laser intensity, the color point of the white light spectrum is fixed at a single point in the color space which is determined by the color of the blue laser, the down-converted spectrum emitted by the wavelength converting element, and the ratio of the power of the two spectra, which is determined by the down-conversion efficiency and the amount of pump laser light scattered by the wavelength converting element. By the addition of an independently controlled green laser, the final color point of the spectrum can be pulled above the Planckian blackbody locus of points. By addition of an independently controlled red laser, the final color point of the spectrum can be pulled below the Planckian blackbody locus of points. By the addition of independently controlled violet or cyan colored lasers, with wavelengths not efficiently absorbed by the wavelength converting element, the color point can be adjusted back towards the blue side of the color gamut. Since each laser is independently driven, the time-average transmitted power of each laser can be tailored to allow for fine adjustment of the color point and CRI of the final white light spectrum.

Optionally, multiple blue pump lasers might be used with respective center wavelengths of 420, 430, and 440 nm while non-converted green and red laser devices are used to adjust the color point of the devices spectrum. Optionally, the non-converted laser devices need not have center wavelengths corresponding to red and green light. For example, the non-converted laser device might emit in the infra-red region at wavelengths between 800 nm and 2 microns. Such a light engine would be advantageous for communication as the infra-red device, while not adding to the luminous efficacy of the white light source, or as a visible light source with a non-visible channel for communications. This allows for data transfer to continue under a broader range of conditions and could enable for higher data rates if the non-visible laser configured for data transmission was more optimally suited for high speed modulation such as a telecom laser or vertical cavity surface emitting laser (VCSEL). Another benefit of using a non-visible laser diode for communication allows the VLC-enabled white light source to use a non-visible emitter capable of effectively transmitting data even when the visible light source is turned off for any reason in applications.

In some embodiments, the white light source is configured to be a smart light source having a beam shaping optical element. Optionally, the beam shaping optical element provides an optical beam where greater than 80% of the emitted light is contained within an emission angle of 30 degrees. Optionally, the beam shaping element provides an optical beam where greater than 80% of the emitted light is contained within an emission angle of 10 degrees. Optionally, the white light source can be formed within the commonly accepted standard shape and size of existing MR, PAR, and AR111 lamps. Optionally, the white light source further contains an integrated electronic power supply to electrically energize the laser-based light module. Optionally, the white light source further contains an integrated electronic power supply with input power within the commonly accepted standards. Of course, there can be other variations, modifications, and alternatives.

In some embodiments, the smart light source containing at least a laser-based light module has one or more beam steering elements to enable communication. Optionally, the beam steering element provides a reflective element that can dynamically control the direction of propagation of the emitted laser light. Optionally, the beam steering element provides a reflective element that can dynamically control the direction of propagation of the emitted laser light and the light emitted from the wavelength converting element. Optionally, the smart light white light source further contains an integrated electronic power supply to electrically energize the beam steering elements. Optionally, the smart light white light source further contains an integrated electronic controller to dynamically control the function of the beam steering elements.

According to an embodiment, the present invention provides a dynamic laser-based light source or light projection apparatus including a micro-display element to provide a dynamic beam steering, beam patterning, or beam pixelating affect. Micro-displays such as a microelectromechanical system (MEMS) scanning mirror, or "flying mirror", a digital light processing (DLP) chip or digital mirror device (DMD), or a liquid crystal on silicon (LCOS) can be included to dynamically modify the spatial pattern and/or color of the emitted light. In one embodiment the light is pixelated to activate certain pixels and not activate other pixels to form a spatial pattern or image of white light. In another example, the dynamic light source is configured for steering or pointing the light beam. The steering or pointing can be accomplished by a user input configured from a dial, switch, or joystick mechanism or can be directed by a feedback loop including sensors.

In an embodiment, a laser driver module is provided. Among other things, the laser driver module is adapted to adjust the amount of power to be provided to the laser diode. For example, the laser driver module generates a drive current based on pixels from digital signals such as frames of images, the drive currents being adapted to drive a laser diode. In a specific embodiment, the laser driver module is configured to generate pulse-modulated light signal at a frequency range of about 50 MHz to 100 GHz.

In an alternative embodiment, DLP or DMD micro-display chip is included in the device and is configured to steer, pattern, and/or pixelate a beam of light by reflecting the light from a 2-dimensional array of micro-mirrors corresponding to pixels at a predetermined angle to turn each pixel on or off. In one example, the DLP or DMD chip is configured to steer a collimated beam of laser excitation light from the one or more laser diodes to generate a predetermined spatial and/or temporal pattern of excitation light on the wavelength conversion or phosphor member. At least a portion of the wavelength converted light from the phosphor member could then be recollimated or shaped using a beam shaping element such as an optic. In this example the micro-display is upstream of the wavelength converter member in the optical pathway. In a second example the DLP or DMD micro-display chip is configured to steer a collimated beam of at least a partially wavelength converted light to generate a predetermined spatial and/or temporal pattern of converted light onto a target surface or into a target space. In this example the micro-display is downstream of the wavelength converter member in the optical pathway. DLP or DMD micro-display chips are configured for dynamic spatial modulation wherein the image is created by tiny mirrors laid out in an array on a semiconductor chip such as a silicon chip. The mirrors can be positionally modulated at rapid rates to reflect light either through an optical beam shaping element such as a lens or into a beam dump. Each of the tiny mirrors represents one or more pixels wherein the pitch may be 5.4 µm or less. The number of mirrors corresponds or correlates to the resolution of the projected image. Common resolutions for such DLP micro-display chips include 800×600, 1024×768, 1280×720, and 1920×1080 (HDTV), and even greater.

According to an embodiment, the present invention provides a dynamic laser-based light source or light projection apparatus including a housing having an aperture. The apparatus can include an input interface for receiving a signal to activate the dynamic feature of the light source. The apparatus can include a video or signal processing module. Additionally, the apparatus includes a light source based on a laser source. The laser source includes a violet laser diode or a blue laser diode. The dynamic light feature output comprised from a phosphor emission excited by the output beam of a laser diode, or a combination of a laser diode and a phosphor member. The violet or blue laser diode is fabricated on a polar, nonpolar, or semipolar oriented Ga-containing substrate. The apparatus can include a laser driver module coupled to the laser source. The apparatus can include a digital light processing (DLP) chip comprising a digital mirror device. The digital mirror device includes a plurality of mirrors, each of the mirrors corresponding to pixels of the frames of images. The apparatus includes a power source electrically coupled to the laser source and the digital light processing chip.

The apparatus can include a laser driver module coupled to the laser source. The apparatus includes an optical member provided within proximity of the laser source, the optical member being adapted to direct the laser beam to the digital light processing chip. The apparatus includes a power source electrically coupled to the laser source and the digital light processing chip. In one embodiment, the dynamic properties of the light source may be initiated by the user of the apparatus. For example, the user may activate a switch, dial, joystick, or trigger to modify the light output from a static to a dynamic mode, from one dynamic mode to a different dynamic mode, or from one static mode to a different static mode.

In an alternative embodiment, a liquid crystal on silicon (LCOS) micro-display chip is included in the device and is configured to steer, pattern, and/or pixelate a beam of light by reflecting or absorbing the light from a 2-dimensional array of liquid crystal mirrors corresponding to pixels at a predetermined angle to turn each pixel on or off. In one example, the LCOS chip is configured to steer a collimated beam of laser excitation light from the one or more laser diodes to generate a predetermined spatial and/or temporal pattern of excitation light on the wavelength conversion or phosphor member. At least a portion of the wavelength converted light from the phosphor member could then be recollimated or shaped using a beam shaping element such as an optic. In this example the micro-display is upstream of the wavelength converter member in the optical pathway. In a second example the LCOS micro-display chip is configured to steer a collimated beam of at least a partially wavelength converted light to generate a predetermined spatial and/or temporal pattern of converted light onto a target surface or into a target space. In this example the micro-display is downstream of the wavelength converter member in the optical pathway. The former example is the preferred example since LCOS chips are polarization sensitive and the output of laser diodes is often highly polarized, for example greater than 70%, 80%, 90%, or greater than 95% polarized. This high polarization ratio of the direct emission from the laser source enables high optical throughput efficiencies for the laser excitation light compared to LEDs or legacy light sources that are unpolarized, which wastes about half of the light.

LCOS micro-display chips are configured spatial light modulation wherein the image is created by tiny active elements laid out in an array on a silicon chip. The elements reflectivity is modulated at rapid rates to selectively reflect light through an optical beam shaping element such as a lens. The number of elements corresponds or correlates to the resolution of the projected image. Common resolutions for such LCOS micro-display chips include 800×600, 1024×768, 1280×720, and 1920×1080 (HDTV), and even greater.

Optionally, the partially converted light emitted from the wavelength conversion element results in a color point, which is white in appearance. Optionally, the color point of the white light is located on the Planckian blackbody locus of points. Optionally, the color point of the white light is located within du'v' of less than 0.010 of the Planckian blackbody locus of points. Optionally, the color point of the white light is preferably located within du'v' of less than 0.03 of the Planckian blackbody locus of points. Optionally, the pump light sources are operated independently, with their relative intensities varied to dynamically alter the color point and color rendering index (CRI) of the white light.

In several preferred embodiments one or more beam shaping elements are included in the present invention. Such beam shaping elements could be included to configure the one or more laser diode excitation beams in the optical pathway prior to incidence on the phosphor or wavelength conversion member. In some embodiments the beam shaping elements are included in the optical pathway after at least a portion of the laser diode excitation light is converted by the phosphor or wavelength conversion member. In additional embodiments the beam shaping elements are included in the optical pathway of the non-converted laser diode light. Of course, in many preferred embodiments, a combination of one or more of each of the beam shaping elements is included in the present invention.

In some embodiments, a laser diode output beam must be configured to be incident on the phosphor material to excite the phosphor. In some embodiments, the laser beam may be directly incident on the phosphor and in other embodiments the laser beam may interact with an optic, reflector, or other object to manipulate or shape the beam prior to incidence on the phosphor. Examples of such optics include, but are not limited to ball lenses, aspheric collimator, aspheric lens, fast or slow axis collimators, dichroic mirrors, turning mirrors, optical isolators, but could be others. In some embodiments, other optics can be included in various combinations for the shaping, collimating, directing, filtering, or manipulating of the optical beam. Examples of such optics include, but are not limited to re-imaging reflectors, ball lenses, aspheric collimator, dichroic mirrors, turning mirrors, optical isolators, but could be others.

In some embodiments, the converted light such as a white light source is combined with one or more optical members to manipulate the generated white light. In an example the converted light source such as the white light source could serve in a spot light system such as a flashlight, spotlight, automobile headlamp or any direction light applications where the light must be directed or projected to a specified location or area. In one embodiment a reflector is coupled to the white light source. Specifically, a parabolic (or paraboloid or paraboloidal) reflector is deployed to project the white light. By positioning the white light source in the focus of a parabolic reflector, the plane waves will be reflected and propagate as a collimated beam along the axis of the parabolic reflector. In another example a lens is used to collimate the white light into a projected beam. In one example a simple aspheric lens would be positioned in front of the phosphor to collimate the white light. In another example, a total internal reflector optic is used for collimation. In other embodiments other types of collimating optics may be used such as spherical lenses or aspherical lenses. In several embodiments, a combination of optics is used.

In some embodiments, the smart white light source containing at least a laser-based light module includes a beam shaping element. Optionally, the beam shaping element provides an optical beam where greater than 80% of the emitted light is contained within an emission angle of 30 degrees. Optionally, the beam shaping element provides an optical beam where greater than 80% of the emitted light is preferably contained within an emission angle of 10 degrees. Optionally, the beam shaping element provides an optical beam where greater than 80% of the emitted light is preferably contained within an emission angle of 5 degrees. In some embodiments collimating optics are used such as parabolic reflectors, total internal reflector (TIR) optics, diffractive optics, other types of optics, and combinations of optics.

Optionally, the smart white light source can be formed within the commonly accepted standard shape and size of existing MR, PAR, and AR111 lamps. Optionally, the solid-state white light source further contains an integrated electronic power supply to electrically energize the laser-based light module. Optionally, the solid-state white light source further contains an integrated electronic power supply with input power within the commonly accepted standards. Of course, there can be other variations, modifications, and alternatives.

In an embodiment, the apparatus is capable of conveying information to the user or another observer through the means of dynamically adjusting certain qualities of the projected light. Such qualities include spot size, shape, hue, and color-point as well as through independent motion of the spot. As an example the apparatus may convey information by dynamically changing the shape of the spot. In an example, the apparatus is used as a flash-light or bicycle light, and while illuminating the path in front of the user it may convey directions or information received from a paired smart phone application. Changes in the shape of the spot which could convey information include, among others: forming the spot into the shape of an arrow that indicates which direction the user should walk along to follow a predetermined path and forming the spot into an icon to indicate the receipt of an email, text message, phone call or other push notification. The white light spot may also be used to convey information by rendering text in the spot. For example, text messages received by the user may be displayed in the spot. As another example, embodiments of the apparatus including mechanisms for altering the hue or color point of the emitted light spectrum could convey information to the user via a change in these qualities. For example, the aforementioned bike light providing directions to the user might change the hue of the emitted light spectrum from white to red rapidly to signal that the user is nearing an intersection or stop-sign that is beyond the range of the lamp.

In a specific embodiment of the present invention including a dual band light source capable of emission in the visible and the IR wavelength bands, one or more emission bands from the light source is activated by a feedback loop including a sensor to create a dynamic illumination source capable of alternating the activation of the illumination bands. Such sensors may be selected from, but not limited to an IR imaging unit including an IR camera or focal plane array, microphone, geophone, hydrophone, a chemical sensor such as a hydrogen sensor, $CO_2$ sensor, or electronic nose sensor, flow sensor, water meter, gas meter, Geiger counter, altimeter, airspeed sensor, speed sensor, range finder, piezoelectric sensor, gyroscope, inertial sensor, accelerometer, MEMS sensor, Hall effect sensor, metal detector, voltage detector, photoelectric sensor, photodetector, photoresistor, pressure sensor, strain gauge, thermistor, thermocouple, pyrometer, temperature gauge, motion detector, passive infrared sensor, Doppler sensor, biosensor, capacitance sensor, video sensor, transducer, image sensor, infrared sensor, radar, SONAR, LIDAR, or others.

In one example, a dynamic illumination feature including a feedback loop with an IR sensor to detect motion or an object. The dynamic light source is configured to generate a visible illumination on the object or location where the motion is detected by sensing the spatial position of the motion and steering the output beam to that location. In another example of a dynamic light feature including a feedback loop with a sensor, such as an accelerometer, is included. The accelerometer is configured to anticipate where the laser light source apparatus is moving toward and steer the output beam to that location even before the user of the apparatus can move the light source to be pointing at the desired location. Of course, these are merely examples of implementations of dynamic light sources with feedback loops including sensors. There can be many other implementations of this invention concept that includes combining dynamic light sources with sensors.

Figure 29A:
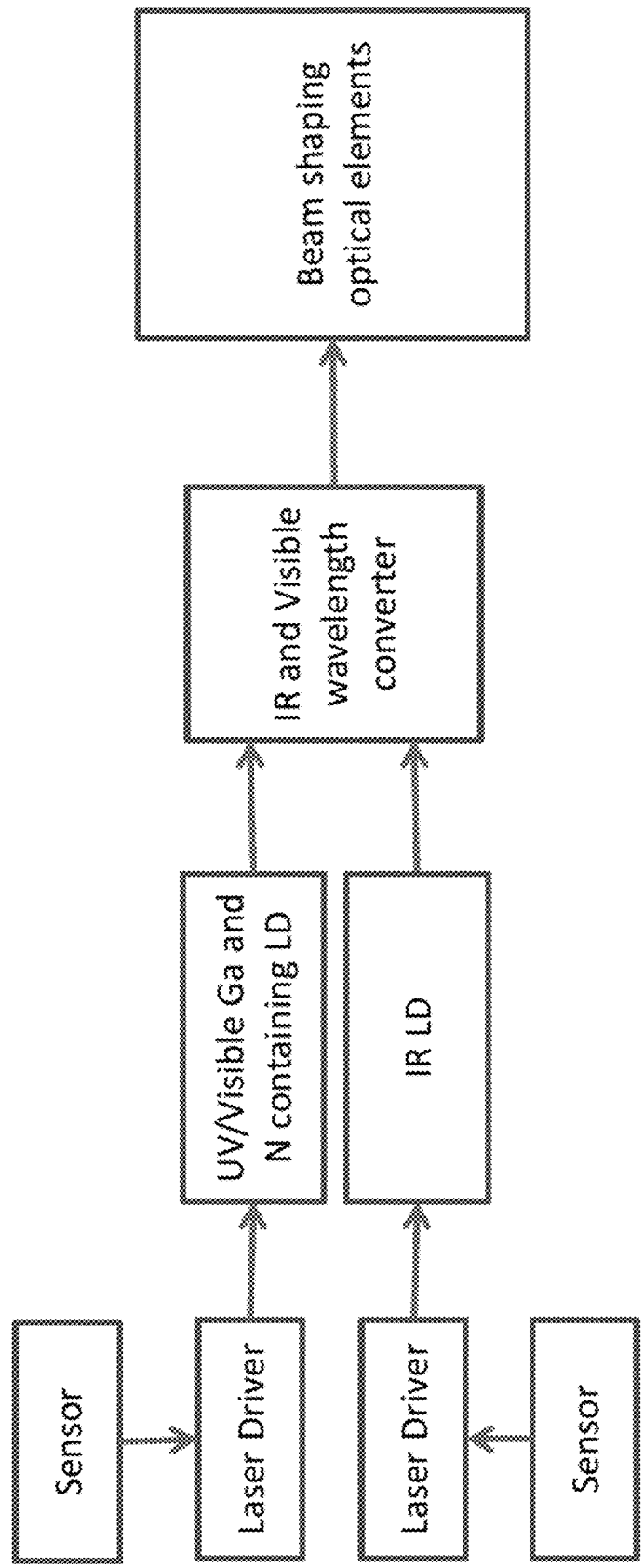
FIG. 29A is a functional block diagram for a laser-based white light source integrated with an IR illumination source containing a UV or blue pump laser, a visible wavelength converting element, an IR emitting laser diode, and sensor members configured for illumination activation based on sensor feedback according to an embodiment of the present invention.

FIG. 29A is a functional block diagram for a laser-based white light source containing a gallium and nitrogen containing violet or blue pump laser and a wavelength converting element to generate a white light emission, an infrared emitting laser diode to generate an IR emission according to an embodiment of the present invention, configured with sensors to form feedback loops. This diagram is merely an example, which should not unduly limit the scope of the claims. Referring to FIG. 29A, a blue or violet laser device emitting a spectrum with a center point wavelength between 390 and 480 nm is provided. The light from the blue laser device is incident on a wavelength converting element, which partially or fully converts the blue light into a broader spectrum of longer wavelength light such that a white light spectrum is produced. A first laser driver is provided which powers the gallium and nitrogen containing laser device to excite the visible emitting wavelength member. Additionally, an IR emitting laser device is included to generate an IR illumination. The directional IR electromagnetic radiation from the laser diode is incident on the wavelength converting element wherein it is reflected from or transmitted through the wavelength converting element such that it follows the same optical path as the white light emission. A second laser driver is included to power the IR emitting laser diode and deliver a controlled amount of current at a sufficiently high voltage to operate the IR laser diode.

The visible and IR emitting illumination source according to the present invention and shown in FIG. 29A is equipped with sensors configured to provide an input to the first and/or the second laser drivers. In one example, the first laser driver is configured with an IR sensor that detects motion or objects using the IR illumination source. Once a detection is triggered using the IR illumination source, the first laser driver activates the first laser diode to generate a white light to shine a visible light on the object or target. There are many examples where it would be useful to covertly detect an object using IR illumination such that it could not be detected by animals or humans.

According to this embodiment shown in FIG. 29A, the IR emission could include a peak wavelength in the 700 nm to 1100 nm range based on gallium and arsenic material system [eg GaAs] for near-IR illumination, or a peak wavelength in the 1100 to 2500 nm range based on an indium and phosphorous containing material system (e.g., InP) for eye-safe wavelength IR illumination, or in the 2500 nm to 15000 nm wavelength range based on quantum cascade laser technology for mid-IR thermal imaging. Optionally, the one or more beam shaping optical elements can be one selected from slow axis collimating lens, fast axis collimating lens, aspheric lens, ball lens, total internal reflector (TIR) optics, parabolic lens optics, refractive optics, or a combination of above.

Of course, any type of sensor could be configured with the present invention to induce a visible or IR illumination response when the sensor was triggered or tripped. Further elements could be incorporated with present invention including sensors. In one embodiment a beam steering element such as a MEMS mirror or DLP is used to pattern or direct the light onto a specific area or a specific object that could be moving. By using a motion sensor or the IR sensor the illumination source configured with the beam steering element could be configured to track the object with visible light and/or with IR illumination. In a scenario where the user did not want the target matter to be aware of their presence, the user could track with the IR illumination. In a scenario where the user did want the subject to be aware of their presence, they could track the subject with visible light. In many jurisdictions, it is important to have photographs or other images under visible light, in which case the visible illumination source would be illuminated. In some embodiments filters may be used to selectively filter the visible light, to selectively filter the IR illumination, and/or to selectively filter both the visible light and the IR illumination.

In one embodiment according to the present invention a LiFi or VLC capability is included with the laser based visible and IR illumination source. In one example, the LiFi capability could be configured to transmit data to a target subject in its field of view once a certain detection or sensor stimulus was triggered. The data could be targeted based on IR sensor input or other sensor input such as a visible camera. In another example, the LiFi or VLC function is used to transmit data to the user or another individual. In one example, the data being transmitted is the IR or visible imagery data acquired by the apparatus. Of course there can be other applications and examples of the present invention that includes a LiFi or VLC capability.

In one embodiment according to the present invention a spatial sensing system that uses the gallium and nitrogen containing laser diode and/or an included IR emitting laser diode is configured with the laser based visible and IR illumination source. In one example, the spatial sensing capability could be configured as a depth detector using a time of flight calculation. See U.S. application Ser. No. 15/841,053, filed Dec. 13, 2017, the contents of which are incorporated herein by reference.

In some embodiments, the invention may be applicable as a visible light communication transceiver for bi-directional communication. Optionally, the transceiver also contains a detector including a photodiode, avalanche photodiode, photomultiplier tube or other means of converting a light signal to electrical energy. The detector is connected to the modem. In this embodiment the modem is also capable of decoding detected light signals into binary data and relaying that data to a control system such as a computer, cell-phone, wristwatch, or other electronic device.

In some embodiments, the present invention provides a smart white light-source to be used on automotive vehicles for illumination of the exterior environment of the vehicle. An exemplary usage would be as a parking light, headlight, fog-light, signal-light or spot-light. In an embodiment, a lighting apparatus is provided including a housing having an aperture. Additionally, the lighting apparatus includes one or more pump light sources including one or more blue lasers or blue SLED sources. The individual blue lasers or SLEDs have an emission spectrum with center wavelength within the range 400 to 480 nm. The one or more of the pump light sources emitting in the blue range of wavelengths illuminates a wavelength converting element which absorbs part of the pump light and reemits a broader spectrum of longer wavelength light. Each pump light source is configured such that both light from the wavelength converting element and light directly emitted from the one or more light sources being combined as a white light spectrum. The lighting apparatus further includes optical elements for focusing and collimating the white light and shaping the white light spot.

In this smart lighting apparatus, each pump light source is independently addressable, and is controlled by a laser driver module configured to generate pulse-modulated light signal at a frequency range of between 10 MHz and 100 GHz. The laser driver includes an input interface for receiving digital or analog signals from sensors and electronic controllers in order to control the modulation of the pump laser sources for the transmission of data. The lighting apparatus can transmit data about the vehicle or fixture to which it is attached via the modulation of the blue or violet lasers or SLED sources to other vehicles which have appropriately configured VLC receivers. For example, the white light source could illuminate oncoming vehicles. Optionally, it could illuminate from behind or sides vehicles travelling in the same direction. As an example the lighting apparatus could illuminate VLC-receiver enabled road signs, road markings, and traffic signals, as well as dedicated VLC receivers installed on or near the highway. The lighting apparatus would then broadcast information to the receiving vehicles and infrastructure about the broadcasting vehicle. Optionally, the lighting apparatus could transmit information on the vehicle's location, speed and heading as well as, in the case of autonomous or semiautonomous vehicles, information about the vehicle's destination or route for purposes of efficiently scheduling signal light changes or coordinating cooperative behavior, such as convoying, between autonomous vehicles.

In some embodiments, the present invention provides a communication device which can be intuitively aimed. An example use of the communication device would be for creation of temporary networks with high bandwidth in remote areas such as across a canyon, in a ravine, between mountain peaks, between buildings separated by a large distance and under water. In these locations, distances may be too large for a standard wireless network or, as in the case of being under water, radio frequency communications may be challenging due to the absorption of radio waves by water. The communication device includes a housing having an aperture. Additionally, the communication device includes one or more blue laser or blue SLED source. The individual blue lasers or SLEDs have an emission spectrum with center wavelength within the range 400 to 480 nm. One or more of the light sources emitting in the blue range of wavelengths illuminates a wavelength converting element which absorbs part of the pump light and reemits a broader spectrum of longer wavelength light. The light source is configured such that both light from the wavelength converting element and the plurality of light sources are emitted as a white light spectrum. The communication device includes optical elements for focusing and collimating the white light and shaping the white light spot. Optionally, each light source in the communication device is independently addressable, and is controlled by a driver module configured to generate pulse-modulated light signal at a modulation frequency range of between 10 MHz and 100 GHz. The driver module includes an input interface for receiving digital or analog signals from sensors and electronic controllers in order to control the modulation of the laser sources for the transmission of data.

The communication device includes one or more optical detectors to act as VLC-receivers and one or more band-pass filters for differentiating between two or more of the laser or SLED sources. Optionally, a VLC-receiver may detect VLC signals using multiple avalanche photodiodes capable of measuring pulse-modulated light signals at a frequency range of about 50 MHz to 100 GHz. Optionally, the communication device contains one or more optical elements, such as mirrors or lenses to focus and collimate the light into a beam with a divergence of less than 5 degrees in a less preferred case and less than 2 degrees in a most preferred case. Two such apparatuses would yield a spot size of between roughly 3 and 10 meters in diameter at a distance of 100 to 300 meters, respectively, and the focused white light spot would enable operators to aim the VLC-transceivers at each other even over long distances simply by illuminating their counterpart as if with a search light.

In some embodiments, the communication device disclosed in the present invention can be applied as flash sources such as camera flashes that carrying data information. Data could be transmitted through the flash to convey information about the image taken. For example, an individual may take a picture in a venue using a camera phone configured with a VLC-enabled solid-state light-source in accordance with an embodiment of this invention. The phone transmits a reference number to VLC-receivers installed in the bar, with the reference number providing a method for identifying images on social media websites taken at a particular time and venue.

In some embodiments, the present invention provides a projection apparatus. The projection apparatus includes a housing having an aperture. The apparatus also includes an input interface for receiving one or more frames of images. The apparatus includes a video processing module. Additionally, the apparatus includes one or more blue laser or blue SLED sources disposed in the housing. The individual blue lasers or SLEDs have an emission spectrum with center wavelength within the range 400 to 480 nm. One or more of the light sources emitting in the blue range of wavelengths illuminates a wavelength converting element which absorbs part of the pump light and reemits a broader spectrum of longer wavelength light. The light source is configured such that both light from the wavelength converting element and the plurality of light sources are emitted as a white light spectrum. Additionally, the apparatus includes optical elements for focusing and collimating the white light and shaping the white light spot. In this apparatus, each light source is independently addressable, and is controlled by a laser driver module configured to generate pulse-modulated light signal at a modulation frequency range of between 10 MHz and 100 GHz. The laser driver also includes an input interface for receiving digital or analog signals from sensors and electronic controllers in order to control the modulation of the laser sources for the transmission of data. Furthermore, the apparatus includes a power source electrically coupled to the laser source and the digital light processing chip. Many variations of this embodiment could exist, such as an embodiment where the green and blue laser diode share the same substrate or two or more of the different color lasers could be housed in the same packaged. The outputs from the blue, green, and red laser diodes would be combined into a single beam.

Fiber scanner has certain performance advantages and disadvantages over scanning mirror as the beam steering optical element in the dynamic light source. Scanning mirror appears to have significantly more advantages for display and imaging applications. For example, the scanning frequency can be achieved much higher for scanning mirror than for fiber scanner. Mirror scanner may raster at near 1000 kHz with higher resolution (<1 μm) but without 2D scanning limitation while fiber scanner may only scan at up to 50 kHz with 2D scanning limitation. Additionally, mirror scanner can handle much higher light intensity than fiber scanner. Mirror scanner is easier to be physically set up with light optimization for white light or RGB light and incorporated with photodetector for image, and is less sensitive to shock and vibration than fiber scanner. Since light beam itself is directly scanned in mirror scanner, no collimation loss, AR loss, and turns limitation exist, unlike the fiber itself is scanned in fiber scanner which carries certain collimation loss and AR loss over curved surfaces. Of course, fiber scanner indeed is advantageous in providing much larger angular displacement (near 80 degrees) over that (about +/−20 degrees) provided by mirror scanner.

This white light or multi-colored dynamic image projection technology according to this invention enables smart lighting benefits to the users or observers. This embodiment of the present invention is configured for the laser-based light source to communicate with users, items, or objects in two different methods wherein the first is through VLC technology such as LiFi that uses high-speed analog or digital modulation of an electromagnetic carrier wave within the system, and the second is by the dynamic spatial patterning of the light to create visual signage and messages for the viewers to see. These two methods of data communication can be used separately to perform two distinct communication functions such as in a coffee shop or office setting where the VLC/LiFi function provides data to users' smart phones and computers to assist in their work or internet exploration while the projected signage or dynamic light function communicates information such as menus, lists, directions, or preferential lighting to inform, assist, or enhance users experience in their venue.

In another aspect, the present invention provides a dynamic light source or "light-engine" that can function as a white light source for general lighting applications with tunable colors.

In an embodiment, the light-engine consists of two or more lasers or SLED light sources. At least one of the light sources emits a spectrum with a center wavelength in the range of 380-450 nm. At least one of the light sources emits a spectrum with a center wavelength in the range of 450-540 nm. In some embodiments the laser diode is comprised from a III-nitride material emitting in the ultraviolet region with a wavelength of about 270 nm to about 390 nm. This embodiment is advantageous in that for many phosphors in order to achieve a particular color point, there will be a significant gap between the wavelength of the laser light source and the shortest wavelength of the spectrum emitted by the phosphor. By including multiple blue lasers of significantly different wavelengths, this gap can be filled, resulting in a similar color point with improved color rendering.

In an embodiment, the green and red laser light beams are incident on the wavelength converting element in a transmission mode and are scattered by the wavelength converting element. In this embodiment the red and green laser light is not strongly absorbed by the wavelength converting element.

In and embodiment, the wavelength converting element consists of a plurality of regions comprised of varying composition or color conversion properties. For example, the wavelength converting element may be comprised by a plurality of regions of alternating compositions of phosphor. One composition absorbs blue or violet laser light in the range of wavelengths of 385 to 450 nm and converts it to a longer wavelength of blue light in the wavelength range of 430 nm to 480 nm. A second composition absorbs blue or violet laser light and converts it to green light in the range of wavelengths of 480-550 nm. A third composition absorbs blue or violet laser light and converts it to red light in the range of wavelengths of 550 to 670 nm. Between the laser light source and the wavelength converting element is a beam steering mechanism such as a MEMS mirror, rotating polygonal mirror, mirror galvanometer, or the like. The beam steering element scans a violet or blue laser spot across the array of regions on the wavelength converting element and the intensity of the laser is synced to the position of the spot on the wavelength converting element such that red, green and blue light emitted or scattered by the wavelength converting element can be varied across the area of the wavelength converting element.

In an embodiment, the phosphor elements are single crystal phosphor platelets.

In an embodiment, the phosphor elements are regions of phosphor powder sintered into platelets or encapsulated by a polymer or glassy binder.

In another embodiment, the plurality of wavelength converting regions comprising the wavelength converting element are composed of an array of semiconductor elements such as InGaN, GaN single or multi-quantum wells for the production of blue or green light and single and multi-quantum-well structures composed of various compositions of AlInGaAsP for production of yellow red light or infrared light, although this is merely an example, which should not unduly limit the scope of the claims. One of ordinary skill in the art would recognize other alternative semiconductor materials or light-converting structures.

In another embodiment, the plurality of wavelength converting regions comprising the wavelength converting element are composed of an array of semiconductor elements such as InGaN GaN quantum dots for the production of blue, red or green light and quantum dots composed of various compositions of AlInGaAsP for production of yellow and red light, although this is merely an example, which should not unduly limit the scope of the claims. One of ordinary skill in the art would recognize other alternative semiconductor materials or light-converting structures.

In another embodiment, the wavelength converting element also contains regions of non-wavelength converting material that scatters the laser light. The advantage of this configuration is that the blue laser light is diffusely scattered without conversion losses, thereby improving the efficiency of the overall light source. Examples of such non-converting but scattering materials are: granules of wide-bandgap ceramics or dielectric materials suspended in a polymer or glassy matrix, wide-bandgap ceramics or dielectric materials with a roughened surface, a dichroic mirror coating overlaid on a roughened or patterned surface, or a metallic mirror or metallic-dielectric hybrid mirror deposited on a rough surface.

In a specific embodiment, the input to the laser driver is a digital or analog signal provided by one or more sensors.

In a specific embodiment, the output from the sensors is measured or read by a microcontroller or other digital circuit which outputs a digital or analog signal which directs the modulation of the laser driver output based on the input signal from the sensors.

In a specific embodiment, the input to the driver is a digital or analog signal provided by a microcontroller or other digital circuit based on input to the microcontroller or digital circuit from one or more sensors.

Optionally, sensors used in the smart-lighting system may include sensors measuring atmospheric and environmental conditions such as pressure sensors, thermocouples, thermistors, resistance thermometers, chronometers or real-time clocks, humidity sensor, ambient light meters, pH sensors, infra-red thermometers, dissolved oxygen meters, magnetometers and hall-effect sensors, colorimeters, soil moister sensors, and microphones among others.

Optionally, sensors used in the smart-lighting system may include sensors for measuring non-visible light and electromagnetic radiation such as UV light sensors, infra-red light sensors, infra-red cameras, infra-red motion detectors, RFID sensors, and infra-red proximity sensors among others.

Optionally, sensors used in the smart-lighting system may include sensors for measuring forces such as strain gages, load cells, force sensitive resistors and piezoelectric transducers among others.

Optionally, sensors used in the smart-lighting system may include sensors for measuring aspects of living organisms such as fingerprint scanner, pulse oximeter, heart-rate monitors, electrocardiography sensors, electroencephalography sensors and electromyography sensors among others.

In an embodiment, the dynamic properties of the light source may be initiated by the user of the apparatus. For example, the user may activate a switch, dial, joystick, or trigger to modify the light output from a static to a dynamic mode, from one dynamic mode to a different dynamic mode, or from one static mode to a different static mode.

In one example of the smart-lighting system, it includes a dynamic light source configured in a feedback loop with a sensor, for example, a motion sensor, being provided. The dynamic light source is configured to illuminate specific locations by steering the output of the white light beam in the direction of detected motion. In another example of a dynamic light feature including a feedback loop with a sensor, an accelerometer is provided. The accelerometer is configured to measure the direction of motion of the light source. The system then steers the output beam towards the direction of motion. Such a system could be used as, for example, a flashlight or hand-held spot-light. Of course, these are merely examples of implementations of dynamic light sources with feedback loops including sensors. There can be many other implementations of this invention concept that includes combining dynamic light sources with sensors.

According to an embodiment, the present invention provides a dynamic laser-based light source or light projection apparatus that is spatially tunable. The apparatus includes a housing with an aperture to hold a light source having an input interface for receiving a signal to activate the dynamic feature of the light source. Optionally, the apparatus can include a video or signal processing module. Additionally, the apparatus includes a laser source disposed in the housing with an aperture. The laser source includes one or more of a violet laser diode or blue laser diode. The dynamic light source features output comprised from the laser diode light spectrum and a phosphor emission excited by the output beam of a laser diode. The violet or blue laser diode is fabricated on a polar, nonpolar, or semipolar oriented Ga-containing substrate. The apparatus can include mirror galvanometer or a microelectromechanical system (MEMS) scanning mirror, or "flying mirror", configured to project the laser light or laser pumped phosphor white light to a specific location in the outside world. By rastering the laser beam using the MEMS mirror a pixel in two dimensions can be formed to create a pattern or image. The apparatus can also include an actuator for dynamically orienting the apparatus to project the laser light or laser pumped phosphor white light to a specific location in the outside world.

According to an embodiment, the present invention provides a dynamic light source or "light-engine" that can function as a white light source for general lighting applications with tunable colors. The light-engine consists of three or more laser or SLED light sources. At least one light source emits a spectrum with a center wavelength in the range of 380-480 nm and acts as a blue light source. At least one light emits a spectrum with a center wavelength in the range of 480-550 nm and acts as a green light source. At least one light emits a spectrum with a center wavelength in the range 600-670 nm and acts as a red light source. Each light source is individually addressable, such that they may be operated independently of one another and act as independent communication channels, or in the case of multiple emitters in the red, green or blue wavelength ranges the plurality of light sources in each range may be addressed collectively, though the plurality of sources in each range are addressable independently of the sources in the other wavelength ranges. One or more of the light sources emitting in the blue range of wavelengths illuminates a wavelength converting element which absorbs part of the pump light and reemits a broader spectrum of longer wavelength light. The light engine is configured such that both light from the wavelength converting element and the plurality of light sources are emitted from the light-engine. A laser or SLED driver module is provided which can dynamically control the light engine based on input from an external source. For example, the laser driver module generates a drive current, with the drive currents being adapted to drive one or more laser diodes, based on one or more signals.

Optionally, the quality of the light emitted by the white light source may be adjusted based on input from one or more sensors. Qualities of the light that can be adjusted in response to a signal include but are not limited to: the total luminous flux of the light source, the relative fraction of long and short wavelength blue light as controlled by adjusting relative intensities of more than one blue laser sources characterized by different center wavelengths and the color point of the white light source by adjusting the relative intensities of red and green laser sources. Such dynamic adjustments of light quality may improve productivity and health of workers by matching light quality to work conditions.

Optionally, the quality of the white light emitted by the white light source is adjusted based on input from sensors detecting the number of individuals in a room. Such sensors may include motion sensors such as infra-red motion sensors, microphones, video cameras, radio-frequency identification (RFID) receivers monitoring RFID enabled badges on individuals, among others.

Optionally, the color point of the spectrum emitted by the white light source is adjusted by dynamically adjusting the intensities of the blue "pump" laser sources relative to the intensities of the green and red sources. The total luminous flux of the light source and the relative proportions are controlled by input from a chronometer, temperature sensor and ambient light sensor measuring to adjust the color point to match the apparent color of the sun during daylight hours and to adjust the brightness of the light source to compensate for changes in ambient light intensity during daylight hours. The ambient light sensor would either be configured by its position or orientation to measure input predominantly from windows, or it would measure ambient light during short periods when the light source output is reduced or halted, with the measurement period being too short for human eyes to notice.

Optionally, the color point of the spectrum emitted by the white light source is adjusted by dynamically adjusting the intensities of the blue "pump" laser sources relative to the intensities of the green and red sources. The total luminous flux of the light source and the relative proportions are controlled by input from a chronometer, temperature sensor and ambient light sensor measuring to adjust the color point to compensate for deficiencies in the ambient environmental lighting. For example, the white light source may automatically adjust total luminous flux to compensate for a reduction in ambient light from the sun due to cloudy skies. In another example, the white light source may add an excess of blue light to the emitted spectrum to compensate for reduced sunlight on cloudy days. The ambient light sensor would either be configured by its position or orientation to measure input predominantly from windows, or it would measure ambient light during short periods when the light source output is reduced or halted, with the measurement period being too short for human eyes to notice.

In a specific embodiment, the white light source contains a plurality of blue laser devices emitting spectra with different center wavelengths spanning a range from 420 nm to 470 nm. For example, the source may contain three blue laser devices emitting at approximately 420, 440 and 460 nm. In another example, the source may contain five blue laser devices emitting at approximately 420, 440, 450, 460 and 470 nm. The total luminous flux of the light source and the relative fraction of long and short wavelength blue light is controlled by input from a chronometer and ambient light sensor such that the emitted white light spectra contains a larger fraction of intermediate wavelength blue light between 440 and 470 nm during the morning or during overcast days in order to promote a healthy circadian rhythm and promote a productive work environment. The ambient light sensor would either be configured by its position or orientation to measure input predominantly from windows, or it would measure ambient light during short periods when the light source output is reduced or halted, with the measurement period being too short for human eyes to notice.

Optionally, the white light source would be provided with a VLC-receiver such that a plurality of such white light sources could form a VLC mesh network. Such a network would enable the white light sources to broadcast measurements from various sensors. In an example, a VLC mesh-network comprised of VLC-enabled white light sources could monitor ambient light conditions using photo sensors and room occupancy using motion detectors throughout a workspace or building as well as coordinate measurement of ambient light intensity such that adjacent light sources do not interfere with these measurements. In an example, such fixtures could monitor local temperatures using temperature sensors such as RTDs and thermistors among others.

In an embodiment, the white light source is provided with a computer controlled video camera. The white light source contains a plurality of blue laser devices emitting spectra with different center wavelengths spanning a range from 420 nm to 470 nm. For example, the white light source may contain three blue laser devices emitting at approximately 420, 440 and 460 nm. In another example, the white light source may contain five blue laser devices emitting at approximately 420, 440, 450, 460 and 470 nm. The total luminous flux of the white light source and the relative fraction of long and short wavelength blue light is controlled by input from facial recognition and machine learning based algorithms that are utilized by the computer control to determine qualities of individuals occupying the room. In an example, number of occupants is measured. In another example, occupants may be categorized by type; for example by sex, size and color of clothing among other differentiable physical features. In another example, mood and activity level of occupants may be quantified by the amount and types of motion of occupants.

Figure 29B:
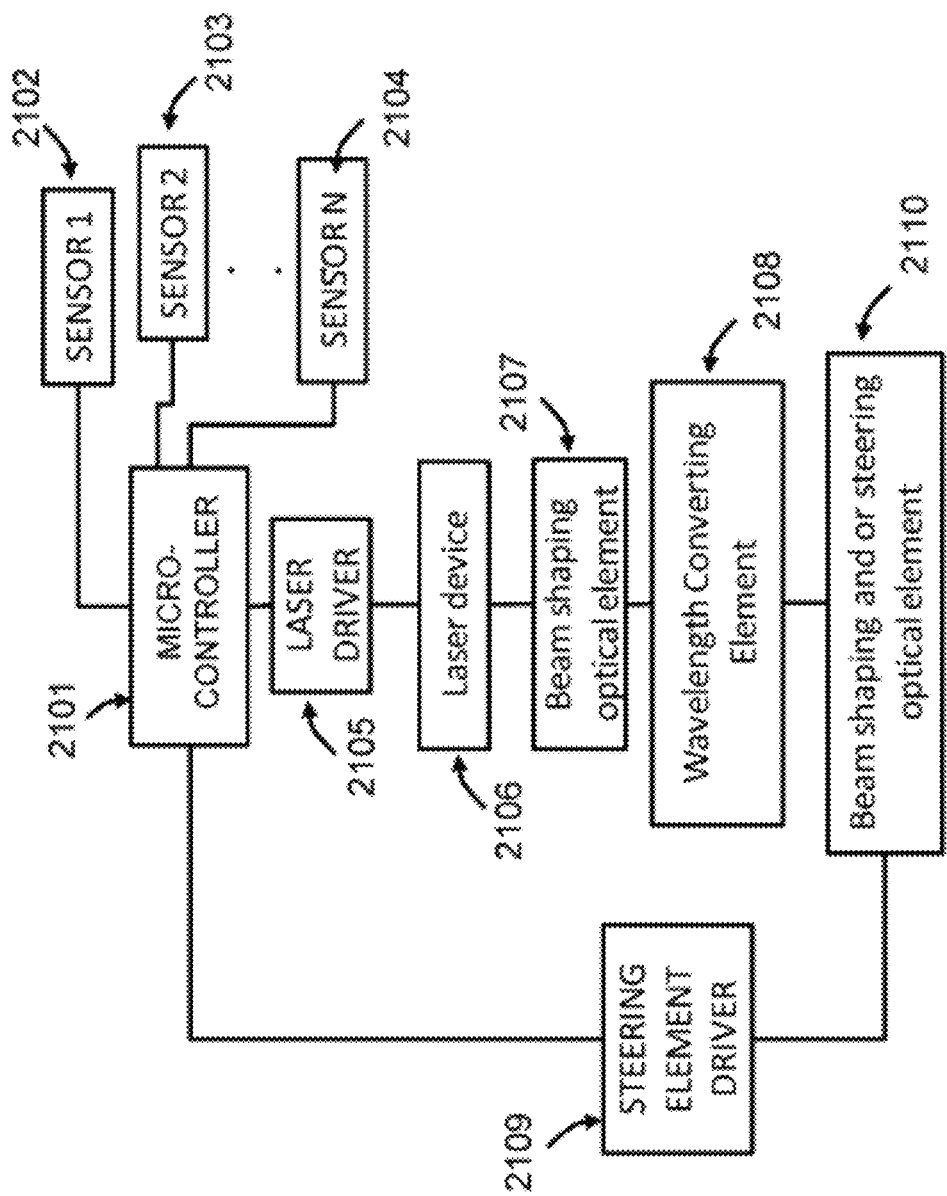
FIG. 29B is a functional diagram for a dynamic, laser-based smart-lighting system according to some embodiments of the present invention.

FIG. 29B is a functional diagram for a dynamic, laser-based smart-lighting system according to some embodiments of the present invention. This diagram is merely an example, which should not unduly limit the scope of the claims. One of ordinary skill in the art would recognize many variations, alternatives, and modifications. As shown, one or more laser devices 2106 are provided along with beam shaping optical elements 2107. The laser devices 2106 and beam shaping optical elements 2107 are configured such that the laser light is incident on a wavelength converting element 2108 that absorbs part or all laser light and emits a longer wavelength spectrum of light. Beam shaping and steering elements 2110 are provided which collect light from the wavelength converting element 2008 along with remaining laser light and direct it out of the light source. The light source is provided with a laser driver 2005 that provides controlled current and voltage to the one or more laser devices 2006. The output of the laser driver 2105 is determined by the digital or analog output of a microcontroller (or other digital or analog control circuit) 2101. The light source is also provided with a steering element driver 2109 which controls the beam steering optical element 2110. The output of the steering element driver 2109 is determined by input from the control circuit. One or more sensors 2102, 2103 and 2104 are provided. A digital or analog output of the sensors is read by the microcontroller 2101 and then converted into a predetermined change or modulation of the output from the control circuit to the laser driver 2105 and steering element driver 2109 such that the output of the light source is dynamically controlled by the output of the sensors.

In some embodiments, the beam steering optical elements include a scanning mirror. In an example, among the one or more laser devices, at least one laser device emits a spectrum with a center wavelength in the range of 380-480 nm and acts as a violet or blue light source. The blue range of wavelengths illuminates the wavelength converting element which absorbs part of the pump light and reemits a broader spectrum of longer wavelength light. Both light from the wavelength converting element and the one or more laser devices are emitted as a white light. Optionally, a laser or SLED driver module is provided for dynamically controlling the one or more laser devices based on input from an external source to form a dynamic light source. For example, the laser driver module generates a drive current, with the drive current being adapted to drive one or more laser diodes, based on one or more signals. The dynamic light source has a scanning mirror and other optical elements for beam steering which collect the emitted white light spectrum, direct them towards the scanning mirror and either collimate or focus the light. A scanning mirror driver is provided which can dynamically control the scanning mirror based on input from an external source. For example, the scanning mirror driver generates either a drive current or a drive voltage, with the drive current or drive voltage adapted to drive the scanning mirror to a specific orientation or through a specific range of motion, based on one or more signals.

Applications for such an embodiment include any where there is aesthetic, informational or artistic value in the color point, position or shape of a spot light being dynamically controlled based on the input from one or more sensors. The primary advantage of the apparatus to such applications is that the apparatus may transition between several configurations, with each configuration providing optimal lighting for different possible contexts. Some example contexts that may require different quality of lighting include: general lighting, highlighting specific objects in a room, spot lighting that follows a moving person or object, lighting that changes color point to match time of day or exterior or ambient lighting, among others.

As an example use case, the apparatus could be used as a light source for illuminating works of art in a museum or art gallery. Motion sensors would trigger the change in the shape and intensity of the emitted spot of light from a spatial and color configuration intended for general lighting to a configuration that highlights in an ascetically pleasing way the work of art corresponding to the triggering motion sensor. Such a configuration would also be advantageous in stores, where the apparatus could provide general illumination until a triggering input causes it to preferentially illuminate one or more items for sale.

The apparatus would be advantageous in lighting applications where one needs to trigger transmission of information based on the input of sensors. As an example application, one may utilize the apparatus as a car head-light. Measurements from a LIDAR or image recognition system would detect the presence of other vehicles in front of the car and trigger the transmission of the cars location, heading and velocity to the other vehicles via VLC.

Applications include selective area VLC as to only transmit data to certain locations within a space or to a certain object which is determined by sensors—spatially selective WiFi/LiFi that can track the recipients location and continuously provide data. You could even do spacetime division multiplexing where convoluted data streams are sent to different users or objects sequentially through modulation of the beam steering device. This could provide for very secure end user data links that could track user's location.

In an embodiment, the apparatus is provided with information about the location of a user based on input from sensors or other electronic systems for determining the location of individuals in the field of the view of the apparatus. The sensors might be motion detectors, digital cameras, ultrasonic range finders or even RF receivers that triangulate the position of people by detecting radio frequency emissions from their electronics. The apparatus provides visible light communication through the dynamically controllable white light spot, while also being able to control the size and location of the white light spot as well as raster the white light spot quickly enough to appear to form a wide spot of constant illumination. The determined location of a user with respect to the apparatus can be used to localize the VLC data transmission intended for a specific user to only in the region of the field of view occupied by the specific user. Such a configuration is advantageous because it provides a beam steering mechanism for multiple VLC transmitters to be used in a room with reduced interference. For example, two conventional LED-light bulb based VLC transmitters placed adjacent to one another in a room would produce a region of high interference in the region of the room where the emitted power from both VLC transmitters incident on a user's VLC receiver is similar or equal. Such an embodiment is advantageous in that when two such light sources are adjacent to one another the region containing VLC data transmission of the first apparatus is more likely to overlap a region from the second apparatus where no VLC data is being transmitted. Since DC offsets in received optical power are easy to filter out of VLC transmissions, this allows multiple VLC enabled light sources to be more closely packed while still providing high transmission rates to multiple users.

In some embodiments, the apparatus received information about where the user is from RF receivers. For example, a user may receive data using VLC but transmits it using a lower-bandwidth WiFi connection. Triangulation and beam-forming techniques can be used to pinpoint the location of the user within a room by analyzing the strength of the user's WiFi transmission at multiple WiFi transmitter antennas.

In some embodiments, the user transmits data either by VLC or WiFi, and the location of the user is determined by measuring the intensity of the VLC signal from the apparatus at the user and then transmitting that data back to the apparatus via WiFi or VLC from the user's VLC enabled device. This allows the apparatus to scan the room with a VLC communication spot and the time when a user detects maximum VLC signal is correlated to the spot position to aim the VLC beam at the user.

In an embodiment, the apparatus is attached to radio-controlled or autonomous unmanned aircraft. The unmanned aircraft could be drones, i.e. small scale vehicles such as miniature helicopters, quad-copters or other multi-rotor or single-rotor vertical takeoff and landing craft, airplanes and the like that were not constructed to carry a pilot or other person. The unmanned aircraft could be full-scale aircraft retrofitted with radio-controls or autopilot systems. The unmanned aircraft could be a craft where lift is provided by buoyancy such as blimps, dirigibles, helium and hydrogen balloons and the like.

Addition of VLC enabled, laser-based dynamic white-light sources to unmanned aircraft is a highly advantageous configuration for applications where targeted lighting must be provided to areas with little or no infrastructure. As an example embodiment, one or more of the apparatuses are provided on an unmanned aircraft. Power for the apparatuses is provided through one or more means such as internal power from batteries, a generator, solar panels provided on the aircraft, wind turbines provided on the aircraft and the like or external power provided by tethers including power lines. Data transmission to the aircraft can be provided either by a dedicated wireless connection to the craft or via transmission lines contained within the tether. Such a configuration is advantageous for applications where lighting must be provided in areas with little or no infrastructure and where the lighting needs to be directional and where the ability to modify the direction of the lighting is important. The small size of the apparatus, combined with the ability of the apparatus to change the shape and size of the white light spot dynamically as well as the ability of the unmanned aircraft to alter its position either through remote control by a user or due to internal programming allow for one or more of these aircraft to provide lighting as well as VLC communications to a location without the need for installation of fixed infrastructure. Situations where this would be advantageous include but are not limited to construction and road-work sites, event sites where people will gather at night, stadiums, coliseums, parking lots, etc. By combining a highly directional light source on an unmanned aircraft, fewer light sources can be used to provide illumination for larger areas with less infrastructures. Such an apparatus could be combined with infra-red imaging and image recognition algorithms, which allow the unmanned aircraft to identify pedestrians or moving vehicles and selectively illuminate them and provide general lighting as well as network connectivity via VLC in their vicinity.

In some preferred embodiments the smart light source is used in Internet of Things (IoT), wherein the laser based smart light is used to communicate with objects such as household appliances (i.e., refrigerator, ovens, stove, etc.), lighting, heating and cooling systems, electronics, furniture such as couches, chairs, tables, beds, dressers, etc., irrigation systems, security systems, audio systems, video systems, etc. Clearly, the laser based smart lights can be configured to communicate with computers, smart phones, tablets, smart watches, augmented reality (AR) components, virtual reality (VR) components, games including game consoles, televisions, and any other electronic devices.

In some embodiments, the apparatus is used for augmented reality applications. One such application is as a light source that is able to provide a dynamic light source that can interact with augmented reality glasses or headsets to provide more information about the environment of the user. For example, the apparatus may be able to communicate with the augmented reality headset via visible light communication (LiFi) as well as rapidly scan a spot of light or project a pattern of light onto objects in the room. This dynamically adjusted pattern or spot of light would be adjusted too quickly for the human eye to perceive as an independent spot. The augmented reality head-set would contain cameras that image the light pattern as they are projected onto objects and infer information about the shape and positioning of objects in the room. The augmented reality system would then be able to provide images from the system display that are designed to better integrate with objects in the room and thus provide a more immersive experience for the user.

For spatially dynamic embodiments, the laser light or the resulting white light must be dynamically aimed. A MEMS mirror is the smallest and most versatile way to do this, but this text covers others such as DLP and LCOS that could be used. A rotating polygon mirror was common in the past, but requires a large system with motors and multiple mirrors to scan in two or more directions. In general, the scanning mirror will be coated to produce a highly reflective surface. Coatings may include metallic coatings such as silver, aluminum and gold among others. Silver and Aluminum are preferred metallic coatings due to their relatively high reflectivity across a broad range of wavelengths. Coatings may also include dichroic coatings consisting of layers of differing refractive index. Such coatings can provide exceptionally high reflectivity across relatively narrow wavelength ranges. By combining multiple dichroic film stacks targeting several wavelength ranges a broad spectrum reflective film can be formed. In some embodiments, both a dichroic film and a metal reflector are utilized. For example, an aluminum film may be deposited first on a mirror surface and then overlaid with a dichroic film that is highly reflective in the range of 650-750 nm. Since aluminum is less reflective at these wavelengths, the combined film stack will produce a surface with relatively constant reflectivity for all wavelengths in the visible spectrum. In an example, a scanning mirror is coated with a silver film. The silver film is overlaid with a dichroic film stack which is greater than 50% reflective in the wavelength range of 400-500 nm.

In some embodiments, the signal from one or more sensors is input directly into the steering element driver, which is provided with circuits that adapt sensor input signals into drive currents or voltages for the one or more scanning mirrors. In other embodiments, a computer, microcontroller, application specific integrated circuit (ASIC) or other control circuit external to the steering element driver is provided and adapts sensor signals into control signals that direct the steering element driver in controlling the one or more scanning mirrors.

In some embodiments, the scanning mirror driver responds to input from motion sensors such as a gyroscope or an accelerometer. In an example embodiment, the white light source acts as a spot-light, providing a narrowly diverging beam of white light. The scanning mirror driver responds to input from one or more accelerometers by angling the beam of light such that it leads the motion of the light source. In an example, the light source is used as a hand-held flash-light. As the flash-light is swept in an arc the scanning mirror directs the output of the light source in a direction that is angled towards the direction of motion of the flash light. In an example embodiment, the white light source acts as a spot-light, providing a narrowly diverging beam of white light. The scanning mirror driver responds to input from one or more accelerometers and gyroscopes by directing the beam such that it illuminates the same spot regardless of the position of the light source. An application for such a device would be self-aiming spot-lights on vehicles such as helicopters or automobiles.

In an embodiment, the dynamic white light source could be used to provide dynamic head-lights for automobiles. Shape, intensity, and color point of the projected beam are modified depending on inputs from various sensors in the vehicle. In an example, a speedometer is used to determine the vehicle speed while in motion. Above a critical threshold speed, the headlamp projected beam brightness and shape are altered to emphasize illumination at distances that increase with increasing speed. In another example, sensors are used to detect the presence of street signs or pedestrians adjacent to the path of travel of the vehicle. Such sensor may include: forward looking infra-red, infra-red cameras, CCD cameras, cameras, Light detection and ranging (LIDAR) systems, and ultrasonic rangefinders among others.

In an example, sensors are used to detect the presence of front, rear or side windows on nearby vehicles. Shape, intensity, and color point of the projected beam are modified to reduce how much of the headlight beam shines on passengers and operators of other vehicles. Such glare-reducing technology would be advantageous in night-time applications where compromises must be made between placement of lamps on vehicles optimized for how well an area is illuminated and placement of the beam to improve safety of other drivers by reducing glare.

At present, the high and low beams are used with headlights and the driver has to switch manually between them with all known disadvantages. The headlight horizontal swivel is used in some vehicles, but it is currently implemented with the mechanical rotation of the whole assembly. Based on the dynamic light source disclosed in this invention, it is possible to move the beam gradually and automatically from the high beam to low beam based on simple sensor(s) sensitive to the distance of the approaching vehicle, pedestrian, bicyclist or obstacle. The feedback from such sensors would move the beam automatically to maintain the best visibility and at the same time prevent blinding of the driver going in the opposite direction. With 2D scanners and the simple sensors, the scanned laser based headlights with horizontal and vertical scanning capability can be implemented.

Optionally, the distance to the incoming vehicles, obstacles, etc. or level of fog can be sensed by a number of ways. The sensors could include the simple cameras, including infrared one for sensing in dark, optical distance sensors, simple radars, light scattering sensor, etc. The distance would provide the signal for the vertical beam positioning, thus resulting in the optimum beam height that provides best visibility and does not blind drivers of the incoming vehicles.

In an alternative embodiment, the dynamic white light source could be used to provide dynamic lighting in restaurants based on machine vision. An infra-red or visible light camera is used to image a table with diners. The number and positions or diners at the table are identified by a computer, microcontroller, ASIC or other computing device. The microcontroller then outputs coordinated signals to the laser driver and the scanning mirror to achieve spatially localized lighting effects that change dynamically throughout the meal. By scanning the white light spot quickly enough the light would appear to the human eye to be a static illumination. For example, the white light source might be provided with red and green lasers which can be used to modulate the color point of the white light illuminating individual diners to complement their clothing color. The dynamic white light source could preferentially illuminate food dishes and drinks. The dynamic white light source could be provided with near-UV laser sources that could be used to highlight certain objects at the table by via fluorescence by preferentially illuminating them with near-UV light. The white light source could measure time of occupancy of the table as well as number of food items on the table to tailor the lighting brightness and color point for individual segments of the meal.

Such a white light source would also have applications in other venues. In another example use, the dynamic white light source could be used to preferentially illuminate people moving through darkened rooms such as theaters or warehouses.

In another alternative embodiment, the dynamic white light source could be used to illuminate work spaces. In an example, human machine interaction may be aided in a factory by using dynamically changing spatial distributions of light as well as light color point to provide information cues to workers about their work environments and tasks. For example, dangerous pieces of equipment could be highlighted in a light spot with a predetermined color point when workers approach. As another example, emergency egress directions customized for individual occupants based on their locations could be projected onto the floor or other surfaces of a building.

In other embodiments, individuals would be tracked using triangulation of RFID badges or triangulation of Wi-Fi transmissions or other means that could be included in devices such as cell phones, smart watches, laptop computers, or any type of device.

In an alternative aspect, the present disclosure provides a smart light system with color and brightness dynamic control. The smart light system includes a microcontroller configured to receive input information for generating one or more control signals. Further, the smart light system includes a laser device configured to be driven by at least one of the one or more control signals to emit at lease a first laser beam with a first peak wavelength in a color range of violet or blue spectrum and a second laser beam with a second peak wavelength longer than the first peak wavelength. Additionally, the smart light system includes a pathway configured to dynamically guide the first laser beam and the second laser beam. The smart light system further includes a wavelength converting member configured to receive either the first laser beam or the second laser beam from the pathway and configured to convert a first fraction of the first laser beam with the first peak wavelength to a first spectrum with a third peak wavelength longer than the first peak wavelength or convert a second fraction of the second laser beam with the second peak wavelength to a second spectrum with a fourth peak wavelength longer than the second peak wavelength. The first spectrum and the second spectrum respectively combine with remaining fraction of the first laser beam with the first peak wavelength and the second laser beam with the second peak wavelength to reemit an output light beam of a broader spectrum dynamically varied from a first color point to a second color point. Furthermore, the smart light system includes a beam shaping optical element configured to collimate and focus the output light beam and a beam steering optical element configured to direct the output light beam. The smart light system further includes a beam steering driver coupled to the microcontroller to receive some of the one or more control signals based on input information for the beam steering optical element to dynamically scan the output light beam substantially in white color to provide spatially modulated illumination and selectively direct one or more of the multiple laser beams with the first peak wavelengths in different color ranges onto one or more of multiple target areas or into one or more of multiple target directions in one or more selected periods. Moreover, the smart light system includes one or more sensors configured in a feedback loop circuit coupled to the controller. The one or more sensors are configured to provide one or more feedback currents or voltages based on the various parameters associated with the target of interest detected in real time to the controller with one or more of light movement response, light color response, light brightness response, spatial light pattern response, and data signal communication response being triggered.

Optionally, the laser device includes one or more first laser diodes for emitting the first laser beam with the first peak wavelength in violet spectrum ranging from 380 to 420 nm or blue spectrum ranging from 420 to 480 nm.

Optionally, the laser device includes one or more second laser diodes for emitting the second laser beam with the second peak wavelength in red spectrum ranging from 600 to 670 nm, or in green spectrum ranging from 480 nm to 550 nm, or in another blue spectrum with the second peak wavelength longer than the first peak wavelength.

Optionally, the one or more first laser diodes include an active region including a gallium and nitrogen containing material configured to be driven by the one or more driving currents.

Optionally, the gallium and nitrogen containing material includes one or more of GaN, AlN, InN, InGaN, AlGaN, InAlN, InAlGaN.

Optionally, the one or more second laser diodes emitting in the red or infrared region include an active region including a gallium and arsenic containing material or an indium and phosphorous containing material configured to be driven by the one or more driving currents.

Optionally, the wavelength converting member includes a first phosphor material selected for absorbing a first ratio of the first laser beam with the first peak wavelength in the violet spectrum and converting to a first spectrum with the third peak wavelength longer than the first peak wavelength to emit a first output light beam with a first color point, a second phosphor material selected for absorbing a second ratio of the first laser beam with the first peak wavelength in the blue spectrum and converting to a second spectrum with the third peak wavelength longer than the first peak wavelength to emit a second output light beam with a second color point, a third phosphor material selected for absorbing a third ratio of the second laser beam with the second peak wavelength and converting to a third spectrum with the fourth wavelength longer than the second peak wavelength to emit a third output light beam with a third color point.

Optionally, the pathway includes an optical fiber to guide either the first laser beam or the second laser beam to the wavelength converter member disposed remotely as a remote light source.

Optionally, the pathway includes a waveguide for guiding either the first laser beam or the second laser beam to the wavelength converter member to generate the output light beam with a dynamically varying color point.

Optionally, the pathway includes free-space optics devices.

Optionally, the beam shaping optical element includes one or a combination of more optical elements selected a list of slow axis collimating lens, fast axis collimating lens, aspheric lens, ball lens, total internal reflector (TIR) optics, parabolic lens optics, refractive optics, and micro-electro-mechanical system (MEMS) mirrors configured to direct, collimate, focus the output light beam with modified angular distribution thereof.

Optionally, beam steering optical element is selected from one of a micro-electromechanical system (MEMS) mirror, a digital light processing (DLP) chip, a digital mirror device (DMD), and a liquid crystal on silicon (LCOS) chip.

Optionally, the beam steering optical element includes a 2-dimensional array of micro-mirrors to steer, pattern, and/or pixelate the multiple output light beams with varying color points by reflecting from corresponding pixels at a predetermined angle to turn each pixel on or off.

Optionally, the 2-dimensional array of micro-mirrors are configured to be activated by some of the one or more control signals received by the beam steering driver from the microcontroller based on the input information to manipulate the multiple output light beams with respective color points being dynamically adjusted to provide a pattern of color and brightness onto a surface of a target area or into a direction of a target space.

What is claimed is:

1. A light source configured for visible light emission and violet or ultraviolet (UV) emission, the light source comprising:
    a nitrogen containing laser diode configured as a first pump-light device;
    the nitrogen containing laser diode comprising an optical cavity; the optical cavity comprising an optical waveguide region and one or more facet regions,
    the nitrogen containing laser diode configured to output directional electromagnetic radiation through at least one of the facet regions;
    the directional electromagnetic radiation from the nitrogen containing laser diode characterized by a first peak wavelength;
    a first wavelength converter optically coupled to a pathway to receive the directional electromagnetic radiation from the first pump-light device, wherein the wavelength converter is configured to convert at least a fraction of the directional electromagnetic radiation with the first peak wavelength to at least a second peak wavelength that is longer than the first peak wavelength and to generate the visible light emission as a white-color emission comprising at least the second peak wavelength;
    the light source configured with an violet or UV emitting laser diode to provide the violet or UV emission;
    the violet or UV emitting laser diode configured to output a directional electromagnetic radiation characterized by a third peak wavelength;
    the third peak wavelength characterized by a wavelength in a violet or UV portion of the electromagnetic spectrum;
    a package member configured with a base member; and
    at least one common support member configured to support at least the nitrogen containing laser diode member and the first wavelength converter member.

2. The light source of claim 1 further comprising an infrared emitting laser diode to provide an infrared emission, the infrared emitting laser diode configured to output an electromagnetic radiation characterized by a fourth peak wavelength in the infrared region.

3. The light source of claim 1 wherein the first peak wavelength is in a blue wavelength rage of 420 nm to 480 nm, and the violet or UV emission is in a UV wavelength range of 270 nm to 390 nm or a violet wavelength range of 390 nm to 425 nm.

4. The light source of claim 1 further comprising a beam shaper configured to direct the visible light emission and the violet or UV emission for illuminating a target of interest.

5. The light source of claim 4, wherein the beam shaper comprises one or a combination of optical elements selected a list of slow axis collimating lens, fast axis collimating lens, aspheric lens, ball lens, total internal reflector (TIR) optics, parabolic lens optics, refractive optics, and micro-electro-mechanical system (MEMS) mirrors configured to direct, collimate, focus the white-color spectrum to at least modify an angular distribution thereof.

6. The light source of claim 1 wherein the nitrogen containing laser diode is a gallium and nitrogen containing laser diode emitting a first peak wavelength in the violet wavelength region of 390 nm to 420 nm or the blue wavelength region of 420 nm to 480 nm.

7. The light source of claim 1 wherein the first wavelength converter member is characterized by a reflective mode operation such that the directional electromagnetic radiation with the first wavelength from the first pump-light is incident on an excitation surface of the wavelength converter member; and wherein the primary emission of the second wavelength from the wavelength converter is emitted from the same excitation surface of the wavelength converter member.

8. The light source of claim 7 wherein the first wavelength converter is optically coupled to the pathway to receive the directional electromagnetic radiation from the violet or UV emitting laser diode, wherein the first wavelength converter is configured to reflect and/or scatter the violet or UV emission; and wherein the violet or UV emission and the visible light emission are overlapping within a same spatial area.

9. The light source of claim 1 wherein the first wavelength converter member is characterized by a transmissive mode operation such that the directional electromagnetic radiation with the first wavelength from the first pump-light is incident on an excitation surface of the wavelength converter member; and wherein the primary emission of the second wavelength from the wavelength converter is emitted from an emission surface; wherein the emission surface is on the opposite side of the wavelength converter from the excitation surface.

10. The light source of claim 9 wherein the first wavelength converter is optically coupled to the pathway to receive the directional electromagnetic radiation from the violet or UV laser diode, wherein the wavelength converter is configured to transmit and/or scatter the violet or UV emission; and wherein the violet or UV emission and the visible light emission are overlapping within a same spatial area.

11. The light source of claim 1, wherein the first wavelength converter member is comprised of a phosphor material; and wherein the phosphor is comprised of a ceramic yttrium aluminum garnet (YAG) doped with Ce, or a single crystal YAG doped with Ce, or a powdered YAG comprising a binder material; and wherein the phosphor member has an optical conversion efficiency of at least 50 lumen per optical watt.

12. The laser diode of claim 1 wherein the violet or UV emitting laser diode is nitrogen containing.

13. The light source of claim 1, wherein the package is a surface mount device (SMD) package and wherein a common support member is configured from the base of the SMD package.

14. The light source of claim 1, wherein the package is selected from a TO can type, a flat package type, or a butterfly type.

15. The light source of claim 1, wherein the visible light emission with at least the second peak wavelength is coupled into an optical fiber member, or wherein the violet or UV light emission with the third peak wavelength is coupled into an optical fiber, or wherein both the visible light emission with at least the second peak wavelength and the violet or UV light emission with the third peak wavelength are coupled into an optical fiber member; wherein the optical fiber is a single mode fiber (SMF) or a multi-mode fiber (MMF); and wherein the optical fiber has a core diameter ranging from about 1 um to 10 um, about 10 um to 50 um, about 50 um to 150 um, about 150 um to 500 um, about 500 um to 1 mm, about 1 mm to 5 mm or greater than 5 mm.

16. The light source of claim 15, wherein the optical fiber includes at least one of a transport fiber or a leaky scattering fiber.

17. The light source of claim 1 further comprising one or more sensors and a controller to provide an input signal to the light source; wherein the one or more sensors are configured in a feedback loop circuit to provide a feedback current or voltage to the controller to tune at least one of the one or more control signals to adjust brightness of the visible light emission and/or the violet or UV emission.

18. The light source of claim 1 configured for use in one or more applications including spotlighting, detection, imaging, projection display, spatially dynamic lighting devices, sensing, LIDAR, LiFi, visible light communication, general lighting, commercial lighting and display, automotive lighting, automotive communication and/or detection, defense and security, search and rescue, industrial processing, internet communications, or agriculture or horticulture.

19. The light source of claim 1 configured for use in one or more applications including purification of water, purification of air, and cleaning of surfaces, or disinfection.

20. A light source configured for visible light emission and violet or ultraviolet (UV) emission, the light source comprising:
a nitrogen containing laser diode configured as a first pump-light device;
the nitrogen containing laser diode comprising an optical cavity; the optical cavity comprising an optical waveguide region and one or more facet regions,
the nitrogen containing laser diode configured to output directional electromagnetic radiation through at least one of the facet regions;
the directional electromagnetic radiation from the nitrogen containing laser diode characterized by a first peak wavelength;
a first wavelength converter optically coupled to a pathway to receive the directional electromagnetic radiation from the first pump-light device, wherein the wavelength converter is configured to convert at least a fraction of the directional electromagnetic radiation with the first peak wavelength to at least a second peak wavelength that is longer than the first peak wavelength and to generate the visible light emission as a white-color emission comprising at least the second peak wavelength, the first wavelength converter configured to provide the visible light emission in a reflective mode such that the directional electromagnetic radiation is incident on an excitation surface of the first wavelength converter and the excitation surface is a primary emission surface of the visible light emission;
the light source configured with an violet or UV emitting laser diode to provide the violet or UV emission;
the violet or UV emitting laser diode configured to output a directional electromagnetic radiation characterized by a third peak wavelength;
the third peak wavelength characterized by a wavelength in a violet or UV portion of the electromagnetic spectrum;
a surface mount device (SMD) package member configured with a base member; and
at least one common support member configured to support at least the nitrogen containing laser diode member and the first wavelength converter member, wherein the at least one common support member comprises the base member of the SMD package.

21. A system comprising:
a light source configured for visible light emission and violet or ultraviolet (UV) emission;
a package configured to enclose the light source, the light source comprising:
a nitrogen containing laser diode configured as a first pump-light device;
the nitrogen containing laser diode comprising an optical cavity; the optical cavity comprising an optical waveguide region and one or more facet regions,
the nitrogen containing laser diode configured to output directional electromagnetic radiation through at least one of the facet regions;
the directional electromagnetic radiation from the nitrogen containing laser diode characterized by a first peak wavelength;
a first wavelength converter optically coupled to the pathway to receive the directional electromagnetic radiation from the first pump-light device, wherein the wavelength converter is configured to convert at least a fraction of the directional electromagnetic radiation with the first peak wavelength to at least a second peak wavelength that is longer than the first peak wavelength and to generate the visible light emission as a white-color emission comprising at least the second peak wavelength;
the light source configured with an violet or UV emitting laser diode to provide the violet or UV emission;
the violet or UV emitting laser diode configured to output a directional electromagnetic radiation characterized by a third peak wavelength;
the third peak wavelength characterized by a wavelength in a violet or UV portion of the electromagnetic spectrum; and
at least one common support member configured to support at least the nitrogen containing laser diode member and the first wavelength converter member.

22. The system of claim 21 configured for use in an application selected from purification, cleaning, or disinfecting.

23. The system of claim 21 configured for use in one or more applications including lighting, sensing, and/or communications, wherein an emission from the violet or UV emitting laser diode is used for the sensing and/or communications applications.

* * * * *